(12) United States Patent
McClurken

(10) Patent No.: US 7,811,282 B2
(45) Date of Patent: Oct. 12, 2010

(54) FLUID-ASSISTED ELECTROSURGICAL DEVICES, ELECTROSURGICAL UNIT WITH PUMP AND METHODS OF USE THEREOF

(75) Inventor: Michael E. McClurken, Durham, NH (US)

(73) Assignee: Salient Surgical Technologies, Inc., Portsmouth, NH (US)

( * ) Notice: Subject to any disclaimer, the term of this patent is extended or adjusted under 35 U.S.C. 154(b) by 1139 days.

(21) Appl. No.: 11/274,908

(22) Filed: Nov. 14, 2005

(65) Prior Publication Data

US 2006/0149225 A1  Jul. 6, 2006

Related U.S. Application Data

(63) Continuation-in-part of application No. 10/488,801, filed on Dec. 16, 2004, which is a continuation of application No. PCT/US02/28488, filed on Sep. 5, 2002, and a continuation-in-part of application No. 09/947,658, filed on Sep. 5, 2001, now Pat. No. 7,115, 139, which is a continuation-in-part of application No. 09/797,049, filed on Mar. 1, 2001, now Pat. No. 6,702, 810.

(60) Provisional application No. 60/356,390, filed on Feb. 12, 2002, provisional application No. 60/368,177, filed on Mar. 27, 2002, provisional application No. 60/187,114, filed on Mar. 6, 2000, provisional application No. 60/630,582, filed on Nov. 23, 2004.

(51) Int. Cl.
*A61B 18/18* (2006.01)

(52) U.S. Cl. .......................... 606/49; 606/50
(58) Field of Classification Search .................... 606/41, 606/45, 48–52
See application file for complete search history.

(56) References Cited

U.S. PATENT DOCUMENTS

| 623,022 | A | 4/1899 | Johnson |
| 1,735,271 | A | 11/1929 | Groff |
| 1,814,791 | A | 7/1931 | Ende |
| 2,002,594 | A | 5/1935 | Wappler et al. |
| 2,031,682 | A | 2/1936 | Wappler et al. |
| 2,102,270 | A | 12/1937 | Hyams |
| 2,275,167 | A | 3/1942 | Bierman |

(Continued)

FOREIGN PATENT DOCUMENTS

DE  1 007 960  5/1957

(Continued)

OTHER PUBLICATIONS

U.S. Office Action issued in related U.S. Appl. No. 11/318,207 dated Dec. 30, 2008.

(Continued)

*Primary Examiner*—Roy D Gibson
(74) *Attorney, Agent, or Firm*—Grossman, Tucker, Perreault & Pfleger, PLLC

(57) ABSTRACT

The invention provides an electrosurgical unit comprising a radio-frequency power source and a pump, with the throughput of fluid expelled by the pump controlled by the RF power level setting and fluid flow rate setting. The invention also provides various electrosurgical devices which may be used with the electrosurgical unit. In one embodiment, the electrosurgical device comprises a first electrode tip spaced next to a second electrode tip with a portion of the first electrode tip facing the second electrode tip and a portion of the second electrode tip facing the first electrode tip, the first electrode tip and the second electrode tip both having a spherical distal end, and a fluid outlet arrangement to expel fluid onto the electrode tips solely at locations remote from the electrode tip portions facing each other.

40 Claims, 108 Drawing Sheets

U.S. PATENT DOCUMENTS

| | | |
|---|---|---|
| 2,888,928 A | 6/1959 | Seiger |
| 3,163,166 A | 12/1964 | Brent et al. |
| 3,682,130 A | 8/1972 | Jeffers |
| 3,750,650 A | 8/1973 | Ruttgers |
| 3,901,241 A | 8/1975 | Allen, Jr. |
| 4,037,590 A | 7/1977 | Dohring et al. |
| 4,060,088 A | 11/1977 | Morrison, Jr. et al. |
| 4,116,198 A | 9/1978 | Roos |
| 4,244,371 A | 1/1981 | Farin |
| 4,276,874 A | 7/1981 | Wolvek et al. |
| 4,301,802 A | 11/1981 | Poler |
| 4,307,720 A | 12/1981 | Weber, Jr. |
| 4,321,931 A | 3/1982 | Hon |
| 4,326,529 A | 4/1982 | Doss et al. |
| 4,342,218 A | 8/1982 | Fox |
| 4,355,642 A | 10/1982 | Alferness |
| 4,381,007 A | 4/1983 | Doss |
| 4,532,924 A | 8/1985 | Auth et al. |
| 4,548,207 A | 10/1985 | Reimels |
| 4,567,890 A | 2/1986 | Ohta et al. |
| 4,602,628 A | 7/1986 | Allen, Jr. |
| 4,671,274 A | 6/1987 | Sorochenko |
| 4,674,499 A | 6/1987 | Pao |
| 4,919,129 A | 4/1990 | Weber, Jr. |
| 4,920,982 A | 5/1990 | Goldstein |
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,976,711 A | 12/1990 | Parins et al. |
| 4,985,030 A | 1/1991 | Melzer et al. |
| 4,998,933 A | 3/1991 | Eggers et al. |
| 5,009,656 A | 4/1991 | Reimels |
| 5,013,312 A | 5/1991 | Parins et al. |
| 5,035,696 A | 7/1991 | Rydell |
| 5,071,419 A | 12/1991 | Rydell et al. |
| 5,080,660 A | 1/1992 | Buelna |
| 5,122,138 A | 6/1992 | Manwaring |
| 5,125,928 A | 6/1992 | Parins et al. |
| 5,147,357 A | 9/1992 | Rose et al. |
| 5,151,102 A | 9/1992 | Kamiyama et al. |
| 5,156,613 A | 10/1992 | Sawyer |
| 5,167,659 A | 12/1992 | Ohtomo et al. |
| 5,171,311 A | 12/1992 | Rydell et al. |
| 5,190,541 A | 3/1993 | Abele et al. |
| 5,195,959 A | 3/1993 | Smith |
| 5,197,963 A | 3/1993 | Parins |
| 5,197,964 A | 3/1993 | Parins |
| 5,217,460 A | 6/1993 | Knoepfler |
| 5,234,428 A | 8/1993 | Kaufman |
| 5,242,441 A | 9/1993 | Avitall |
| 5,242,442 A | 9/1993 | Hirschfeld |
| 5,254,117 A | 10/1993 | Rigby |
| 5,269,780 A | 12/1993 | Roos |
| 5,269,781 A | 12/1993 | Hewell, III |
| 5,277,696 A | 1/1994 | Hagen |
| 5,281,215 A | 1/1994 | Milder |
| 5,281,216 A | 1/1994 | Klicek |
| 5,282,799 A | 2/1994 | Rydell |
| 5,290,286 A | 3/1994 | Parins |
| 5,300,087 A | 4/1994 | Knoepfler |
| 5,313,943 A | 5/1994 | Houser et al. |
| 5,318,589 A | 6/1994 | Lichtman |
| 5,322,503 A | 6/1994 | Desai |
| 5,330,521 A | 7/1994 | Cohen |
| 5,334,193 A | 8/1994 | Nardella |
| 5,336,220 A | 8/1994 | Ryan |
| 5,342,357 A | 8/1994 | Nardella |
| 5,342,359 A | 8/1994 | Rydell |
| 5,348,554 A | 9/1994 | Imran et al. |
| 5,364,394 A | 11/1994 | Mehl |
| 5,383,874 A | 1/1995 | Jackson et al. |
| 5,383,876 A | 1/1995 | Nardella |
| 5,395,312 A | 3/1995 | Desai |
| 5,395,363 A | 3/1995 | Billings et al. |
| 5,401,272 A | 3/1995 | Perkins |
| 5,403,311 A | 4/1995 | Abele et al. |
| 5,403,312 A | 4/1995 | Yates et al. |
| 5,405,344 A | 4/1995 | Williamson et al. |
| 5,405,376 A | 4/1995 | Mulier et al. |
| 5,417,672 A | 5/1995 | Nita et al. |
| 5,417,709 A | 5/1995 | Slater |
| 5,431,168 A | 7/1995 | Webster, Jr. |
| 5,431,649 A | 7/1995 | Mulier et al. |
| 5,433,708 A | 7/1995 | Nichols et al. |
| 5,437,662 A | 8/1995 | Nardella |
| 5,437,664 A | 8/1995 | Cohen et al. |
| 5,441,498 A | 8/1995 | Perkins |
| 5,441,503 A | 8/1995 | Considine et al. |
| 5,445,638 A | 8/1995 | Rydell et al. |
| 5,456,682 A | 10/1995 | Edwards et al. |
| 5,456,684 A | 10/1995 | Schmidt et al. |
| 5,458,596 A | 10/1995 | Lax et al. |
| 5,458,597 A | 10/1995 | Edwards et al. |
| 5,458,598 A | 10/1995 | Feinberg et al. |
| 5,460,629 A | 10/1995 | Shlain et al. |
| 5,462,521 A | 10/1995 | Brucker et al. |
| 5,472,441 A | 12/1995 | Edwards et al. |
| 5,472,443 A | 12/1995 | Cordis et al. |
| 5,487,385 A | 1/1996 | Avitall |
| 5,490,819 A | 2/1996 | Nicholas et al. |
| 5,500,012 A | 3/1996 | Brucker et al. |
| 5,514,130 A | 5/1996 | Baker |
| 5,522,815 A | 6/1996 | Durgin, Jr. et al. |
| 5,536,267 A | 7/1996 | Edwards et al. |
| 5,540,562 A | 7/1996 | Giter |
| 5,542,928 A | 8/1996 | Evans et al. |
| 5,542,945 A | 8/1996 | Fritzsch |
| 5,556,397 A | 9/1996 | Long |
| 5,558,671 A | 9/1996 | Yates |
| 5,562,503 A | 10/1996 | Ellman et al. |
| 5,562,702 A | 10/1996 | Huitema et al. |
| 5,562,703 A | 10/1996 | Desai |
| 5,564,440 A | 10/1996 | Swartz et al. |
| 5,569,242 A | 10/1996 | Lax et al. |
| 5,569,243 A | 10/1996 | Kortenbach et al. |
| 5,573,424 A | 11/1996 | Poppe |
| 5,573,533 A | 11/1996 | Strul |
| 5,575,810 A | 11/1996 | Swanson et al. |
| 5,584,872 A | 12/1996 | LaFontaine et al. |
| 5,599,346 A | 2/1997 | Edwards et al. |
| 5,599,350 A | 2/1997 | Schulze et al. |
| 5,605,539 A | 2/1997 | Buelna et al. |
| 5,609,151 A | 3/1997 | Mulier et al. |
| 5,633,578 A | 5/1997 | Eggers et al. |
| 5,637,110 A | 6/1997 | Pennybacker et al. |
| 5,640,955 A | 6/1997 | Ockuly et al. |
| 5,643,197 A | 7/1997 | Brucker et al. |
| 5,647,869 A | 7/1997 | Goble et al. |
| 5,647,871 A | 7/1997 | Levine et al. |
| 5,653,692 A | 8/1997 | Masterson et al. |
| 5,660,836 A | 8/1997 | Knowlton |
| 5,676,662 A | 10/1997 | Fleischhacker et al. |
| 5,676,693 A | 10/1997 | LaFontaine |
| 5,681,282 A | 10/1997 | Eggers et al. |
| 5,681,294 A | 10/1997 | Osborne et al. |
| 5,683,366 A | 11/1997 | Eggers et al. |
| 5,683,384 A | 11/1997 | Gough et al. |
| 5,687,723 A | 11/1997 | Avitall |
| 5,688,270 A | 11/1997 | Yates et al. |
| 5,693,045 A | 12/1997 | Eggers |
| 5,697,281 A | 12/1997 | Eggers et al. |
| 5,697,536 A | 12/1997 | Eggers et al. |
| 5,697,882 A | 12/1997 | Eggers et al. |

| | | | | | |
|---|---|---|---|---|---|
| 5,697,909 A | 12/1997 | Eggers et al. | 5,954,716 A | 9/1999 | Sharkey et al. |
| 5,697,927 A | 12/1997 | Imran et al. | 5,957,919 A | 9/1999 | Laufer |
| 5,709,680 A | 1/1998 | Yates et al. | 5,964,755 A | 10/1999 | Edwards |
| 5,713,896 A | 2/1998 | Nardella | 5,971,983 A | 10/1999 | Lesh |
| 5,718,241 A | 2/1998 | Ben-Haim et al. | 5,976,128 A | 11/1999 | Schilling et al. |
| 5,718,701 A | 2/1998 | Shai et al. | 5,980,504 A | 11/1999 | Sharkey et al. |
| 5,718,703 A | 2/1998 | Chin | 5,980,516 A | 11/1999 | Mulier |
| 5,722,400 A | 3/1998 | Ockuly et al. | 5,989,248 A | 11/1999 | Tu et al. |
| 5,725,524 A | 3/1998 | Mulier et al. | 5,992,418 A | 11/1999 | De La Rama et al. |
| 5,730,127 A | 3/1998 | Avitall | 5,993,412 A | 11/1999 | Deily et al. |
| 5,735,846 A | 4/1998 | Panescu et al. | 6,003,517 A | 12/1999 | Sheffield et al. |
| 5,743,903 A | 4/1998 | Stern et al. | 6,004,316 A | 12/1999 | Laufer |
| 5,746,739 A | 5/1998 | Sutter | 6,004,319 A | 12/1999 | Goble et al. |
| 5,749,869 A | 5/1998 | Lindenmeier et al. | 6,007,570 A | 12/1999 | Sharkey et al. |
| 5,755,717 A | 5/1998 | Yates et al. | 6,010,500 A | 1/2000 | Sherman et al. |
| 5,755,753 A | 5/1998 | Knowlton | 6,015,391 A | 1/2000 | Rishton et al. |
| 5,766,153 A | 6/1998 | Eggers et al. | 6,015,407 A | 1/2000 | Rieb et al. |
| 5,766,167 A | 6/1998 | Eggers et al. | 6,016,809 A | 1/2000 | Mulier et al. |
| 5,785,705 A | 7/1998 | Baker | 6,017,338 A | 1/2000 | Brucker et al. |
| 5,785,706 A | 7/1998 | Bednarek | 6,018,676 A | 1/2000 | Davis et al. |
| 5,792,140 A | 8/1998 | Tu et al. | 6,019,757 A | 2/2000 | Scheldrup |
| 5,797,905 A | 8/1998 | Fleischman et al. | 6,024,733 A | 2/2000 | Eggers et al. |
| 5,797,960 A | 8/1998 | Stevens et al. | 6,027,501 A | 2/2000 | Goble et al. |
| 5,800,413 A | 9/1998 | Swartz et al. | 6,030,379 A | 2/2000 | Panescu et al. |
| 5,800,482 A | 9/1998 | Pomeranz et al. | 6,030,381 A | 2/2000 | Jones |
| 5,807,393 A | 9/1998 | Williamson et al. | 6,032,077 A | 2/2000 | Pomeranz |
| 5,807,395 A | 9/1998 | Mulier et al. | 6,032,674 A | 3/2000 | Eggers et al. |
| 5,810,764 A | 9/1998 | Eggers et al. | 6,033,398 A | 3/2000 | Farley et al. |
| 5,810,805 A | 9/1998 | Sutcu et al. | 6,035,238 A | 3/2000 | Ingle et al. |
| 5,810,811 A | 9/1998 | Yates et al. | 6,036,687 A | 3/2000 | Laufer et al. |
| 5,817,093 A | 10/1998 | Williamson et al. | 6,045,532 A | 4/2000 | Eggers et al. |
| 5,823,956 A | 10/1998 | Roth et al. | 6,047,700 A | 4/2000 | Eggers et al. |
| 5,827,271 A | 10/1998 | Buysse et al. | 6,048,333 A | 4/2000 | Lennox et al. |
| 5,827,281 A | 10/1998 | Levin | 6,053,172 A | 4/2000 | Hovda et al. |
| 5,833,703 A | 11/1998 | Manushakian | 6,053,912 A | 4/2000 | Panescu et al. |
| 5,843,019 A | 12/1998 | Eggers et al. | 6,056,744 A | 5/2000 | Edwards |
| 5,843,021 A | 12/1998 | Edwards et al. | 6,056,745 A | 5/2000 | Panescu et al. |
| 5,843,078 A | 12/1998 | Sharkey | 6,056,746 A | 5/2000 | Goble |
| 5,843,152 A | 12/1998 | Tu et al. | 6,056,747 A | 5/2000 | Saadat et al. |
| 5,855,614 A | 1/1999 | Stevens et al. | 6,059,781 A | 5/2000 | Yamanashi et al. |
| 5,860,951 A | 1/1999 | Eggers et al. | 6,063,079 A | 5/2000 | Hovda et al. |
| 5,860,974 A | 1/1999 | Abele | 6,063,081 A | 5/2000 | Mulier et al. |
| 5,861,002 A | 1/1999 | Desai | 6,066,134 A | 5/2000 | Eggers et al. |
| 5,861,021 A | 1/1999 | Thome et al. | 6,066,139 A | 5/2000 | Ryan et al. |
| 5,868,739 A | 2/1999 | Lindenmeier et al. | 6,068,627 A | 5/2000 | Orszulak et al. |
| 5,871,469 A | 2/1999 | Eggers | 6,068,653 A | 5/2000 | LaFontaine |
| 5,871,524 A | 2/1999 | Knowlton | 6,071,280 A | 6/2000 | Edwards et al. |
| 5,873,855 A | 2/1999 | Eggers | 6,073,051 A | 6/2000 | Sharkey et al. |
| 5,876,398 A | 3/1999 | Mulier et al. | 6,074,389 A | 6/2000 | Levine et al. |
| 5,879,348 A | 3/1999 | Owens et al. | 6,080,151 A | 6/2000 | Swartz et al. |
| 5,888,198 A | 3/1999 | Eggers et al. | 6,081,749 A | 6/2000 | Ingle et al. |
| 5,891,095 A | 4/1999 | Eggers et al. | 6,083,237 A | 7/2000 | Huitema et al. |
| 5,891,141 A | 4/1999 | Rydell | 6,086,585 A | 7/2000 | Hovda et al. |
| 5,891,142 A | 4/1999 | Eggers et al. | 6,086,586 A | 7/2000 | Hooven |
| 5,893,848 A | 4/1999 | Negus et al. | 6,091,995 A | 7/2000 | Ingle et al. |
| 5,895,355 A | 4/1999 | Schaer | 6,093,186 A | 7/2000 | Goble |
| 5,895,417 A | 4/1999 | Pomeranz et al. | 6,095,149 A | 8/2000 | Sharkey et al. |
| 5,897,553 A | 4/1999 | Mulier et al. | 6,096,037 A | 8/2000 | Mulier et al. |
| 5,902,272 A | 5/1999 | Eggers et al. | 6,099,514 A | 8/2000 | Sharkey et al. |
| 5,902,328 A | 5/1999 | LaFontaine et al. | 6,102,046 A | 8/2000 | Weinstein et al. |
| 5,904,711 A | 5/1999 | Flom et al. | 6,105,581 A | 8/2000 | Eggers et al. |
| 5,906,613 A | 5/1999 | Mulier et al. | 6,109,268 A | 8/2000 | Thapliyal et al. |
| 5,913,854 A | 6/1999 | Maguire et al. | 6,113,596 A | 9/2000 | Hooven |
| 5,913,856 A | 6/1999 | Chia et al. | 6,113,597 A | 9/2000 | Eggers et al. |
| 5,919,191 A | 7/1999 | Lennox et al. | 6,117,109 A | 9/2000 | Eggers et al. |
| 5,919,219 A | 7/1999 | Knowlton | 6,122,549 A | 9/2000 | Sharkey et al. |
| 5,921,982 A | 7/1999 | Lesh et al. | H1904 H | 10/2000 | Yates et al. |
| 5,921,983 A | 7/1999 | Shannon, Jr. | 6,126,682 A | 10/2000 | Sharkey et al. |
| 5,925,045 A | 7/1999 | Reimels et al. | 6,135,999 A | 10/2000 | Fanton et al. |
| 5,935,123 A | 8/1999 | Edwards et al. | 6,141,576 A | 10/2000 | Littmann et al. |
| 5,944,715 A | 8/1999 | Goble | 6,142,992 A | 11/2000 | Cheng et al. |
| 5,948,011 A | 9/1999 | Knowlton | 6,149,620 A | 11/2000 | Baker et al. |
| 5,951,549 A | 9/1999 | Richardson et al. | 6,159,194 A | 12/2000 | Eggers et al. |

| | | |
|---|---|---|
| 6,159,208 A | 12/2000 | Hovda et al. |
| 6,165,169 A | 12/2000 | Panescu et al. |
| 6,165,175 A | 12/2000 | Wampler et al. |
| 6,168,594 B1 | 1/2001 | LaFontaine et al. |
| 6,171,275 B1 | 1/2001 | Webster, Jr. |
| 6,174,308 B1 | 1/2001 | Goble et al. |
| 6,174,309 B1 | 1/2001 | Wrublewski et al. |
| 6,176,857 B1 | 1/2001 | Ashley |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,190,384 B1 | 2/2001 | Ouchi |
| 6,193,715 B1 | 2/2001 | Wrublewski et al. |
| 6,193,716 B1 | 2/2001 | Shannon, Jr. |
| 6,203,542 B1 | 3/2001 | Ellsberry et al. |
| 6,210,402 B1 | 4/2001 | Olsen et al. |
| 6,210,406 B1 | 4/2001 | Webster |
| 6,210,410 B1 | 4/2001 | Farin et al. |
| 6,210,411 B1 | 4/2001 | Hofmann et al. |
| 6,212,426 B1 | 4/2001 | Swanson |
| 6,216,704 B1 | 4/2001 | Ingle et al. |
| 6,217,576 B1 | 4/2001 | Tu et al. |
| 6,221,039 B1 | 4/2001 | Durgin et al. |
| 6,221,069 B1 | 4/2001 | Daikuzono |
| 6,224,592 B1 | 5/2001 | Eggers et al. |
| 6,224,593 B1 | 5/2001 | Ryan et al. |
| 6,226,554 B1 | 5/2001 | Tu et al. |
| 6,228,078 B1 | 5/2001 | Eggers et al. |
| 6,228,082 B1 | 5/2001 | Baker et al. |
| 6,231,591 B1 | 5/2001 | Desai |
| 6,235,020 B1 | 5/2001 | Cheng et al. |
| 6,236,891 B1 | 5/2001 | Ingle et al. |
| 6,238,387 B1 | 5/2001 | Miller, III |
| 6,238,391 B1 | 5/2001 | Olsen et al. |
| 6,238,393 B1 | 5/2001 | Mulier et al. |
| 6,241,753 B1 | 6/2001 | Knowlton |
| 6,241,754 B1 | 6/2001 | Swanson et al. |
| 6,251,110 B1 | 6/2001 | Wampler |
| 6,254,600 B1 | 7/2001 | Willink et al. |
| 6,258,086 B1 | 7/2001 | Ashley et al. |
| 6,258,087 B1 | 7/2001 | Edwards et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,654 B1 | 7/2001 | Swartz et al. |
| 6,266,551 B1 | 7/2001 | Osadchy et al. |
| 6,277,112 B1 | 8/2001 | Underwood et al. |
| 6,280,440 B1 | 8/2001 | Gocho |
| 6,283,961 B1 | 9/2001 | Underwood et al. |
| 6,283,988 B1 | 9/2001 | Laufer et al. |
| 6,283,989 B1 | 9/2001 | Laufer et al. |
| 6,290,715 B1 | 9/2001 | Sharkey et al. |
| 6,293,942 B1 | 9/2001 | Goble et al. |
| 6,293,945 B1 | 9/2001 | Parins et al. |
| 6,296,636 B1 | 10/2001 | Cheng et al. |
| 6,296,638 B1 | 10/2001 | Davison et al. |
| 6,296,640 B1 | 10/2001 | Wampler et al. |
| 6,299,633 B1 | 10/2001 | Laufer |
| 6,302,903 B1 | 10/2001 | Mulier et al. |
| 6,306,134 B1 | 10/2001 | Goble et al. |
| 6,309,387 B1 | 10/2001 | Eggers et al. |
| 6,311,090 B1 | 10/2001 | Knowlton |
| 6,312,408 B1 | 11/2001 | Eggers et al. |
| 6,312,430 B1 | 11/2001 | Wilson et al. |
| 6,315,777 B1 | 11/2001 | Comben |
| 6,322,549 B1 | 11/2001 | Eggers et al. |
| 6,322,559 B1 | 11/2001 | Daulton et al. |
| 6,327,505 B1 | 12/2001 | Medhkour et al. |
| 6,328,735 B1 | 12/2001 | Curley et al. |
| 6,328,736 B1 | 12/2001 | Mulier et al. |
| 6,336,926 B1 | 1/2002 | Goble |
| 6,350,262 B1 | 2/2002 | Ashley |
| 6,350,276 B1 | 2/2002 | Knowlton |
| 6,352,533 B1 | 3/2002 | Ellman et al. |
| 6,355,032 B1 | 3/2002 | Hovda et al. |
| 6,358,245 B1 | 3/2002 | Edwards et al. |
| 6,358,248 B1 | 3/2002 | Mulier et al. |
| 6,363,937 B1 | 4/2002 | Hovda et al. |
| 6,371,956 B1 | 4/2002 | Wilson et al. |
| 6,379,350 B1 | 4/2002 | Sharkey et al. |
| 6,379,351 B1 | 4/2002 | Thapliyal et al. |
| 6,391,025 B1 | 5/2002 | Weinstein et al. |
| 6,391,028 B1 | 5/2002 | Fanton et al. |
| 6,402,742 B1 | 6/2002 | Blewett et al. |
| 6,409,722 B1 * | 6/2002 | Hoey et al. ................. 606/34 |
| 6,409,723 B1 | 6/2002 | Edwards |
| H2037 H | 7/2002 | Yates et al. |
| 6,416,507 B1 | 7/2002 | Eggers et al. |
| 6,416,508 B1 | 7/2002 | Eggers et al. |
| 6,419,509 B2 | 7/2002 | Goble et al. |
| 6,425,877 B1 | 7/2002 | Edwards |
| 6,432,103 B1 | 8/2002 | Ellsberry et al. |
| 6,440,130 B1 | 8/2002 | Mulier et al. |
| 6,443,952 B1 | 9/2002 | Mulier et al. |
| 6,451,017 B1 | 9/2002 | Moutafis et al. |
| 6,458,123 B1 | 10/2002 | Brucker et al. |
| 6,458,130 B1 | 10/2002 | Frazier et al. |
| 6,461,350 B1 | 10/2002 | Underwood et al. |
| 6,461,354 B1 | 10/2002 | Olsen et al. |
| 6,461,357 B1 | 10/2002 | Sharkey et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,275 B1 | 10/2002 | Wampler et al. |
| 6,471,698 B1 | 10/2002 | Edwards et al. |
| 6,475,216 B2 | 11/2002 | Mulier et al. |
| 6,478,793 B1 | 11/2002 | Cosman et al. |
| 6,482,202 B1 | 11/2002 | Goble et al. |
| 6,485,490 B2 | 11/2002 | Wampler et al. |
| 6,488,680 B1 | 12/2002 | Francischelli et al. |
| 6,493,589 B1 | 12/2002 | Medhkour et al. |
| 6,494,902 B2 | 12/2002 | Hoey et al. |
| 6,497,704 B2 | 12/2002 | Ein-Gal |
| 6,497,705 B2 | 12/2002 | Comben |
| 6,506,189 B1 | 1/2003 | Rittman, III et al. |
| 6,508,815 B1 | 1/2003 | Strul et al. |
| 6,517,536 B2 | 2/2003 | Hooven et al. |
| 6,526,320 B2 | 2/2003 | Mitchell |
| 6,537,248 B2 | 3/2003 | Mulier et al. |
| 6,537,272 B2 | 3/2003 | Christopherson et al. |
| 6,539,265 B2 | 3/2003 | Medhkour et al. |
| 6,558,379 B1 | 5/2003 | Batchelor et al. |
| 6,558,385 B1 | 5/2003 | McClurken et al. |
| 6,575,969 B1 | 6/2003 | Rittman, III et al. |
| 6,577,902 B1 | 6/2003 | Laufer et al. |
| 6,579,288 B1 | 6/2003 | Swanson et al. |
| 6,585,732 B2 | 7/2003 | Mulier et al. |
| 6,602,248 B1 | 8/2003 | Sharps et al. |
| 6,603,988 B2 | 8/2003 | Dowlatshahi |
| 6,610,060 B2 | 8/2003 | Mulier et al. |
| 6,613,048 B2 | 9/2003 | Mulier et al. |
| 6,623,515 B2 | 9/2003 | Mulier et al. |
| 6,626,899 B2 | 9/2003 | Houser et al. |
| 6,635,034 B1 | 10/2003 | Cosmescu |
| 6,645,202 B1 | 11/2003 | Pless et al. |
| 6,666,862 B2 | 12/2003 | Jain et al. |
| 6,669,692 B1 | 12/2003 | Nelson et al. |
| 6,676,660 B2 | 1/2004 | Wampler |
| 6,679,882 B1 | 1/2004 | Kornerup |
| 6,682,501 B1 * | 1/2004 | Nelson et al. ................. 604/22 |
| 6,682,527 B2 | 1/2004 | Strul |
| 6,682,528 B2 | 1/2004 | Frazier et al. |
| 6,685,700 B2 | 2/2004 | Behl et al. |
| 6,685,701 B2 | 2/2004 | Orszulak et al. |

| | | | |
|---|---|---|---|
| 6,685,704 B2 | 2/2004 | Greep |
| 6,689,129 B2 | 2/2004 | Baker |
| 6,689,131 B2 | 2/2004 | McClurken |
| 6,692,489 B1 | 2/2004 | Heim et al. |
| 6,694,984 B2 | 2/2004 | Habib |
| 6,695,837 B2 | 2/2004 | Howell |
| 6,695,840 B2 | 2/2004 | Schulze |
| 6,699,240 B2 | 3/2004 | Francischelli |
| 6,699,242 B2 | 3/2004 | Heggeness |
| 6,699,244 B2 | 3/2004 | Carranza et al. |
| 6,699,268 B2 | 3/2004 | Kordis et al. |
| 6,702,810 B2 | 3/2004 | McClurken et al. |
| 6,702,812 B2 | 3/2004 | Cosmescu |
| 6,706,039 B2 | 3/2004 | Mulier et al. |
| 6,712,074 B2 | 3/2004 | Edwards et al. |
| 6,712,811 B2 | 3/2004 | Underwood et al. |
| 6,712,813 B2 | 3/2004 | Ellman et al. |
| 6,712,816 B2 | 3/2004 | Hung et al. |
| 6,716,211 B2 | 4/2004 | Mulier et al. |
| 6,719,754 B2 | 4/2004 | Underwood et al. |
| 6,723,094 B1 | 4/2004 | Desinger |
| 6,726,683 B1 | 4/2004 | Shaw |
| 6,726,684 B1 | 4/2004 | Woloszko et al. |
| 6,726,686 B2 | 4/2004 | Buysse et al. |
| 6,730,081 B1 | 5/2004 | Desai |
| 6,733,496 B2 | 5/2004 | Sharkey et al. |
| 6,733,498 B2 | 5/2004 | Paton et al. |
| 6,733,501 B2 | 5/2004 | Levine |
| 6,736,810 B2 | 5/2004 | Hoey et al. |
| 6,740,058 B2 | 5/2004 | Lal et al. |
| 6,740,079 B1 | 5/2004 | Eggers et al. |
| 6,740,082 B2 | 5/2004 | Shadduck |
| 6,740,084 B2 | 5/2004 | Ryan |
| 6,740,102 B2 | 5/2004 | Hess et al. |
| 6,743,197 B1 | 6/2004 | Edwards |
| 6,743,229 B2 | 6/2004 | Buysse et al. |
| 6,743,230 B2 | 6/2004 | Lutze et al. |
| 6,746,447 B2 | 6/2004 | Davison et al. |
| 6,755,825 B2 | 6/2004 | Shoenman et al. |
| 6,755,827 B2 | 6/2004 | Mulier et al. |
| 6,757,565 B2 | 6/2004 | Sharkey et al. |
| 6,758,846 B2 | 7/2004 | Goble et al. |
| 6,761,718 B2 | 7/2004 | Madsen |
| 6,764,487 B2 | 7/2004 | Mulier et al. |
| 6,766,202 B2 * | 7/2004 | Underwood et al. ......... 607/99 |
| 6,766,817 B2 | 7/2004 | da Silva |
| 6,770,070 B1 | 8/2004 | Balbierz |
| 6,770,071 B2 | 8/2004 | Woloszko et al. |
| 6,770,072 B1 | 8/2004 | Truckai et al. |
| 6,772,012 B2 | 8/2004 | Ricart et al. |
| 6,772,013 B1 | 8/2004 | Ingle et al. |
| 6,775,575 B2 | 8/2004 | Bommannan et al. |
| 6,776,780 B2 | 8/2004 | Mulier et al. |
| 6,780,177 B2 | 8/2004 | Shafirstein et al. |
| 6,780,180 B1 | 8/2004 | Goble et al. |
| 6,786,906 B1 | 9/2004 | Cobb |
| 6,796,981 B2 | 9/2004 | Wham et al. |
| 6,800,077 B1 | 10/2004 | Mucko et al. |
| 6,802,842 B2 | 10/2004 | Ellman et al. |
| 6,802,843 B2 | 10/2004 | Truckai et al. |
| 6,808,525 B2 | 10/2004 | Latterell et al. |
| 6,813,520 B2 | 11/2004 | Truckai et al. |
| 6,814,714 B1 | 11/2004 | Novak et al. |
| 6,814,731 B2 | 11/2004 | Swanson |
| 6,821,273 B2 | 11/2004 | Mollenauer |
| 6,827,713 B2 | 12/2004 | Bek et al. |
| 6,827,725 B2 | 12/2004 | Batchelor et al. |
| 6,832,996 B2 | 12/2004 | Woloszko |
| 6,832,997 B2 | 12/2004 | Uchida et al. |
| 6,835,195 B2 | 12/2004 | Schulze et al. |
| 6,836,688 B2 | 12/2004 | Ingle et al. |
| 6,843,789 B2 | 1/2005 | Goble |
| 6,845,264 B1 | 1/2005 | Skladnev et al. |
| 6,849,073 B2 | 2/2005 | Hoey et al. |
| 6,855,145 B2 | 2/2005 | Ciarrocca |
| 6,858,028 B2 | 2/2005 | Mulier et al. |
| 6,860,882 B2 | 3/2005 | Battles et al. |
| 6,863,669 B2 | 3/2005 | Spitzer |
| 6,864,686 B2 | 3/2005 | Novak et al. |
| 6,881,214 B2 | 4/2005 | Cosman et al. |
| 6,882,885 B2 | 4/2005 | Levy, Jr. et al. |
| 6,887,237 B2 | 5/2005 | McGaffigan |
| 6,887,240 B1 | 5/2005 | Lands et al. |
| 6,893,435 B2 | 5/2005 | Goble |
| 6,893,440 B2 | 5/2005 | Durgin et al. |
| 6,896,672 B1 | 5/2005 | Eggers et al. |
| 6,896,674 B1 | 5/2005 | Woloszko et al. |
| 6,899,712 B2 | 5/2005 | Moutafis et al. |
| 6,905,497 B2 | 6/2005 | Truckai et al. |
| 6,905,499 B1 | 6/2005 | Mucko et al. |
| 6,911,019 B2 | 6/2005 | Mulier et al. |
| 6,915,806 B2 | 7/2005 | Pacek et al. |
| 6,918,404 B2 | 7/2005 | Dias da Silva |
| 6,921,398 B2 | 7/2005 | Carmel et al. |
| 6,921,399 B2 | 7/2005 | Carmel et al. |
| 6,923,803 B2 | 8/2005 | Goble |
| 6,923,805 B1 | 8/2005 | LaFontaine et al. |
| 6,926,706 B1 | 8/2005 | Sealfon |
| 6,926,716 B2 | 8/2005 | Baker et al. |
| 6,926,717 B1 | 8/2005 | Garito et al. |
| 6,929,640 B1 | 8/2005 | Underwood et al. |
| 6,929,641 B2 | 8/2005 | Goble et al. |
| 6,929,642 B2 | 8/2005 | Xiao et al. |
| 6,929,644 B2 | 8/2005 | Truckai et al. |
| 6,929,645 B2 | 8/2005 | Battles et al. |
| 6,932,810 B2 | 8/2005 | Ryan |
| 6,932,815 B2 | 8/2005 | Sutter |
| 6,942,661 B2 | 9/2005 | Swanson |
| 6,949,096 B2 | 9/2005 | Davison et al. |
| 6,949,098 B2 | 9/2005 | Mulier et al. |
| 6,951,559 B1 | 10/2005 | Greep |
| 6,953,461 B2 | 10/2005 | McClurken et al. |
| 6,960,204 B2 | 11/2005 | Eggers et al. |
| 6,960,207 B2 | 11/2005 | Vanney et al. |
| 6,960,210 B2 | 11/2005 | Lands et al. |
| 6,962,589 B2 | 11/2005 | Mulier et al. |
| 6,964,274 B1 | 11/2005 | Ryan et al. |
| 6,964,661 B2 | 11/2005 | Rioux et al. |
| 6,966,907 B2 | 11/2005 | Goble |
| 6,966,909 B2 | 11/2005 | Marshall et al. |
| 6,971,394 B2 | 12/2005 | Sliwa, Jr. et al. |
| 6,974,452 B1 | 12/2005 | Gille et al. |
| 6,974,453 B2 | 12/2005 | Woloszko et al. |
| 6,979,332 B2 | 12/2005 | Adams |
| 6,984,231 B2 | 1/2006 | Goble et al. |
| 6,986,769 B2 | 1/2006 | Nelson et al. |
| 6,991,631 B2 | 1/2006 | Woloszko et al. |
| 7,001,380 B2 | 2/2006 | Goble |
| 7,001,382 B2 | 2/2006 | Gallo, Sr. |
| 7,004,941 B2 | 2/2006 | Tvinnereim et al. |
| 7,004,942 B2 | 2/2006 | Laird et al. |
| 7,008,419 B2 | 3/2006 | Shadduck |
| 7,008,421 B2 | 3/2006 | Daniel et al. |
| 7,033,348 B2 | 4/2006 | Alfano et al. |
| 7,033,356 B2 | 4/2006 | Latterell et al. |
| 7,041,096 B2 | 5/2006 | Malis et al. |
| 7,041,101 B2 | 5/2006 | Eggers |
| 7,041,102 B2 | 5/2006 | Truckai et al. |
| 7,052,494 B2 | 5/2006 | Goble et al. |
| 7,060,064 B2 | 6/2006 | Allen et al. |
| 7,063,670 B2 | 6/2006 | Sampson et al. |
| 7,066,586 B2 | 6/2006 | da Silva |
| 7,066,932 B1 | 6/2006 | Morgan et al. |
| 7,066,936 B2 | 6/2006 | Ryan |
| 7,070,596 B1 | 7/2006 | Woloszko et al. |
| 7,070,604 B1 | 7/2006 | Garito et al. |

| | | | | | | |
|---|---|---|---|---|---|---|
| 7,074,217 | B2 | 7/2006 | Strul et al. | 2002/0169446 A1 | 11/2002 | Mulier et al. |
| 7,074,219 | B2 | 7/2006 | Levine et al. | 2002/0177846 A1 | 11/2002 | Mulier et al. |
| 7,083,601 | B1 | 8/2006 | Cosmescu | 2002/0183733 A1 | 12/2002 | Mulier et al. |
| 7,087,051 | B2 | 8/2006 | Bourne et al. | 2002/0188284 A1 | 12/2002 | To et al. |
| 7,087,053 | B2 | 8/2006 | Vanney | 2002/0193851 A1 | 12/2002 | Silverman et al. |
| 7,094,215 | B2 | 8/2006 | Davison et al. | 2002/0198524 A1 | 12/2002 | Mulier et al. |
| 7,101,387 | B2 | 9/2006 | Garabedian et al. | 2003/0004510 A1 | 1/2003 | Wham et al. |
| 7,104,986 | B2 | 9/2006 | Hovda et al. | 2003/0014050 A1 | 1/2003 | Sharkey et al. |
| 7,112,199 | B2 | 9/2006 | Cosmescu | 2003/0032954 A1 | 2/2003 | Carranza et al. |
| 7,115,139 | B2 | 10/2006 | McClurken et al. | 2003/0032955 A1 | 2/2003 | Mulier et al. |
| 7,125,406 | B2 | 10/2006 | Given | 2003/0073989 A1 | 4/2003 | Hoey et al. |
| 7,147,634 | B2 | 12/2006 | Nesbitt | 2003/0073993 A1 | 4/2003 | Ciarrocca |
| 7,147,635 | B2 | 12/2006 | Ciarrocca | 2003/0114850 A1 | 6/2003 | McClurken et al. |
| 7,147,637 | B2 | 12/2006 | Goble | 2003/0181902 A1 | 9/2003 | Mulier et al. |
| 7,147,638 | B2 | 12/2006 | Chapman et al. | 2003/0204185 A1 | 10/2003 | Sherman et al. |
| 7,150,746 | B2 | 12/2006 | DeCesare et al. | 2003/0216733 A1 | 11/2003 | McClurken et al. |
| 7,150,747 | B1 | 12/2006 | McDonald et al. | 2004/0015162 A1 | 1/2004 | McGaffigan |
| 7,150,748 | B2 | 12/2006 | Ebbutt et al. | 2004/0015163 A1 | 1/2004 | Buysse et al. |
| 7,153,300 | B2 | 12/2006 | Goble | 2004/0015215 A1 | 1/2004 | Fredricks et al. |
| 7,156,845 | B2 | 1/2007 | Mulier et al. | 2004/0015216 A1 | 1/2004 | DeSisto |
| 7,166,105 | B2 | 1/2007 | Mulier et al. | 2004/0015218 A1 | 1/2004 | Finch et al. |
| 7,166,106 | B2 | 1/2007 | Bartel et al. | 2004/0019350 A1 | 1/2004 | O'Brien et al. |
| 7,169,143 | B2 | 1/2007 | Eggers et al. | 2004/0024395 A1 | 2/2004 | Ellman et al. |
| 7,169,144 | B2 | 1/2007 | Hoey et al. | 2004/0024396 A1 | 2/2004 | Eggers |
| 7,207,471 | B2 | 4/2007 | Heinrich et al. | 2004/0024398 A1 | 2/2004 | Hovda et al. |
| 7,232,440 | B2 | 6/2007 | Dumbauld et al. | 2004/0024399 A1 | 2/2004 | Sharps et al. |
| 7,247,155 | B2 | 7/2007 | Hoey et al. | 2004/0030327 A1 | 2/2004 | Golan |
| 7,261,711 | B2 | 8/2007 | Mulier et al. | 2004/0030328 A1 | 2/2004 | Eggers et al. |
| 7,309,325 | B2 | 12/2007 | Mulier et al. | 2004/0030330 A1 | 2/2004 | Brassell et al. |
| 7,311,708 | B2 | 12/2007 | McClurken | 2004/0030332 A1 | 2/2004 | Knowlton et al. |
| 7,322,974 | B2 | 1/2008 | Swoyer et al. | 2004/0030333 A1 | 2/2004 | Goble |
| 7,361,175 | B2 | 4/2008 | Suslov | 2004/0034340 A1 | 2/2004 | Biscup |
| 7,364,579 | B2 | 4/2008 | Mulier et al. | 2004/0034346 A1 | 2/2004 | Stern et al. |
| 2001/0014819 | A1 | 8/2001 | Ingle et al. | 2004/0034349 A1 | 2/2004 | Kirwan, Jr. et al. |
| 2001/0020167 | A1 | 9/2001 | Woloszko et al. | 2004/0034400 A1 | 2/2004 | Ingle et al. |
| 2001/0023365 | A1 | 9/2001 | Medhkour et al. | 2004/0039429 A1 | 2/2004 | Daniel et al. |
| 2001/0025178 | A1 | 9/2001 | Mulier et al. | 2004/0044341 A1 | 3/2004 | Truckai et al. |
| 2001/0032002 | A1 | 10/2001 | McClurken et al. | 2004/0054363 A1 | 3/2004 | Vaska et al. |
| 2001/0039419 | A1 | 11/2001 | Francischelli et al. | 2004/0054365 A1 | 3/2004 | Goble |
| 2001/0041921 | A1 | 11/2001 | Mulier et al. | 2004/0054366 A1 | 3/2004 | Davison et al. |
| 2001/0051802 | A1 | 12/2001 | Woloszko et al. | 2004/0054369 A1 | 3/2004 | Nelson et al. |
| 2001/0051804 | A1 | 12/2001 | Mulier et al. | 2004/0054370 A1 | 3/2004 | Given |
| 2002/0002393 | A1 | 1/2002 | Mitchell | 2004/0059328 A1 | 3/2004 | Daniel et al. |
| 2002/0010463 | A1 | 1/2002 | Mulier et al. | 2004/0059363 A1 | 3/2004 | Alvarez et al. |
| 2002/0013582 | A1 | 1/2002 | Mulier et al. | 2004/0064023 A1 | 4/2004 | Ryan et al. |
| 2002/0016589 | A1 | 2/2002 | Swartz et al. | 2004/0064137 A1 | 4/2004 | Pellegrino et al. |
| 2002/0019628 | A1 | 2/2002 | Comben | 2004/0068306 A1 | 4/2004 | Shadduck |
| 2002/0022870 | A1 | 2/2002 | Truckai et al. | 2004/0068307 A1 | 4/2004 | Goble |
| 2002/0026186 | A1 | 2/2002 | Woloszko et al. | 2004/0073205 A1 | 4/2004 | Treat et al. |
| 2002/0026187 | A1 | 2/2002 | Swanson | 2004/0073208 A1 | 4/2004 | Sutter |
| 2002/0029036 | A1 | 3/2002 | Goble et al. | 2004/0078034 A1 | 4/2004 | Acker et al. |
| 2002/0035361 | A1 | 3/2002 | Houser et al. | 2004/0078037 A1 | 4/2004 | Batchelor et al. |
| 2002/0035387 | A1 | 3/2002 | Mulier et al. | 2004/0078038 A1 | 4/2004 | Desinger et al. |
| 2002/0049438 | A1 | 4/2002 | Sharkey et al. | 2004/0082946 A1 | 4/2004 | Malis et al. |
| 2002/0049439 | A1 | 4/2002 | Mulier et al. | 2004/0082952 A1 | 4/2004 | Dycus et al. |
| 2002/0049483 | A1 | 4/2002 | Knowlton | 2004/0087937 A1 | 5/2004 | Eggers et al. |
| 2002/0058933 | A1 | 5/2002 | Christopherson et al. | 2004/0087939 A1 | 5/2004 | Eggers et al. |
| 2002/0058935 | A1 | 5/2002 | Hoey et al. | 2004/0087940 A1 | 5/2004 | Jahns et al. |
| 2002/0062123 | A1 | 5/2002 | McClurken et al. | 2004/0087943 A1 | 5/2004 | Dycus et al. |
| 2002/0095150 | A1 | 7/2002 | Goble | 2004/0088029 A1 | 5/2004 | Yamamoto |
| 2002/0095151 | A1 | 7/2002 | Dahla et al. | 2004/0092925 A1 | 5/2004 | Rizoiu et al. |
| 2002/0095152 | A1 | 7/2002 | Ciarrocca et al. | 2004/0092926 A1 | 5/2004 | Hoey et al. |
| 2002/0099366 | A1 | 7/2002 | Dahla et al. | 2004/0097919 A1 | 5/2004 | Wellman et al. |
| 2002/0115991 | A1 | 8/2002 | Edwards | 2004/0102770 A1 | 5/2004 | Goble |
| 2002/0115992 | A1 | 8/2002 | Utley et al. | 2004/0102824 A1 | 5/2004 | Sharkey et al. |
| 2002/0120259 | A1 | 8/2002 | Lettice et al. | 2004/0111136 A1 | 6/2004 | Sharkey et al. |
| 2002/0120260 | A1 | 8/2002 | Morris et al. | 2004/0111137 A1 | 6/2004 | Sharkey et al. |
| 2002/0120261 | A1 | 8/2002 | Morris et al. | 2004/0116923 A1 | 6/2004 | Desinger |
| 2002/0128650 | A1 | 9/2002 | McClurken | 2004/0122420 A1 | 6/2004 | Amoah |
| 2002/0133148 | A1 | 9/2002 | Daniel et al. | 2004/0122423 A1 | 6/2004 | Dycus et al. |
| 2002/0151884 | A1 | 10/2002 | Hoey et al. | 2004/0122494 A1 | 6/2004 | Eggers et al. |
| 2002/0156511 | A1 | 10/2002 | Habib | 2004/0138654 A1 | 7/2004 | Goble |
| 2002/0161364 | A1 | 10/2002 | Mulier et al. | 2004/0138655 A1 | 7/2004 | McClurken et al. |

| | | |
|---|---|---|
| 2004/0138657 A1 | 7/2004 | Bourne et al. |
| 2004/0143257 A1 | 7/2004 | Fuimaono |
| 2004/0143258 A1 | 7/2004 | Fuimaono |
| 2004/0143259 A1 | 7/2004 | Mulier et al. |
| 2004/0143263 A1 | 7/2004 | Schechter et al. |
| 2004/0147902 A1 | 7/2004 | McGuckin, Jr. et al. |
| 2004/0147916 A1 | 7/2004 | Baker |
| 2004/0147922 A1 | 7/2004 | Keppel |
| 2004/0147925 A1 | 7/2004 | Buysse et al. |
| 2004/0162552 A1 | 8/2004 | McClurken |
| 2004/0162554 A1 | 8/2004 | Lee et al. |
| 2004/0162557 A1 | 8/2004 | Tetzlaff et al. |
| 2004/0162572 A1 | 8/2004 | Sauer |
| 2004/0167508 A1 | 8/2004 | Wham et al. |
| 2004/0172111 A1 | 9/2004 | Hijii et al. |
| 2004/0176760 A1 | 9/2004 | Qiu |
| 2004/0176761 A1 | 9/2004 | Desinger |
| 2004/0176762 A1 | 9/2004 | Lawes et al. |
| 2004/0181219 A1 | 9/2004 | Goble et al. |
| 2004/0181250 A1 | 9/2004 | Adams et al. |
| 2004/0186469 A1 | 9/2004 | Woloszko et al. |
| 2004/0186470 A1 | 9/2004 | Goble et al. |
| 2004/0186535 A1 | 9/2004 | Knowlton |
| 2004/0193148 A1 | 9/2004 | Wham et al. |
| 2004/0193150 A1 | 9/2004 | Sharkey et al. |
| 2004/0193152 A1 | 9/2004 | Sutton et al. |
| 2004/0193211 A1 | 9/2004 | Voegele et al. |
| 2004/0199156 A1 | 10/2004 | Rioux et al. |
| 2004/0199160 A1 | 10/2004 | Slater |
| 2004/0206365 A1 | 10/2004 | Knowlton |
| 2004/0210213 A1 | 10/2004 | Fuimaono et al. |
| 2004/0210214 A1 | 10/2004 | Knowlton |
| 2004/0215181 A1 | 10/2004 | Christopherson et al. |
| 2004/0215182 A1 | 10/2004 | Lee |
| 2004/0215183 A1 | 10/2004 | Hoey et al. |
| 2004/0215184 A1 | 10/2004 | Eggers et al. |
| 2004/0215185 A1 | 10/2004 | Truckai et al. |
| 2004/0215188 A1 | 10/2004 | Mulier et al. |
| 2004/0215235 A1 | 10/2004 | Jackson et al. |
| 2004/0215296 A1 | 10/2004 | Ganz et al. |
| 2004/0220561 A1 | 11/2004 | Kirwan, Jr. et al. |
| 2004/0220562 A1 | 11/2004 | Garabedian et al. |
| 2004/0225288 A1 | 11/2004 | Buysse et al. |
| 2004/0230190 A1 | 11/2004 | Dahla et al. |
| 2004/0236322 A1 | 11/2004 | Mulier et al. |
| 2004/0236324 A1 | 11/2004 | Muller et al. |
| 2004/0243125 A1 | 12/2004 | Dycus et al. |
| 2004/0243163 A1 | 12/2004 | Casiano et al. |
| 2004/0249371 A1 | 12/2004 | Dycus et al. |
| 2004/0249374 A1 | 12/2004 | Tetzlaff et al. |
| 2004/0249425 A1 | 12/2004 | Roy et al. |
| 2004/0260279 A1 | 12/2004 | Goble et al. |
| 2004/0260280 A1 | 12/2004 | Sartor |
| 2004/0260368 A1 | 12/2004 | Ingle et al. |
| 2005/0010205 A1 | 1/2005 | Hovda et al. |
| 2005/0010212 A1 | 1/2005 | McClurken et al. |
| 2005/0015085 A1 | 1/2005 | McClurken et al. |
| 2005/0015086 A1 | 1/2005 | Platt |
| 2005/0015130 A1 | 1/2005 | Gill |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0033292 A1 | 2/2005 | Teitelbaum et al. |
| 2005/0038471 A1 | 2/2005 | Chan et al. |
| 2005/0043728 A1 | 2/2005 | Ciarrocca |
| 2005/0049583 A1 | 3/2005 | Swanson |
| 2005/0049586 A1 | 3/2005 | Daniel et al. |
| 2005/0055019 A1 | 3/2005 | Skarda |
| 2005/0055020 A1 | 3/2005 | Skarda |
| 2005/0059966 A1 | 3/2005 | McClurken et al. |
| 2005/0070888 A1 | 3/2005 | Dimatteo et al. |
| 2005/0070891 A1 | 3/2005 | DeSisto |
| 2005/0070894 A1 | 3/2005 | McClurken |
| 2005/0070896 A1 | 3/2005 | Daniel et al. |
| 2005/0080410 A1 | 4/2005 | Rioux et al. |
| 2005/0080413 A1 | 4/2005 | Canady |
| 2005/0085804 A1 | 4/2005 | McGaffigan |
| 2005/0085809 A1 | 4/2005 | Mucko et al. |
| 2005/0085880 A1 | 4/2005 | Truckai et al. |
| 2005/0090816 A1 | 4/2005 | McClurken et al. |
| 2005/0090819 A1 | 4/2005 | Goble |
| 2005/0096649 A1 | 5/2005 | Adams |
| 2005/0096651 A1 | 5/2005 | Truckai et al. |
| 2005/0101951 A1 | 5/2005 | Wham et al. |
| 2005/0101952 A1 | 5/2005 | Lands et al. |
| 2005/0101965 A1 | 5/2005 | Ryan |
| 2005/0107778 A1 | 5/2005 | Rioux et al. |
| 2005/0107779 A1 | 5/2005 | Ellman et al. |
| 2005/0107784 A1 | 5/2005 | Moses et al. |
| 2005/0107786 A1 | 5/2005 | Canady |
| 2005/0113820 A1 | 5/2005 | Goble et al. |
| 2005/0113825 A1 | 5/2005 | Cosmescu |
| 2005/0124987 A1 | 6/2005 | Goble |
| 2005/0130929 A1 | 6/2005 | Boyd |
| 2005/0131402 A1 | 6/2005 | Ciarrocca et al. |
| 2005/0137590 A1 | 6/2005 | Lawes et al. |
| 2005/0137662 A1 | 6/2005 | Morris et al. |
| 2005/0143729 A1 | 6/2005 | Francischelli et al. |
| 2005/0154385 A1 | 7/2005 | Heim et al. |
| 2005/0154433 A1 | 7/2005 | Levy, Jr. et al. |
| 2005/0159739 A1 | 7/2005 | Paul et al. |
| 2005/0159740 A1 | 7/2005 | Paul et al. |
| 2005/0159778 A1 | 7/2005 | Heinrich et al. |
| 2005/0159797 A1 | 7/2005 | Chandran et al. |
| 2005/0165444 A1 | 7/2005 | Hart et al. |
| 2005/0171524 A1 | 8/2005 | Stern et al. |
| 2005/0171526 A1 | 8/2005 | Rioux et al. |
| 2005/0171532 A1 | 8/2005 | Ciarrocca |
| 2005/0171533 A1 | 8/2005 | Latterell et al. |
| 2005/0171534 A1 | 8/2005 | Habib |
| 2005/0171583 A1 | 8/2005 | Mosher et al. |
| 2005/0177150 A1 | 8/2005 | Amoah et al. |
| 2005/0177209 A1 | 8/2005 | Leung et al. |
| 2005/0187543 A1 | 8/2005 | Underwood et al. |
| 2005/0187599 A1 | 8/2005 | Sharkey et al. |
| 2005/0203503 A1 | 9/2005 | Edwards et al. |
| 2005/0203504 A1 | 9/2005 | Wham et al. |
| 2005/0209591 A1 | 9/2005 | Sutter |
| 2005/0209621 A1 | 9/2005 | Gordon et al. |
| 2005/0222602 A1 | 10/2005 | Sutter et al. |
| 2005/0222611 A1 | 10/2005 | WeitKamp |
| 2005/0228372 A1 | 10/2005 | Truckai et al. |
| 2005/0245918 A1 | 11/2005 | Sliwa, Jr. et al. |
| 2005/0245921 A1 | 11/2005 | Strul et al. |
| 2005/0245922 A1 | 11/2005 | Goble |
| 2005/0245923 A1 | 11/2005 | Christopherson et al. |
| 2005/0250477 A1 | 11/2005 | Eastwood et al. |
| 2005/0251128 A1 | 11/2005 | Amoah |
| 2005/0251134 A1 | 11/2005 | Woloszko et al. |
| 2005/0256519 A1 | 11/2005 | Goble et al. |
| 2005/0261676 A1 | 11/2005 | Hall et al. |
| 2005/0261677 A1 | 11/2005 | Hall et al. |
| 2005/0267465 A1 | 12/2005 | Hillier et al. |
| 2005/0267467 A1 | 12/2005 | Paul et al. |
| 2005/0267468 A1 | 12/2005 | Truckai et al. |
| 2005/0267469 A1 | 12/2005 | Blocher |
| 2005/0273092 A1 | 12/2005 | G. et al. |
| 2005/0273097 A1 | 12/2005 | Ryan |
| 2005/0277915 A1 | 12/2005 | DeCesare et al. |
| 2005/0277916 A1 | 12/2005 | DeCesare et al. |
| 2005/0277917 A1 | 12/2005 | Garito et al. |
| 2005/0283147 A1 | 12/2005 | Yachi |
| 2005/0283148 A1 | 12/2005 | Janssen et al. |
| 2005/0283149 A1 | 12/2005 | Thorne et al. |
| 2005/0283150 A1 | 12/2005 | Moutafis et al. |

| | | |
|---|---|---|
| 2005/0283151 A1 | 12/2005 | Ebbutt et al. |
| 2005/0288661 A1 | 12/2005 | Sauvageau et al. |
| 2005/0288665 A1 | 12/2005 | Woloszko |
| 2006/0004356 A1 | 1/2006 | Bilski et al. |
| 2006/0009760 A1 | 1/2006 | Mulier et al. |
| 2006/0009762 A1 | 1/2006 | Whayne |
| 2006/0015097 A1 | 1/2006 | Mulier et al. |
| 2006/0020265 A1 | 1/2006 | Ryan |
| 2006/0025765 A1 | 2/2006 | Landman et al. |
| 2006/0025766 A1 | 2/2006 | Heinrich et al. |
| 2006/0030912 A1 | 2/2006 | Eggers et al. |
| 2006/0036235 A1 | 2/2006 | Swoyer et al. |
| 2006/0036237 A1 | 2/2006 | Davison et al. |
| 2006/0036239 A1 | 2/2006 | Canady |
| 2006/0041254 A1 | 2/2006 | Francischelli et al. |
| 2006/0041255 A1 | 2/2006 | Eggers et al. |
| 2006/0047275 A1 | 3/2006 | Goble |
| 2006/0047280 A1 | 3/2006 | Goble et al. |
| 2006/0047331 A1 | 3/2006 | Lax et al. |
| 2006/0052770 A1 | 3/2006 | Mulier et al. |
| 2006/0064085 A1 | 3/2006 | Schechter et al. |
| 2006/0064101 A1 | 3/2006 | Arramon |
| 2006/0074411 A1 | 4/2006 | Carmel et al. |
| 2006/0074414 A1 | 4/2006 | Mulier et al. |
| 2006/0079872 A1 | 4/2006 | Eggleston |
| 2006/0079888 A1 | 4/2006 | Mulier et al. |
| 2006/0084968 A1 | 4/2006 | Truckai et al. |
| 2006/0095026 A1 | 5/2006 | Ricart et al. |
| 2006/0095031 A1 | 5/2006 | Ormsby |
| 2006/0095034 A1 | 5/2006 | Garito et al. |
| 2006/0095075 A1 | 5/2006 | Burkinshaw et al. |
| 2006/0095103 A1 | 5/2006 | Eggers et al. |
| 2006/0100619 A1 | 5/2006 | McClurken et al. |
| 2006/0106376 A1 | 5/2006 | Godara et al. |
| 2006/0106379 A1 | 5/2006 | O'Brien et al. |
| 2006/0111705 A1 | 5/2006 | Janzen et al. |
| 2006/0111709 A1 | 5/2006 | Goble et al. |
| 2006/0111710 A1 | 5/2006 | Goble et al. |
| 2006/0111711 A1 | 5/2006 | Goble |
| 2006/0111741 A1 | 5/2006 | Nardella |
| 2006/0116675 A1 | 6/2006 | McClurken et al. |
| 2006/0122593 A1 | 6/2006 | Jun et al. |
| 2006/0129145 A1 | 6/2006 | Woloszko et al. |
| 2006/0129185 A1 | 6/2006 | Paternuosto |
| 2006/0142757 A1 | 6/2006 | Daniel et al. |
| 2006/0149225 A1 | 7/2006 | McClurken |
| 2006/0167446 A1 | 7/2006 | Pozzato |
| 2006/0167449 A1 | 7/2006 | Mulier et al. |
| 2006/0167451 A1 | 7/2006 | Cropper |
| 2006/0178667 A1 | 8/2006 | Sartor et al. |
| 2006/0178668 A1 | 8/2006 | Albritton, IV |
| 2006/0178670 A1 | 8/2006 | Woloszko et al. |
| 2006/0178699 A1 | 8/2006 | Surti |
| 2006/0184164 A1 | 8/2006 | Malis et al. |
| 2006/0184167 A1 | 8/2006 | Vaska et al. |
| 2006/0189977 A1 | 8/2006 | Allen et al. |
| 2006/0189979 A1 | 8/2006 | Esch et al. |
| 2006/0195079 A1 | 8/2006 | Eberl |
| 2006/0200123 A1 | 9/2006 | Ryan |
| 2006/0217700 A1 | 9/2006 | Garito et al. |
| 2006/0217701 A1 | 9/2006 | Young et al. |
| 2006/0217707 A1 | 9/2006 | Daniel et al. |
| 2006/0224154 A1 | 10/2006 | Shadduck et al. |
| 2006/0235286 A1 | 10/2006 | Stone et al. |
| 2006/0235377 A1 | 10/2006 | Earley et al. |
| 2006/0235379 A1 | 10/2006 | McClurken et al. |
| 2006/0241577 A1 | 10/2006 | Balbierz et al. |
| 2006/0241587 A1 | 10/2006 | Heim et al. |
| 2006/0241588 A1 | 10/2006 | Heim et al. |
| 2006/0241589 A1 | 10/2006 | Heim et al. |
| 2006/0247614 A1 | 11/2006 | Sampson et al. |
| 2006/0259025 A1 | 11/2006 | Dahla |
| 2006/0259031 A1 | 11/2006 | Carmel et al. |
| 2006/0259070 A1 | 11/2006 | Livneh |
| 2006/0264927 A1 | 11/2006 | Ryan |
| 2006/0264929 A1 | 11/2006 | Goble et al. |
| 2006/0264931 A1 | 11/2006 | Chapman et al. |
| 2006/0271033 A1 | 11/2006 | Ein-Gal |
| 2006/0271036 A1 | 11/2006 | Garabedian et al. |
| 2006/0271042 A1 | 11/2006 | Latterell et al. |
| 2006/0276783 A1 | 12/2006 | Cosmescu |
| 2006/0276785 A1 | 12/2006 | Asahara et al. |
| 2007/0000501 A1 | 1/2007 | Wert et al. |
| 2007/0010812 A1 | 1/2007 | Mittelstein et al. |
| 2007/0016182 A1 | 1/2007 | Lipson et al. |
| 2007/0049920 A1 | 3/2007 | McClurken et al. |
| 2007/0093808 A1 | 4/2007 | Mulier et al. |
| 2007/0118114 A1 | 5/2007 | Mulier et al. |
| 2007/0208332 A1 | 9/2007 | Mulier et al. |
| 2008/0015563 A1 | 1/2008 | Hoey et al. |
| 2008/0071270 A1 | 3/2008 | Desinger et al. |

FOREIGN PATENT DOCUMENTS

| | | |
|---|---|---|
| EP | 0 175 595 | 3/1986 |
| EP | 0895756 | 2/1999 |
| EP | 1 095 627 A1 | 5/2001 |
| EP | 1 157 666 A1 | 11/2001 |
| FR | 2 235 669 | 1/1975 |
| JP | 57-117843 | 7/1982 |
| JP | 5-092009 | 4/1993 |
| JP | 7-124245 | 5/1995 |
| WO | WO 90/03152 | 4/1990 |
| WO | WO 94/02077 A2 | 2/1994 |
| WO | WO 94/26228 | 11/1994 |
| WO | WO 95/05781 | 3/1995 |
| WO | WO 95/09570 | 4/1995 |
| WO | WO 95/17222 | 6/1995 |
| WO | WO 96/34571 | 11/1996 |
| WO | WO 97/05829 A1 | 2/1997 |
| WO | WO 97/16127 | 5/1997 |
| WO | WO 98/14131 | 4/1998 |
| WO | WO 98/38932 A1 | 9/1998 |
| WO | WO 99/03414 | 1/1999 |
| WO | WO 99/20213 A1 | 4/1999 |
| WO | WO 99/58070 A2 | 11/1999 |
| WO | WO 99/66850 A1 | 12/1999 |
| WO | WO 00/78240 A1 | 12/2000 |
| WO | WO 01/26570 A1 | 4/2001 |
| WO | WO 01/28444 A1 | 4/2001 |
| WO | WO 01/35845 A1 | 5/2001 |
| WO | WO 01/60273 A1 | 8/2001 |
| WO | WO 01/66026 A2 | 9/2001 |
| WO | WO 01/80757 A2 | 11/2001 |
| WO | WO 2005/122938 A1 | 12/2005 |
| WO | WO 2006/062916 A2 | 6/2006 |
| WO | WO 2006/062939 A2 | 6/2006 |

OTHER PUBLICATIONS

U.S. Office Action issued in related U.S. Appl. No. 10/488,801 dated Dec. 2, 2008.
U.S. Office Action issued in related U.S. Appl. No. 10/265,170 dated Jan. 12, 2009.
European Search Report issued in related European Patent Application No. 08153786.2 -2305 dated Jun. 24, 2008.
European Office Action dated Nov. 25, 2008 issued in related European Patent Application No. 05851938.0-2305.
European Office Action dated Feb. 20, 2009 issued in related European Patent Application No. 02798936.7.
European Office Action dated May 6, 2009 issued in related European Patent Application No. 05851938.0.
European Office Action dated Nov. 25, 2008 issued in related European Patent Application No. 05851938.0.
Office Action dated Dec. 24, 2009 issued in related U.S. Appl. No. 10/813,736.

U.S. Office Action dated Jul. 16, 2009 issued in related U.S. Appl. No. 10/746,222.
Office Action dated Jul. 2, 2009 issued in related U.S. Appl. No. 10/813,736.
Office Action dated Sep. 8, 2009 issued in related U.S. Appl. No. 10/488,801.
Office Action dated Sep. 15, 2009 issued in related U.S. Appl. No. 10/365,170.
Office Action dated Apr. 14, 2009 issued in related U.S. Appl. No. 10/547,881.
Office Action dated Sep. 17, 2009 issued in related U.S. Appl. No. 11/318,207.
Office Action dated Jun. 22, 2009 issued in related U.S. Appl. No. 10/486,807.
United States Office Action dated Aug. 4, 2009 issued in related U.S. Appl. No. 11/537,852.
Office Action dated Jan. 27, 2010 issued in related U.S. Appl. No. 10/746,222.
Office Action dated Jan. 29, 2010 issued in related U.S. Appl. No. 10/488,801.
Office Action dated Jun. 21, 2006 issued in related U.S. Appl. No. 10/746,222.
Office Action dated Jun. 21, 2007 issued in related U.S. Appl. No. 10/746,222.
Office Action dated Nov. 15, 2007 issued in related U.S. Appl. No. 10/746,222.
Office Action dated Aug. 27, 2008 issued in related U.S. Appl. No. 10/746,222.
Office Action dated Mar. 18, 2010 issued in related U.S. Appl. No. 10/365,170.
Office Action dated Apr. 5, 2010 issued in related U.S. Appl. No. 11/318,207.
Office Action dated Apr. 26, 2010 issued in related U.S. Appl. No. 11/537,852.

* cited by examiner

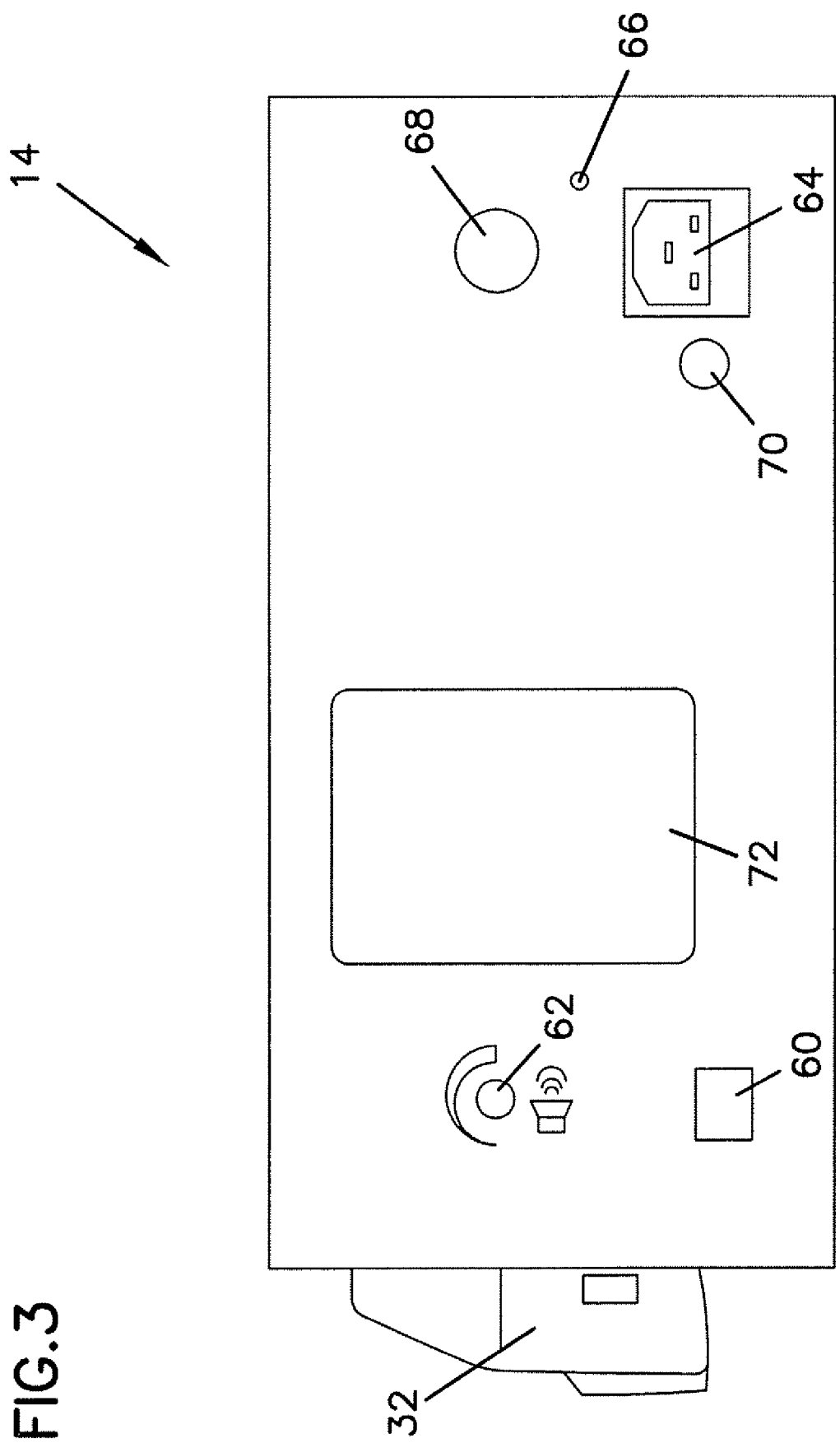

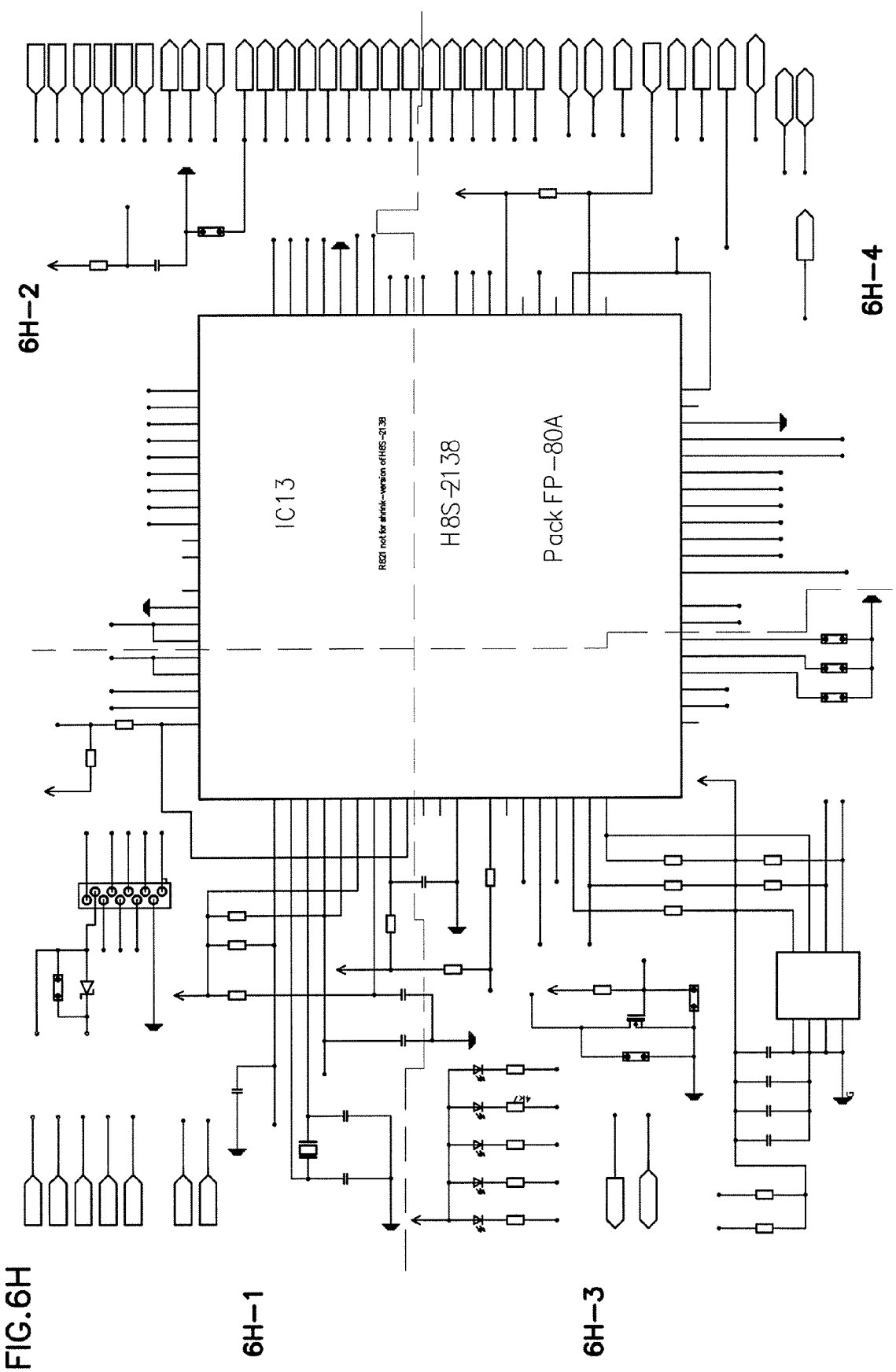

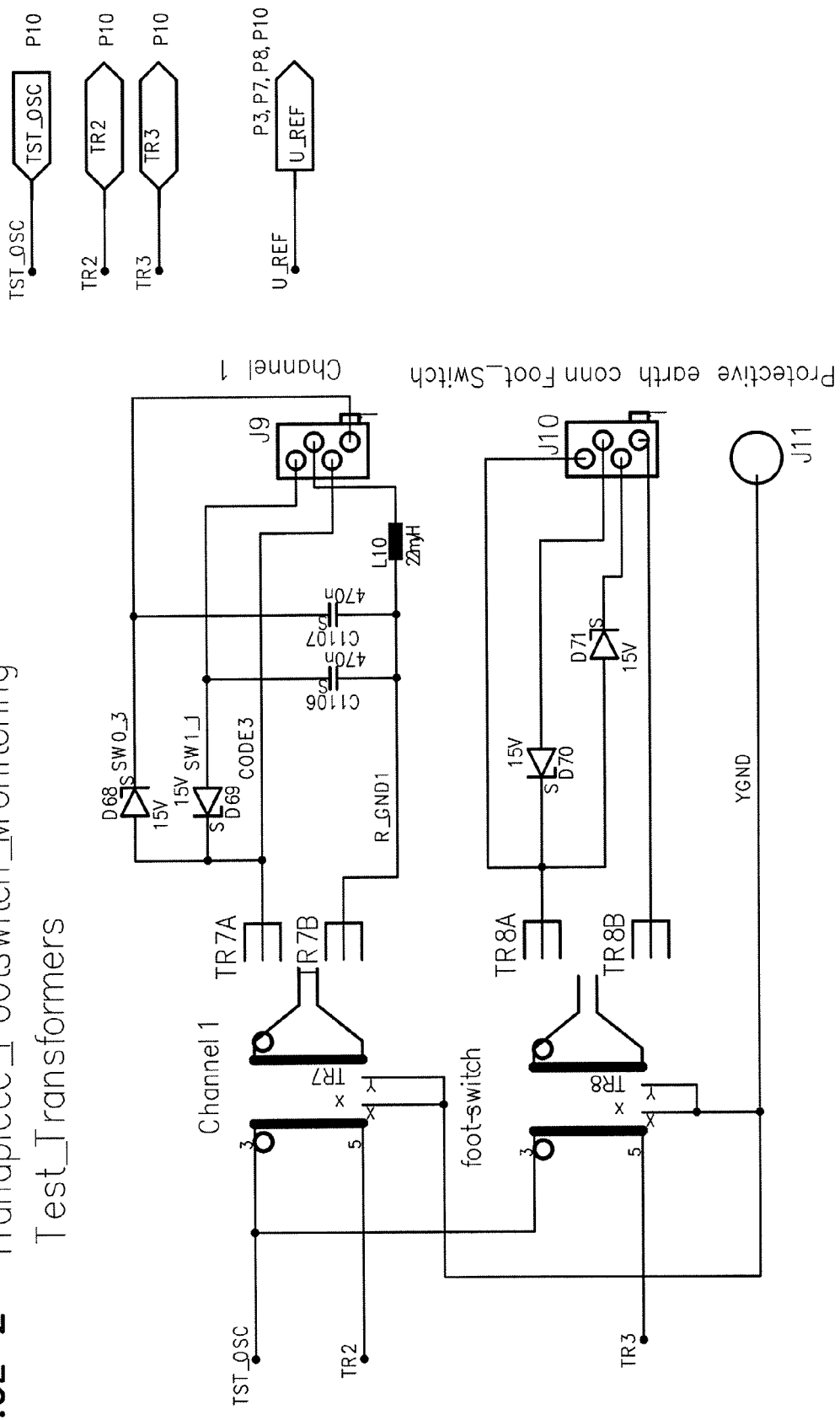
FIG.6L-2 Handpiece_Footswitch_Monitoring Test_Transformers

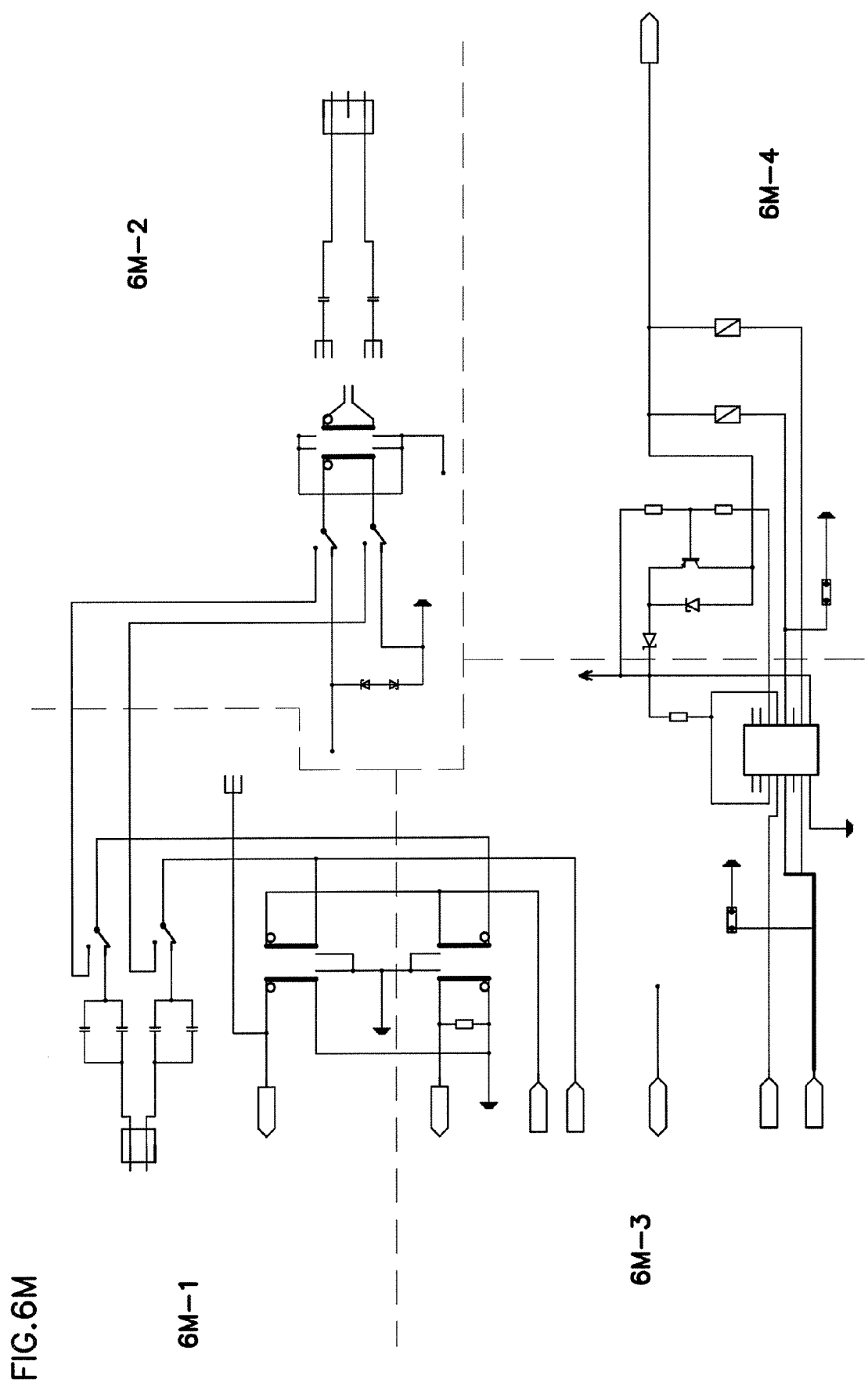

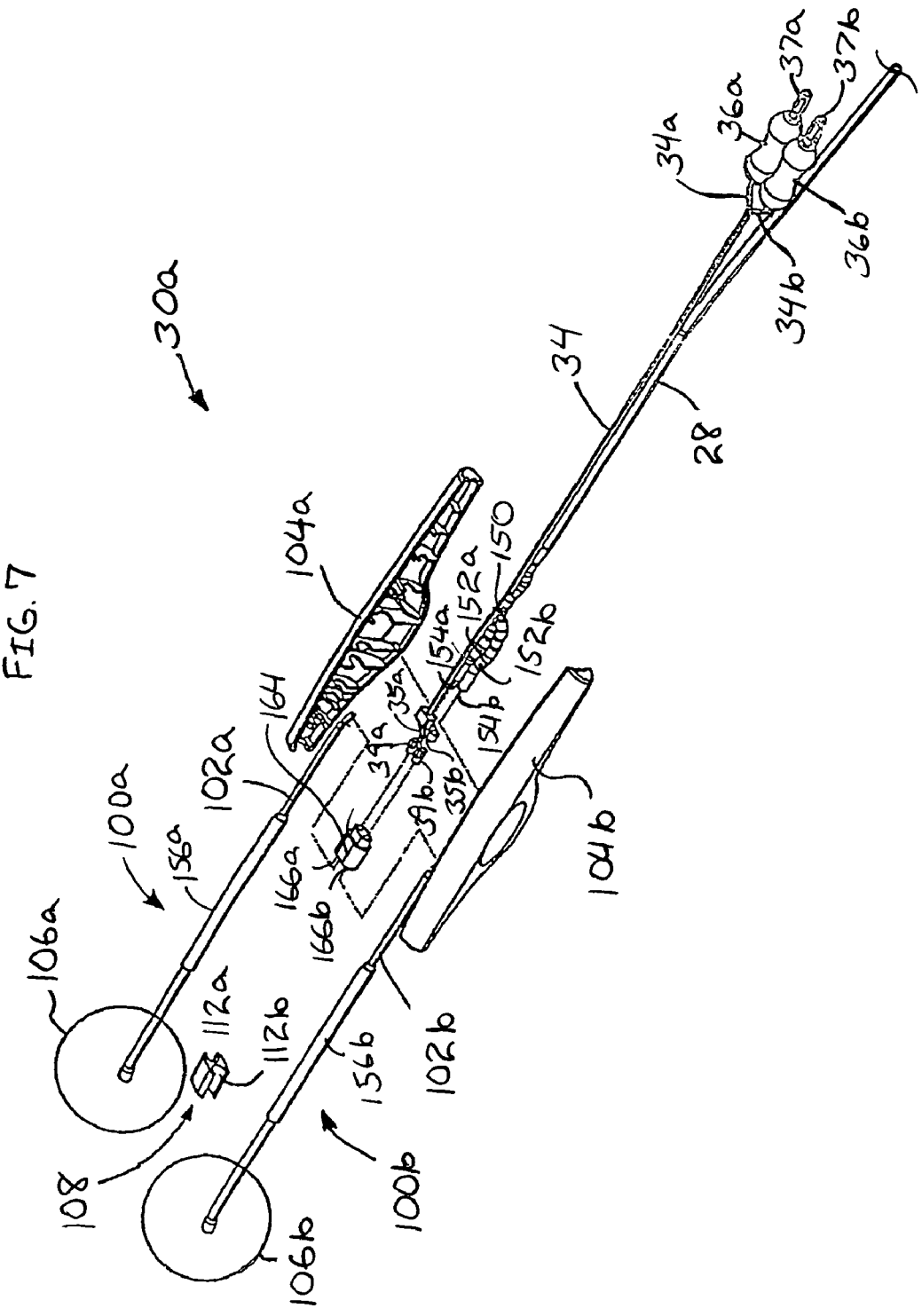

FLUID-ASSISTED ELECTROSURGICAL DEVICES, ELECTROSURGICAL UNIT WITH PUMP AND METHODS OF USE THEREOF

CROSS REFERENCE TO RELATED APPLICATIONS

This patent application is a continuation-in-part of U.S. patent application Ser. No. 10/488,801, filed Dec. 16, 2004, now pending, which is a U.S. national stage continuation of PCT patent application serial no. PCT/US02/28488, filed Sep. 5, 2002, which claims priority to and is a continuation-in-part of U.S. provisional application Ser. No. 60/356,390, filed Feb. 12, 2002 and No. 60/368,177, filed Mar. 27, 2002; and is a continuation-in-part of U.S. patent application Ser. No. 09/947,658, filed Sep. 5, 2001, now U.S. Pat. No. 7,115,139, which is a continuation-in-part of U.S. patent application Ser. No. 09/797,049, filed Mar. 1, 2001, now U.S. Pat. No. 6,702,810, which claims priority to U.S. provisional application Ser. No. 60/187,114, filed Mar. 6, 2000.

This patent application also claims priority to and is a continuation-in-part of U.S. provisional application Ser. No. 60/630,582, filed Nov. 23, 2004.

The entire disclosure of each of these patent applications is incorporated herein by reference to the extent it is consistent.

FIELD

This invention relates generally to the field of medical devices, systems and methods for use upon a body during surgery. More particularly, the invention relates to electrosurgical devices, systems and methods for use upon tissues of a human body during surgery, particularly open surgery and minimally invasive surgery such as laparoscopic surgery.

BACKGROUND

A dry tip electrosurgical device, such as a Bovie pencil, can cause the temperature of tissue being treated to rise significantly higher than 100° C., resulting in tissue desiccation, tissue sticking to the electrodes, tissue perforation, char formation and smoke generation.

More recently, fluid-assisted electrosurgical devices have been developed use saline to inhibit undesirable effects such as tissue desiccation, electrode sticking, smoke production and char formation. However, too much saline can provide too much electrical dispersion and cooling at the electrode/tissue interface. This reduces the temperature of the tissue being treated and, in turn, can result in longer treatment time needed to achieve the desired tissue temperature for treatment of the tissue. Long treatment times are undesirable for surgeons since it is in the best interest of the patient, physician and hospital to perform surgical procedures as quickly as possible.

SUMMARY OF THE INVENTION

This invention, in one embodiment, provides an electrosurgical apparatus to provide controlled delivery of radio-frequency power and a fluid to an electrosurgical hand device to treat tissue. The apparatus comprises a radio-frequency generator to deliver the radio-frequency power, with the radio frequency power from the radio-frequency generator selectable at a radio-frequency power level; a pump to deliver the fluid; a primer to prime the hand device with the fluid; a control system to control a flow of the fluid delivered by the pump with a functional relationship between the radio-frequency power level and the flow of the fluid, the functional relationship to increase the flow of the fluid in response to an increase in the radio-frequency power level and to decrease the flow of the fluid in response to a decrease in the radio-frequency power level; and a fluid flow selector which changes the functional relationship between the radio-frequency power level and the flow of the fluid.

In certain embodiments, the functional relationship is stored in the apparatus in the form of a mathematical equation having a proportionality constant and the fluid flow selector changes the proportionality constant. In other embodiments, the mathematical equation comprises a linear equation. In still other embodiments, the functional relationship is stored in the apparatus in the form of a look-up table.

In certain embodiments, the fluid flow selector provides a plurality of fluid flow settings. In other embodiments, the plurality of fluid flow settings can include a low fluid flow setting and a high fluid flow setting. In still other embodiments, the fluid flow selector comprises at least one switch, and this at least one switch could be a push switch, a membrane switch or a plurality of switches.

In certain embodiments, the control system of the apparatus is open loop with respect to the tissue.

In certain embodiments, the pump used is a peristaltic pump, which could be a rotary peristaltic pump.

In another embodiment, the invention provides a noncoaptive bipolar electrosurgical device to treat tissue by moving along a tissue surface in a presence of radio frequency energy and a fluid provided simultaneously from the device. The device comprises a first electrode tip spaced next to a second electrode tip with a surface portion of the first electrode tip facing alongside the second electrode tip and a surface portion of the second electrode tip facing alongside the first electrode tip, the first electrode tip and the second electrode tip both having a spherical distal end, and a fluid outlet arrangement to expel fluid onto the electrode tips solely at locations remote from the electrode tip surface portions alongside each other.

In certain embodiments, the fluid outlet arrangement has a first fluid outlet and a second fluid outlet with the first fluid outlet to expel fluid onto the first electrode tip at a first electrode tip location remote from the surface portion of the first electrode tip facing alongside the second electrode tip and the second fluid outlet to expel fluid onto the second electrode tip at a second electrode tip location remote from the surface portion of the second electrode tip facing alongside the first electrode tip.

In certain embodiments, the first fluid outlet to expel fluid onto the first electrode tip at a first electrode tip location remote from the surface portion of the first electrode tip facing alongside the second electrode tip expels the fluid onto a lateral surface portion of the first electrode tip and the second fluid outlet to expel fluid onto the second electrode tip at a second electrode tip location remote from the surface portion of the second electrode tip facing alongside the first electrode tip expels the fluid onto a lateral surface portion of the second electrode tip.

In certain embodiments, the lateral surface portion of the first electrode tip comprises a semi-cylindrical or arcuate surface portion of the first electrode tip and the lateral surface portion of the second electrode tip comprises a semi-cylindrical or arcuate surface portion of the second electrode tip. In other embodiments, the surface portion of the first electrode tip has a cylindrical arc or arcuate arc of about 180 degrees and the surface portion of the second electrode tip has a cylindrical arc or arcuate arc of about 180 degrees.

In certain embodiments, a plane, e.g., a flat plane, passes through a longitudinal axis of the first electrode tip and a longitudinal axis of the second electrode tip with the first fluid outlet provided within a localized area of the lateral surface portion of the first electrode tip, the localized area comprising a surface portion, such as a semi-cylindrical surface portion, having a cylindrical or arcuate arc of about 150 degrees provided equally on each side of the plane and the second fluid outlet is provided within a localized area of the lateral surface portion of the second electrode tip, the localized area comprising a surface portion having a cylindrical or arcuate arc of about 150 degrees provided equally on each side of the plane. In other embodiments, the arc for each electrode tip may comprise about 120 degrees, about 90 degrees, about 60 degrees and about 30 degrees. In still other embodiments, the first fluid outlet is provided on the plane and the second fluid outlet is provided on the plane.

In certain embodiments, the first electrode tip location remote from the surface portion of the first electrode tip facing alongside the second electrode tip is provided by a lateral surface portion of the first electrode tip and the second electrode tip location remote from the surface portion of the second electrode tip facing alongside the first electrode tip is provided by a lateral surface portion of the second electrode tip. In other embodiments, the lateral surface portion of the first electrode tip comprises a semi-cylindrical surface portion of the first electrode tip and the lateral surface portion of the second electrode tip comprises a semi-cylindrical surface portion of the second electrode tip. In still other embodiments, the semi-cylindrical surface portion of the first electrode tip has a cylindrical arc of about 180 degrees and the semi-cylindrical surface portion of the second electrode has a cylindrical arc of about 180 degrees.

In certain embodiments, the surface portion of the first electrode tip facing alongside the second electrode tip is provided by a medial surface portion of the first electrode tip and the surface portion of the second electrode tip facing alongside the first electrode tip is provided by a medial surface portion of the second electrode tip. In other embodiments, the medial surface portion of the first electrode tip comprises a semi-cylindrical surface portion of the first electrode tip and the medial surface portion of the second electrode tip comprises a semi-cylindrical surface portion of the second electrode tip. In still other embodiments, the semi-cylindrical surface portion of the first electrode tip has a cylindrical arc of about 180 degrees and the semi-cylindrical surface portion of the second electrode tip has a cylindrical arc of about 180 degrees.

In certain embodiments, the medial surface portion of the first electrode tip has an electrically insulative coating thereon and the medial surface portion of the second electrode tip has an electrically insulative coating thereon. In other embodiments, a flat plane passes through a longitudinal axis of the first electrode tip and a longitudinal axis the second electrode tip with the electrically insulative coating on the first electrode tip provided within a localized area of the medial surface portion of the first electrode tip, the localized area comprising a semi-cylindrical surface portion having a cylindrical arc of about 90 degrees provided equally on each side of the plane and the electrically insulative coating on the second electrode tip provided within a localized area of the medial surface portion of the second electrode tip, the localized area comprising a semi-cylindrical surface portion having a cylindrical arc of about 90 degrees provided equally on each side of the plane passing.

In certain embodiments, the surface portion of the first electrode tip facing alongside the second electrode tip and the surface portion of the second electrode tip facing alongside the first electrode tip are mirror images of each other.

In certain embodiments, the first electrode tip spherical distal end further comprises a hemi-spherical distal end and the second electrode tip spherical distal end further comprises a hemi-spherical distal end. In other embodiments, the first electrode tip spherical distal end has a spherical arc of about 180 degrees and the second electrode tip spherical distal end has a spherical arc of about 180 degrees.

In certain embodiments, the first electrode tip further comprises a first electrode tip cylindrical portion and the second electrode tip further comprises a second electrode tip cylindrical portion. In other embodiments, the first electrode tip cylindrical portion is located proximally adjacent to the first electrode tip spherical distal end and the second electrode tip cylindrical portion is located proximally adjacent to the second electrode tip spherical distal end.

In certain embodiments, the first fluid outlet is at least partially defined by the first electrode tip and the second fluid outlet is at least partially defined by the second electrode tip.

In certain embodiments, the first fluid outlet is located proximal to the first electrode tip spherical distal end and the second fluid outlet is located proximal to the second electrode tip spherical distal end. In other embodiments, the first fluid outlet expels fluid onto the first electrode tip at the first electrode tip cylindrical portion and the second fluid outlet expels fluid onto the second electrode tip at the second electrode tip cylindrical portion.

In certain embodiments, the first electrode tip further comprises a first electrode tip fluid flow channel in fluid communication with the first fluid outlet and the second electrode tip further comprises a second electrode tip fluid flow channel in fluid communication with the second fluid outlet.

In certain embodiments, the first electrode tip fluid flow channel to carries fluid expelled from the first fluid outlet distally along a length of the first electrode tip and remote from the surface portion of the first electrode tip facing alongside the second electrode tip and the second electrode tip fluid flow channel to carries fluid expelled from the second fluid outlet distally along a length of the second electrode tip and remote from the surface portion of the second electrode tip facing alongside the first electrode tip.

In certain embodiments, the first electrode tip fluid flow channel is provided by a first electrode tip elongated recess oriented longitudinally on the first electrode tip and the second electrode tip fluid flow channel is provided by a second electrode tip elongated recess oriented longitudinally on the second electrode tip. In other embodiments, the first fluid outlet is at least partially defined by the first electrode tip elongated recess and the second fluid outlet is at least partially defined by the second electrode tip elongated recess. In still other embodiments, the first electrode tip elongated recess terminates adjacent to the first electrode tip spherical distal end and the second electrode tip elongated recess terminates adjacent to the second electrode tip spherical distal end. In still other embodiments, the first electrode tip elongated recess terminates proximal to the first electrode tip spherical distal end and the second electrode tip elongated recess terminates proximal to the second electrode tip spherical distal end.

In certain embodiments, the first electrode tip is provided at a distal end of a first stationary arm and the second electrode tip is provided at a distal end of a second stationary arm. In other embodiments, a distal portion of the first arm is at an angle relative to an adjoining portion of the first arm and a distal portion of the second arm is at an angle relative to an adjoining portion of the second arm. In still other embodiments, the distal portion of the first arm and the distal portion of the second arm are parallel.

In certain embodiments, the first stationary arm comprises a first shaft having a first shaft distal end with the first electrode tip extending distally beyond the first shaft distal end and the second stationary arm comprises a second shaft having a second shaft distal end with the second electrode tip extending distally beyond the second shaft distal end. In other embodiments, the first fluid outlet is located at the first shaft distal end and the second fluid outlet is located at the second shaft distal end. In still other embodiments, the first shaft further comprises a first shaft distal end opening with the first fluid outlet at least partially defined by the first shaft distal end opening and the second shaft further comprises a second shaft distal end opening with the second fluid outlet at least partially defined by the second shaft distal end opening. In still other embodiments, the first fluid outlet is located between a portion of the first electrode tip and the first shaft distal end and the second fluid outlet is located between a portion of the second electrode tip and the second shaft distal end. In still other embodiments, the first shaft further comprises a first shaft fluid passage with the first shaft fluid passage in fluid communication with the first fluid outlet and the second shaft further comprises a second shaft fluid passage with the second shaft fluid passage in fluid communication with the second fluid outlet.

In certain embodiments, the device comprises a first fluid flow passage and a second fluid flow passage with the first fluid flow passage in fluid communication with the first fluid outlet and the second fluid flow passage in fluid communication with the second fluid outlet. In other embodiments, at least one of the first fluid flow passage and the second fluid flow passage having a circular cross-sectional shape. In still other embodiments, at least one of the first fluid flow passage and the second fluid flow passage is provided by a lumen of a hollow metal tubing.

In certain embodiments, the first electrode tip further comprises a surface having a contact angle with fluid expelled from the first fluid outlet onto the first electrode tip of less than about 90 degrees; and the second electrode tip further comprises a surface having a contact angle with fluid expelled from the second fluid outlet onto the second electrode tip of less than about 90 degrees.

In certain embodiments, the first electrode tip and the second electrode tip are parallel. In other embodiments, the first electrode tip and the second electrode tip are in a side-by-side arrangement. In still other embodiments the first electrode tip and the second electrode tip are a same shape or a same size.

In certain embodiments, the first electrode tip has a diameter in the range between and including about 1 mm to about 7 mm and the second electrode tip has a diameter in the range between and including about 1 mm to about 7 mm. In other embodiments, the first electrode tip has a diameter in the range between and including about 2 mm to about 5 mm and the second electrode tip has a diameter in the range between and including about 2 mm to about 5 mm.

In certain embodiments, the first electrode tip spherical distal end has a radius in the range between and including about 0.5 mm to about 3.5 mm and the second electrode tip spherical distal end has a radius in the range between and including about 0.5 mm to about 3.5 mm. In other embodiments, the first electrode tip spherical distal end has a radius in the range between and including about 1 mm to about 2.5 mm and the second electrode tip spherical distal end has a radius in the range between and including about 1 mm to about 2.5 mm.

In certain embodiments, the first electrode tip is spaced from the second electrode tip by a gap of at least about 2 mm. In other embodiments, the first electrode tip is spaced from the second electrode tip by a gap in the range between and including about 1.3 mm to about 4 mm. In other embodiments, the first electrode tip is spaced from the second electrode tip by a gap in the range between and including about 2 mm to about 3 mm.

It is understood that the specific features described in these embodiments can be rearranged among the various embodiments to provide devices, apparatus, and systems that fall within the scope of this disclosure.

BRIEF DESCRIPTION OF THE DRAWINGS

FIG. 7 is an exploded perspective view of an assembly of an electrosurgical device according to the present invention;

DETAILED DESCRIPTION

Figure 1:
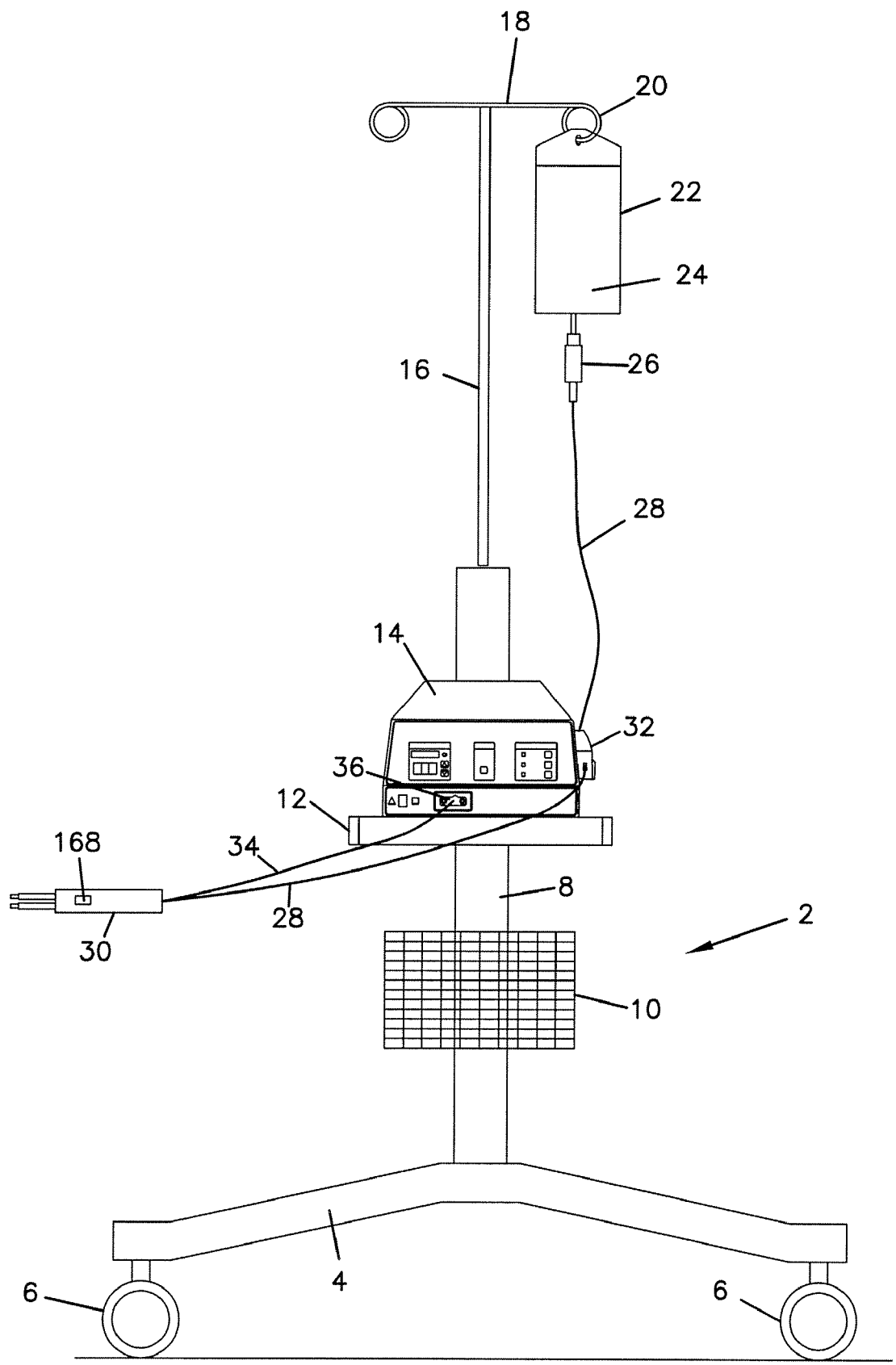
FIG. 1 is a front view of one embodiment of a system of the present invention having an electrosurgical unit in combination with a fluid source and handheld electrosurgical device.

Throughout the description, like reference numerals and letters indicate corresponding structure throughout the several views. Also, any particular feature(s) of a particular exemplary embodiment may be equally applied to any other exemplary embodiment(s) of this specification as suitable. In other words, features between the various exemplary embodiments described herein are interchangeable as suitable, and not exclusive. From the specification, it should be clear that any use of the terms "distal" and "proximal" are made in reference from the user of the device, and not the patient.

The invention provides devices, systems and methods for controlling tissue temperature at a tissue treatment site during an electrosurgical procedure. This is particularly useful for procedures where it is desirable to shrink, coagulate and seal tissue against blood loss, for example, by shrinking lumens of blood vessels (e.g., arteries, veins).

The invention will now be discussed with reference to the figures, with FIG. 1 showing a front view of one embodiment of a system of the present invention having an electrosurgical unit 14 in combination with a fluid source 22 and a handheld electrosurgical device 30. FIG. 1 shows a movable cart 2 having a chassis 4 which is provided with four wheels 6 for easy transportation. The chassis 4 carries a support member 8 comprising a hollow cylindrical post to which a storage basket 10 may be fastened and used to store the electrosurgical unit's user manual, as well as additional unused devices. Furthermore, the support member 8 carries a platform 12 comprising a pedestal table to provide a flat, stable surface for location of the electrosurgical unit 14.

As shown cart 2 further comprises a fluid source carrying pole 16 having a height which may be adjusted by sliding the carrying pole 16 up and down within the support member 8 and thereafter secured in position with a set screw. On the top of the fluid source carrying pole 16 is a cross support 18 provided with loops 20 at the ends thereof to provide a hook for carrying fluid source 22.

As shown in FIG. 1, fluid source 22 comprises a bag of fluid from which the fluid 24 flows through a drip chamber 26 after the bag is penetrated with a spike located at the end of the drip chamber 26. Thereafter, fluid 24 flows through flexible delivery tubing 28 to handheld electrosurgical device 30. Preferably the fluid delivery tubing 28 is made from a polymer material.

Figure 6:
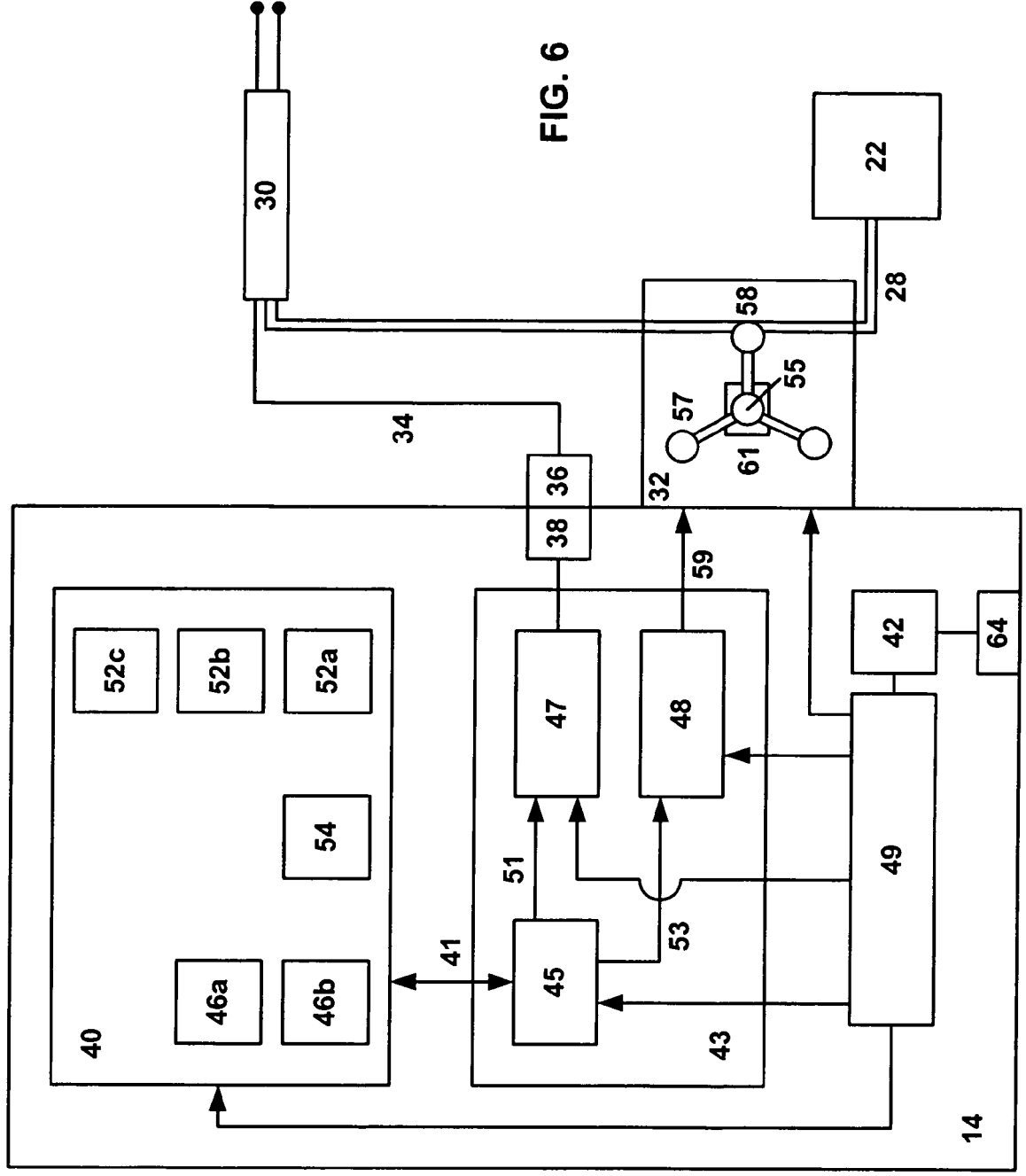
FIG. 6 is a block diagram showing one embodiment of how the electrosurgical unit processes the inputs of RF power setting $P_S$ and the fluid flow rate setting, either $Q_L$, $Q_M$ or $Q_H$, to control the pump speed.

As shown in FIG. 1, the fluid delivery tubing 28 passes through pump 32. As shown pump 32 comprises a peristaltic pump and, more specifically, a rotary peristaltic pump. With a rotary peristaltic pump, a portion of the delivery tubing 28 is loaded into the pump head by raising and lower the pump head in a known manner. As best shown in FIG. 6, fluid 24 is conveyed within the delivery tubing 28 by waves of contraction placed externally on the tubing 28 which are produced mechanically, typically by rotating pinch rollers 57 which rotate on a drive shaft 55 and intermittently compress the tubing 28 against an anvil support 58. Alternatively, pump 32 may comprise a linear peristaltic pump. With a linear peristaltic pump, fluid 24 is conveyed within the delivery tubing 28 by waves of contraction placed externally on the tubing 28 which are produced mechanically, typically by a series of compression fingers or pads which sequentially squeeze the tubing 28 against a support. Peristaltic pumps are generally preferred, as the electromechanical force mechanism, here rollers driven by electric motor, does not make contact the fluid 24, thus reducing the likelihood of inadvertent contamination.

In a preferred embodiment the fluid 24 comprises saline, and even more preferably, normal (physiologic) saline. Although the description herein may make reference to saline as the fluid 24, other electrically conductive fluids can be used in accordance with the invention.

While a conductive fluid is preferred, as will become more apparent with further reading of this specification, fluid 24 may also comprise an electrically non-conductive fluid. The use of a non-conductive fluid is less preferred than a conductive fluid, however, the use of a non-conductive fluid still provides certain advantages over the use of a dry electrode including, for example, reduced occurrence of tissue sticking to the electrode of device 5 and cooling of the electrode and/or tissue. Therefore, it is also within the scope of the invention to include the use of a non-conducting fluid, such as, for example, deionized water.

Figure 2:
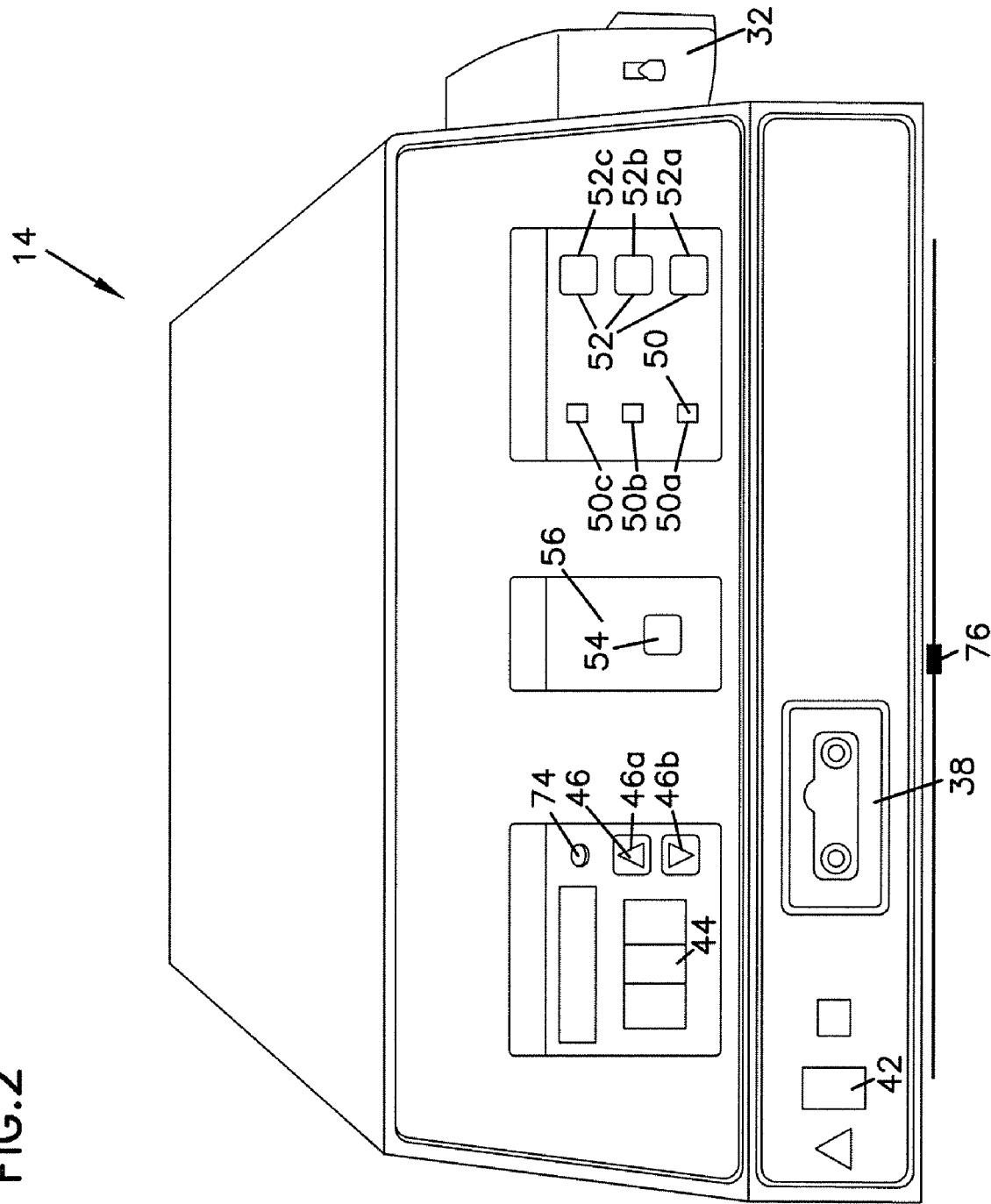
FIG. 2 is a front perspective view of the electrosurgical unit of FIG. 1.

As shown in FIG. 1, electrosurgical device 30 is connected to electrosurgical unit 14 via a cable 34 which comprises a plurality of electrically insulated wire conductors and at least one plug 36 at the end thereof. The electrosurgical unit 14 provides radio-frequency (RF) energy via cable 34 to electrosurgical device 30. As shown in FIG. 2, plug receptacle 38 of electrosurgical unit 14 receives the plug 36 of device 30 therein to electrically connect device 30 to the electrosurgical unit 14. Preferably the fluid delivery tubing 28 is provided as part of cable 34 and produced with the electrically insulated wires via plastic co-extrusion.

FIG. 2 shows the front panel of the electrosurgical unit 14. A power switch 42 is used to turn the electrosurgical unit 14 on and off. After turning the electrosurgical unit 14 on, the RF power setting display 44 is used to display the RF power setting numerically in watts. Preferably the power setting display comprises a liquid crystal display (LCD). Additionally, this display 44 is used to display errors, in which case the display 44 will show "Err" and blink alternately with a special error code number(s).

The RF power selector comprises RF power setting switches 46a, 46b which are used to select the RF power setting. Pushing the switch 46a increases the RF power setting, while pushing the switch 46b decreases the RF power setting. RF power output may be set in 5 watt increments in the range of 20 to 100 watts, and 10 watt increments in the range of 100 to 200 watts. Additionally, electrosurgical unit 14 includes an RF power activation display comprising an indicator light which illuminates when RF power is activated. Switches 46a, 46b may comprise membrane switches.

In addition to having a RF power setting display, electrosurgical unit 14 further includes a fluid flow rate setting display. Flow rate setting display comprises three indicator lights 50a, 50b and 50c with a first light 50a corresponding to a fluid flow rate setting of low, a second light 50b corresponding to a fluid flow rate setting of medium (intermediate) and a third light 50c corresponding to a flow rate setting of high. One of these three indicator lights will illuminate when a fluid flow rate setting is selected.

A fluid flow selector comprising flow rate setting switches 52a, 52b and 52c are used to select or switch the flow rate setting. Three push switches are provided with the first switch 52a corresponding to a fluid flow rate setting of low, the second switch 52b corresponding to a fluid flow rate setting of medium (intermediate) and the third switch 52c corresponding to a flow rate setting of high. Pushing one of these three switches selects the corresponding flow rate setting of either low, medium (intermediate) or high. The medium, or intermediate, flow rate setting is automatically selected as the default setting if no setting is manually selected. Switches 52a, 52b and 52c may comprise membrane switches.

Before starting a surgical procedure, it is desirable to prime device 30 with fluid 24. Priming is desirable to inhibit RF power activation without the presence of fluid 24. A priming switch 54 is used to initiate priming of device 30 with fluid 24. Pushing switch 54 once initiates operation of pump 32 for a predetermined time period to prime device 30. After the time period is complete, the pump 32 shuts off automatically. When priming of device 30 is initiated, a priming display 56 comprising an indicator light illuminates during the priming cycle.

On the front panel the bipolar activation indicator 74 illuminates when RF power is activated from the electrosurgical unit 14, either via a handswitch 168 on device 30 or a footswitch. A pullout drawer 76 is located under the electrosurgical unit 14 where the user of electrosurgical unit 14 may find a short form of the user's manual.

Figure 6A:
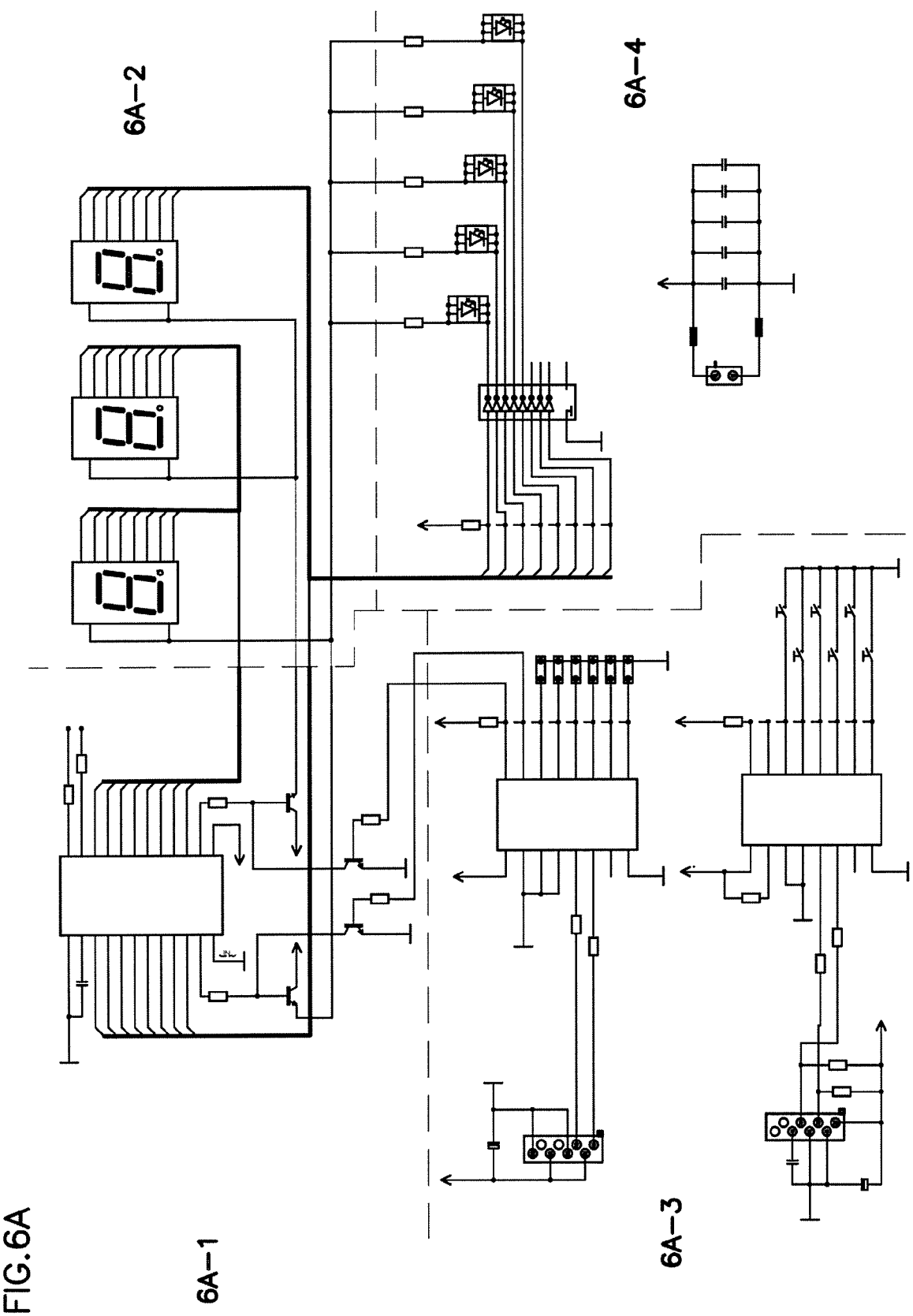
FIGS. 6A-6O are detailed drawings showing one specific embodiment of an electrosurgical unit.
Figures 1, 6A:
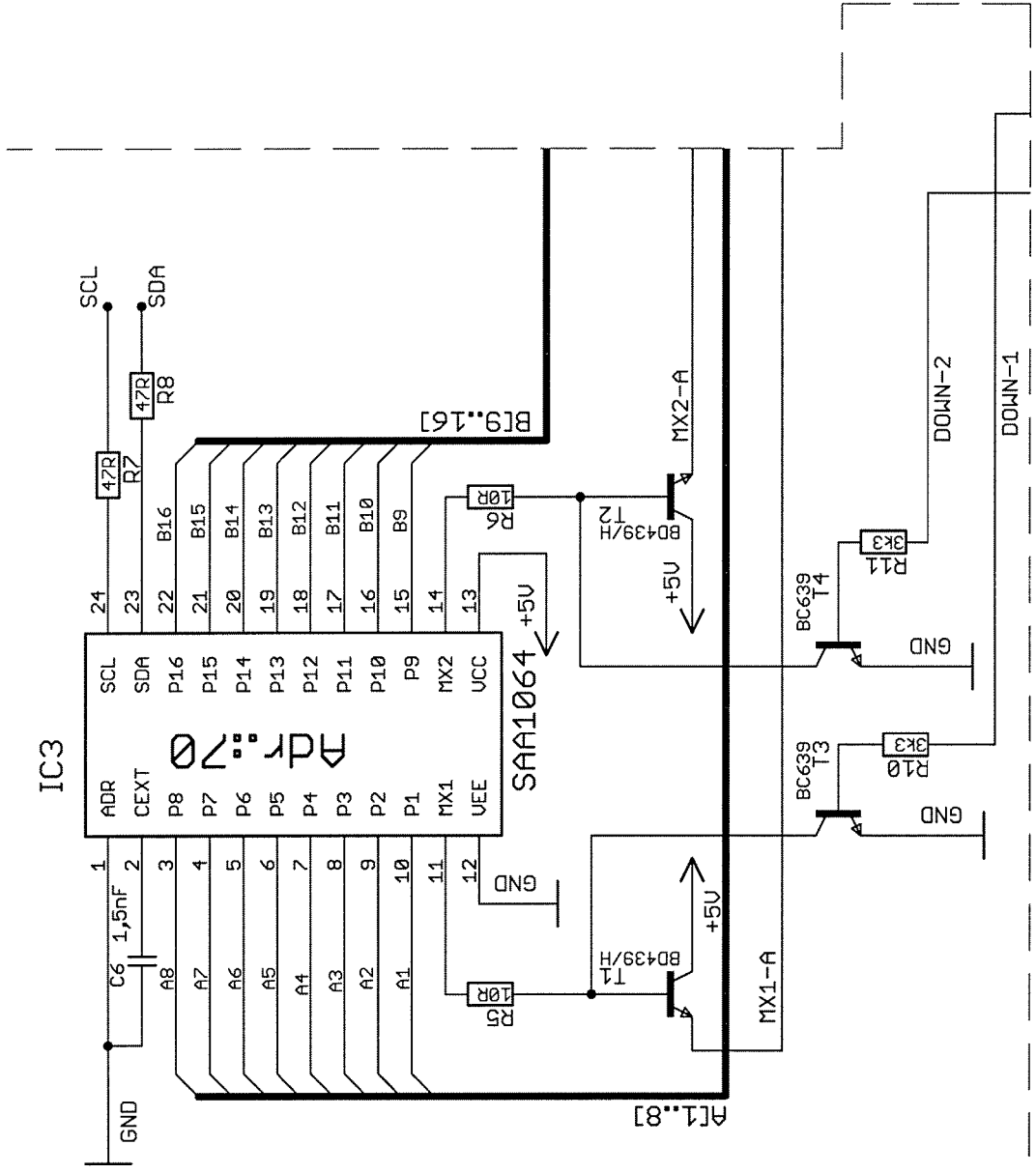
Figures 2, 6A:
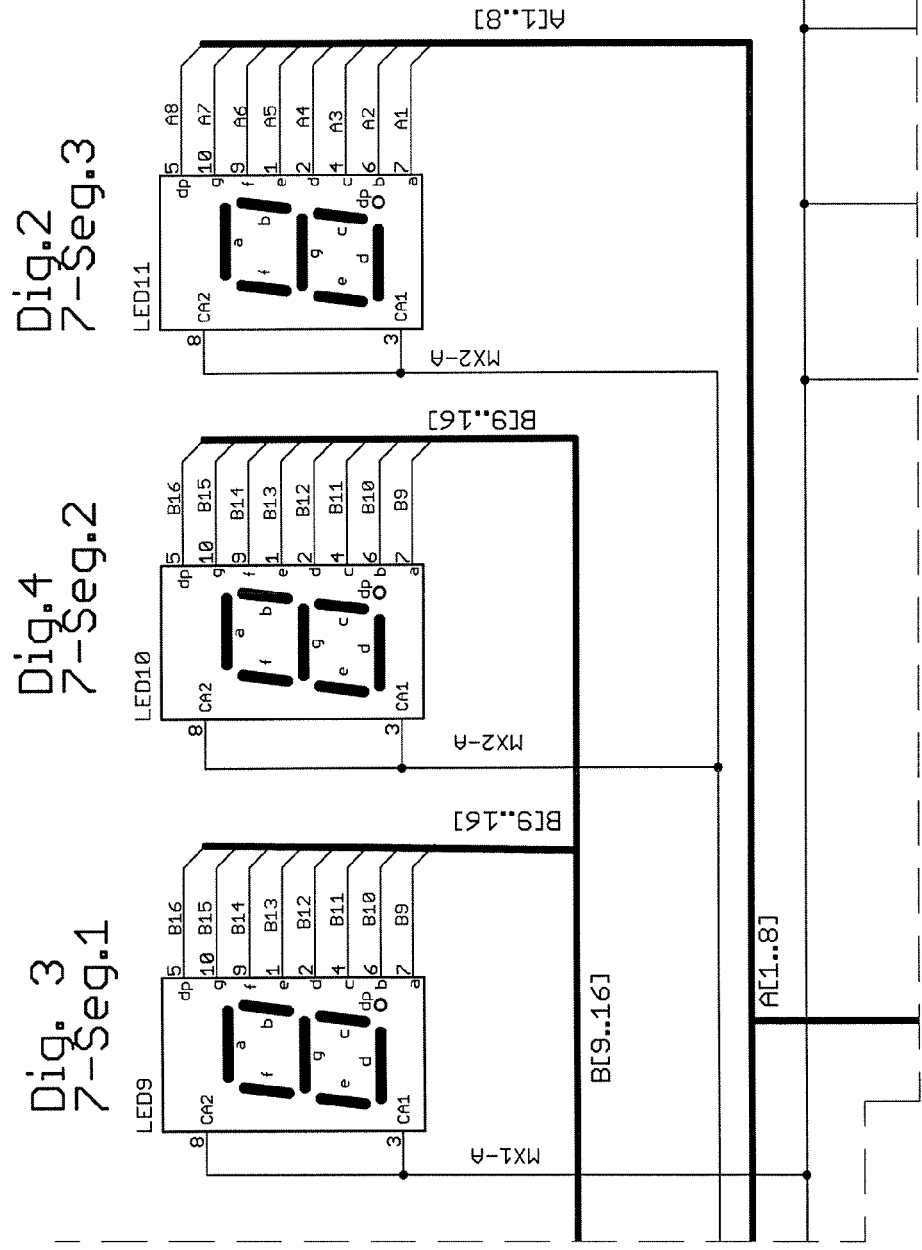
Figures 3, 6A:
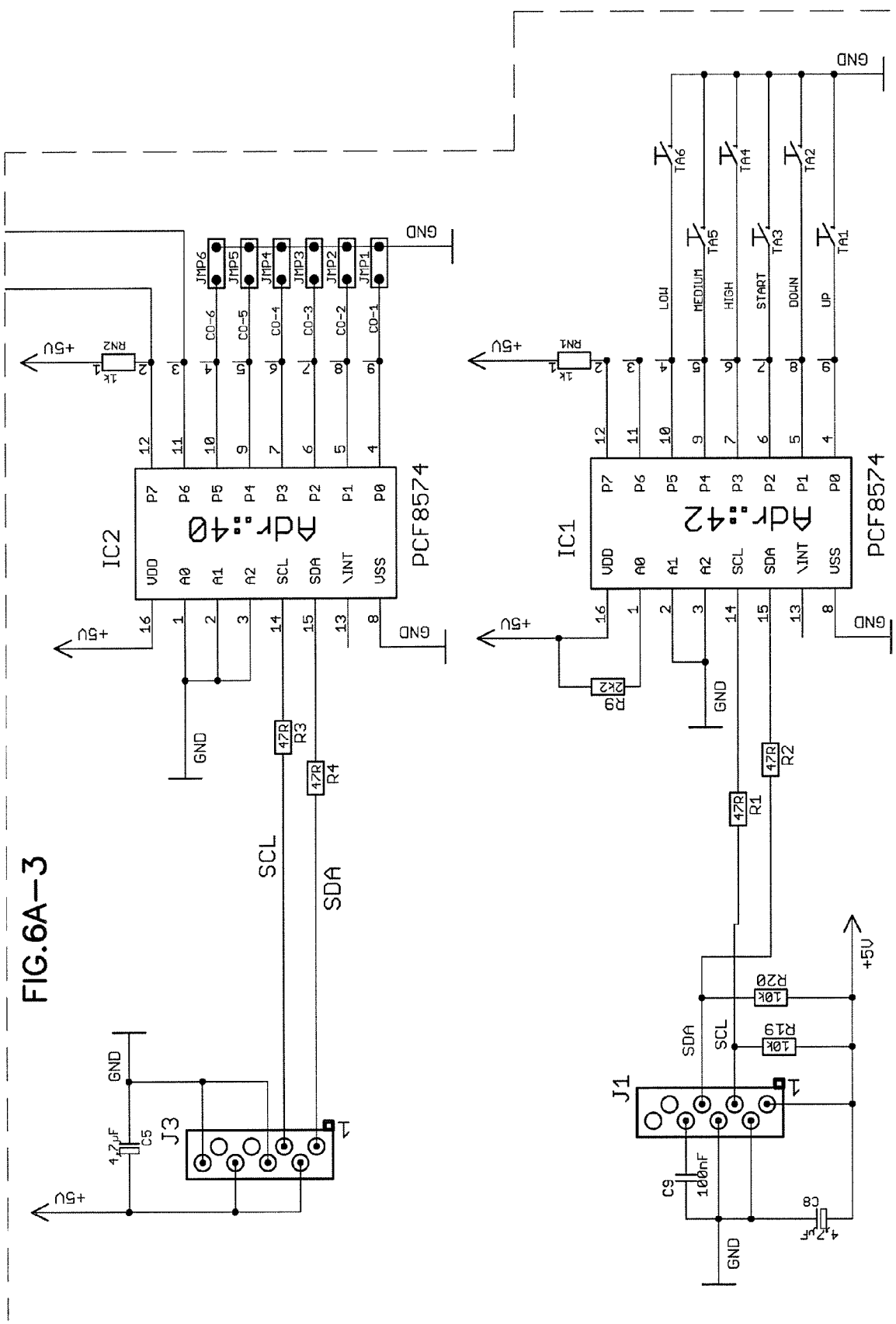
FIG. 3 is a rear view of the electrosurgical unit of FIG. 1.
Figures 4, 6A:
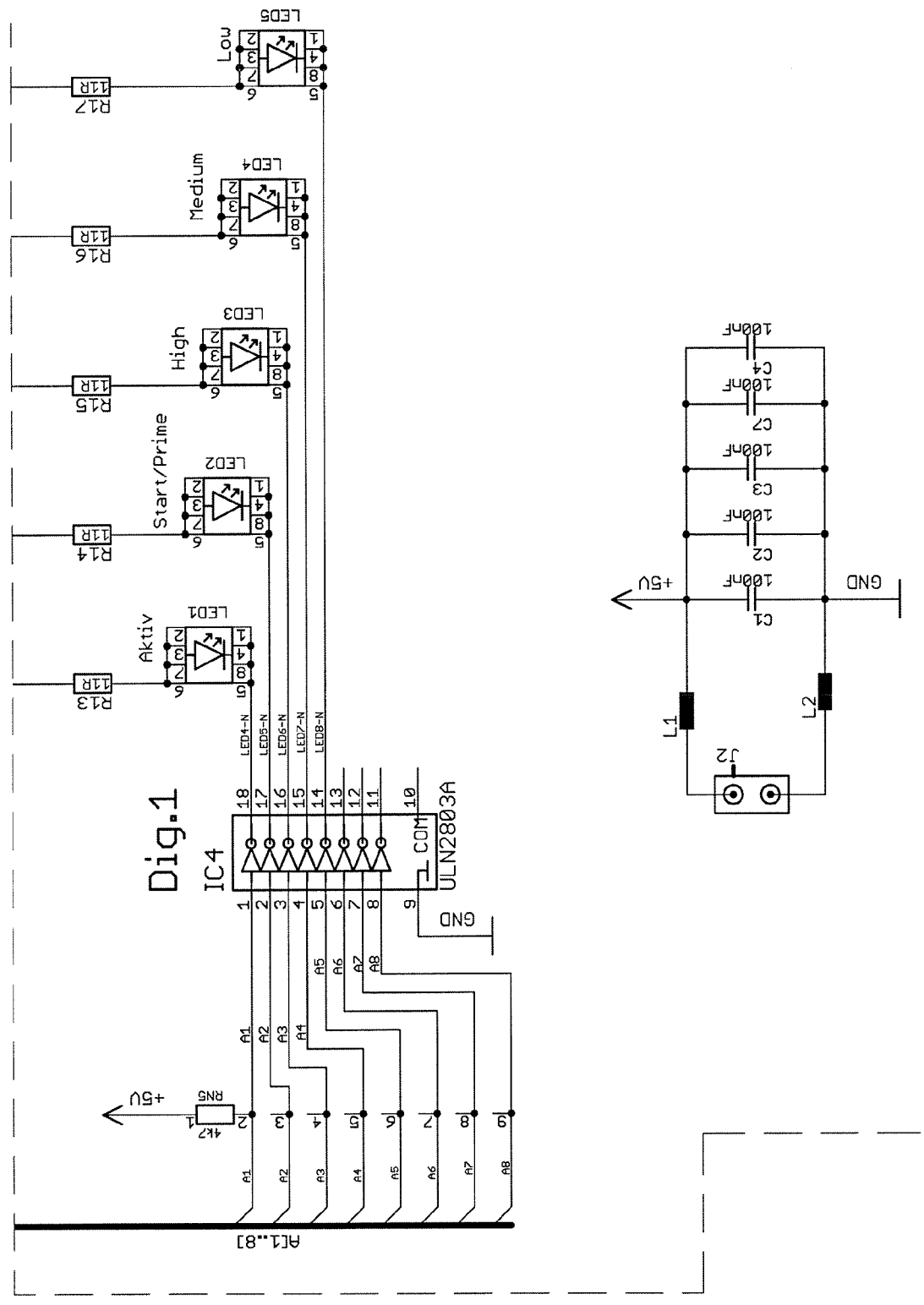
Figure 6B:
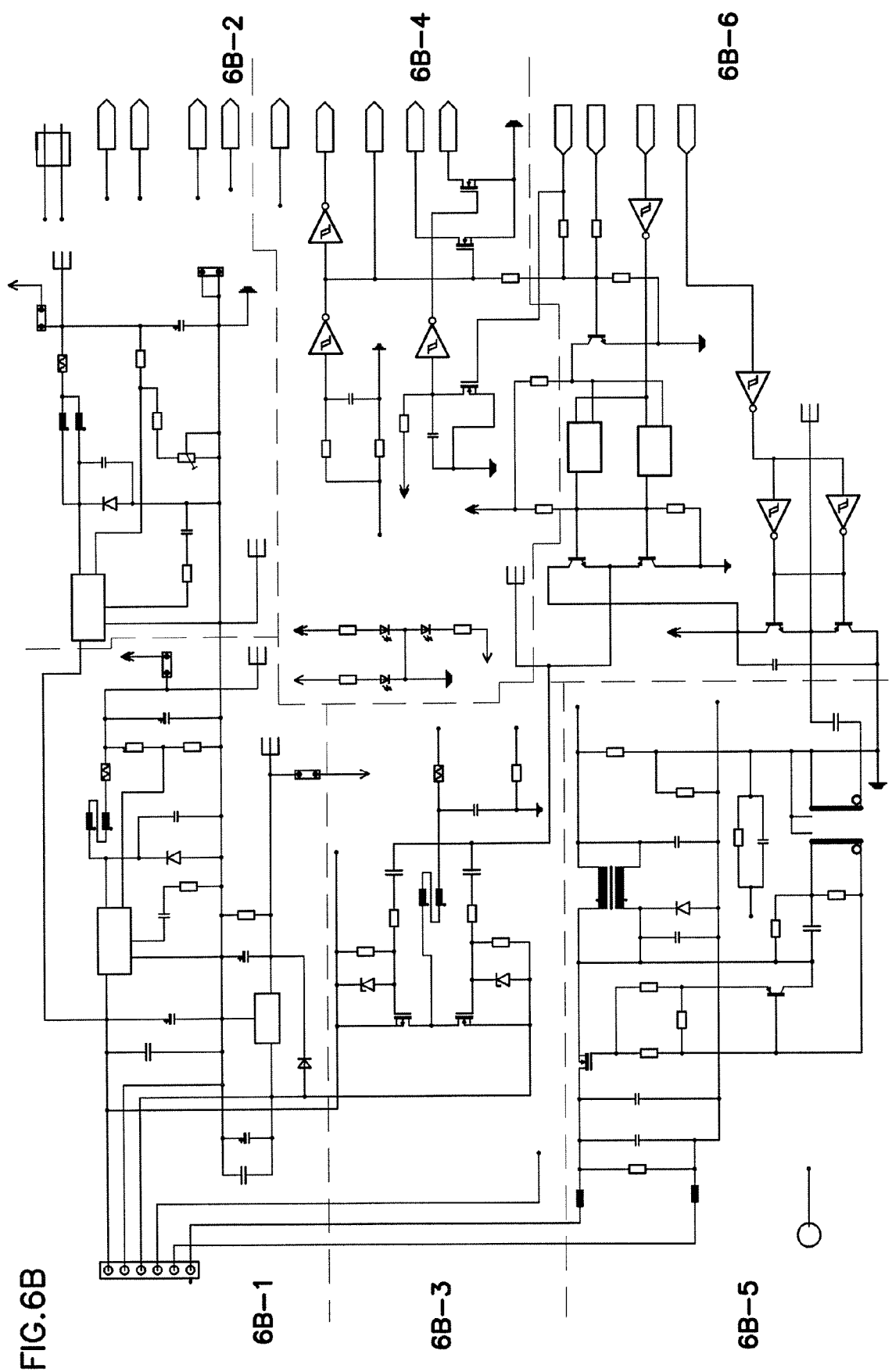
Figures 1, 6B:
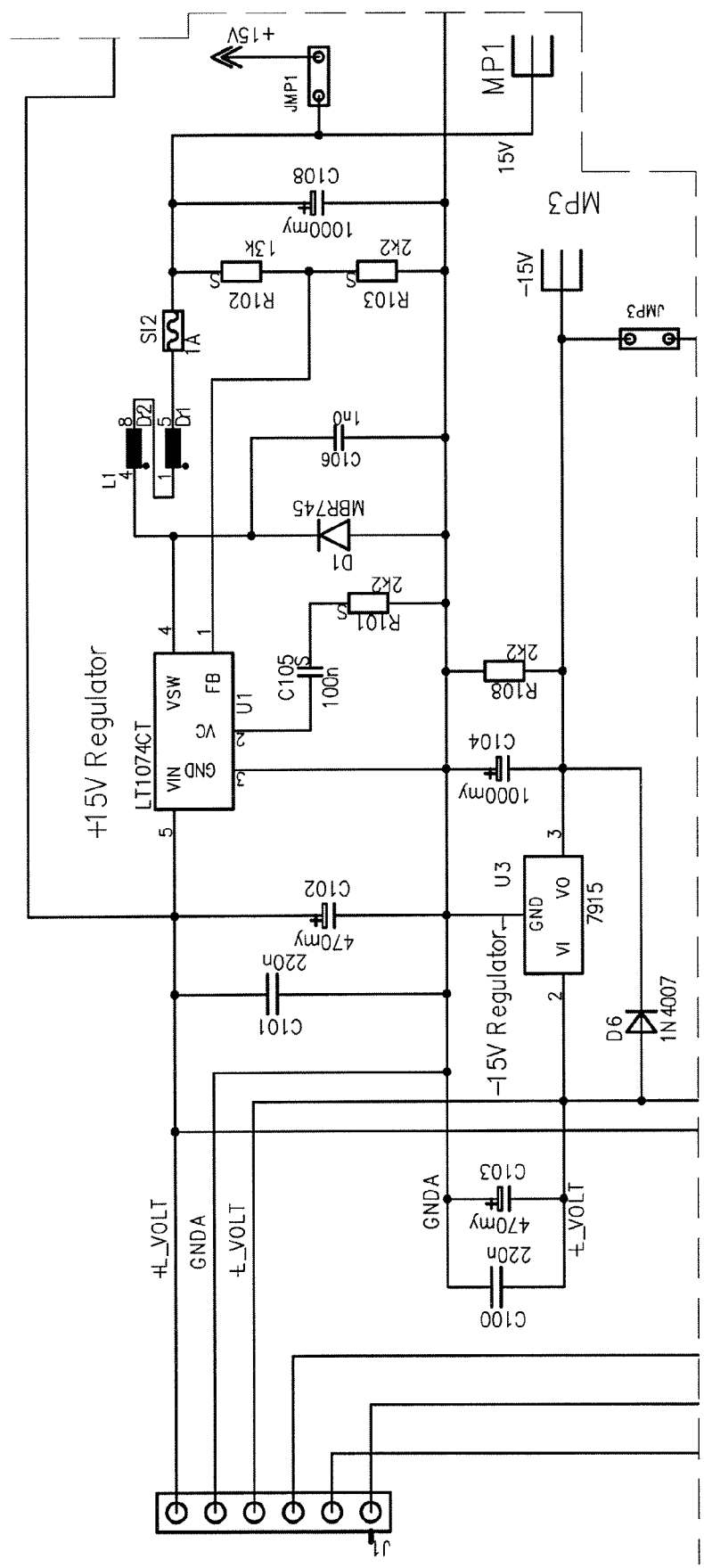
Figures 2, 6B:
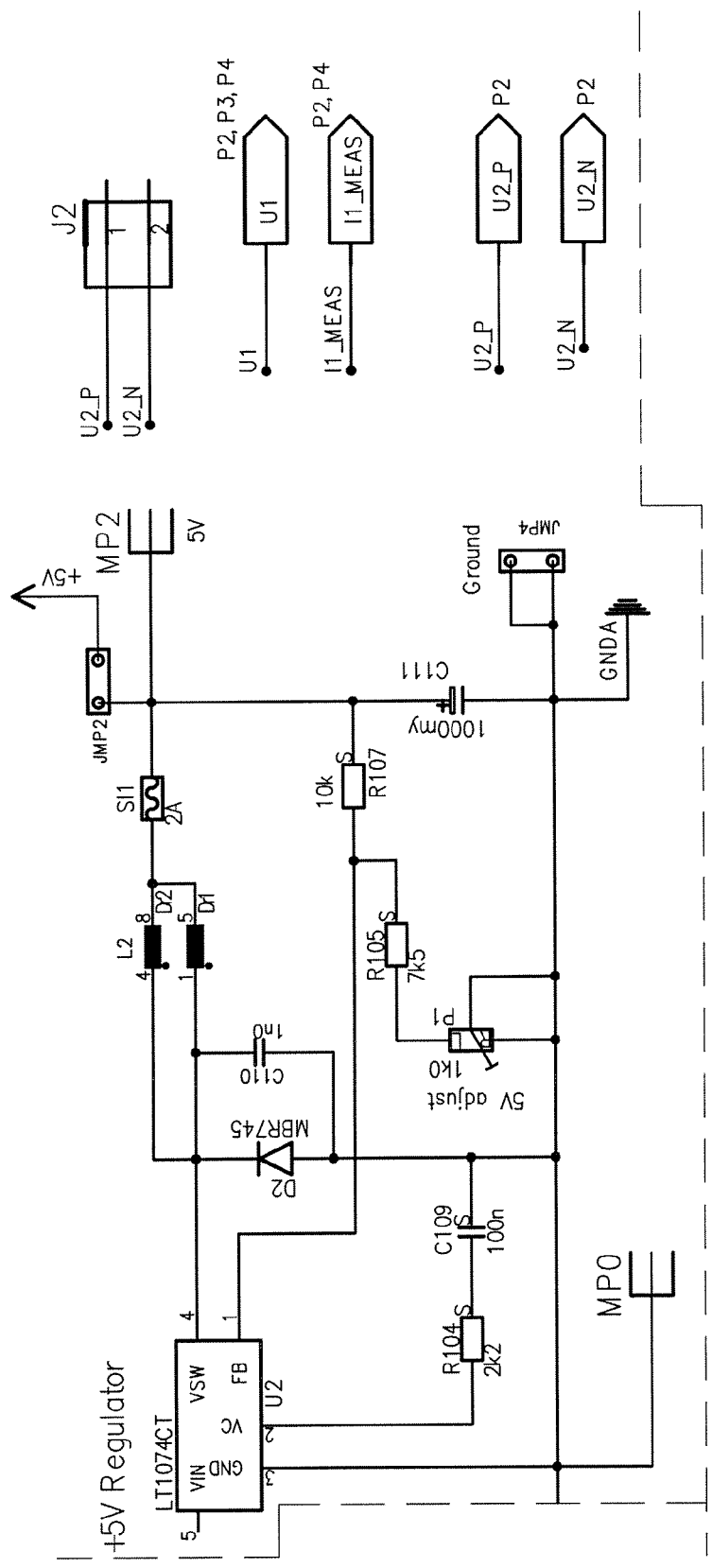
Figures 3, 6B:
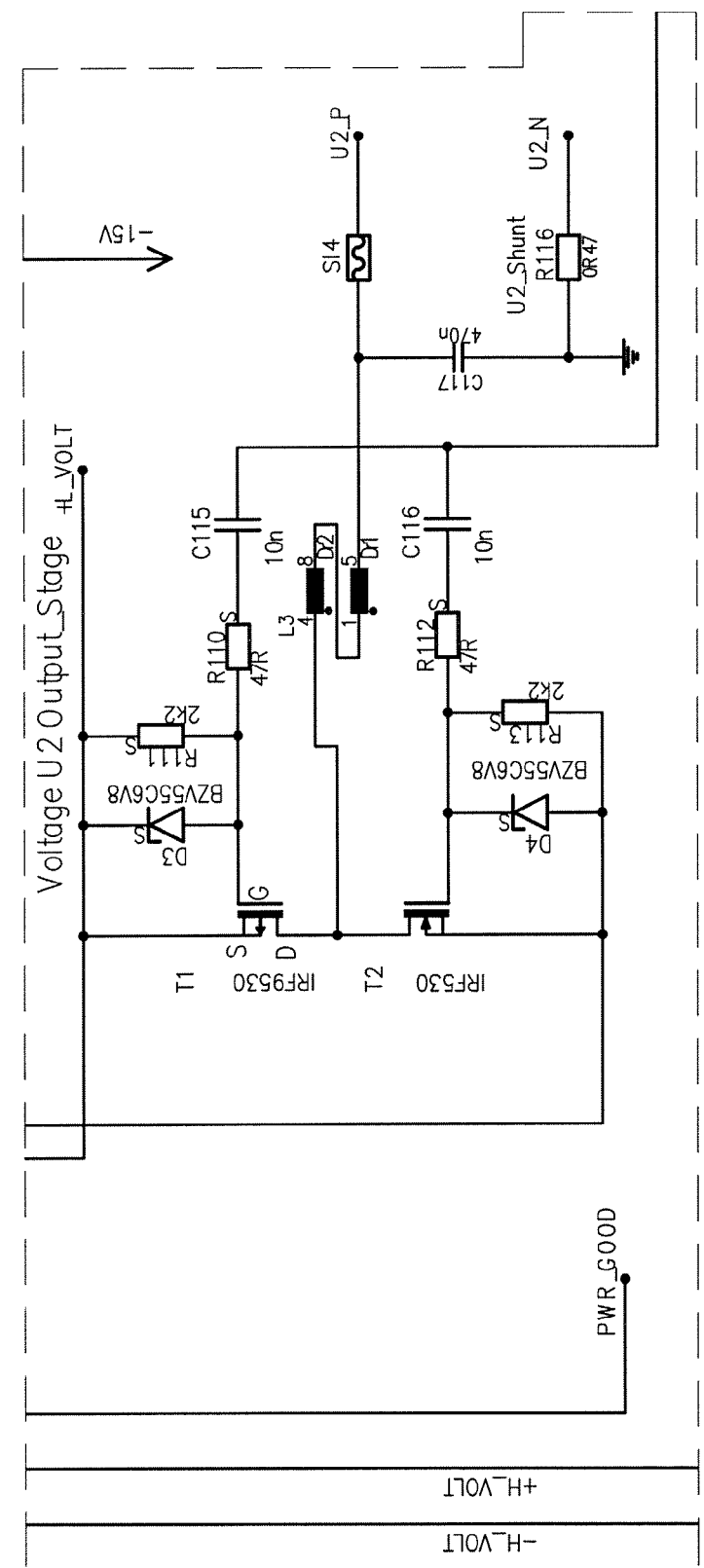
Figures 4, 6B:
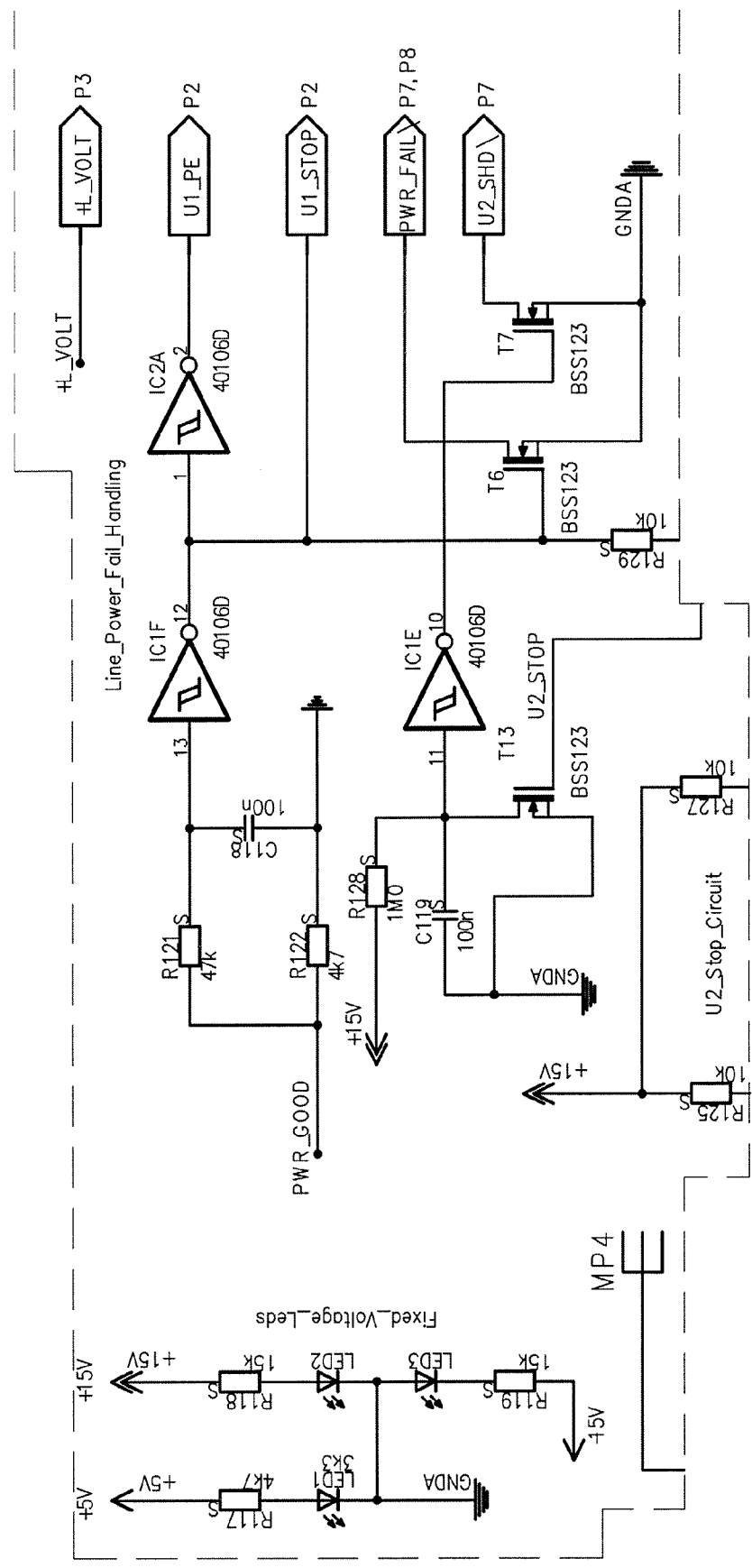
Figures 5, 6B:
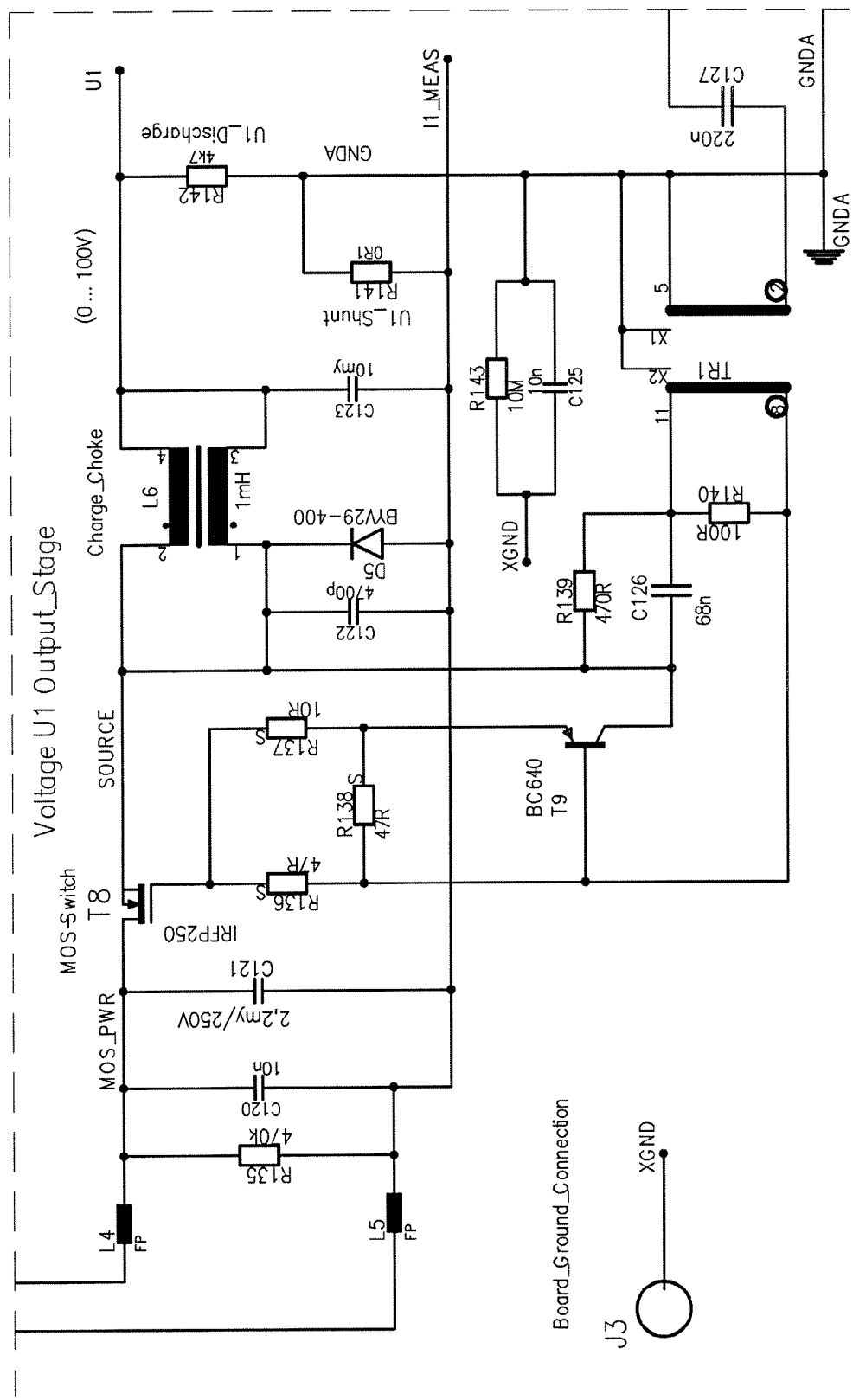
Figures 6, 6B:
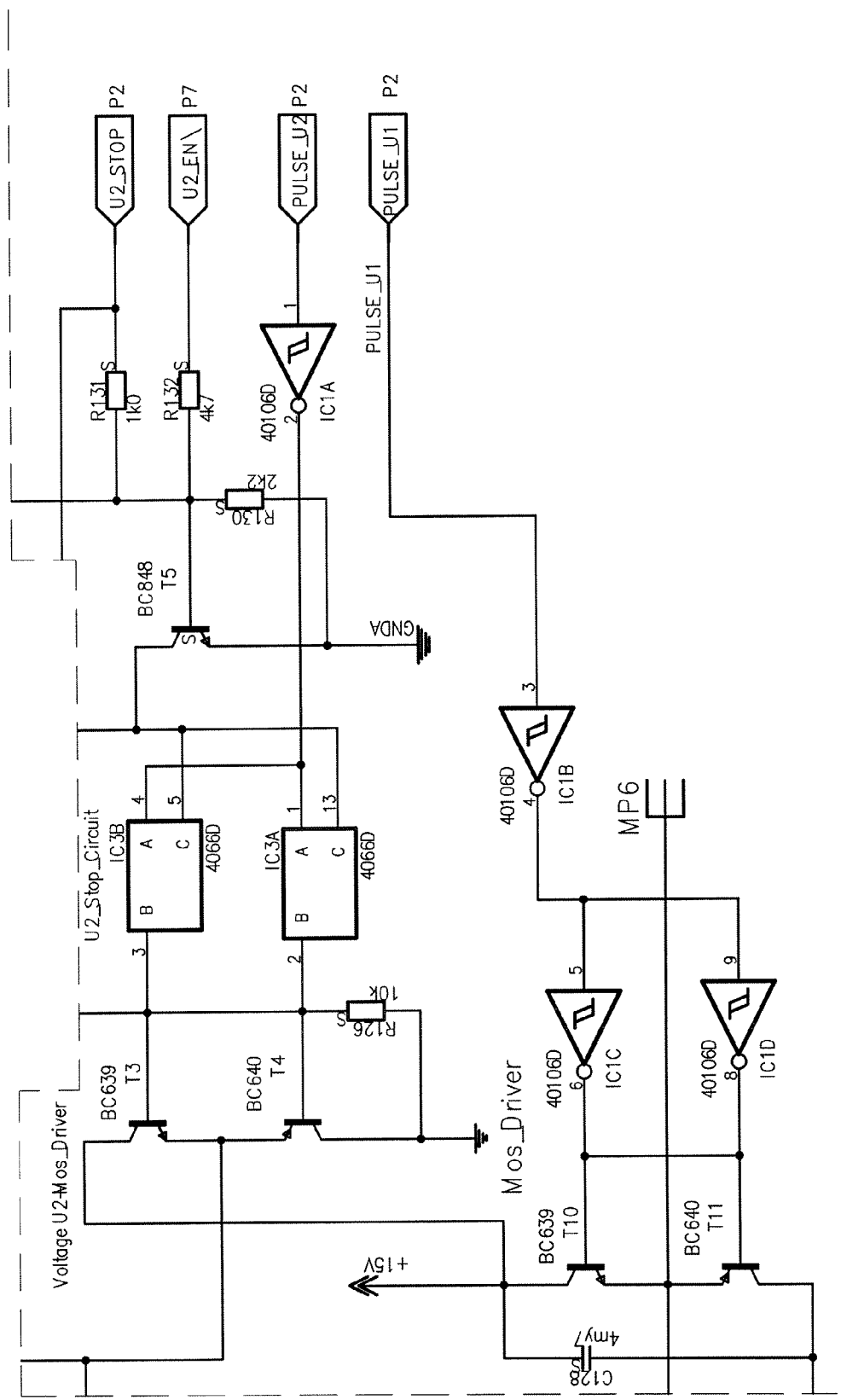
Figure 6C:
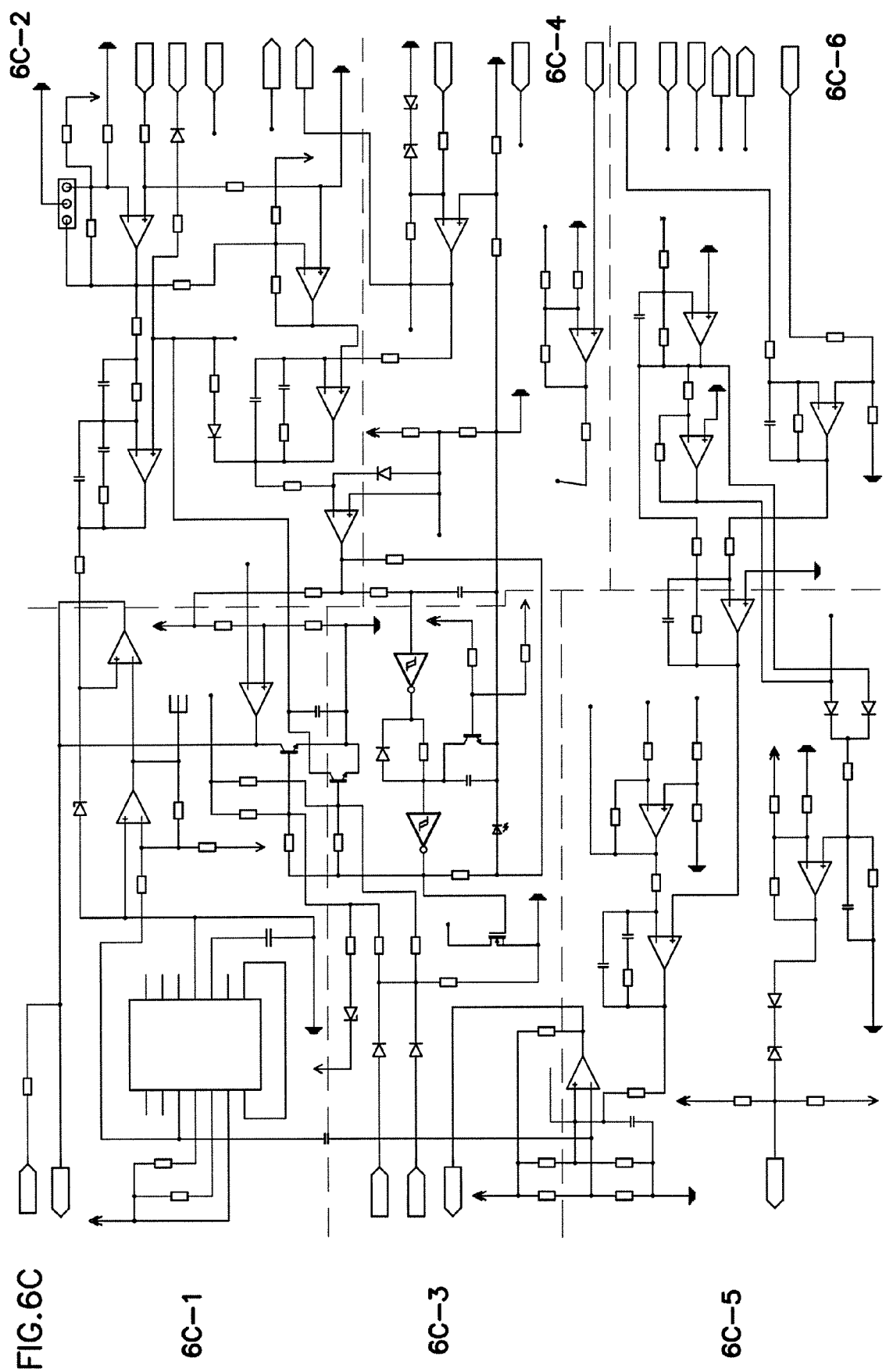
Figures 1, 6C:
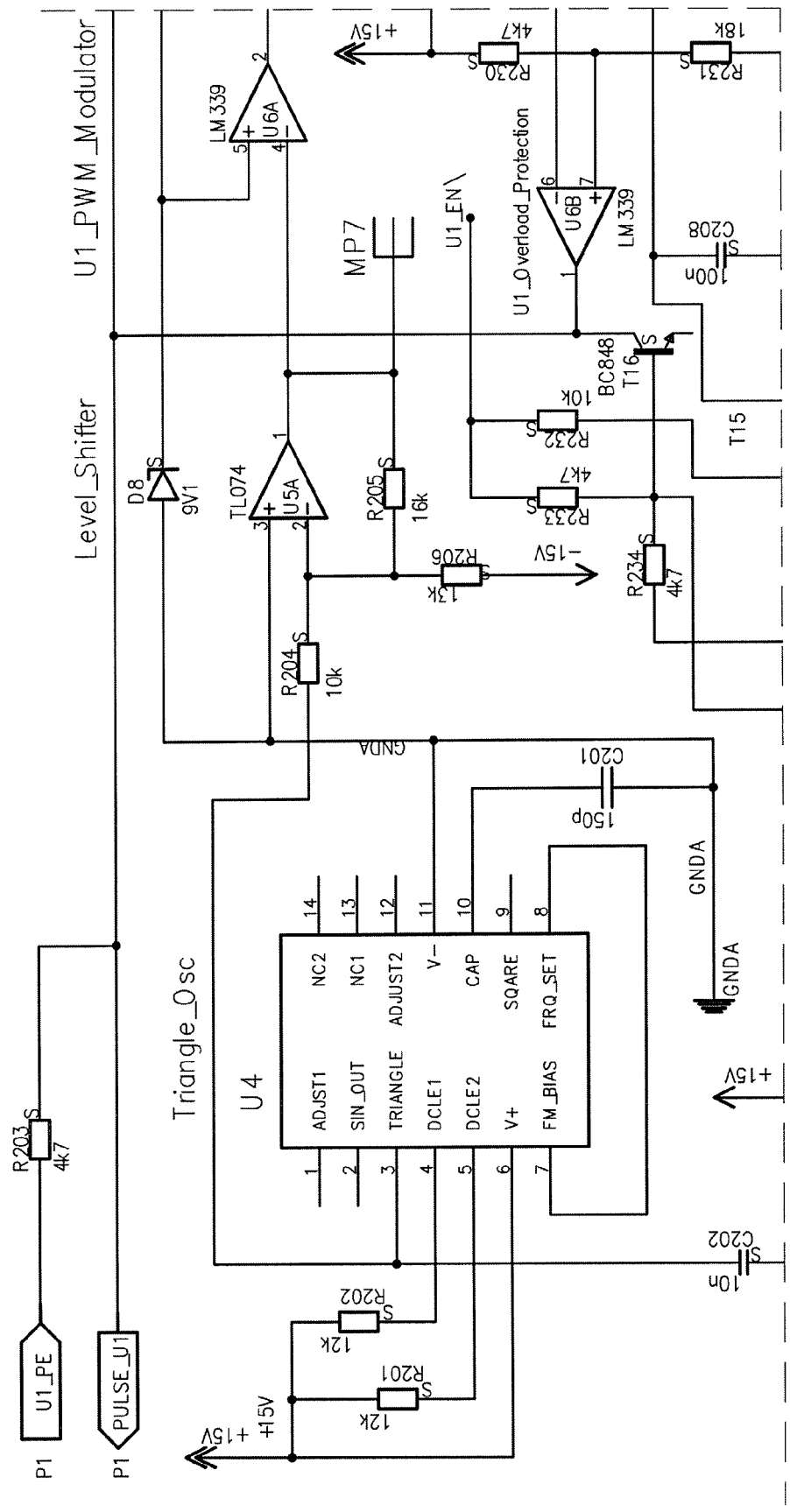
Figures 2, 6C:
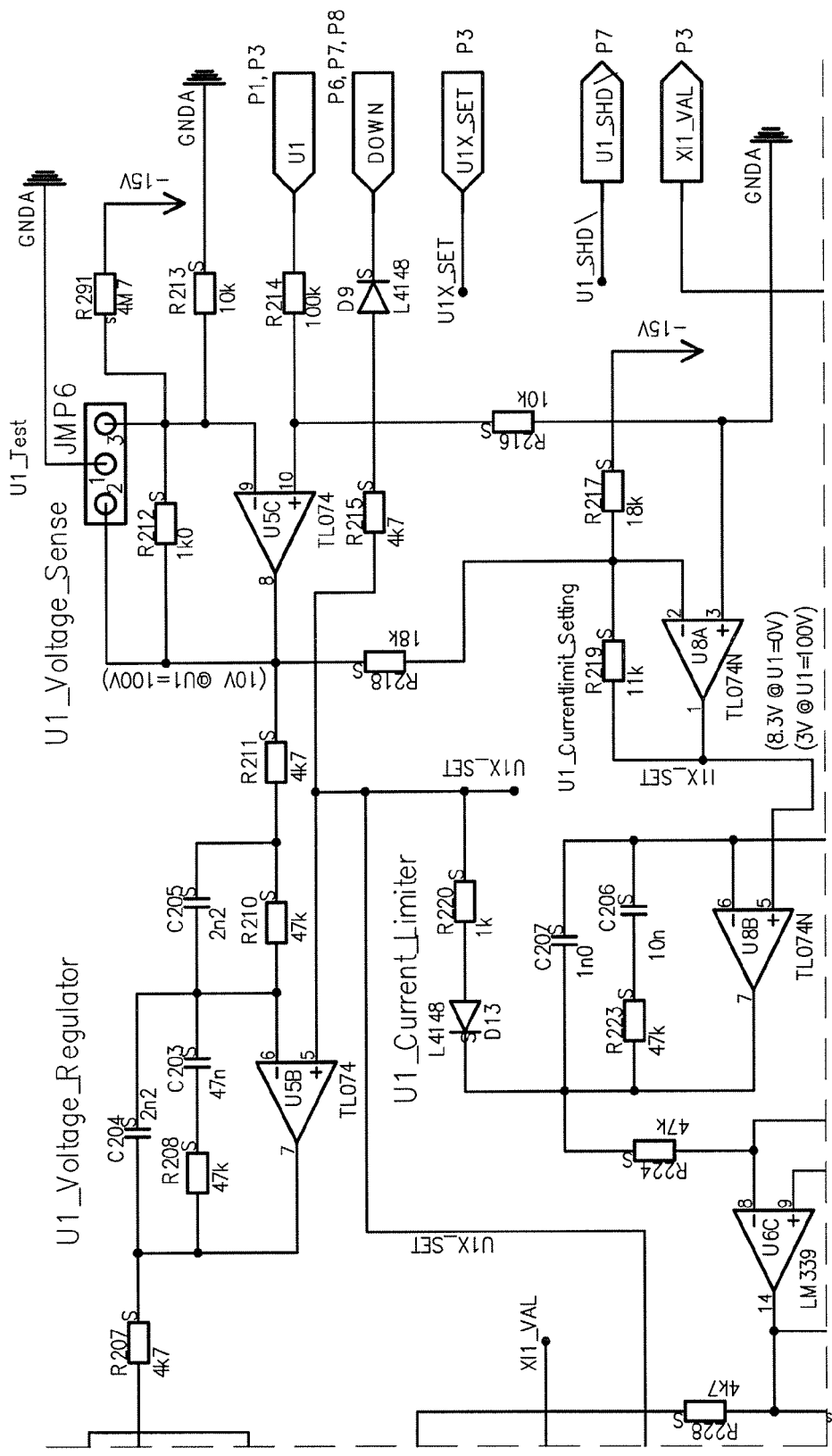
Figures 3, 6C:
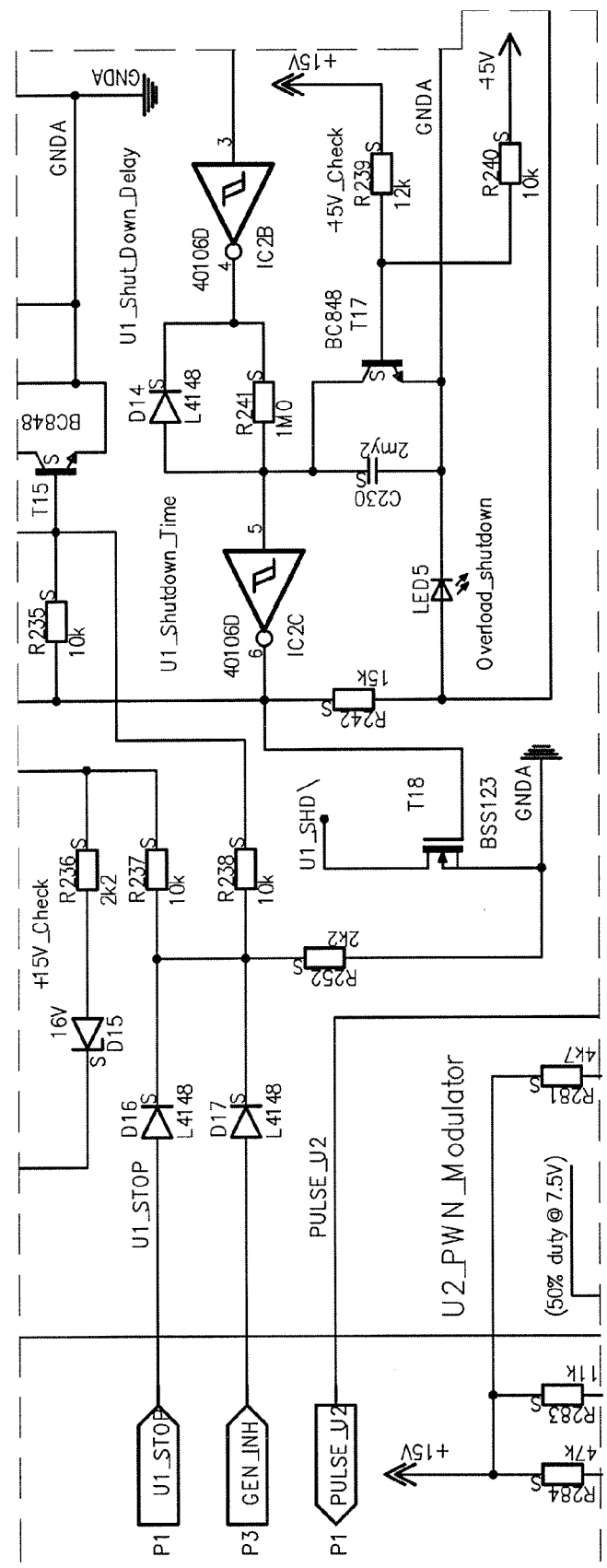
Figures 4, 6C:
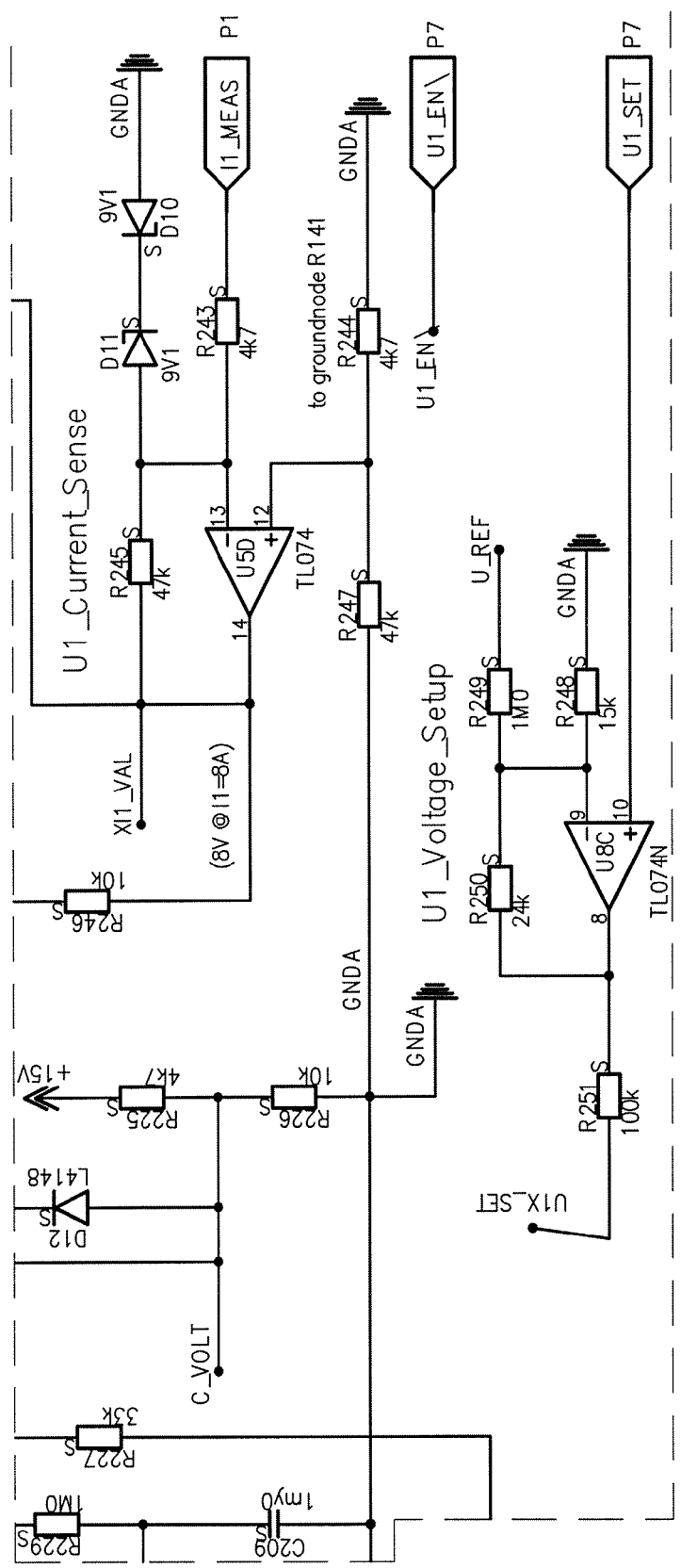
Figures 5, 6C:
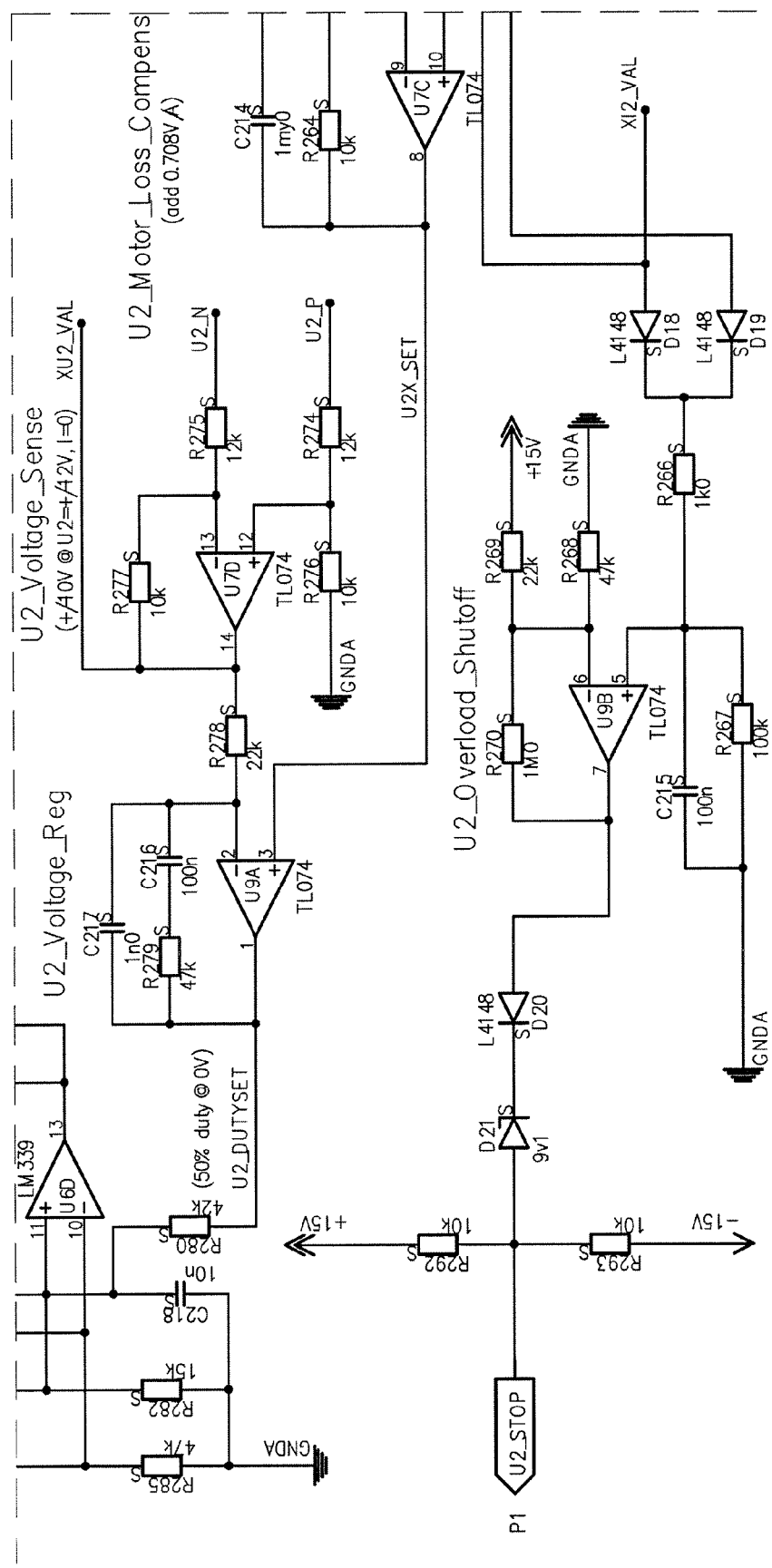
Figures 6, 6C:
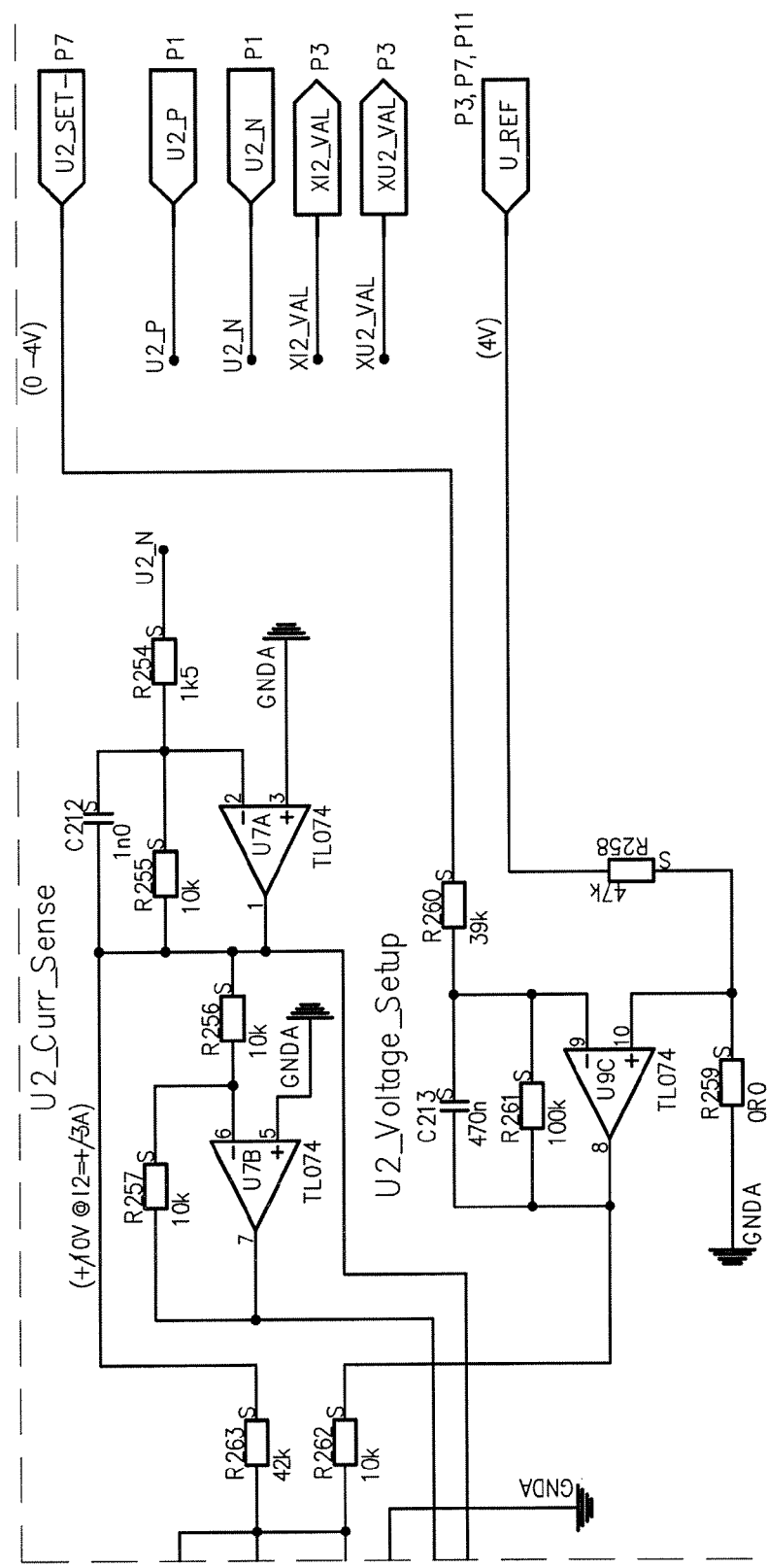
Figure 6D:
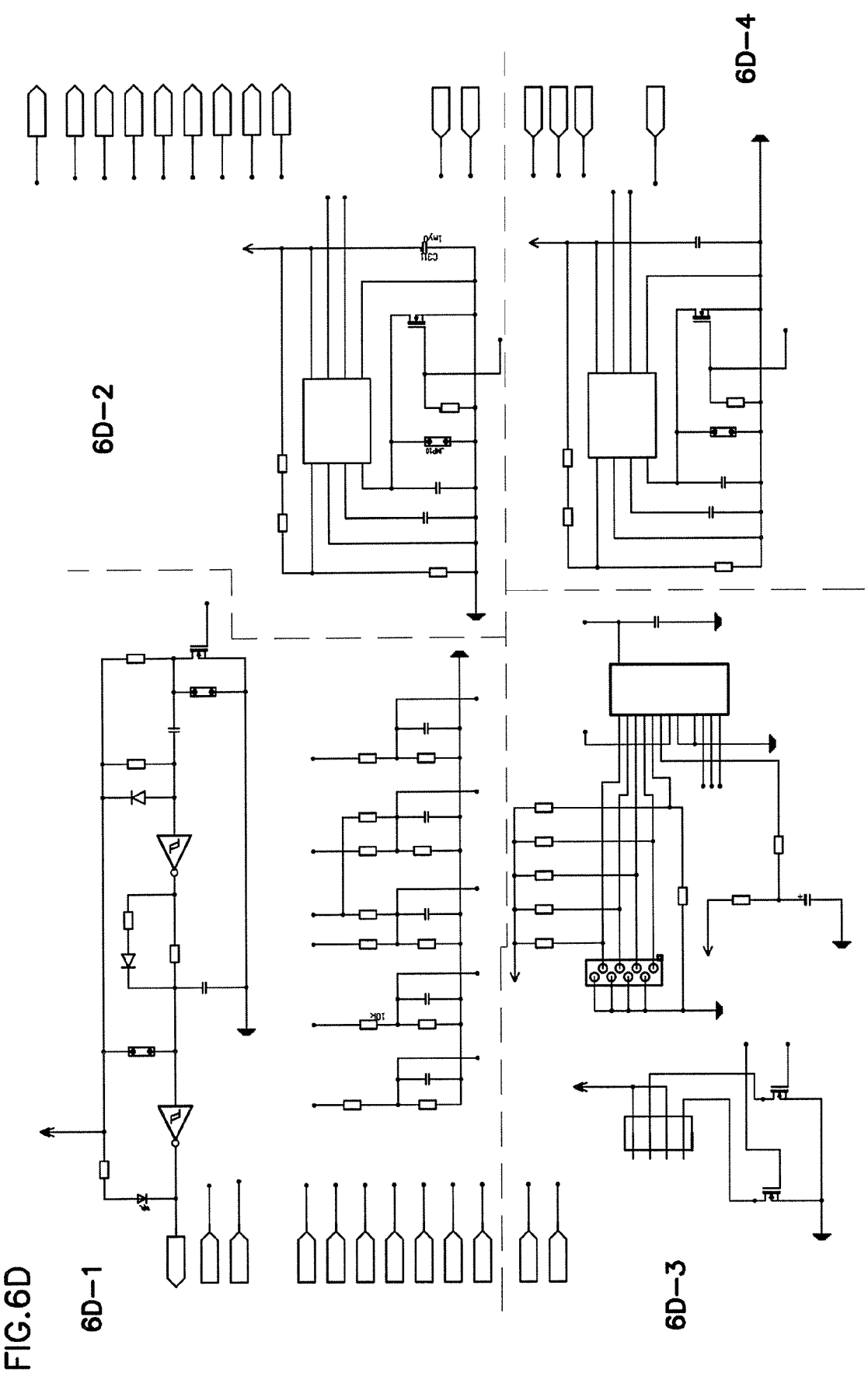
Figures 1, 6D:
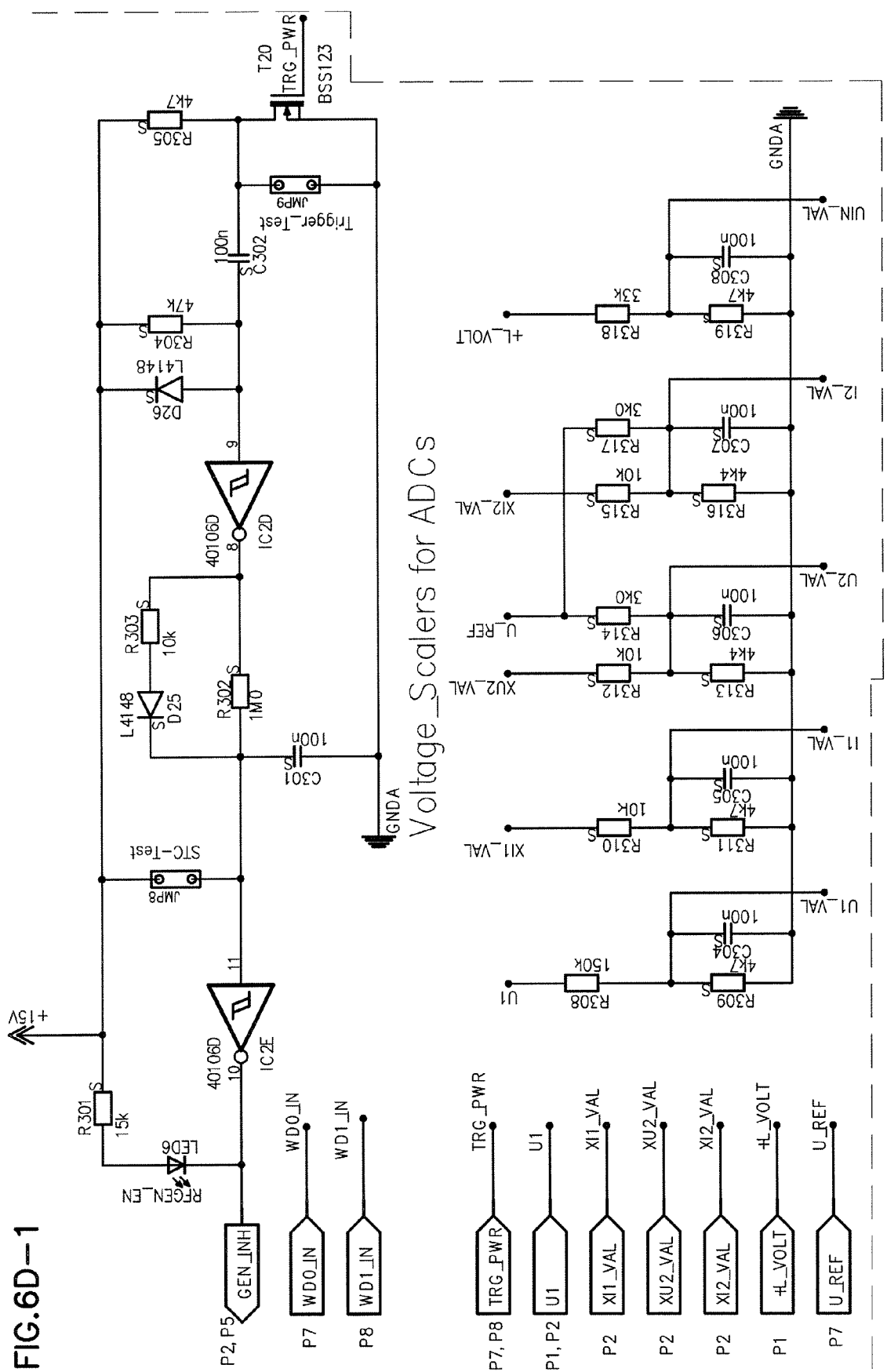
Figures 2, 6D:
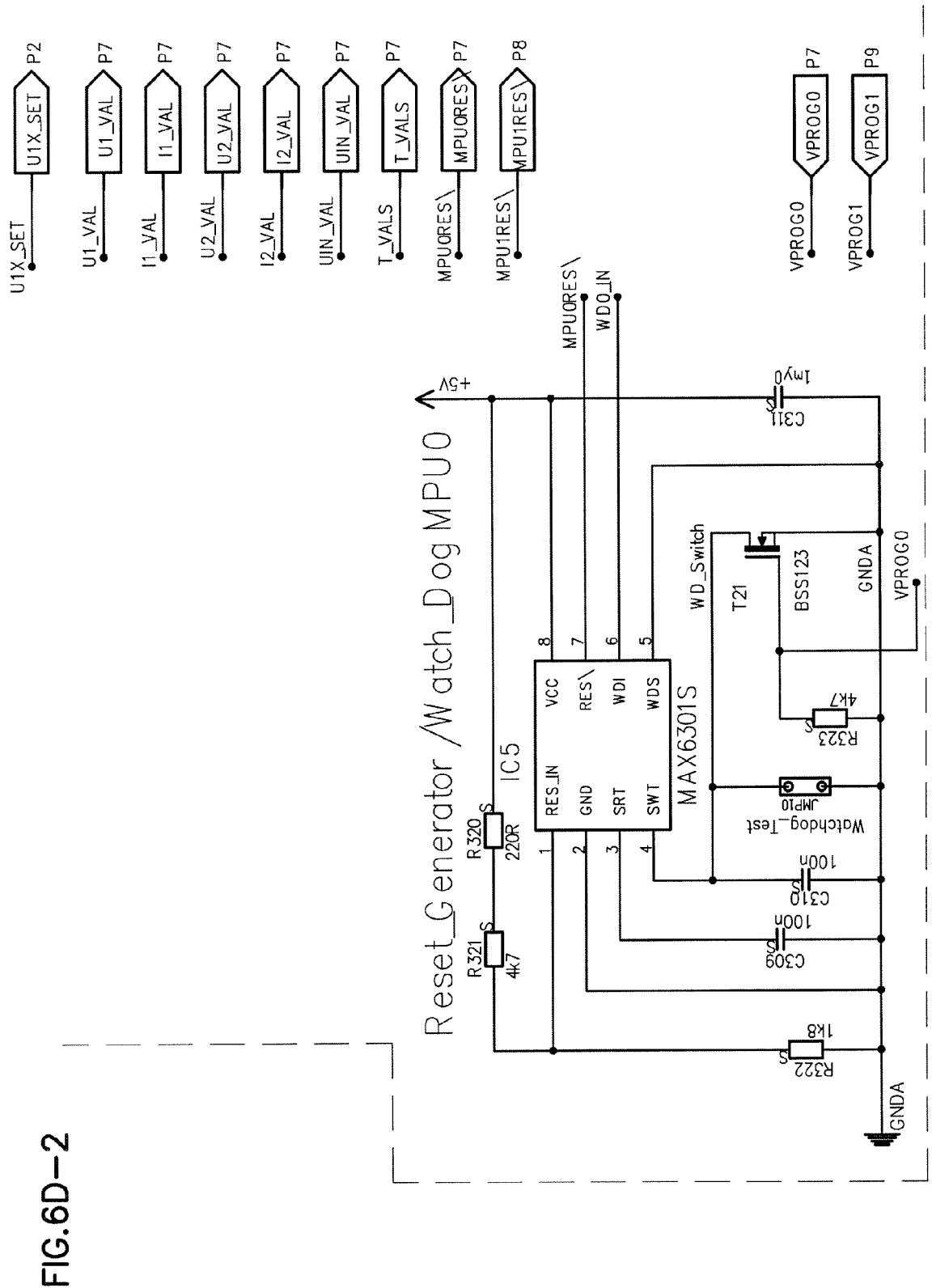
Figures 3, 6D:
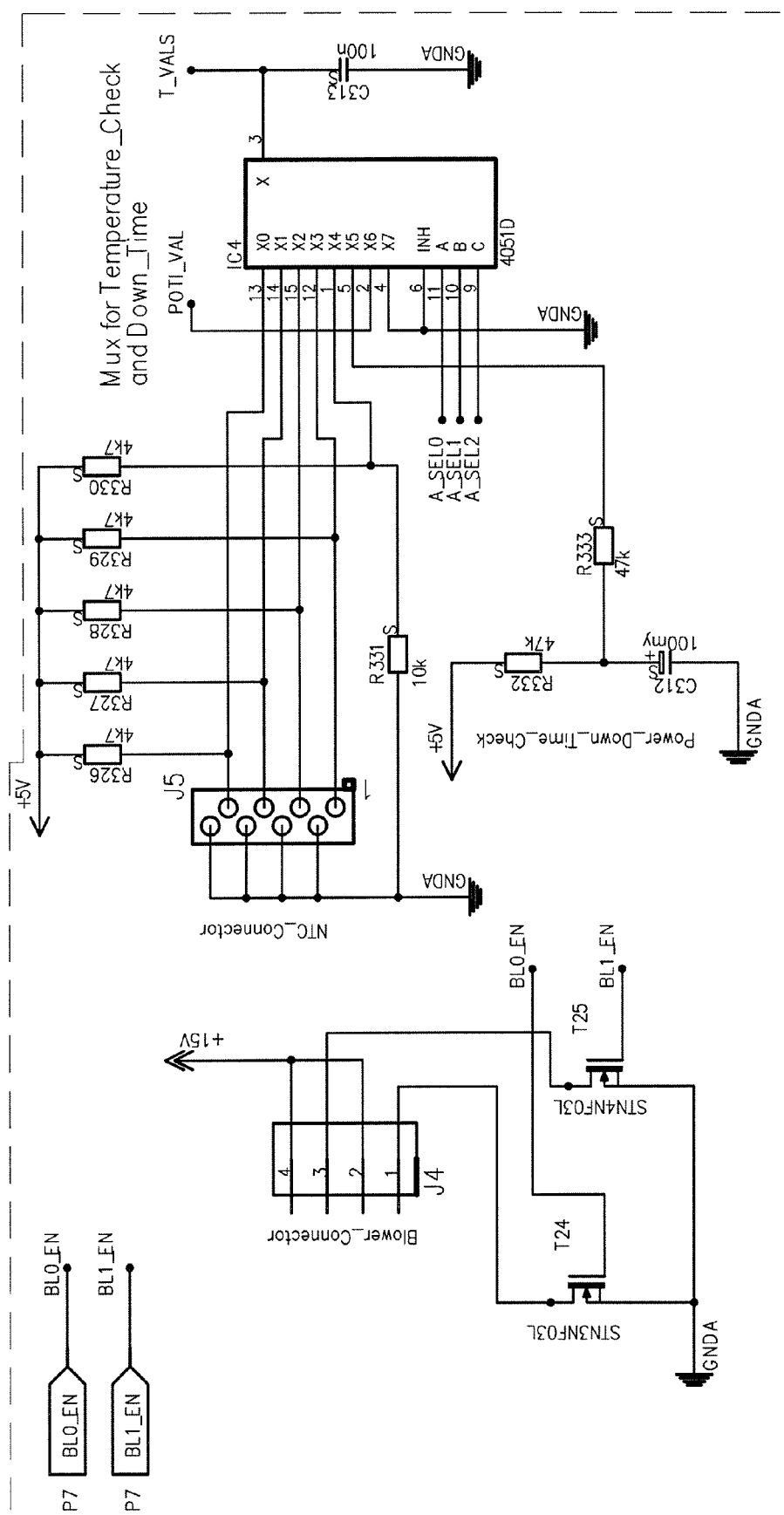
Figures 4, 6D:
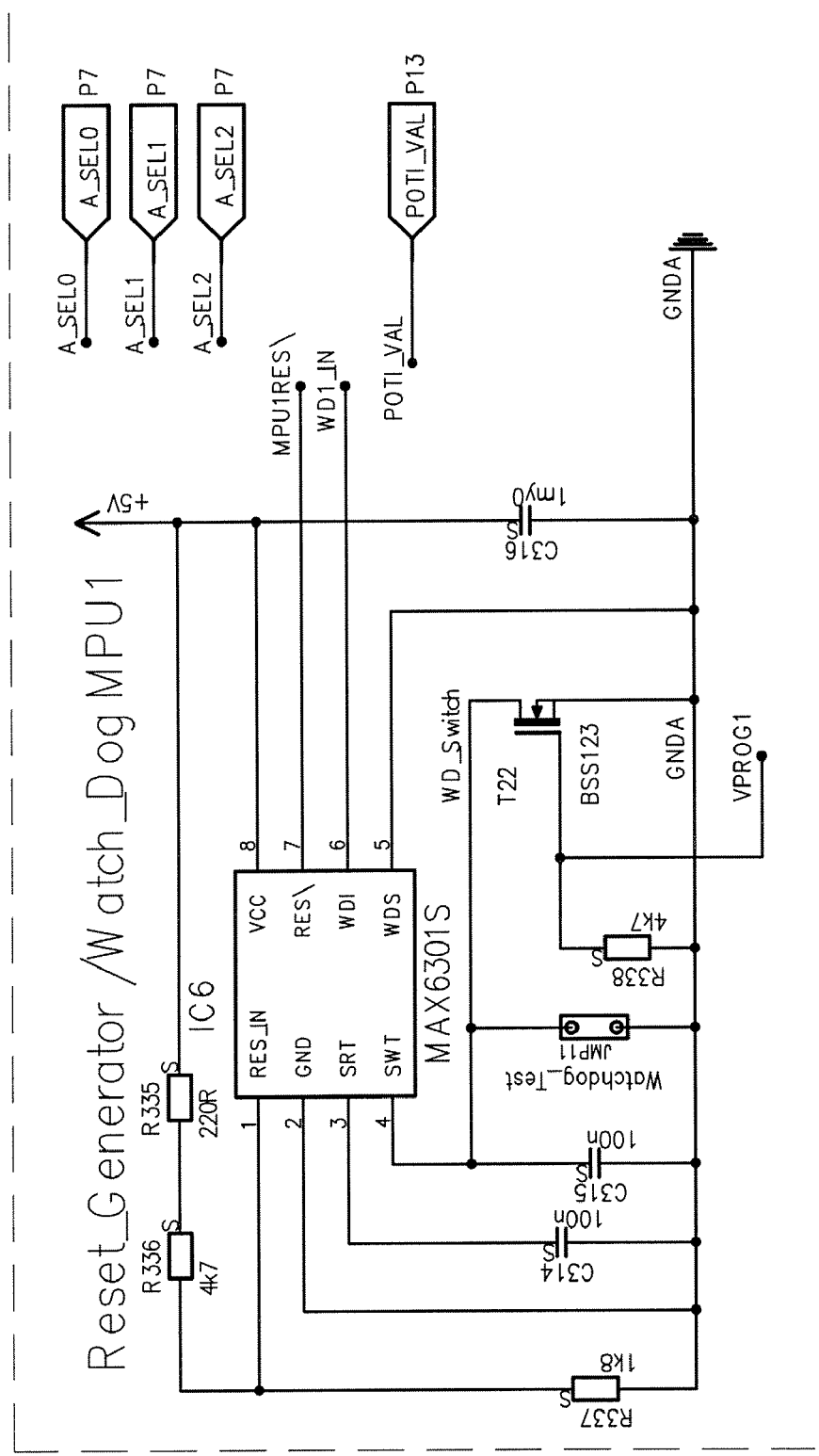
Figure 6E:
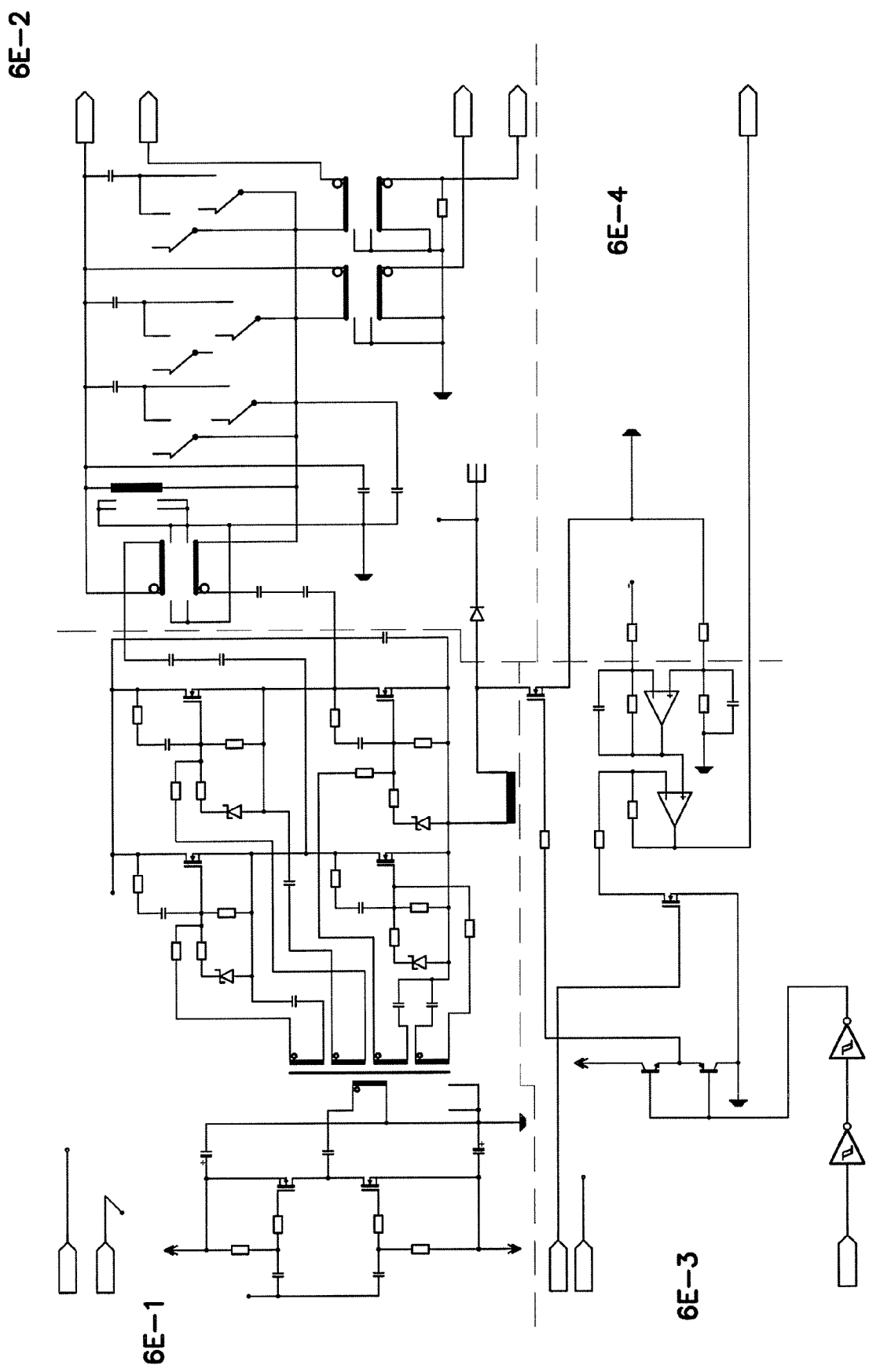
Figures 1, 6E:
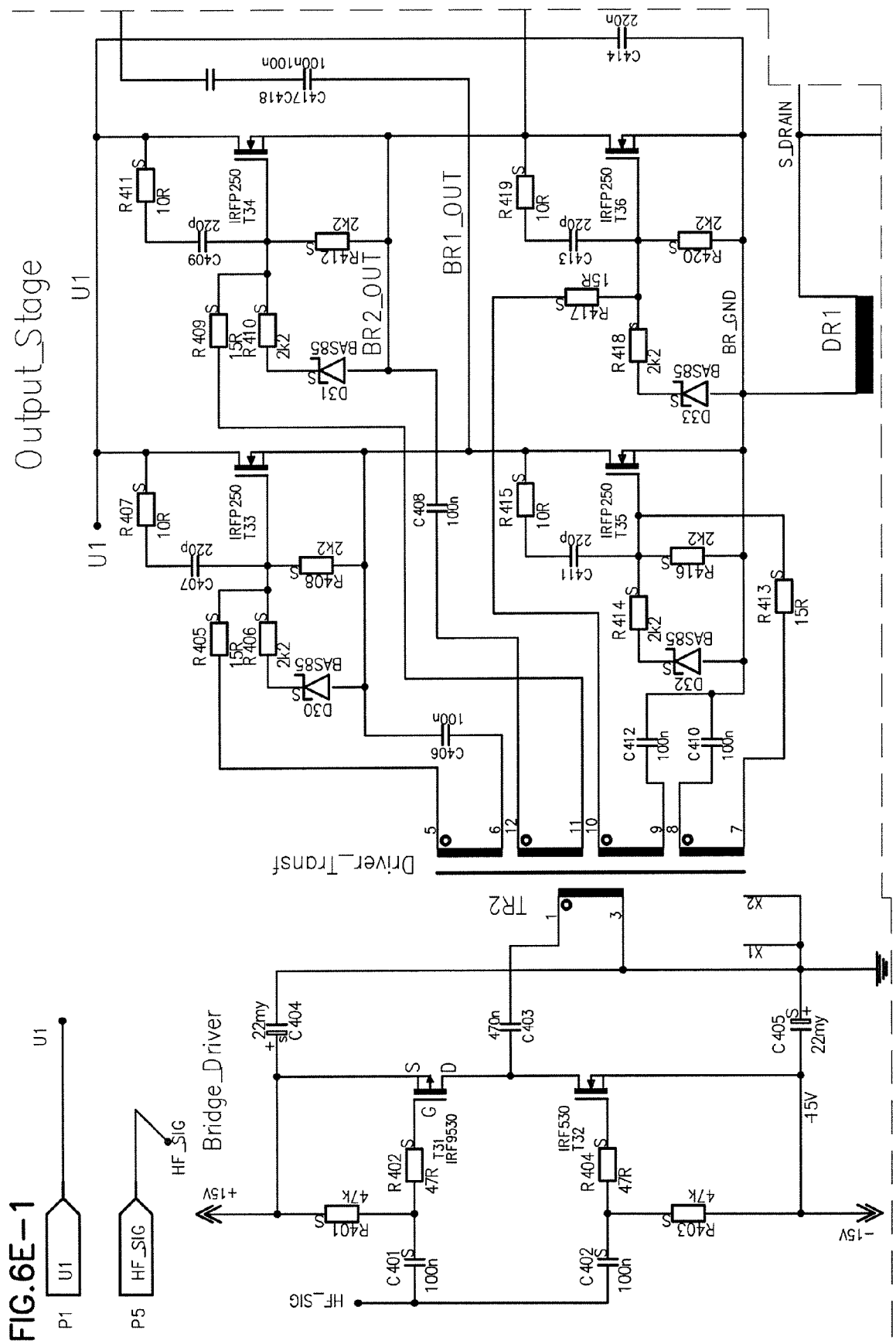
Figures 2, 6E:
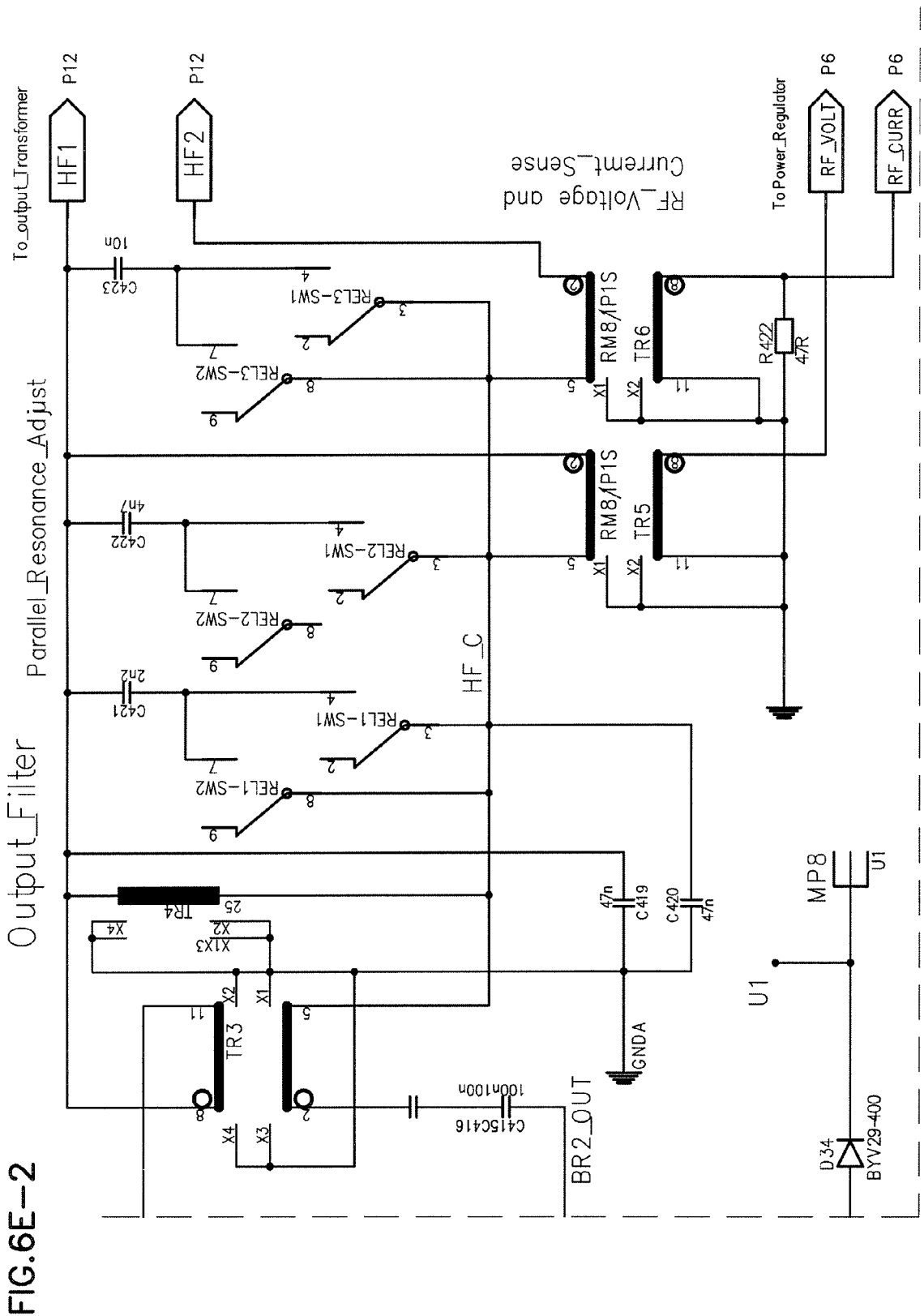
Figures 3, 6E:
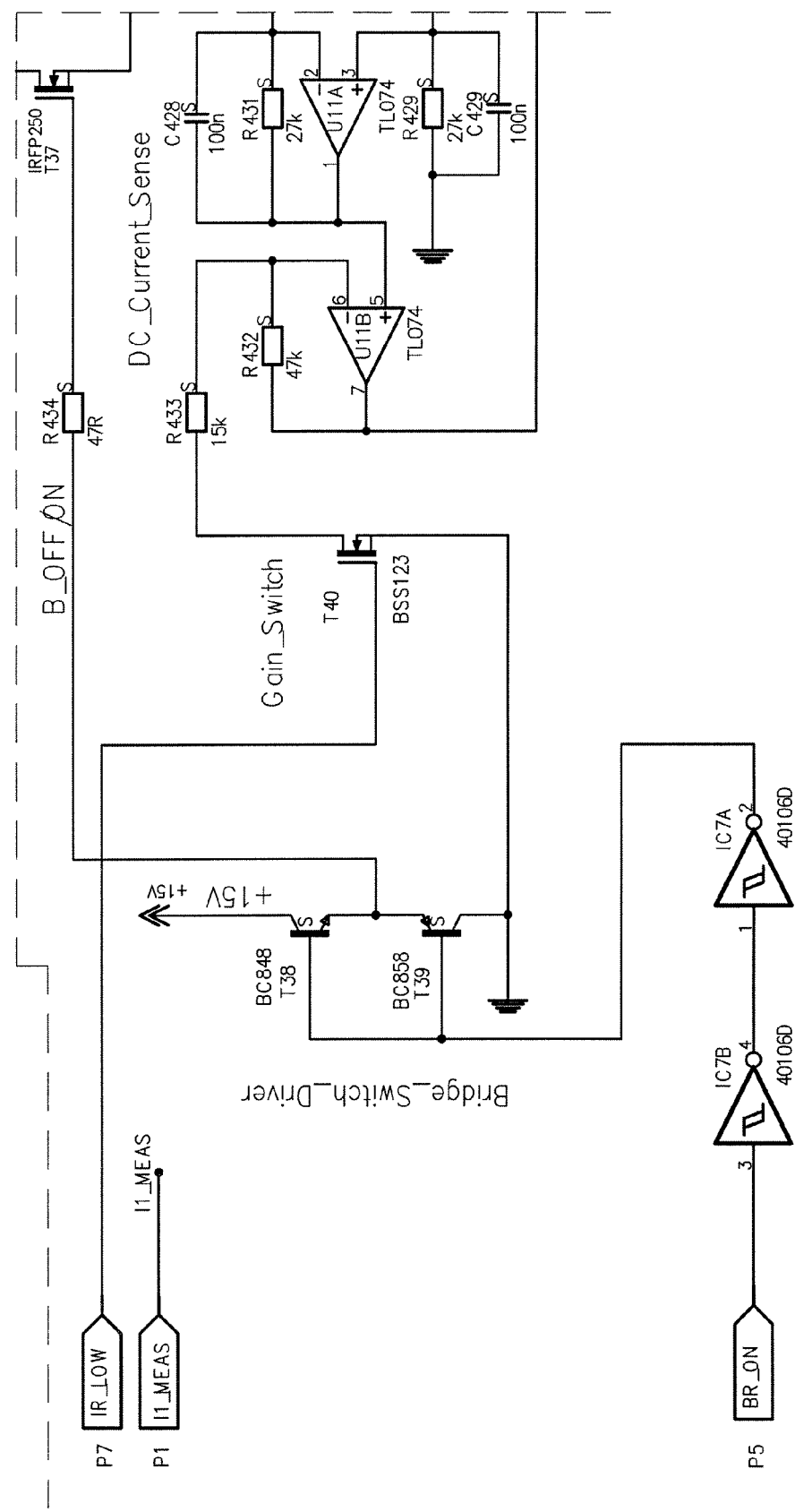
Figures 4, 6E:
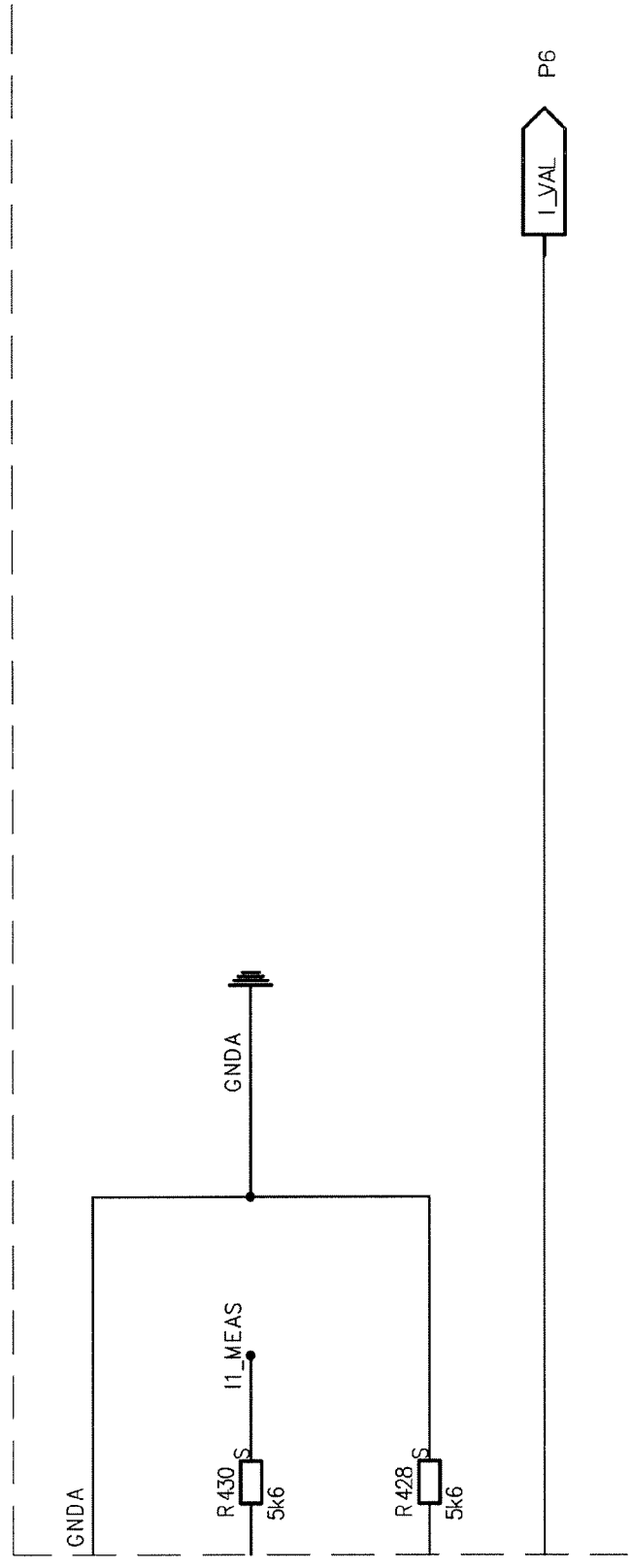
Figure 6F:
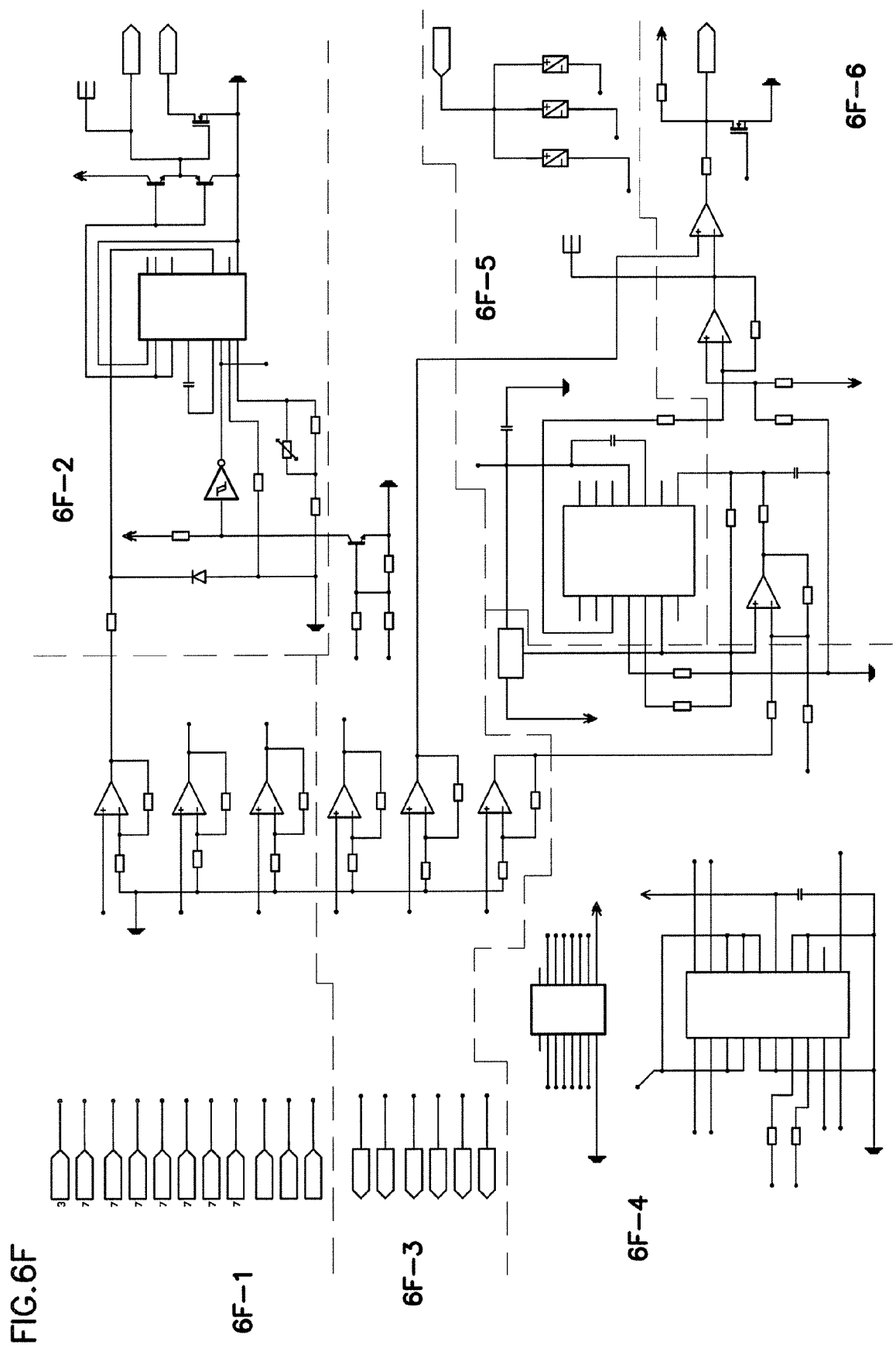
Figures 1, 6F:
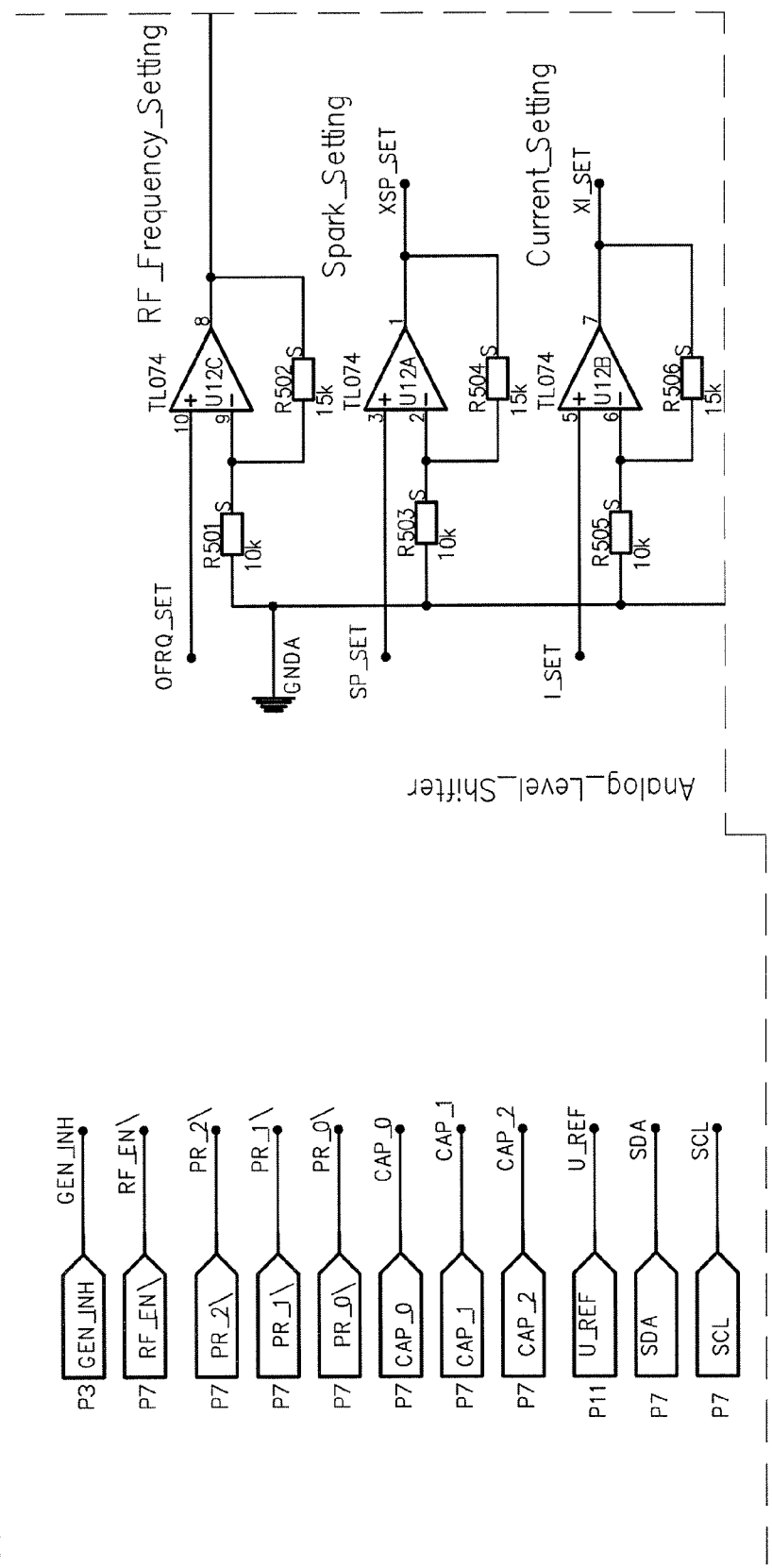
Figures 2, 6F:
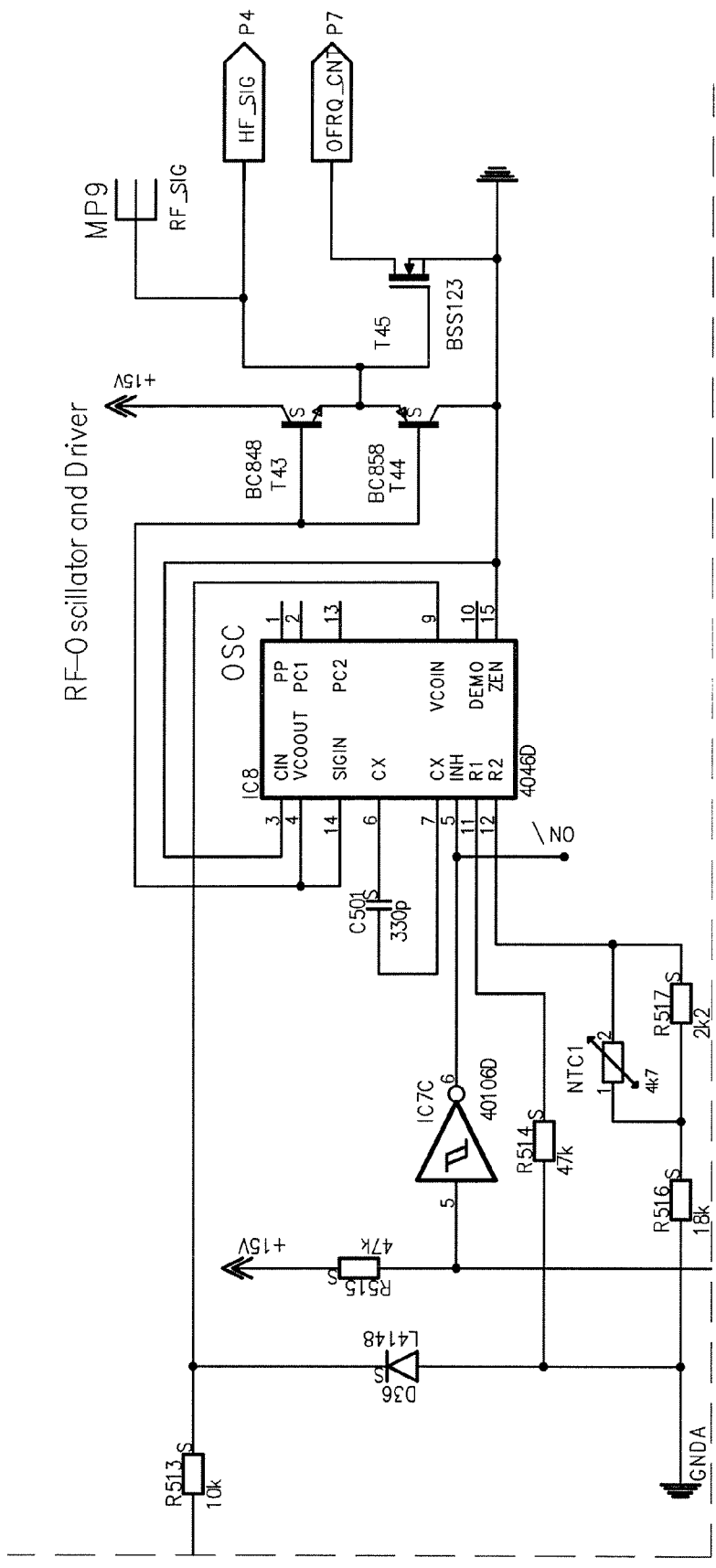
Figures 3, 6F:
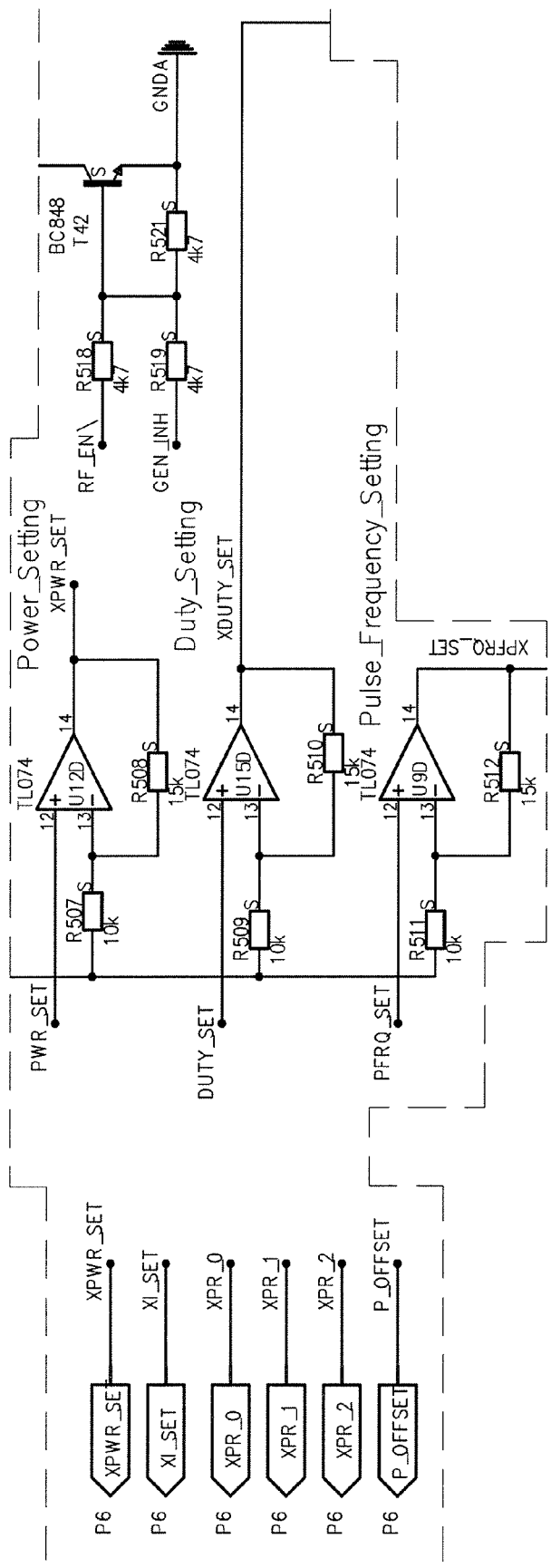
Figures 4, 6F:
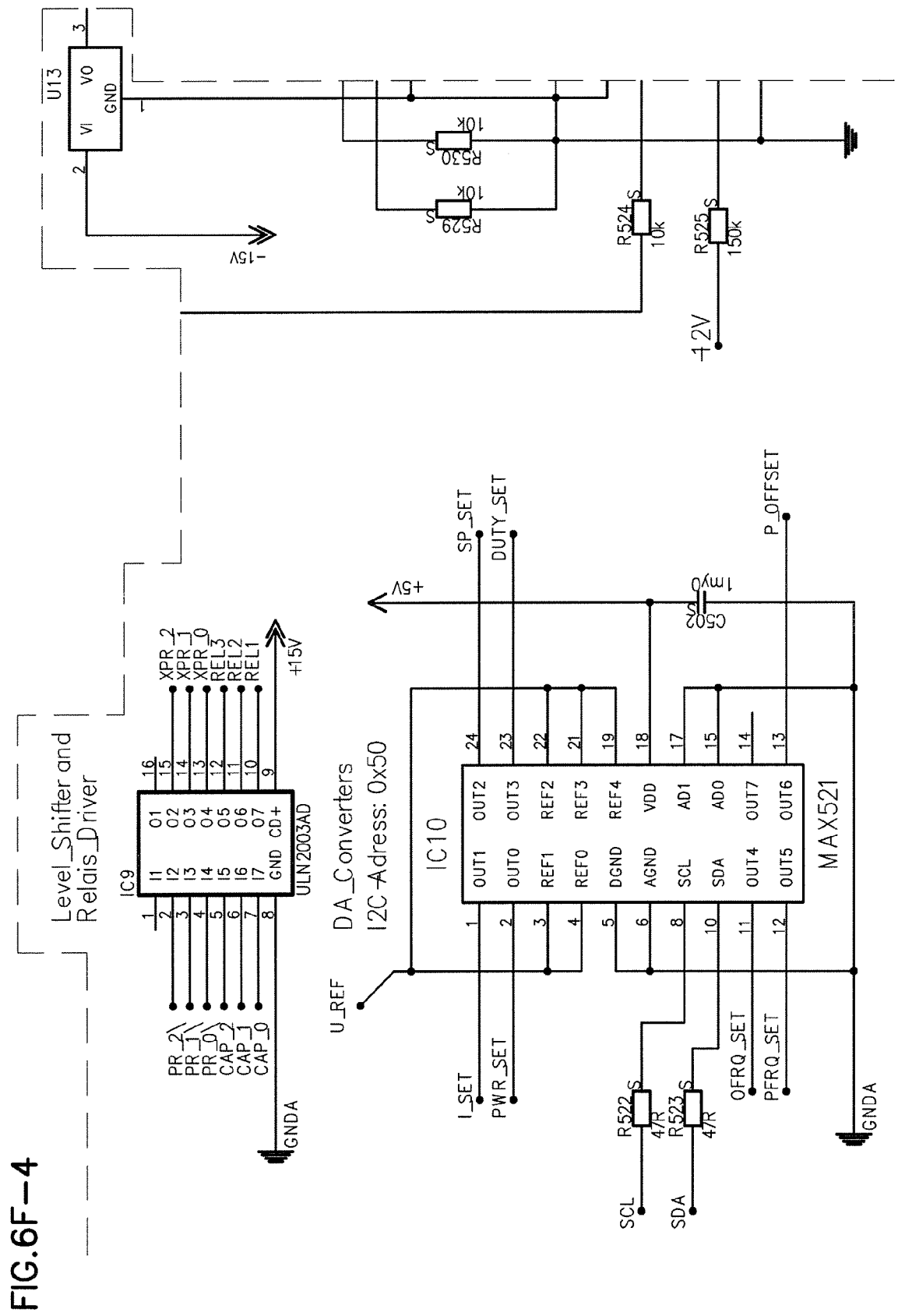
Figures 5, 6F:
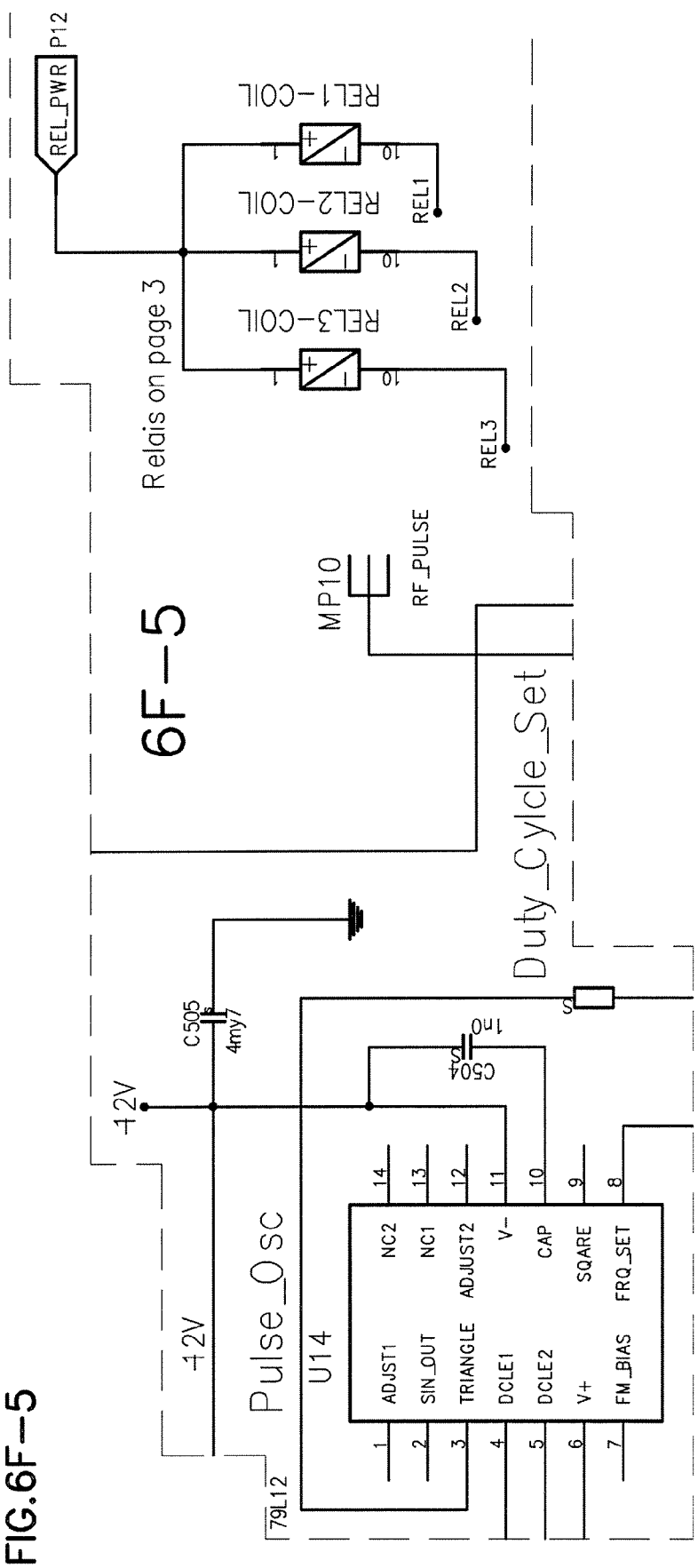
Figures 6, 6F:
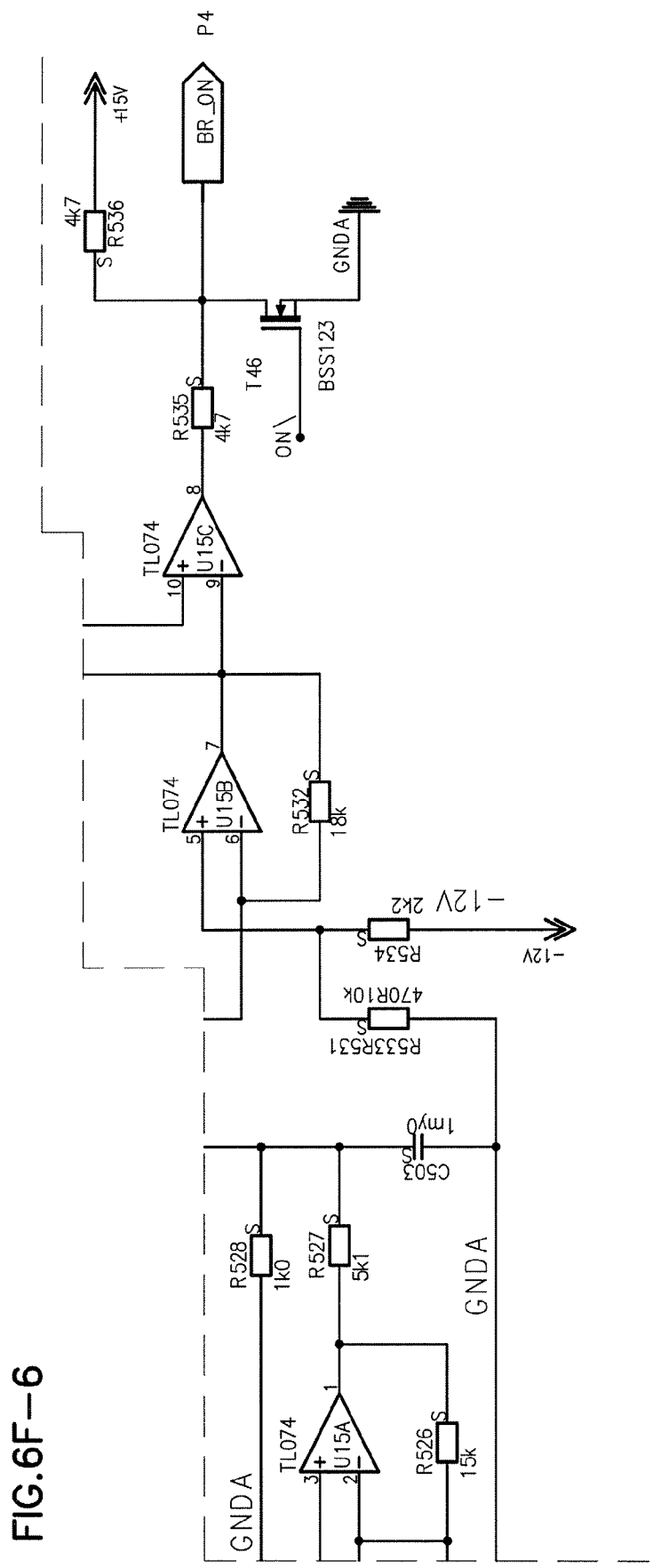
Figure 6G:
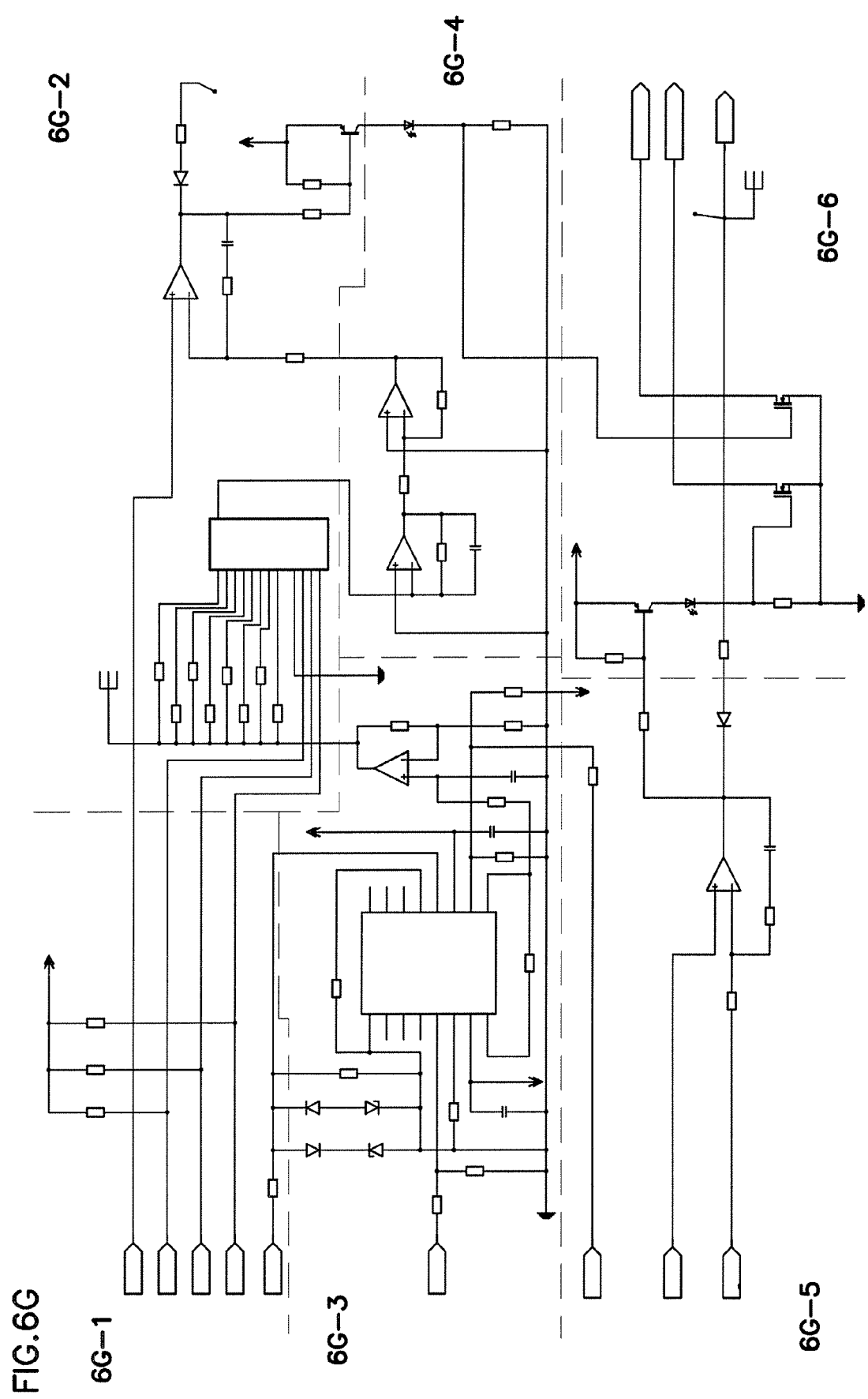
Figures 1, 6G:
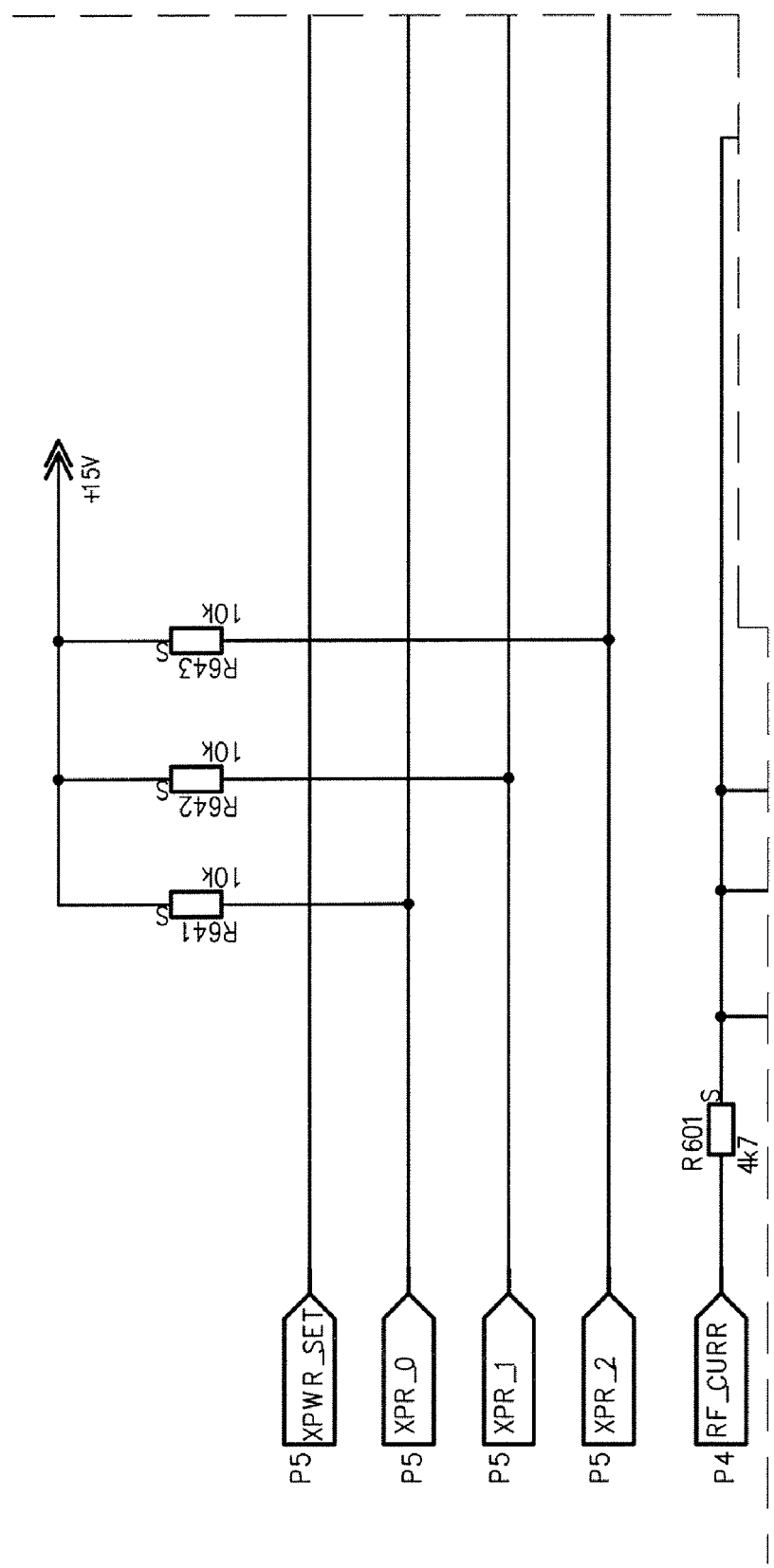
Figures 2, 6G:
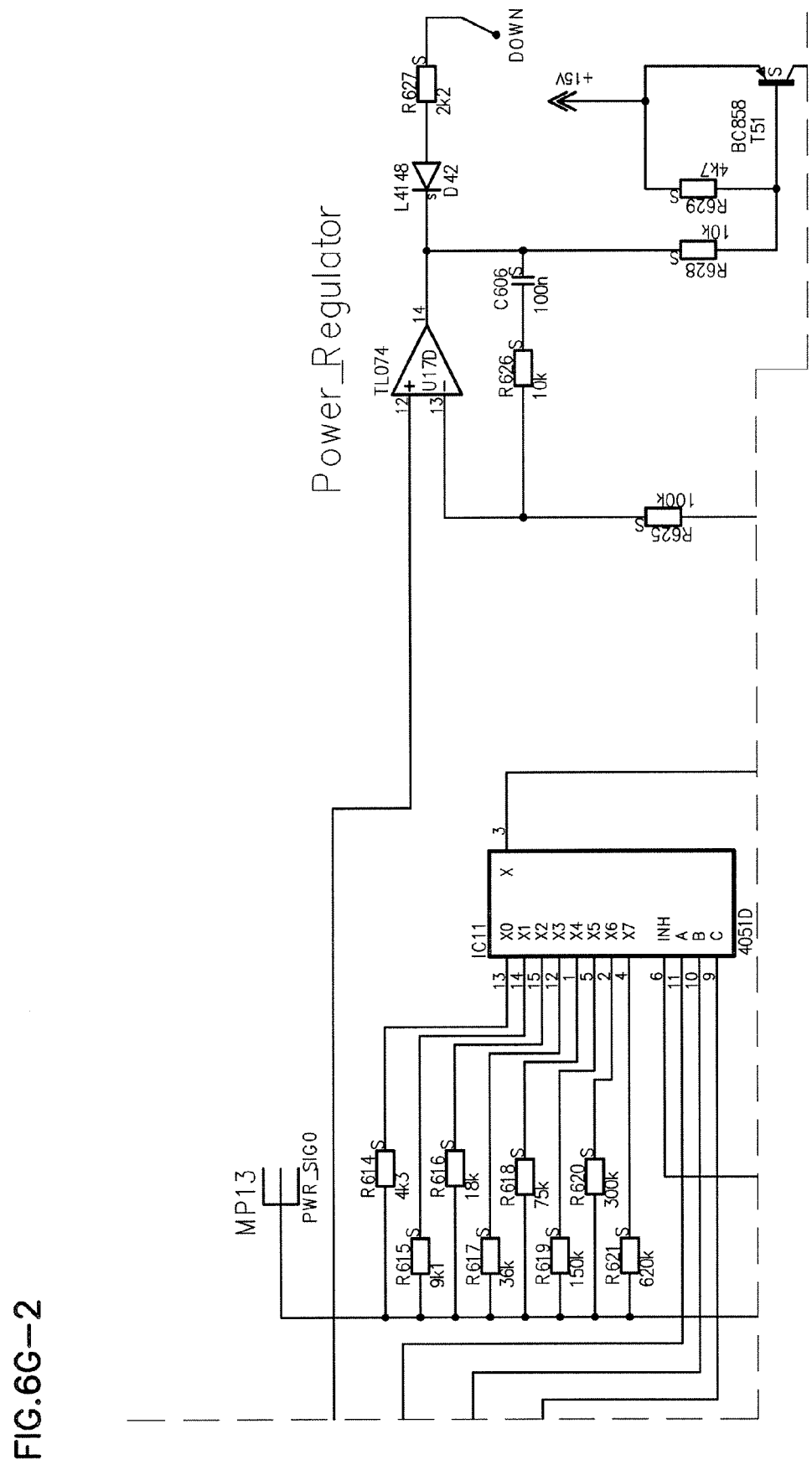
Figures 3, 6G:
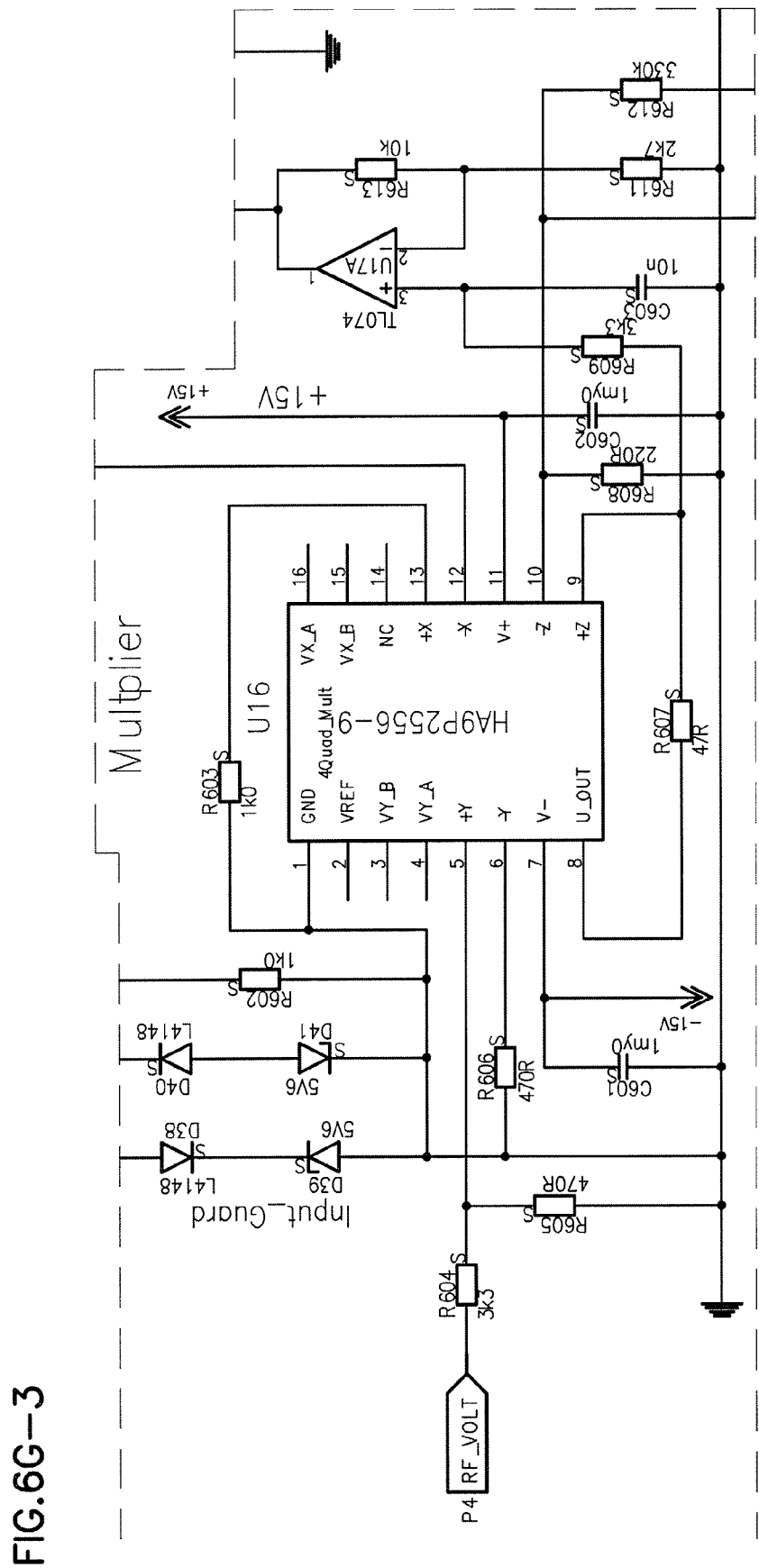
Figures 4, 6G:
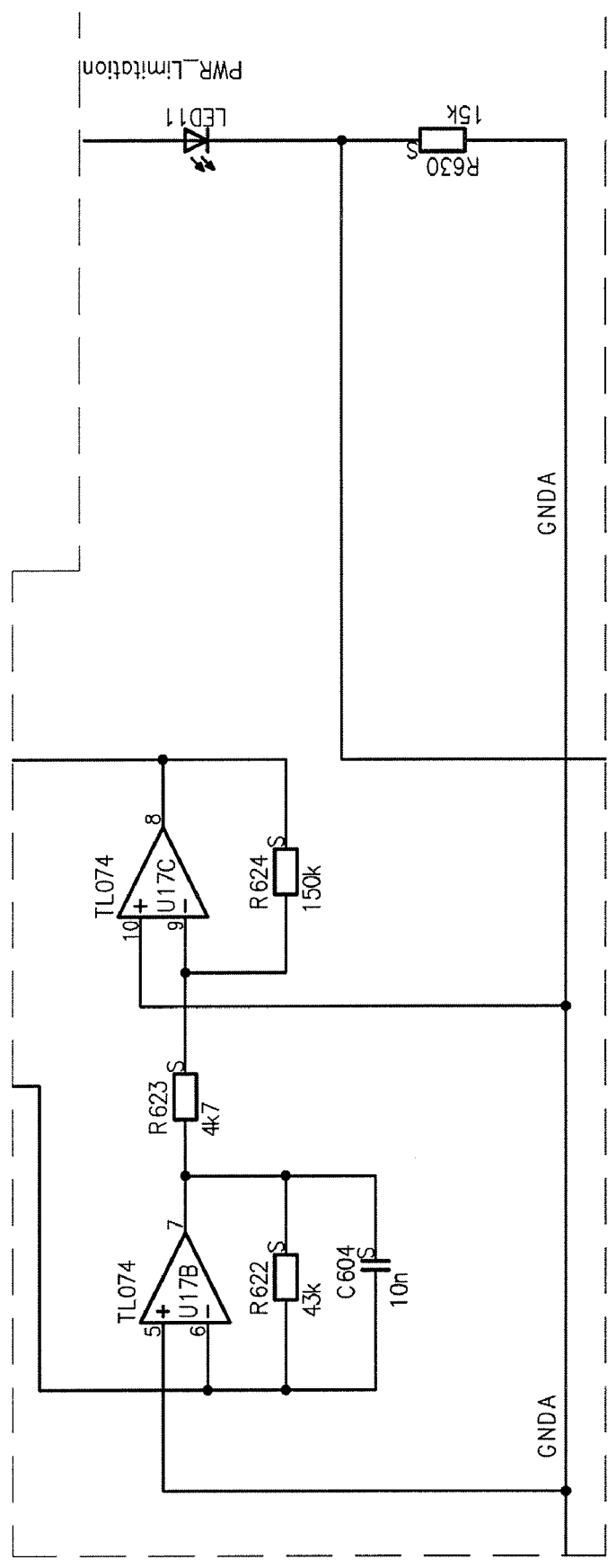
Figures 5, 6G:
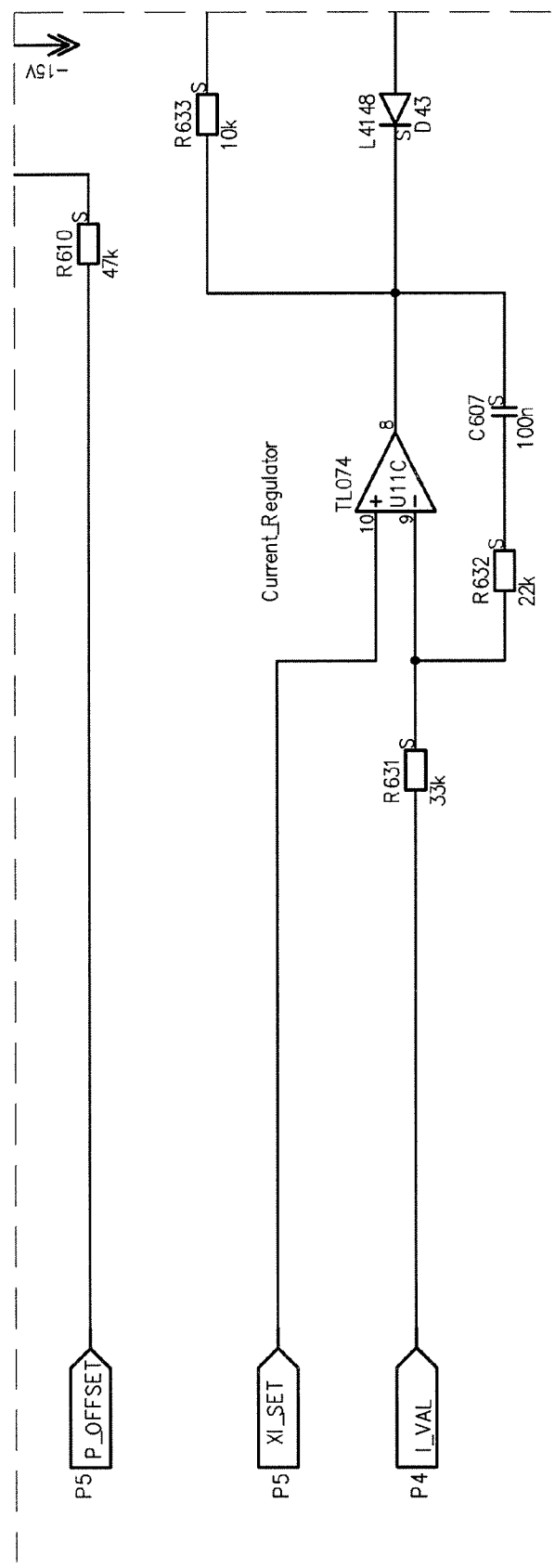
Figures 6, 6G:
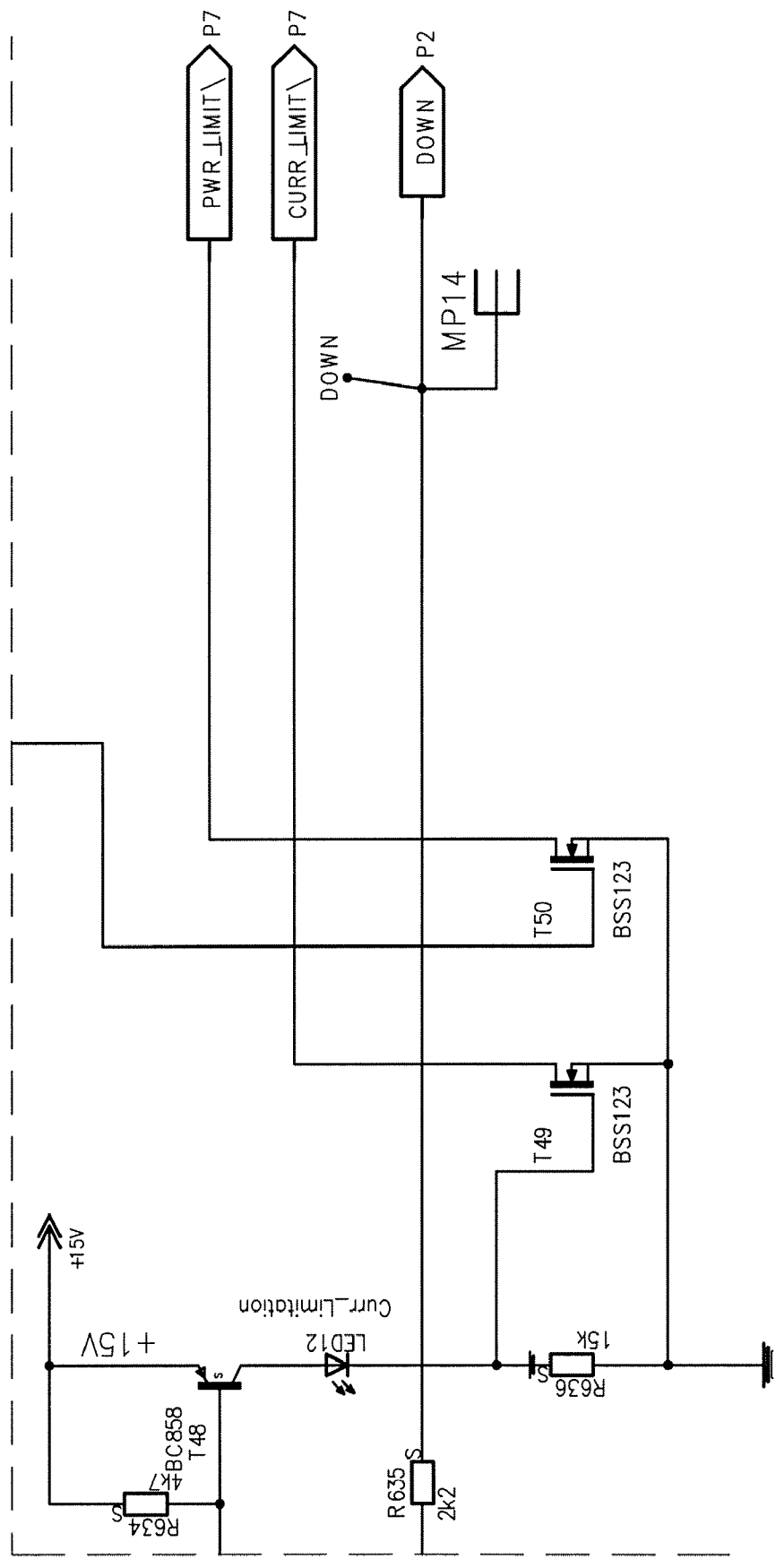
Figures 1, 6H:
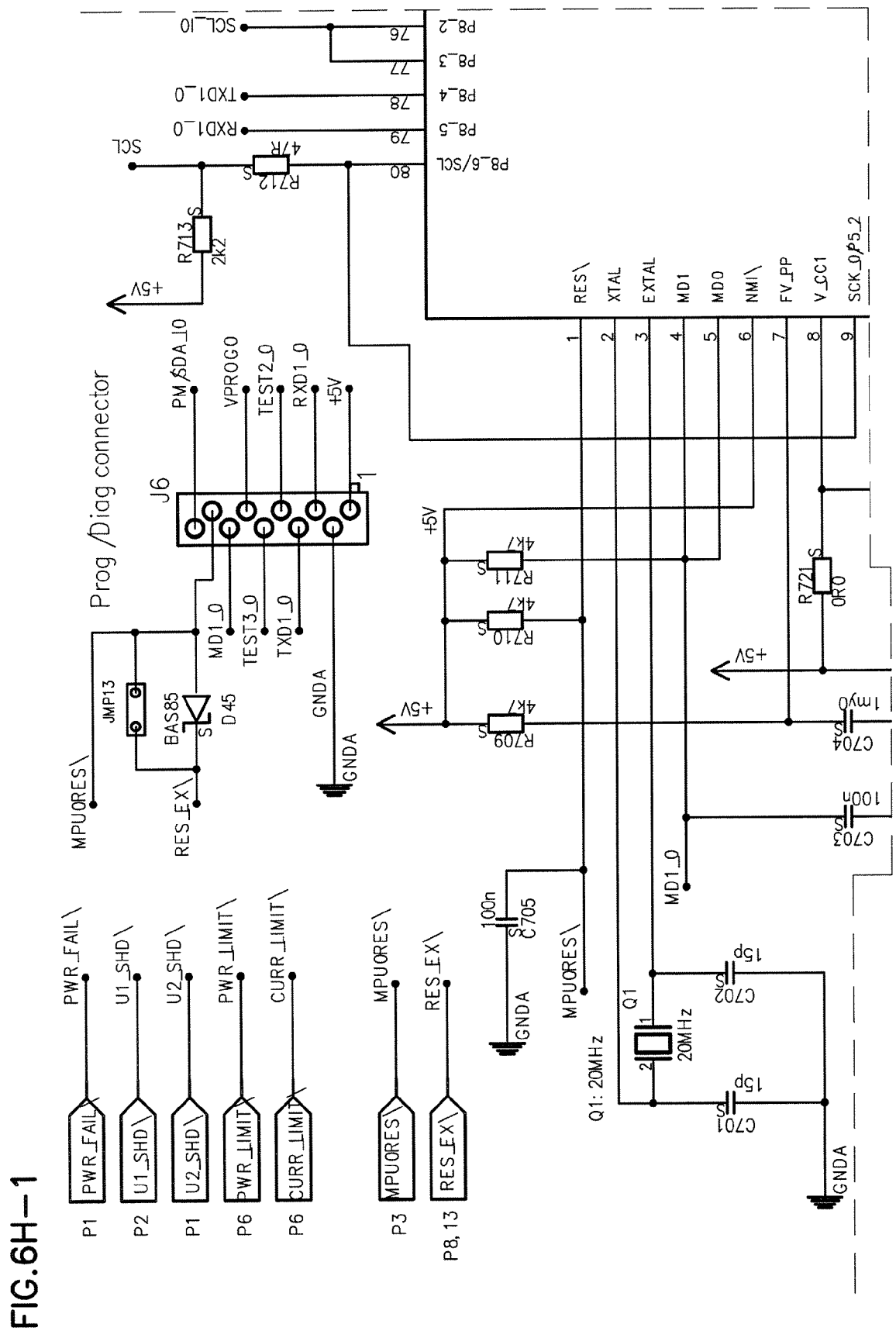
Figures 2, 6H:
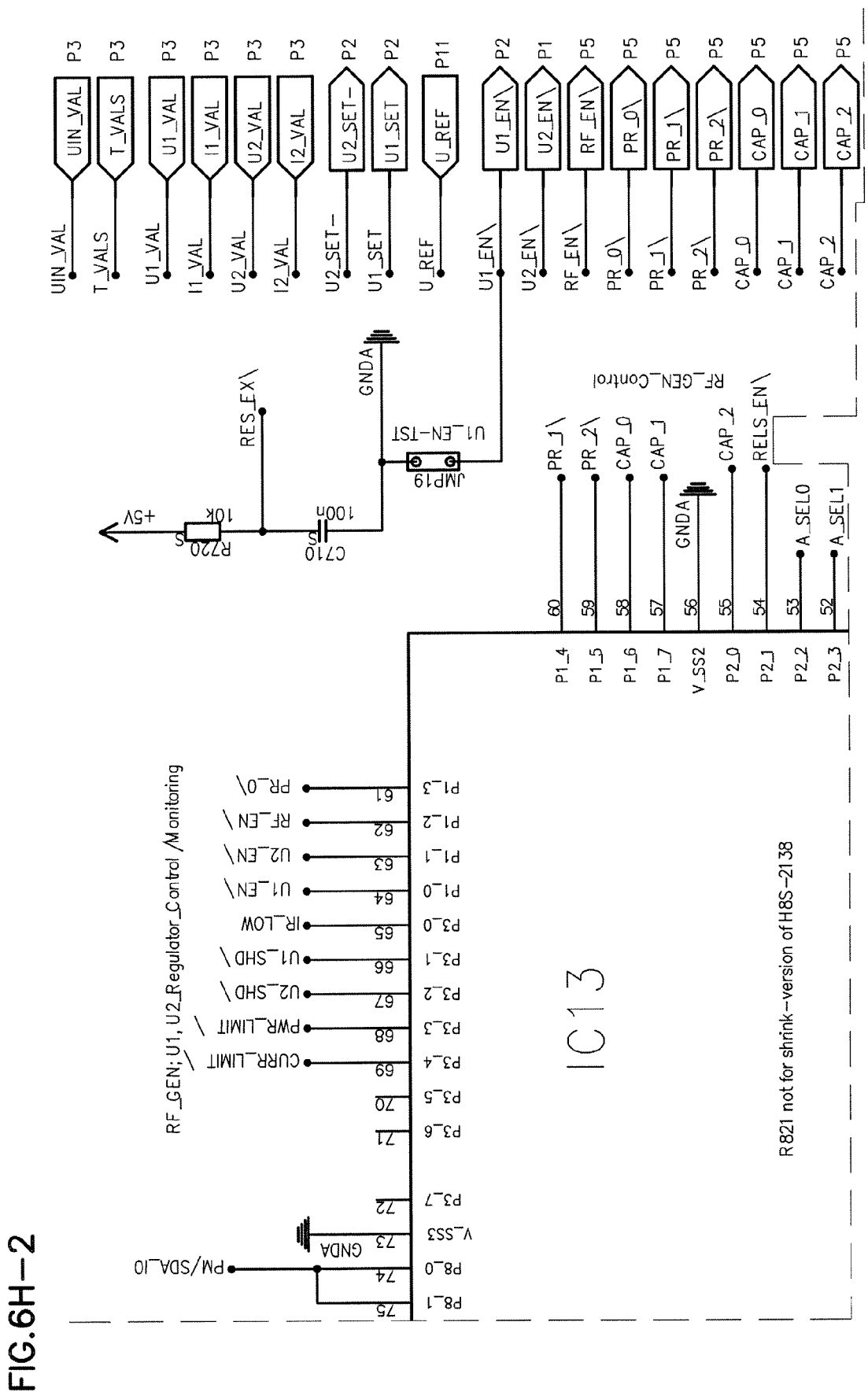
Figures 3, 6H:
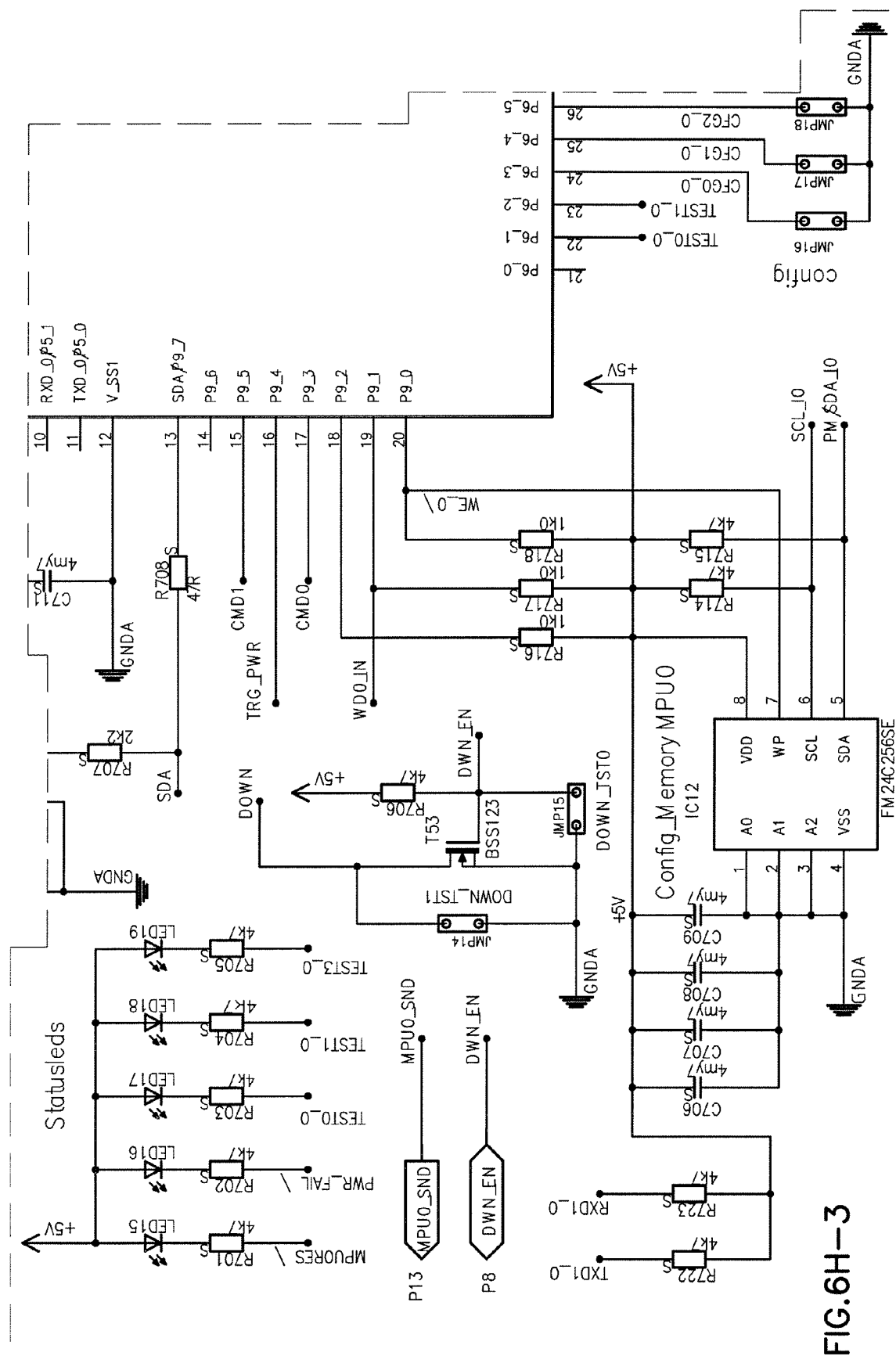
Figures 4, 6H:
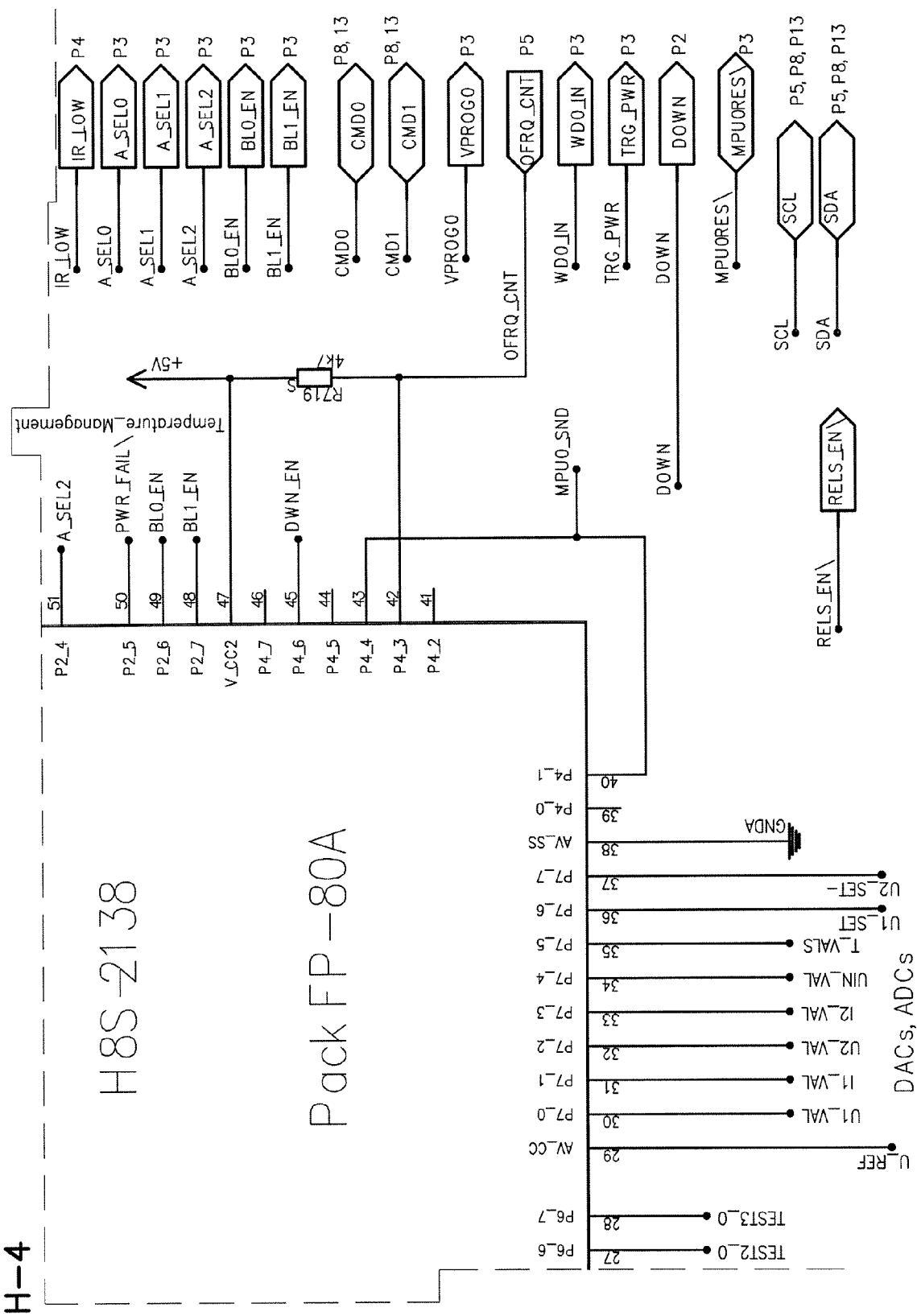
Figure 6I:
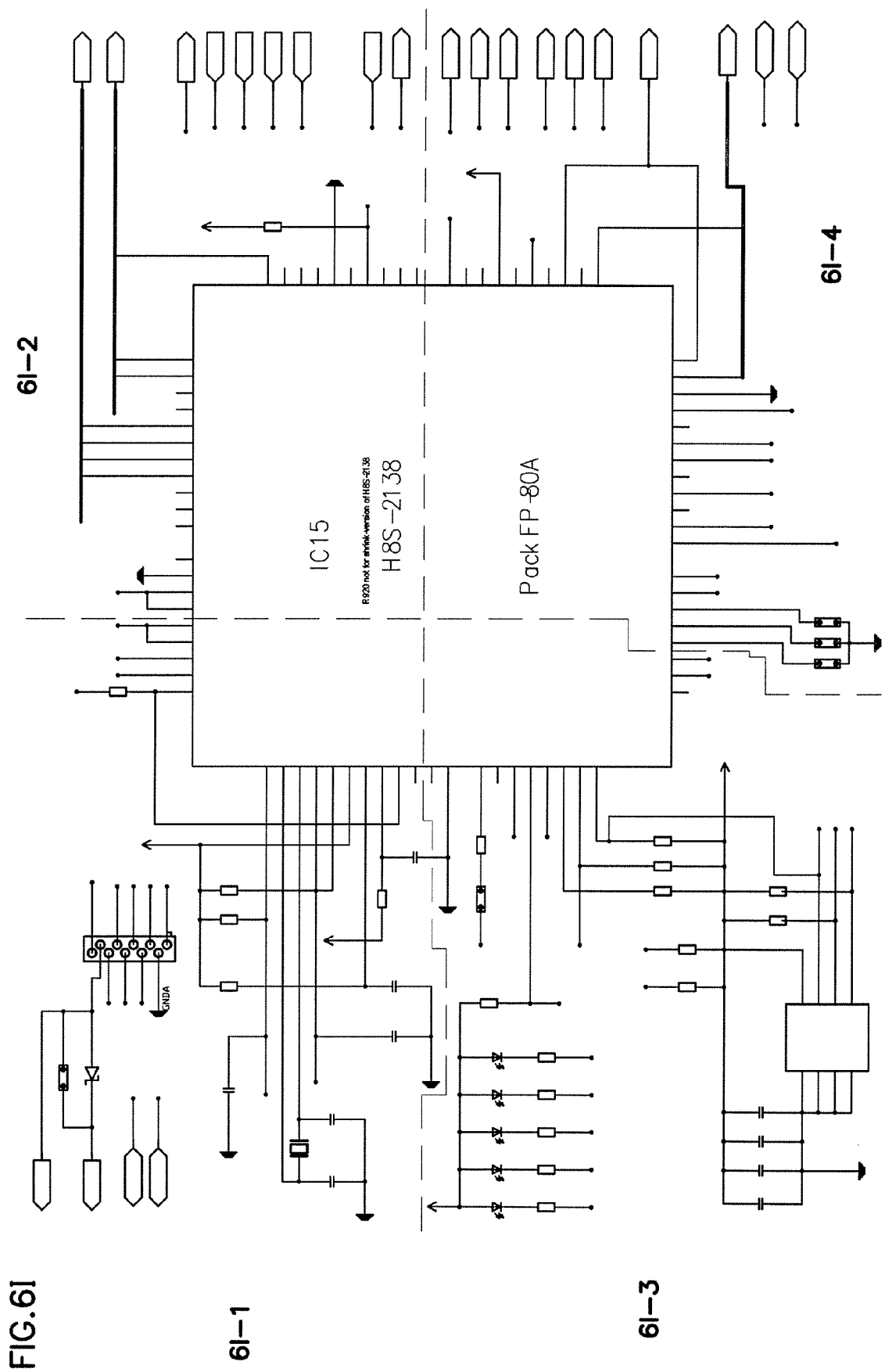
Figures 1, 6I:
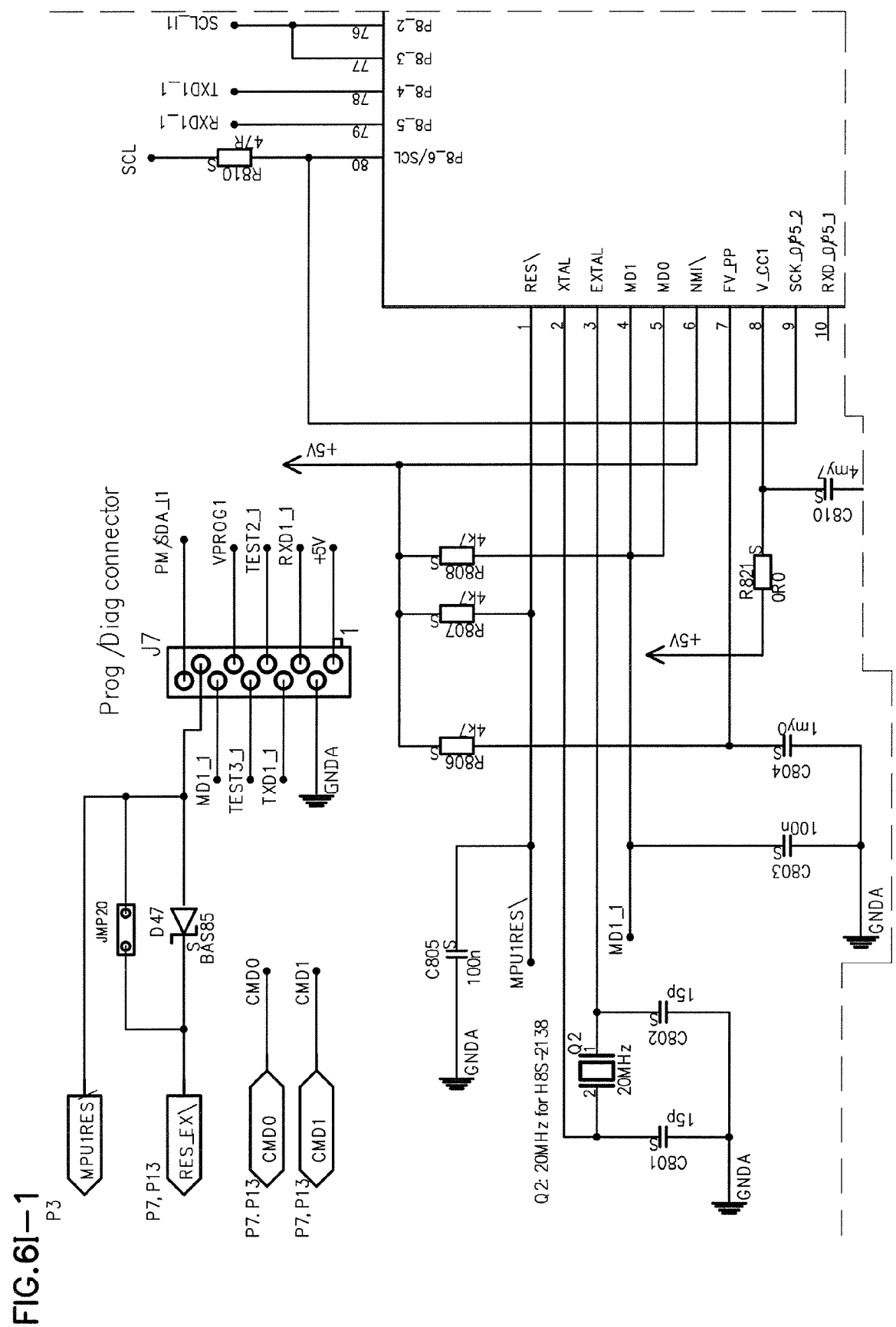
Figures 2, 61:
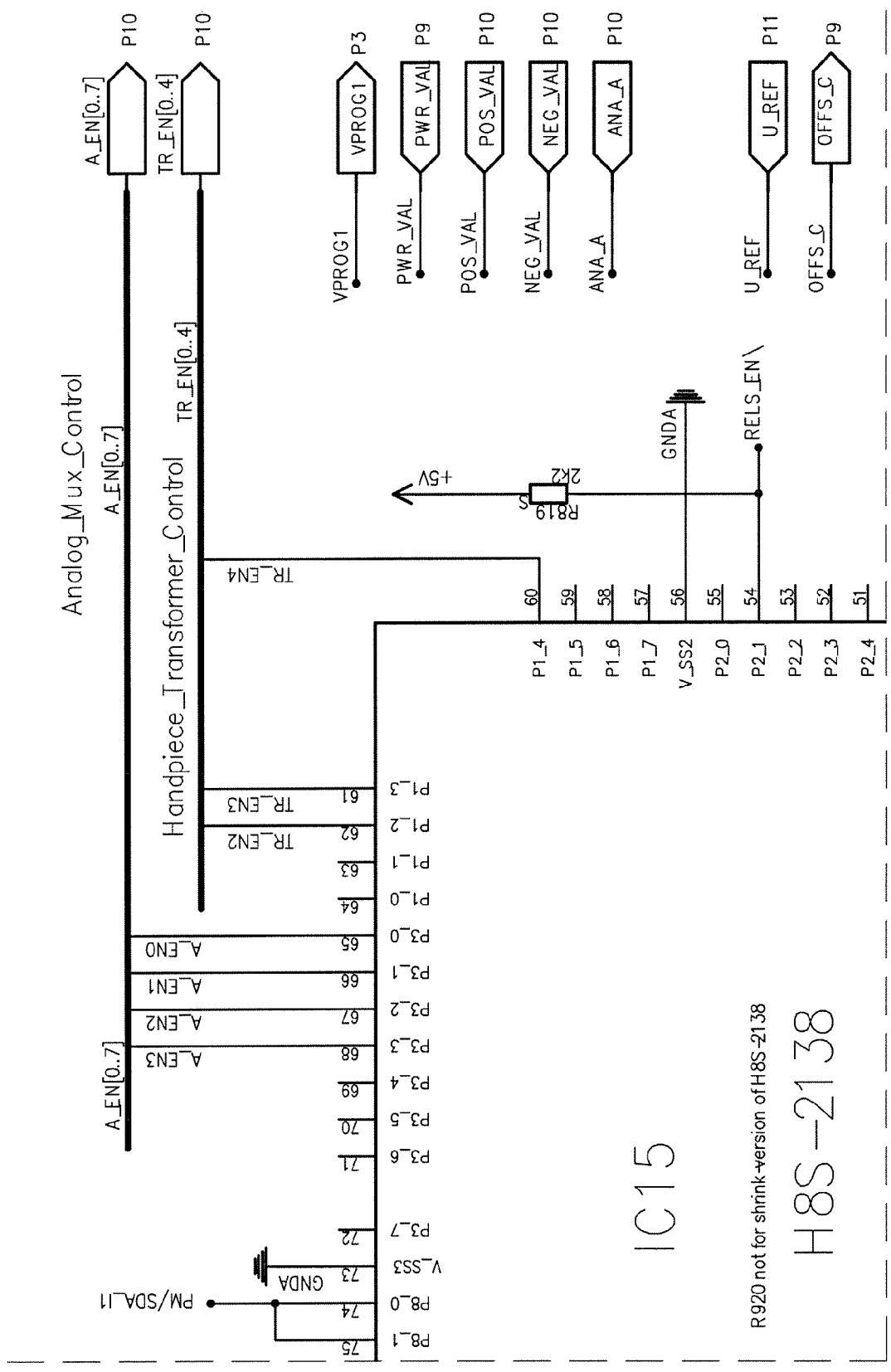
Figures 3, 61:
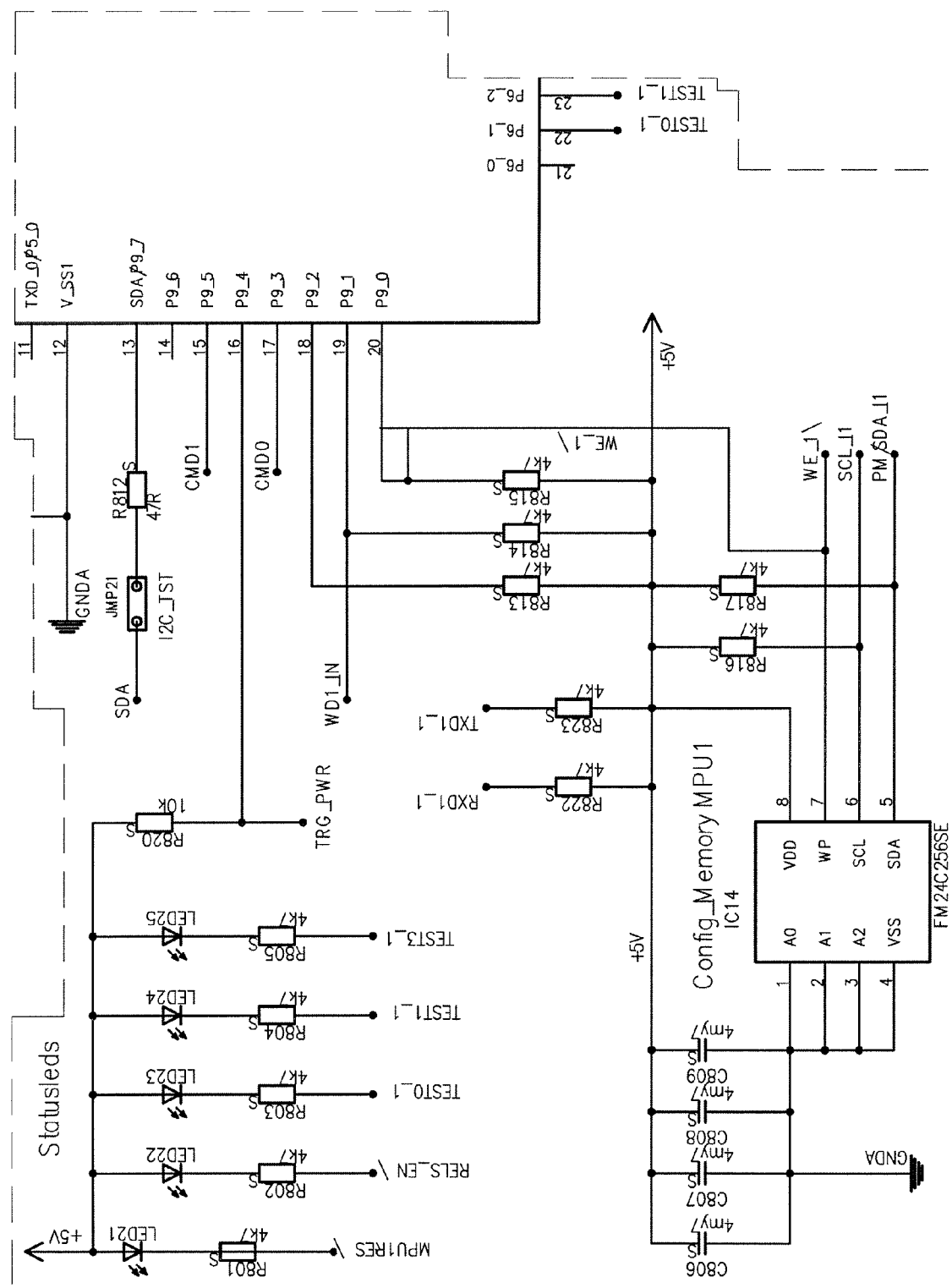
Figures 4, 61:
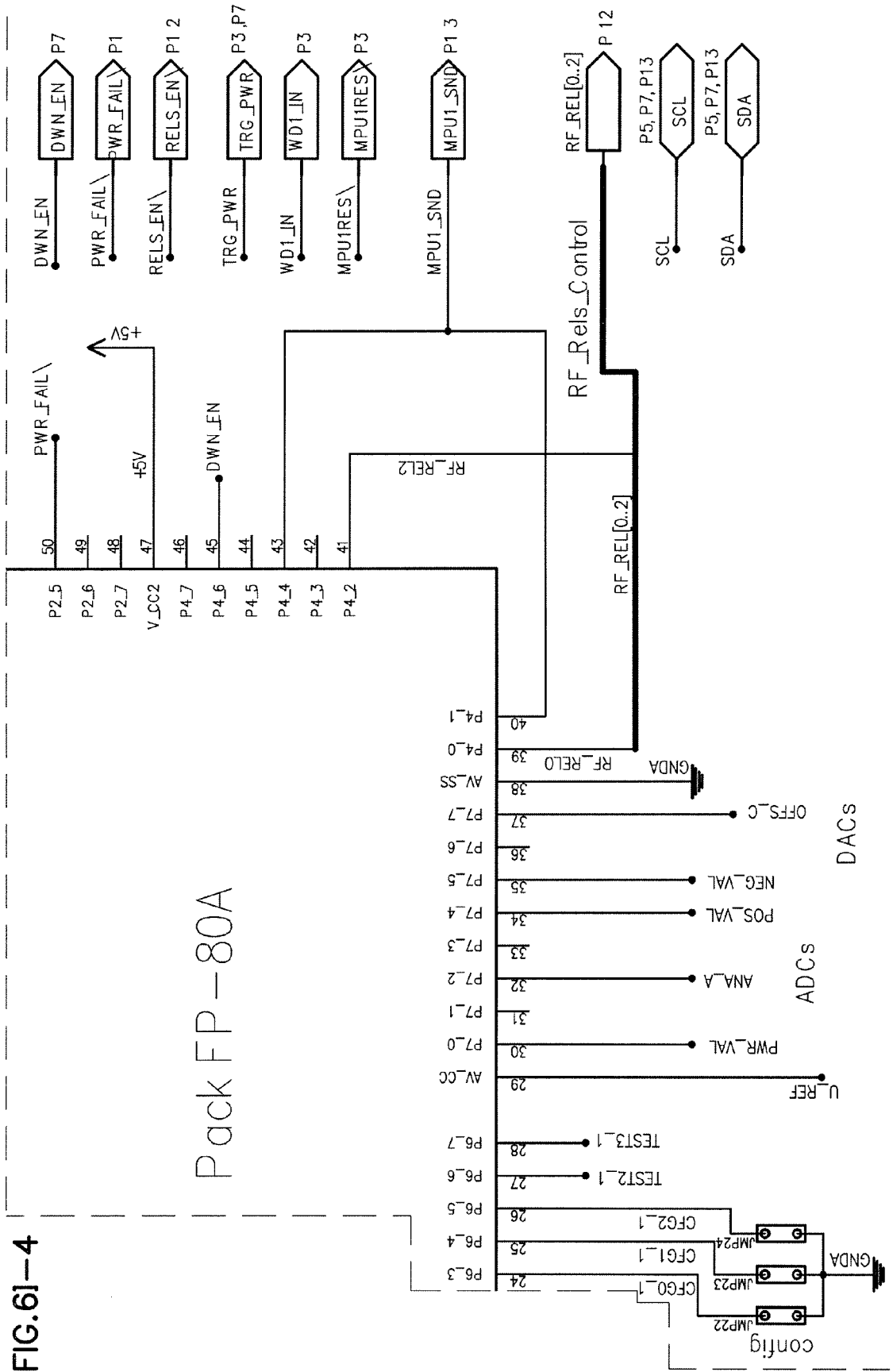
Figure 6J:
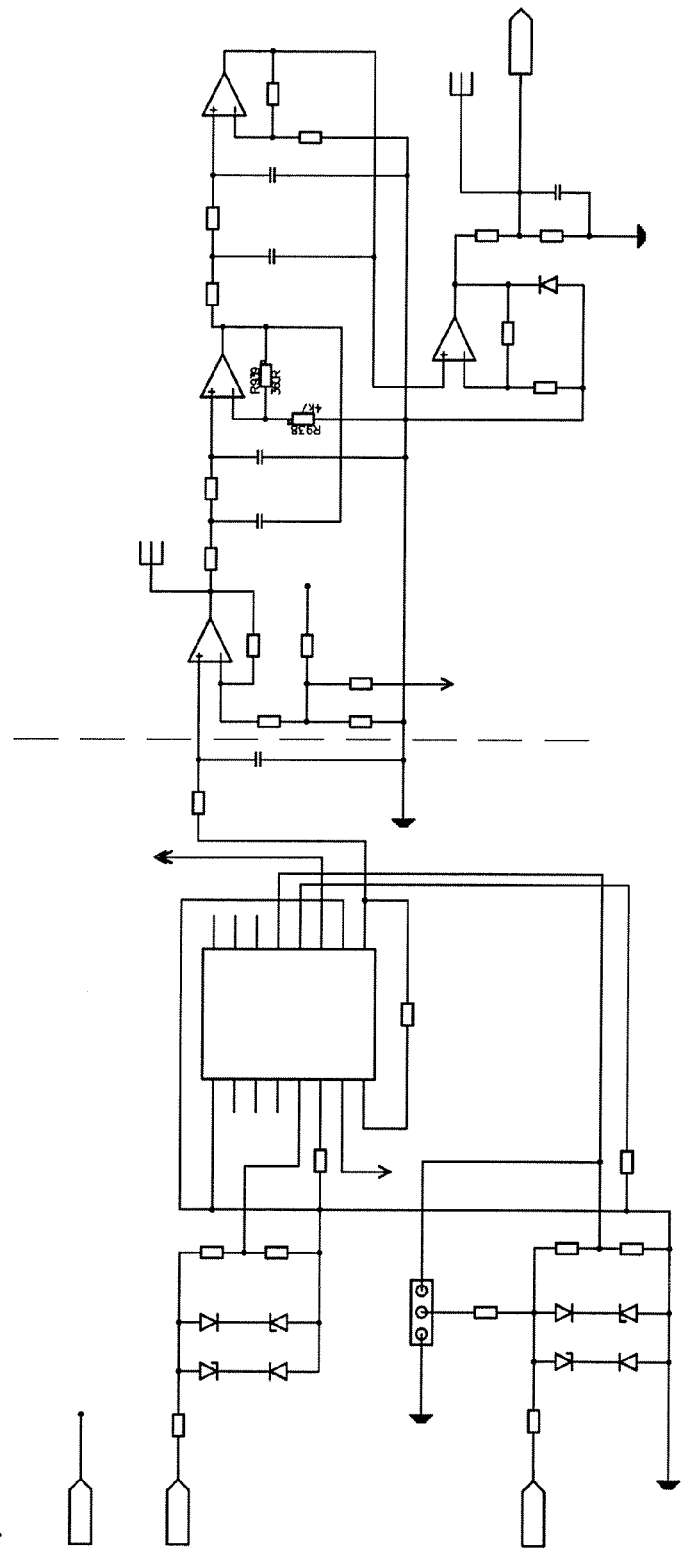
Figures 1, 6J:
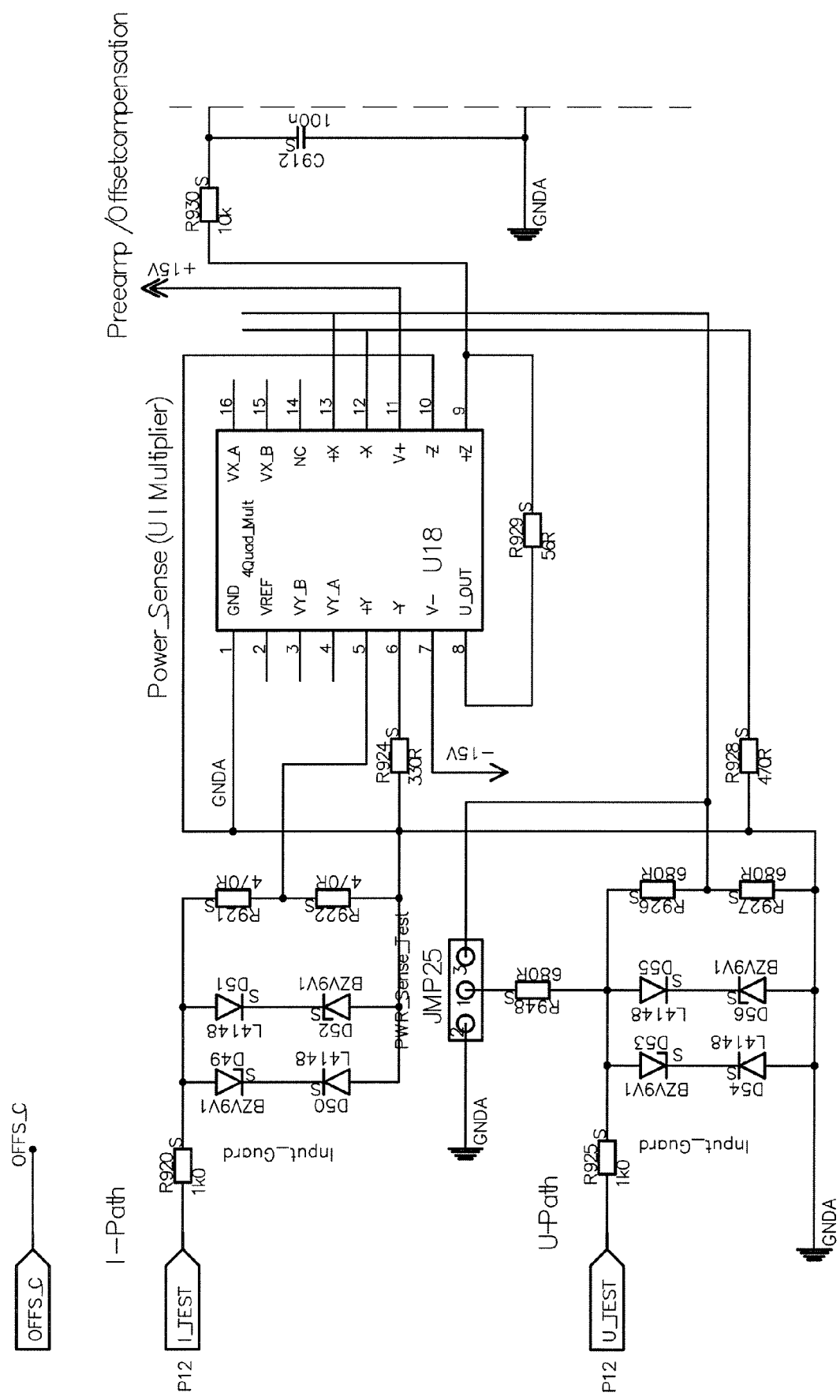
Figures 2, 6J:
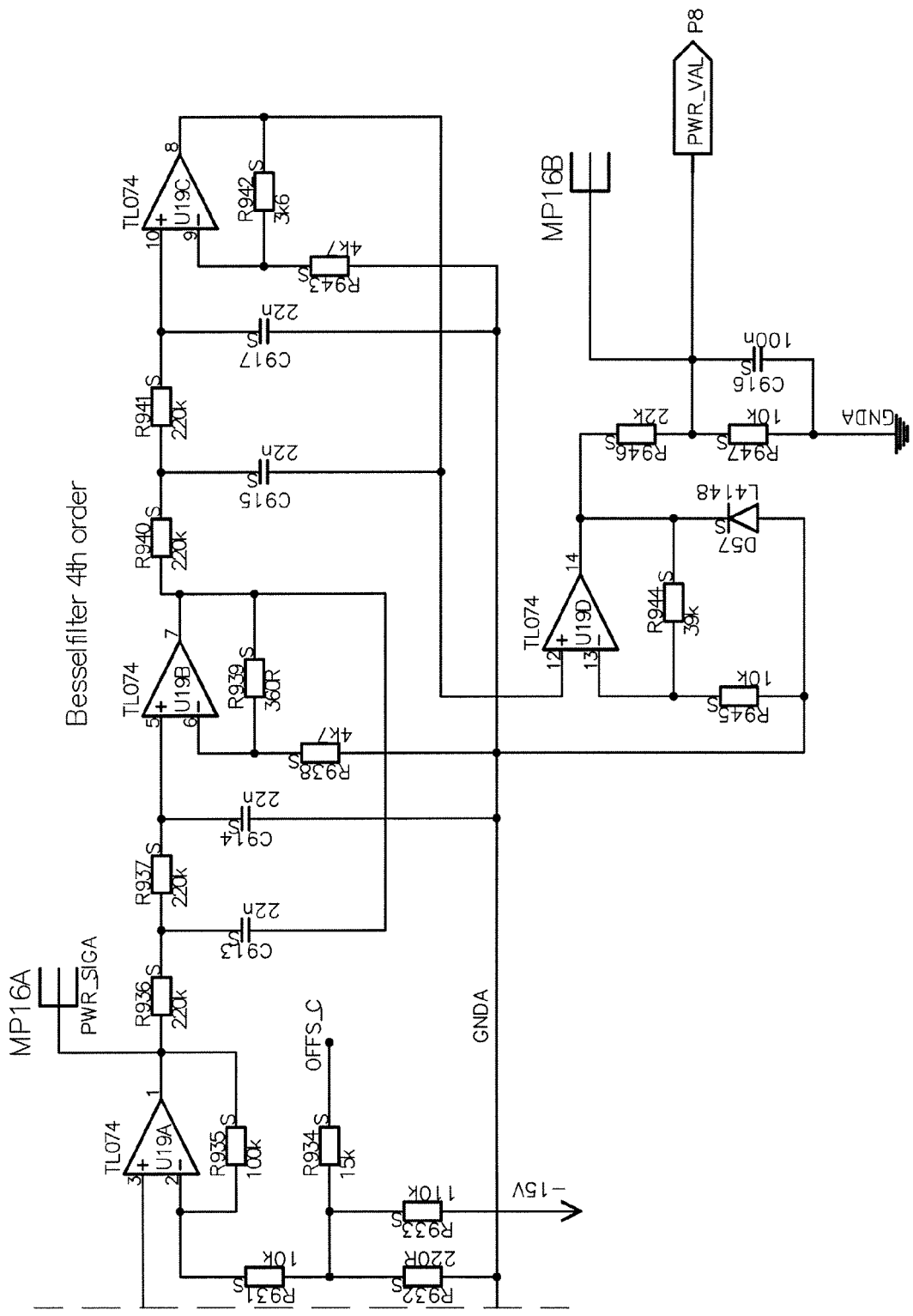
Figure 6K:
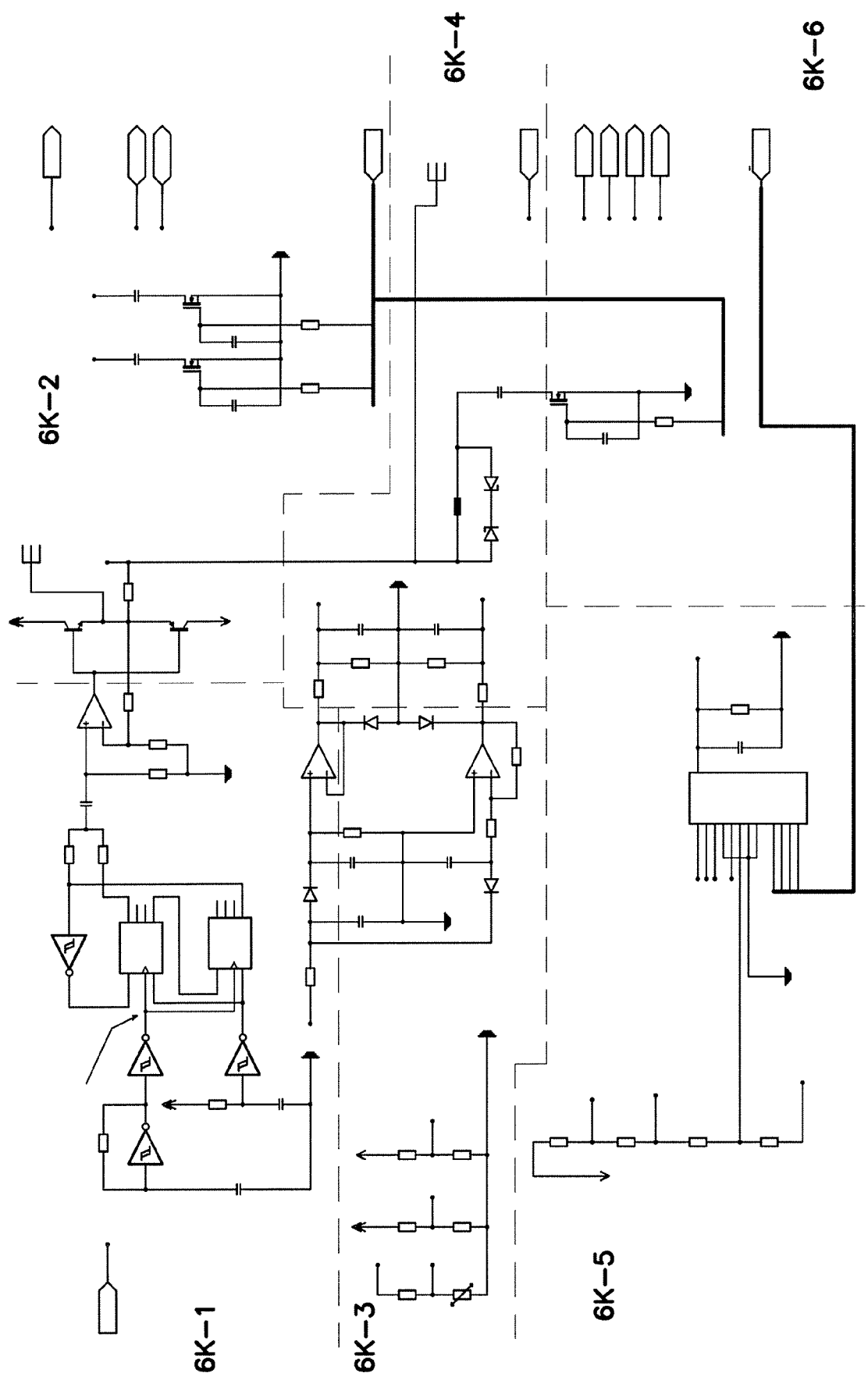
Figure 6K:
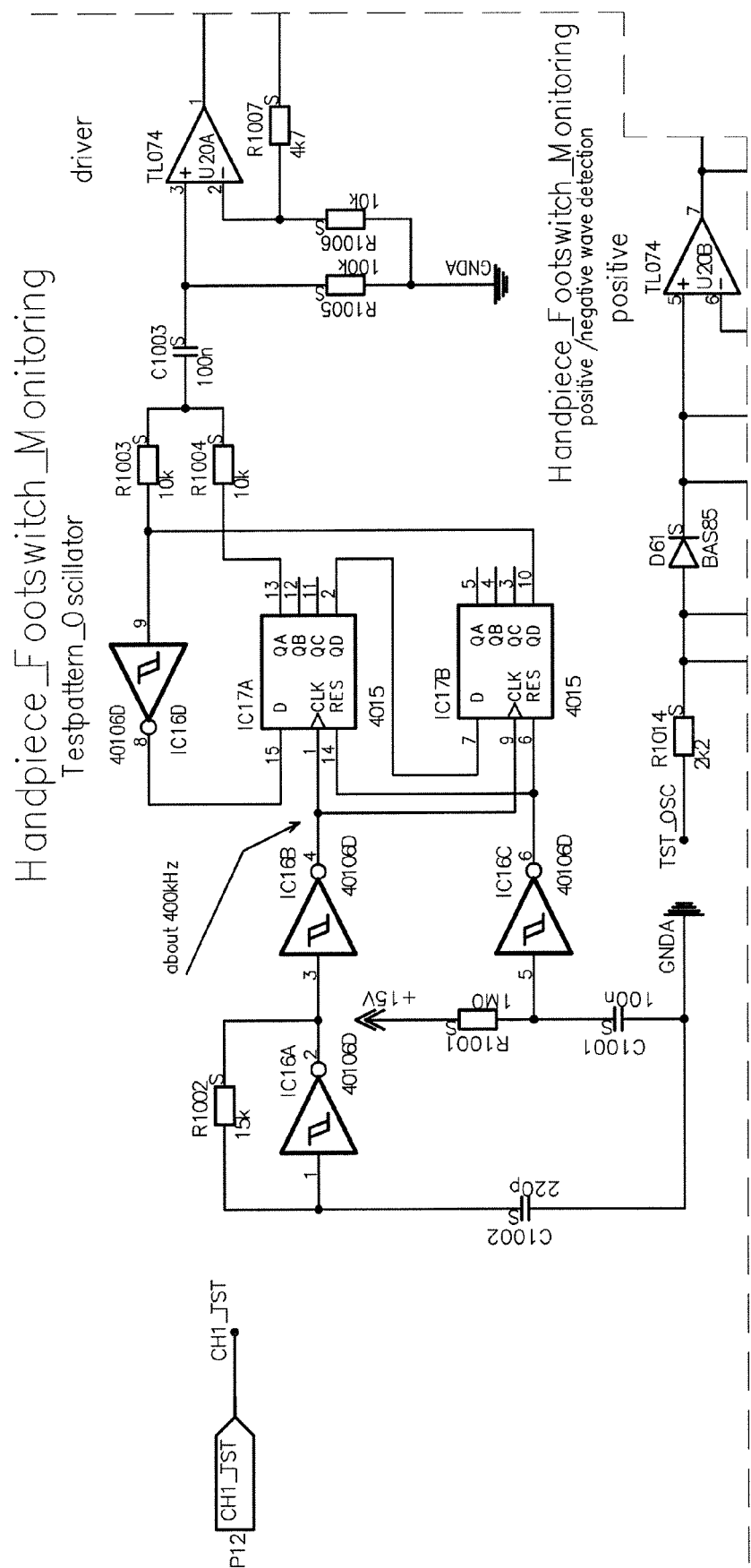
Figures 2, 6K:
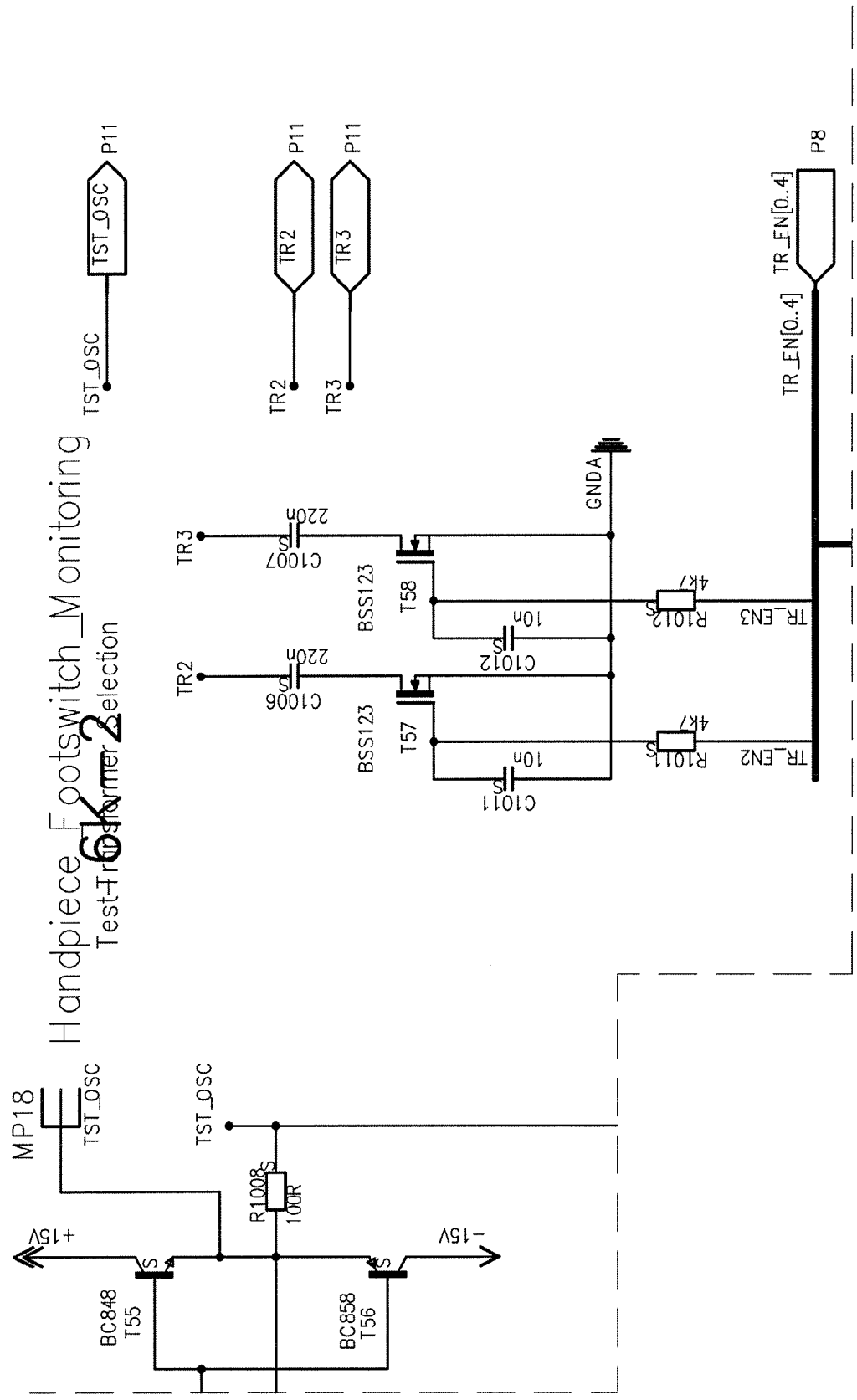
Figures 3, 6K:
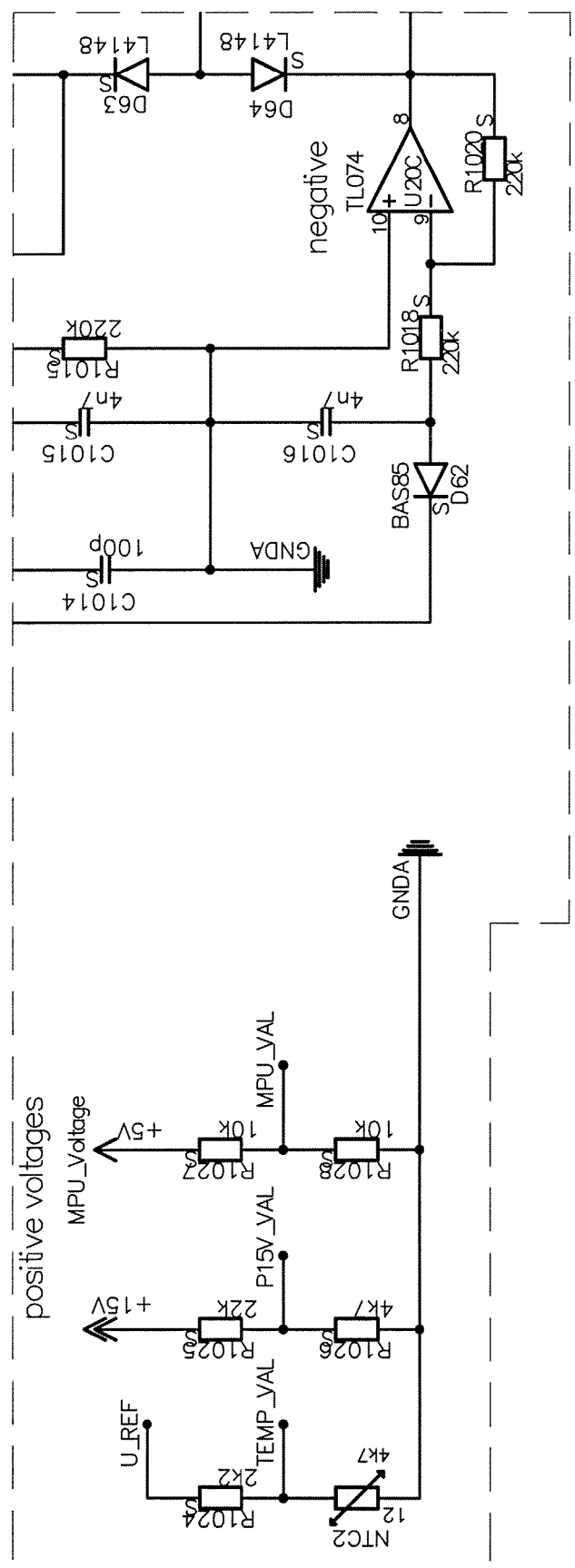
Figures 4, 6K:
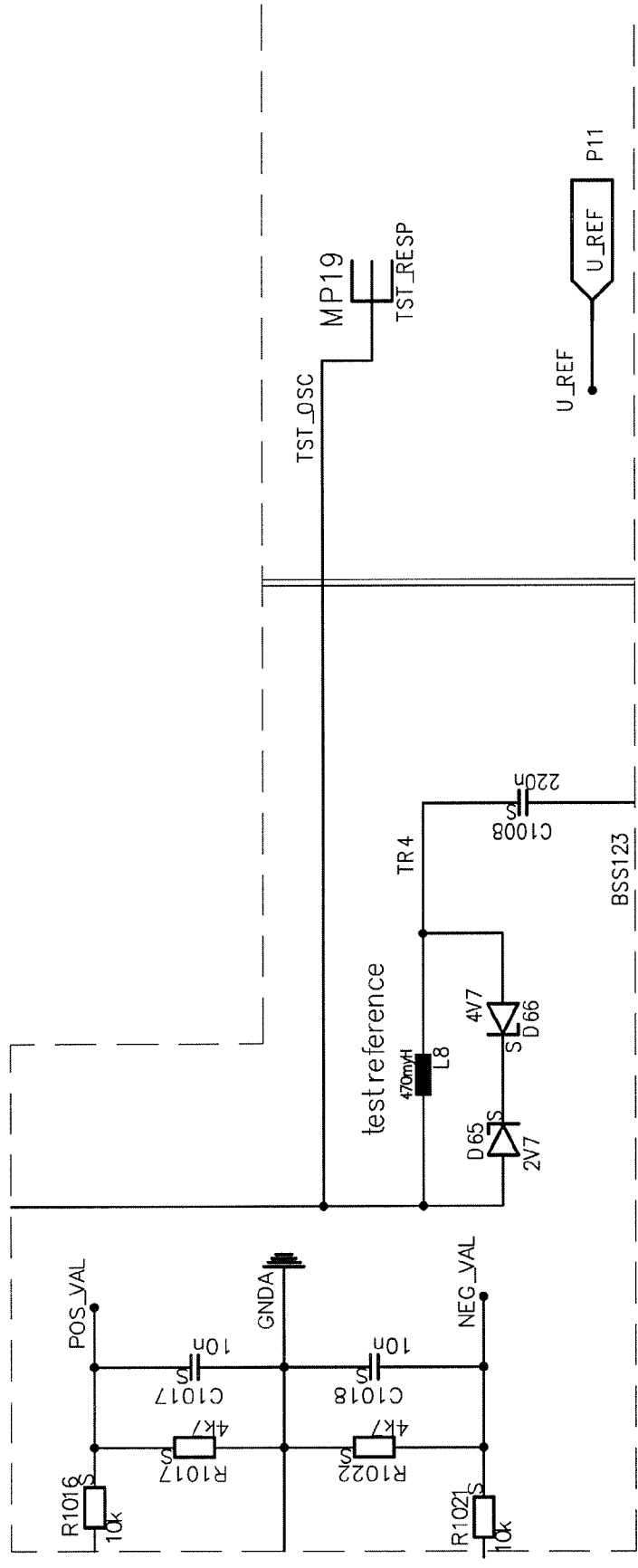
Figures 5, 6K:
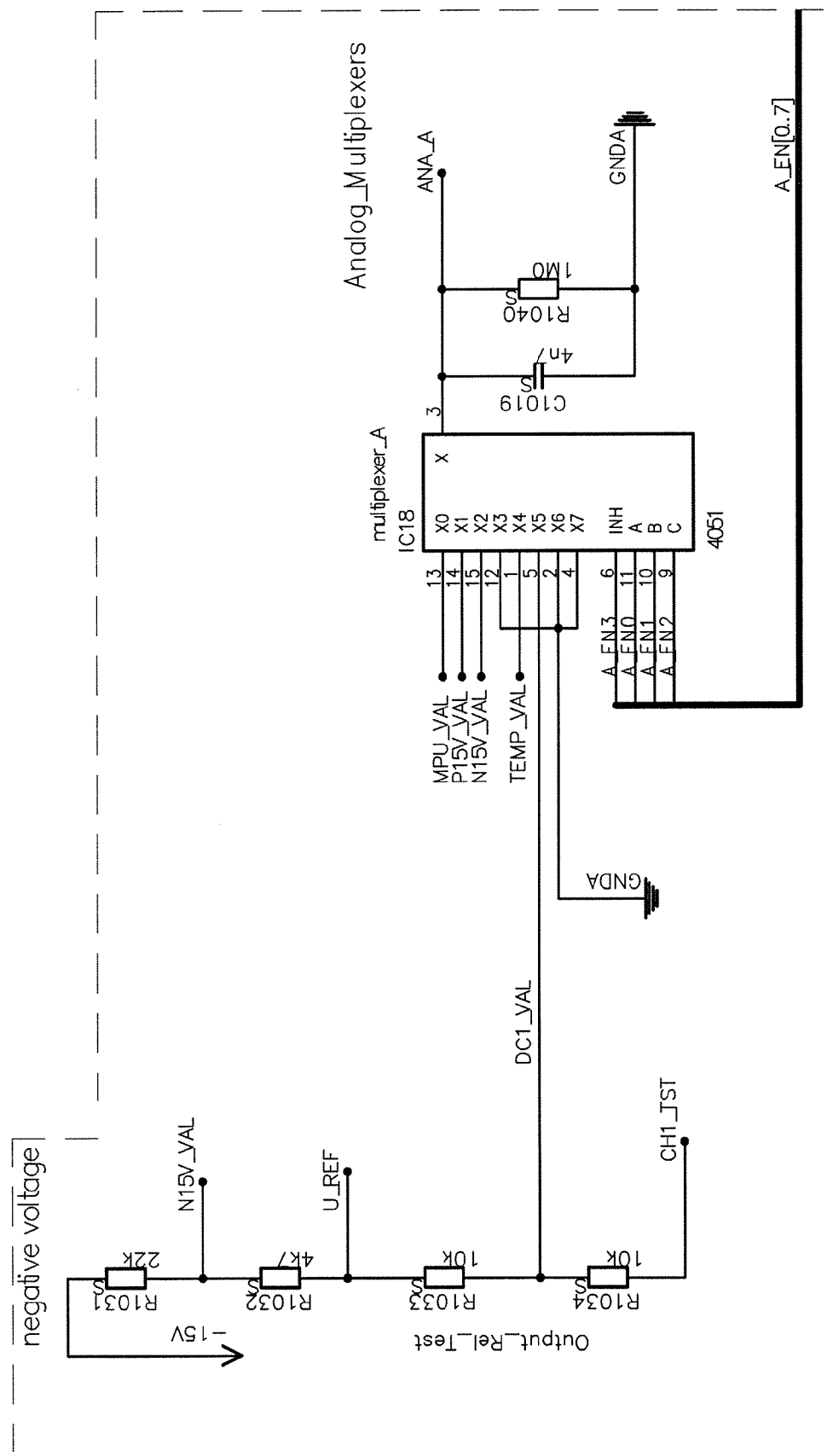
Figures 6, 6K:
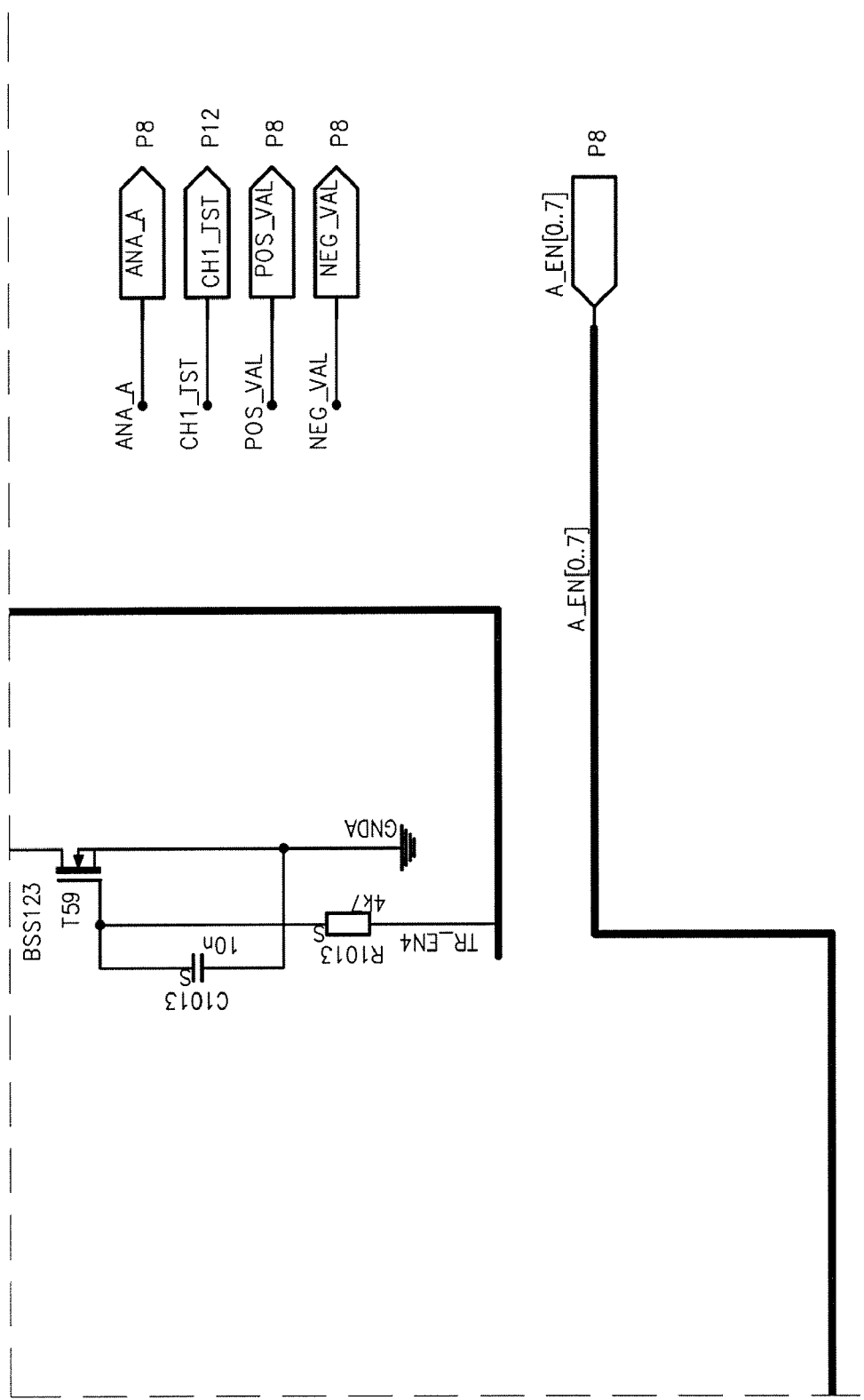
Figure 6L:
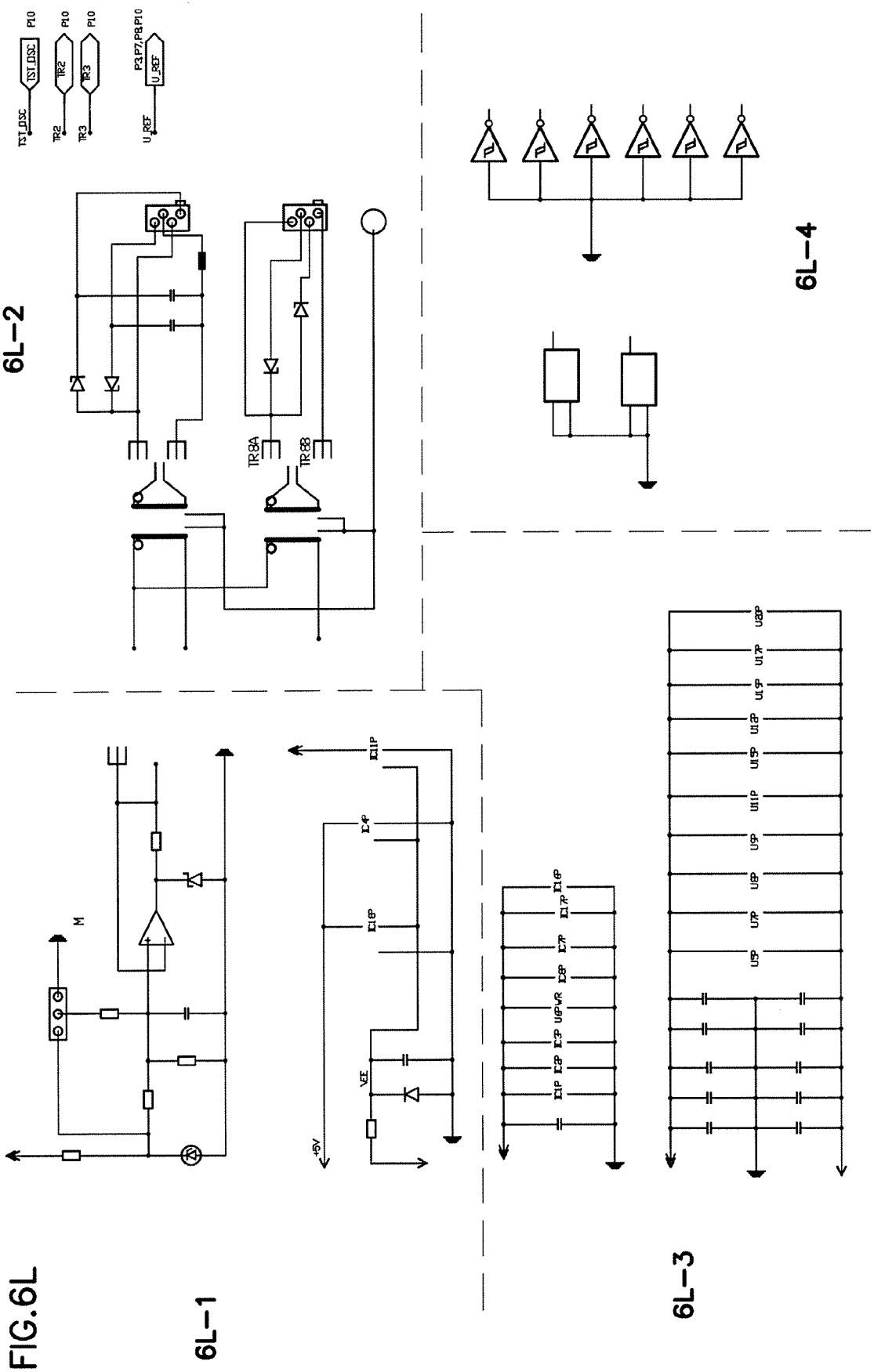
Figures 1, 6L:
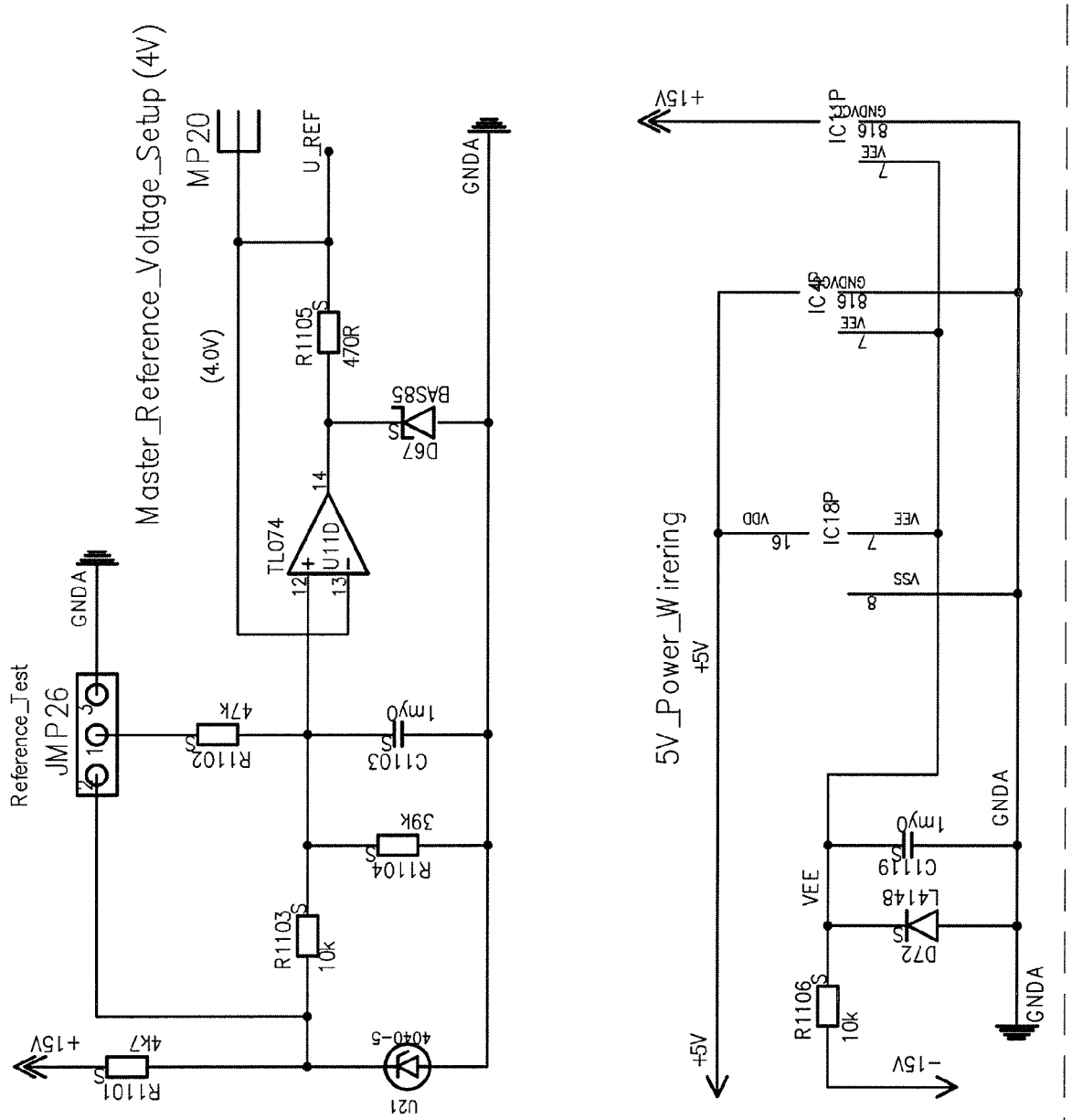
Figures 3, 6L:
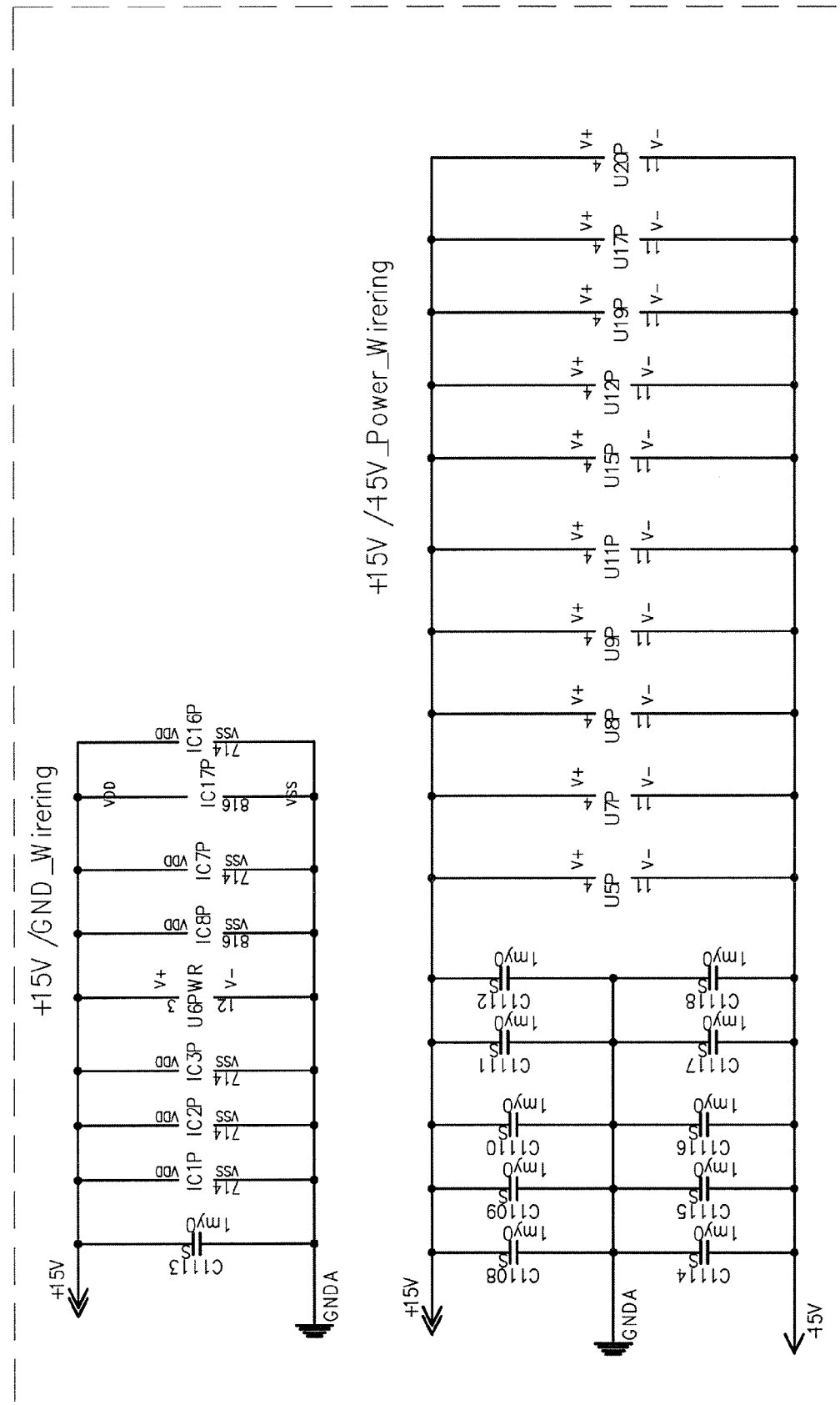
Figures 4, 6L:
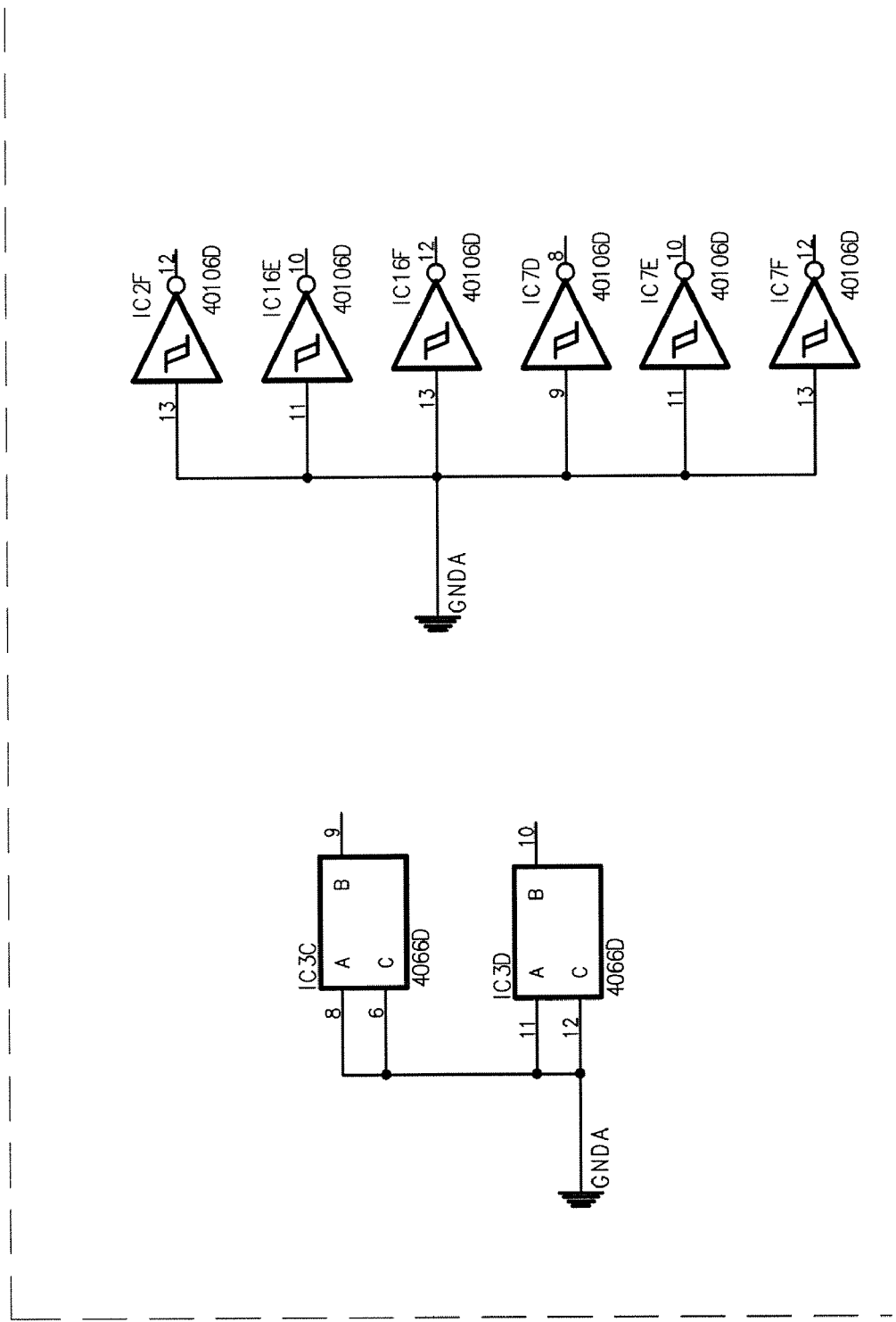
Figures 1, 6M:
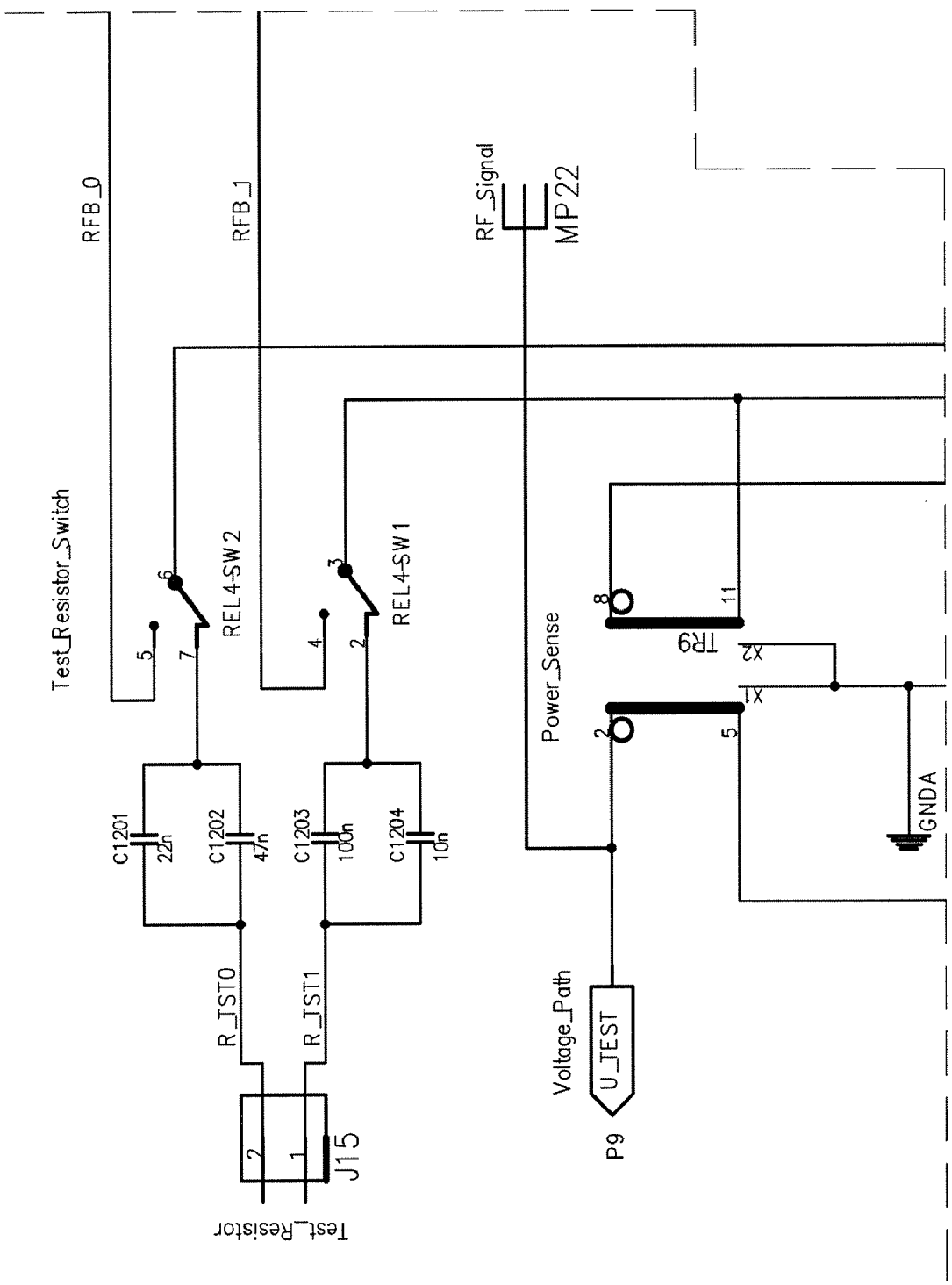
Figures 2, 6M:
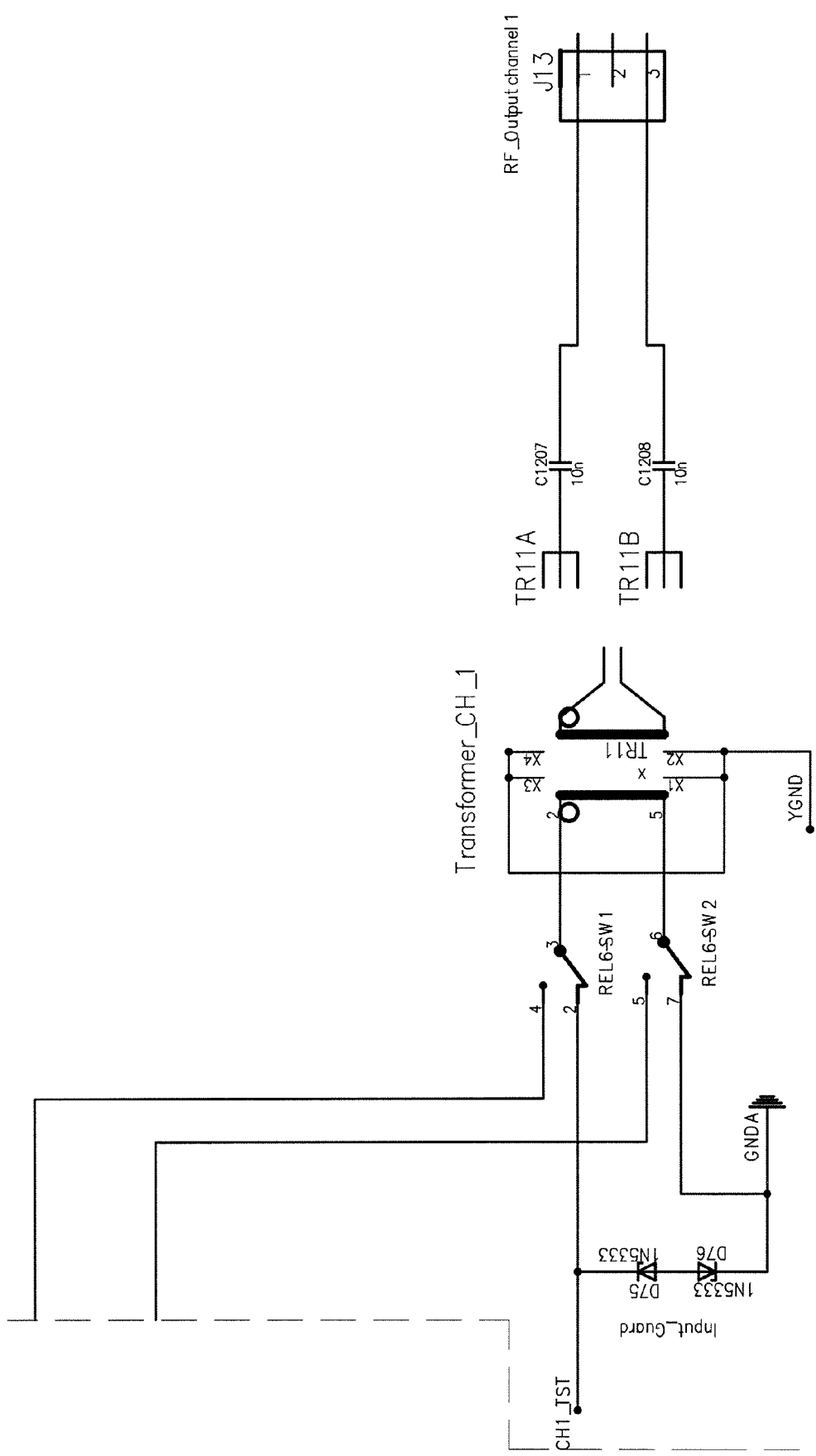
Figures 3, 6M:
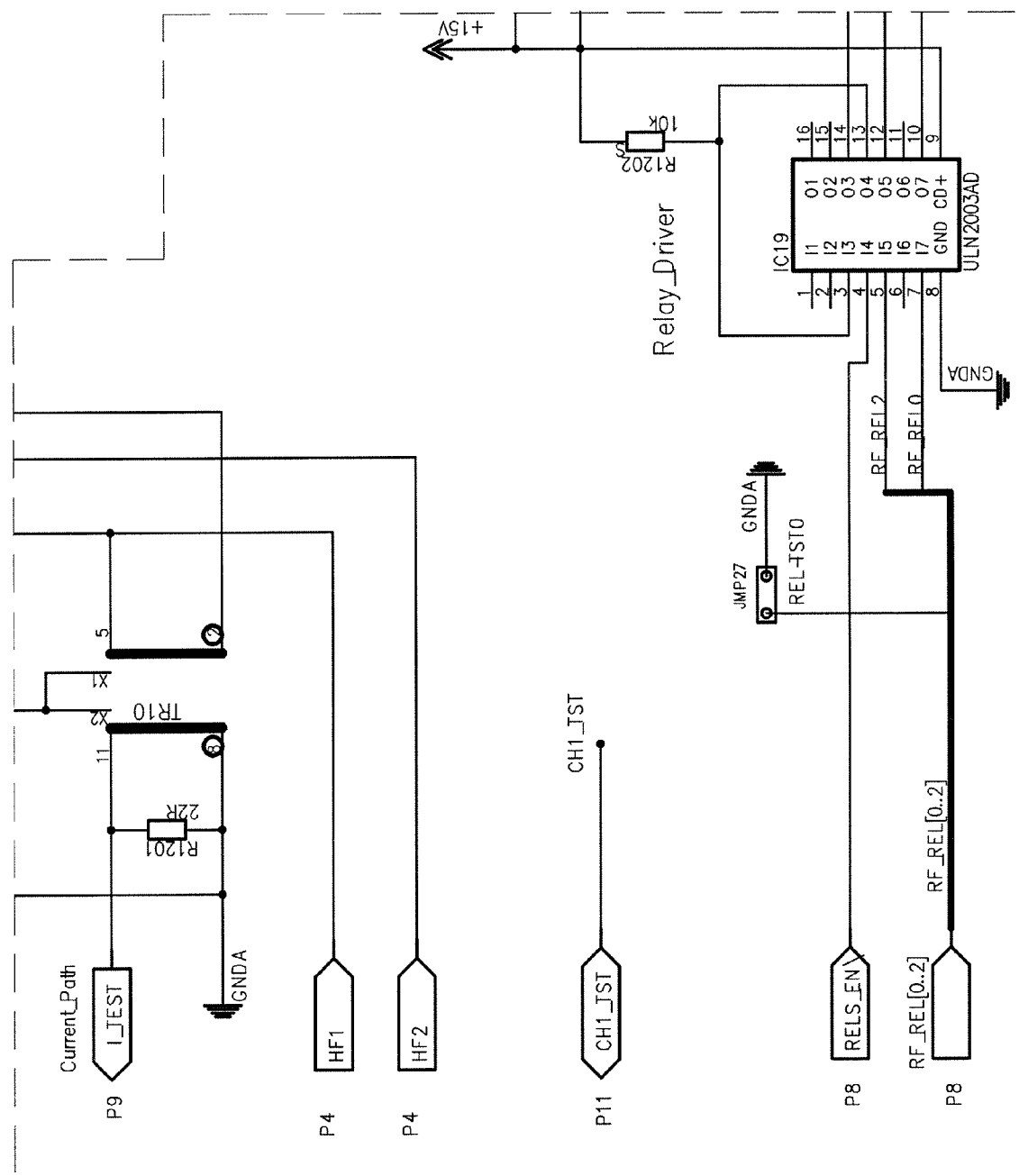
Figures 4, 6M:
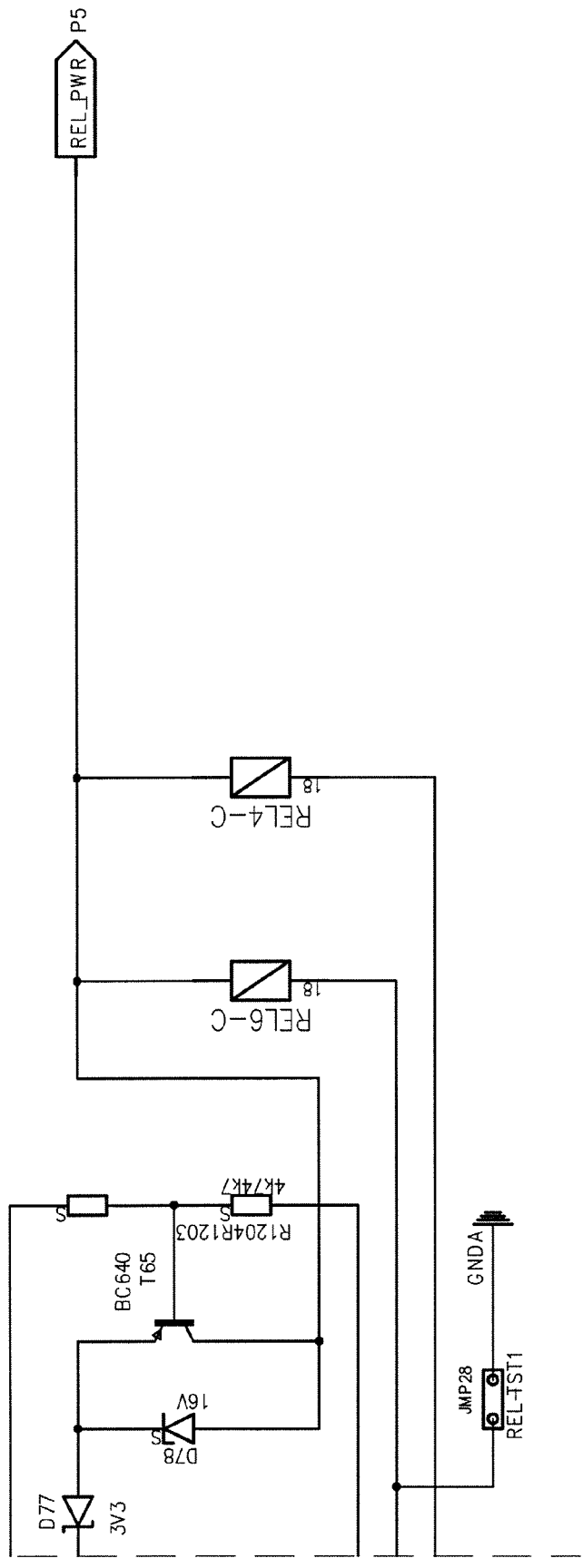
Figure 6N:
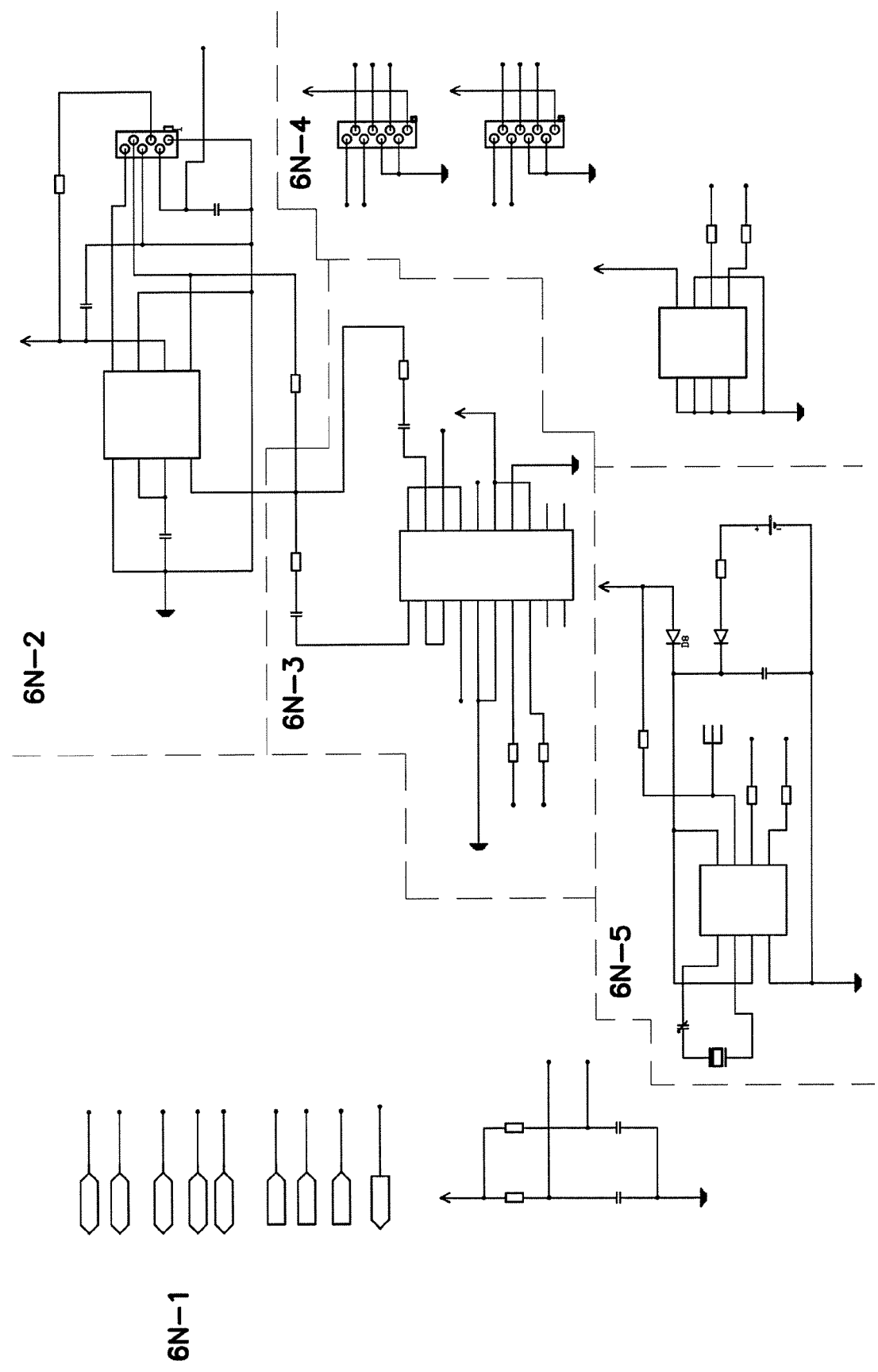
Figure 6N:
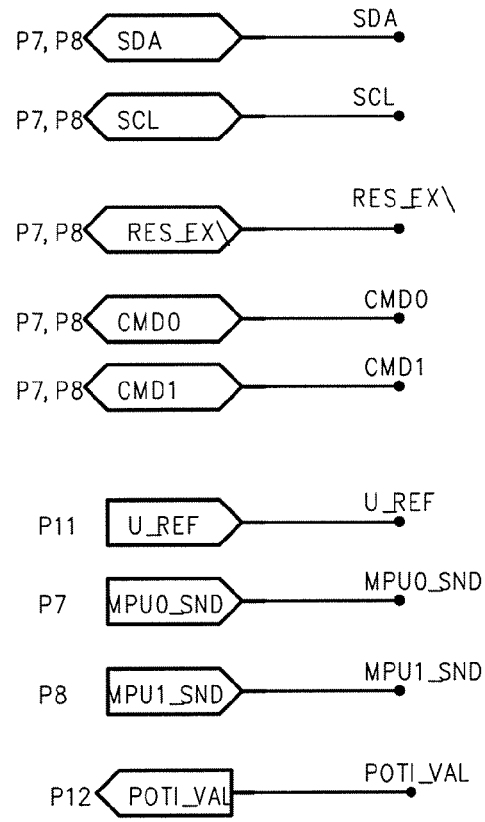
Figure 1:
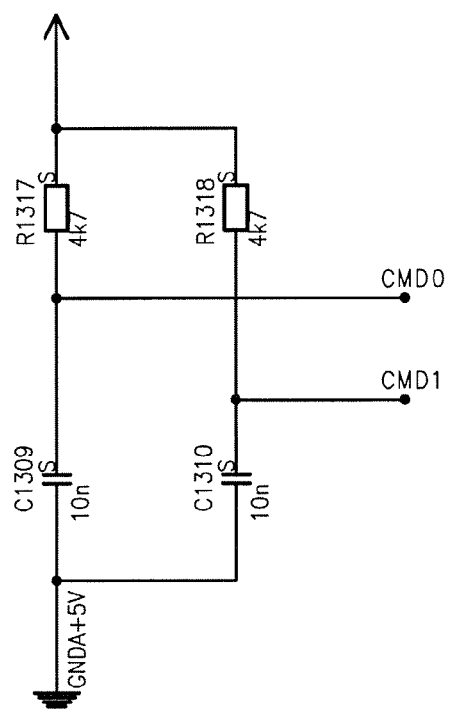
Figures 2, 6N:
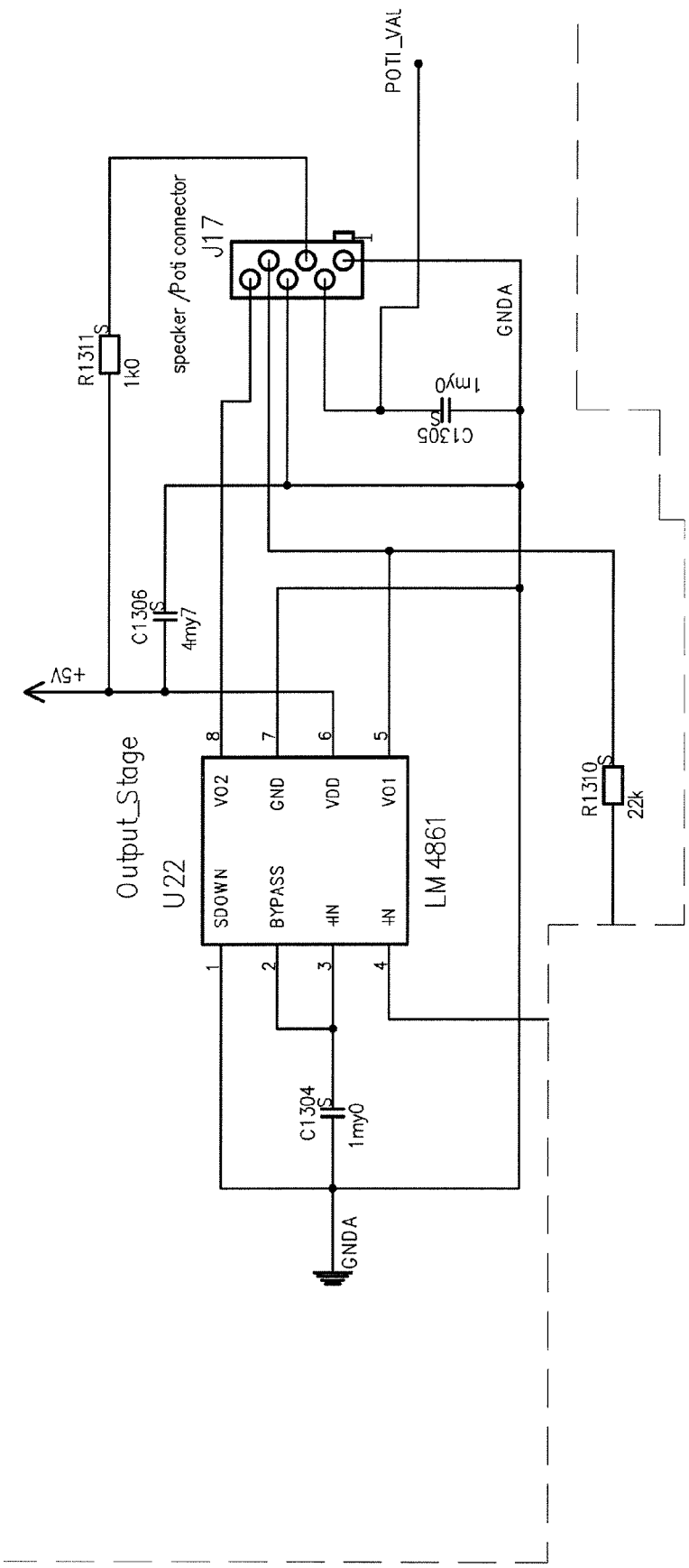
Figures 3, 6N:
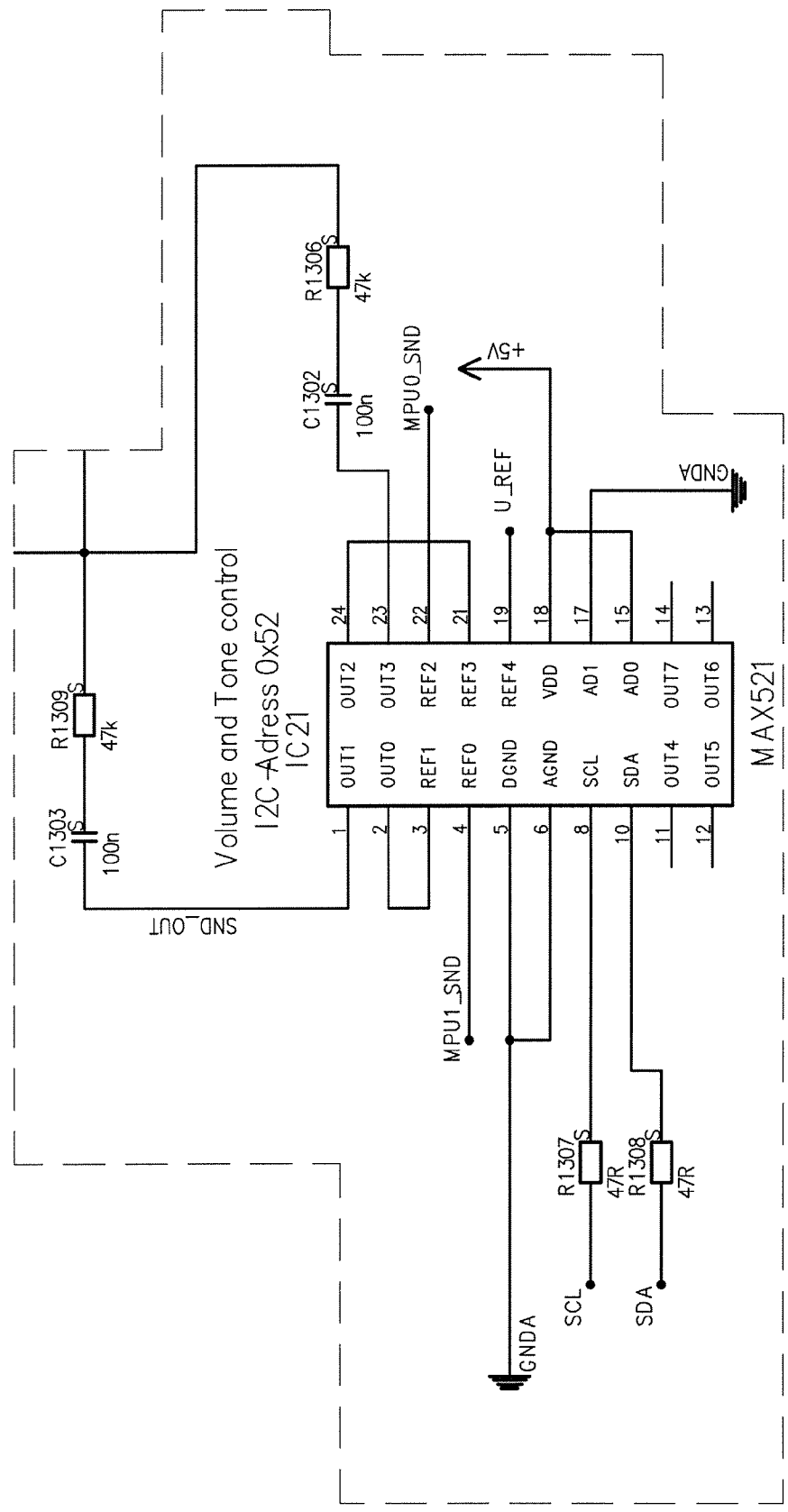
Figures 4, 6N:
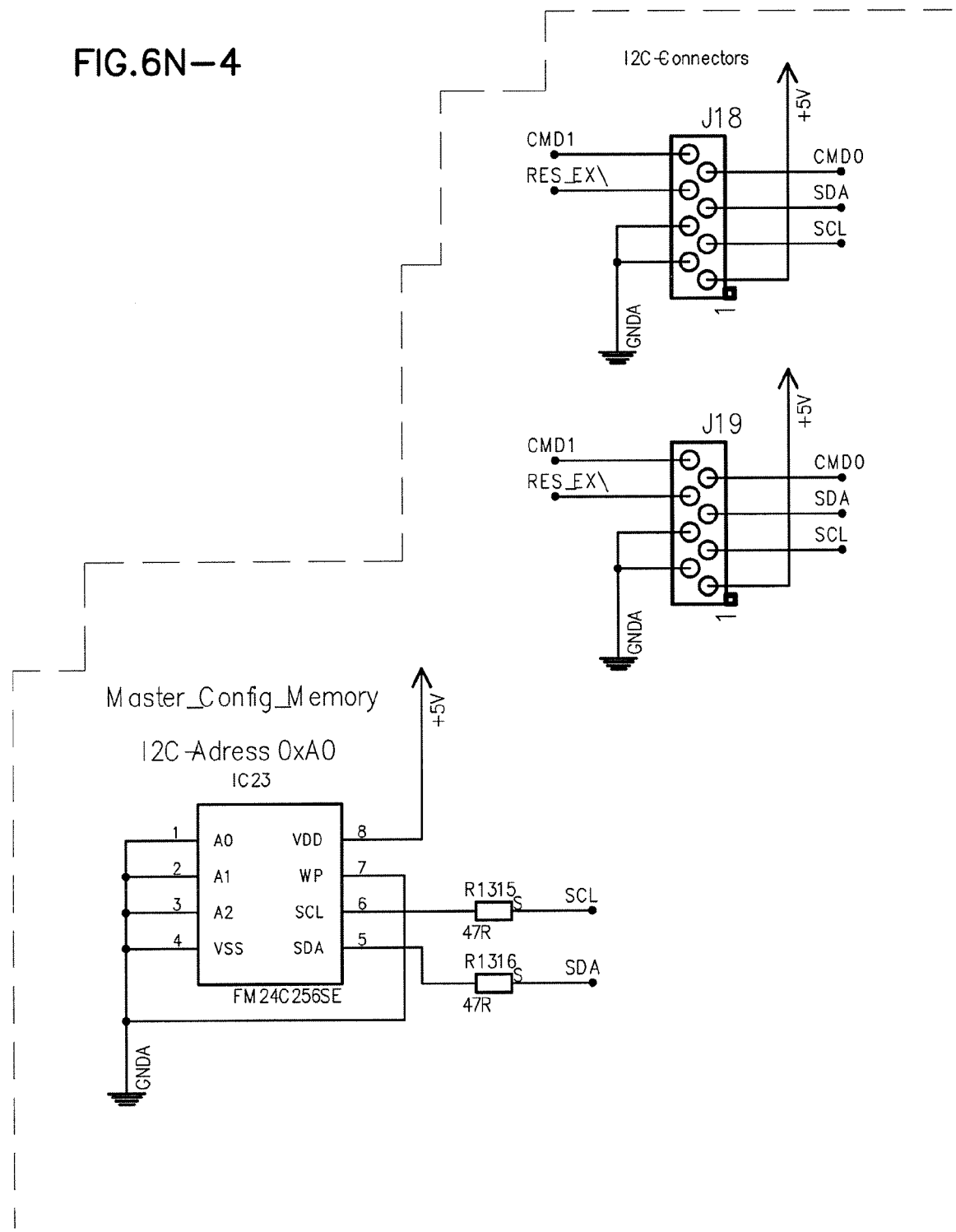
Figures 5, 6N:
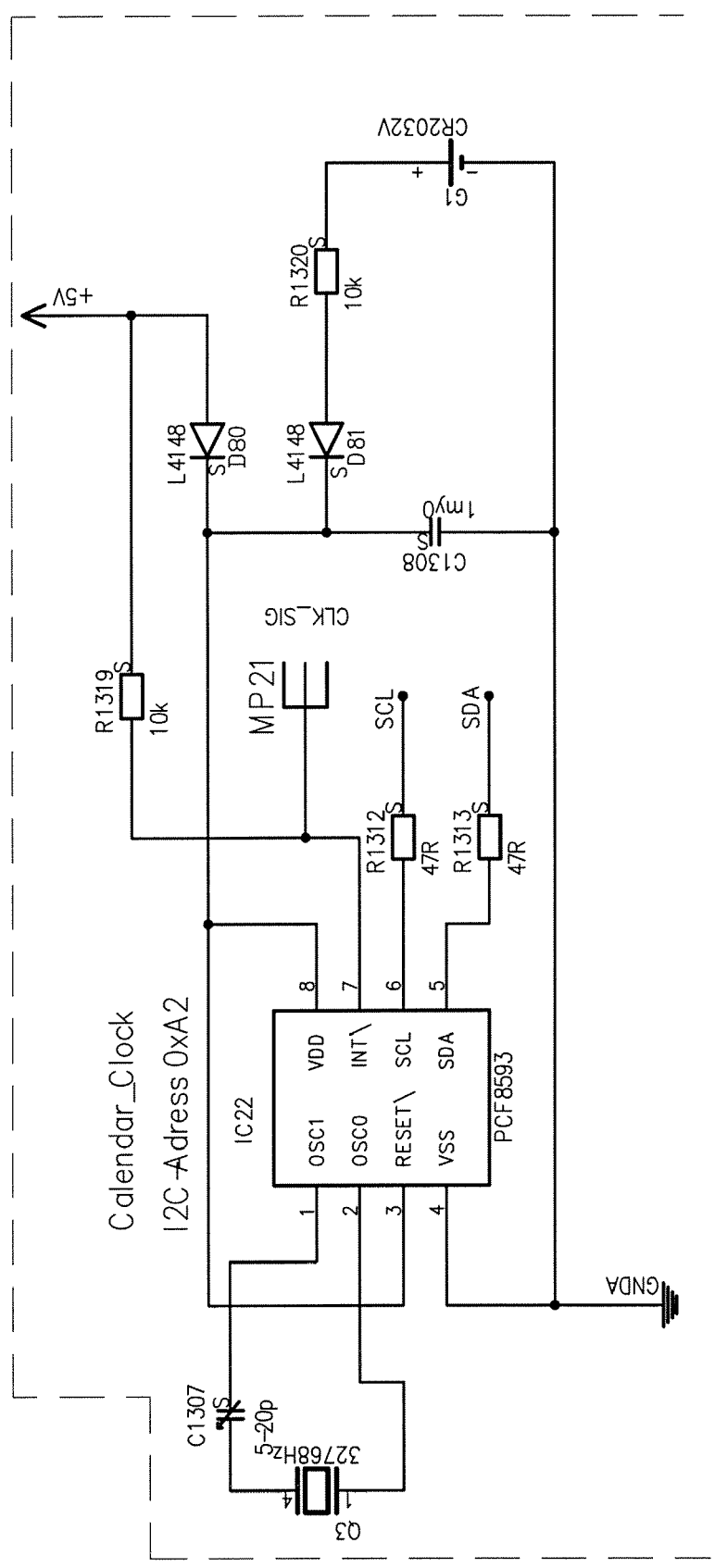
Figure 60:
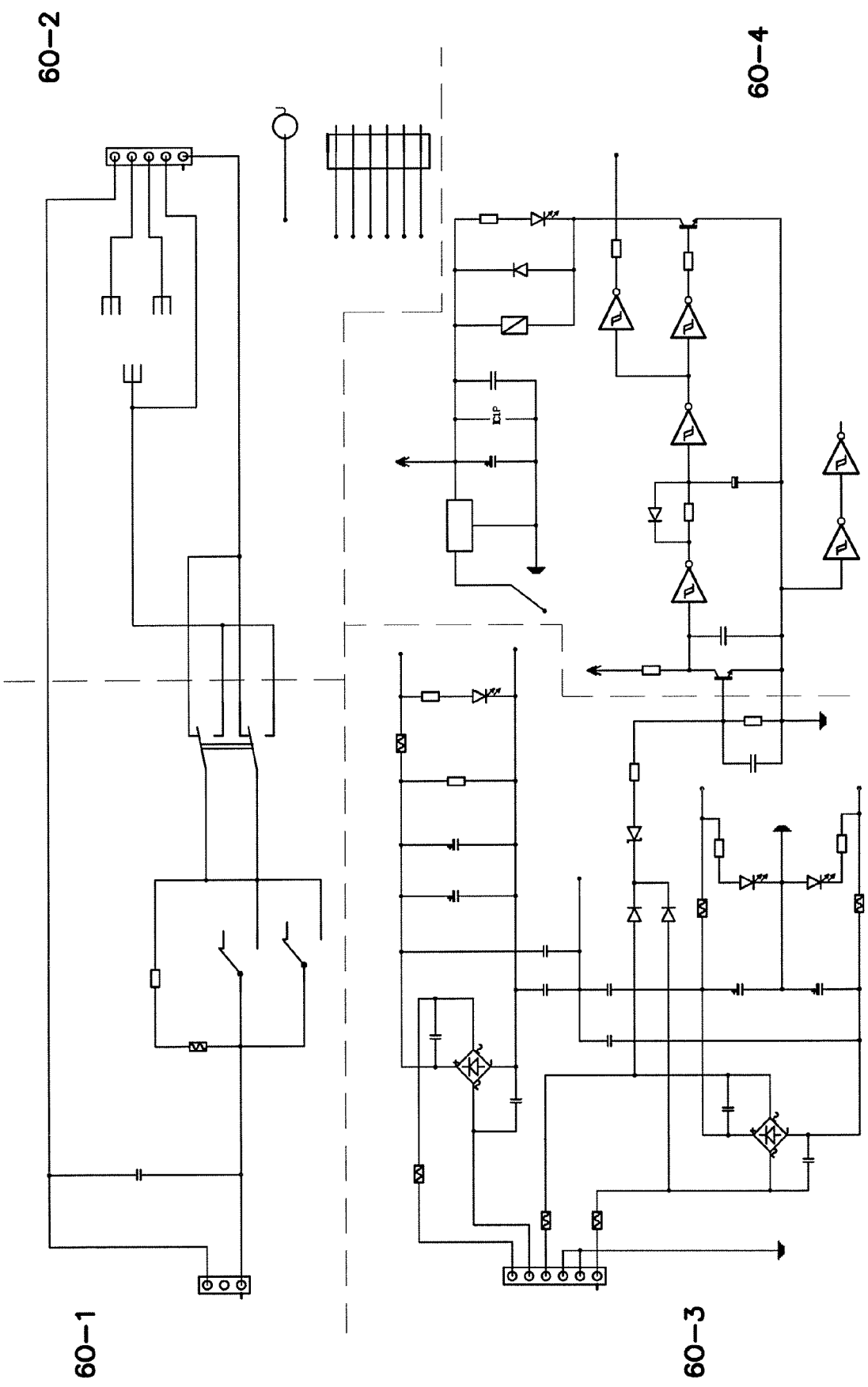
Figures 1, 60:
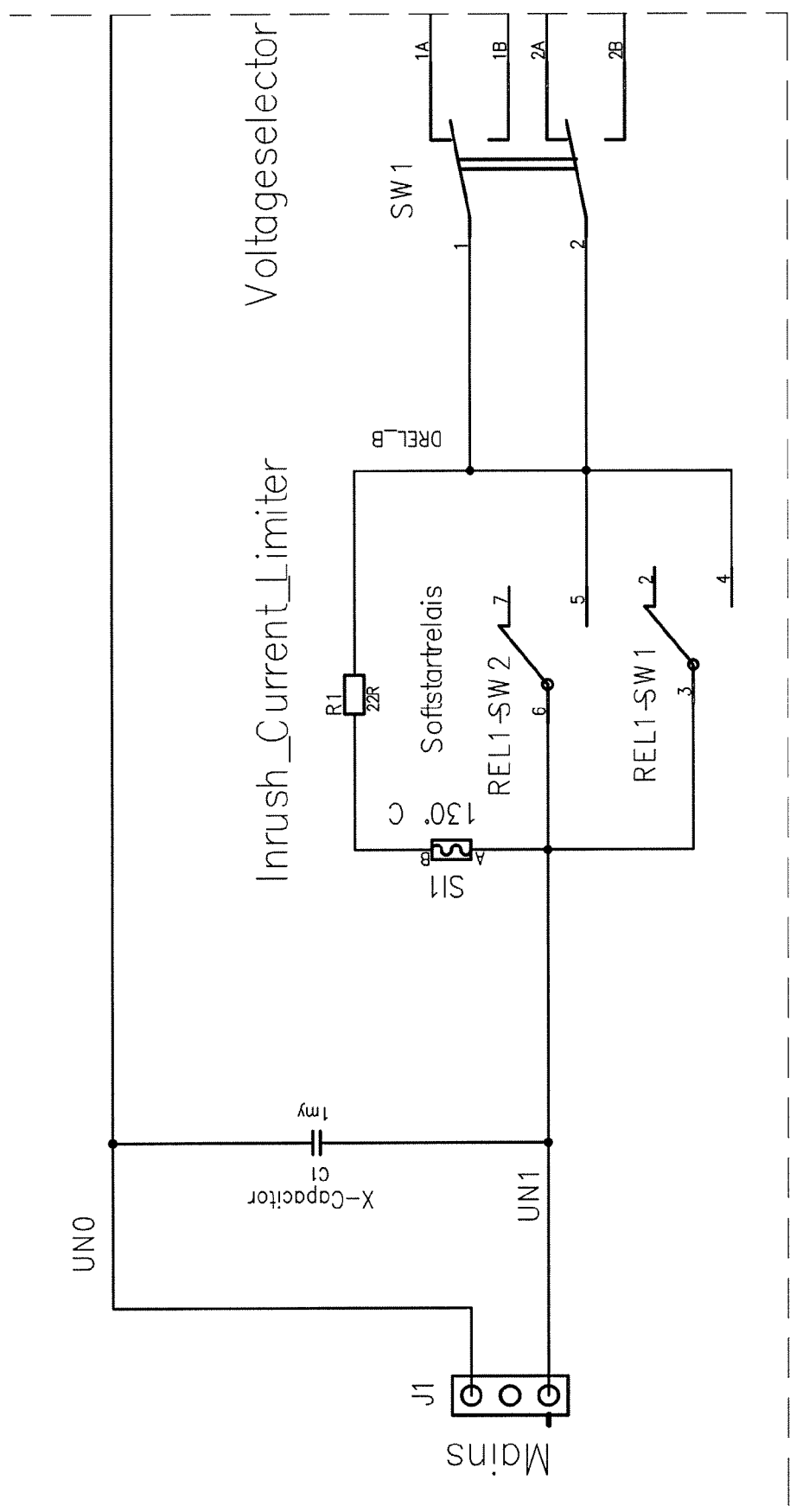
Figures 2, 60:
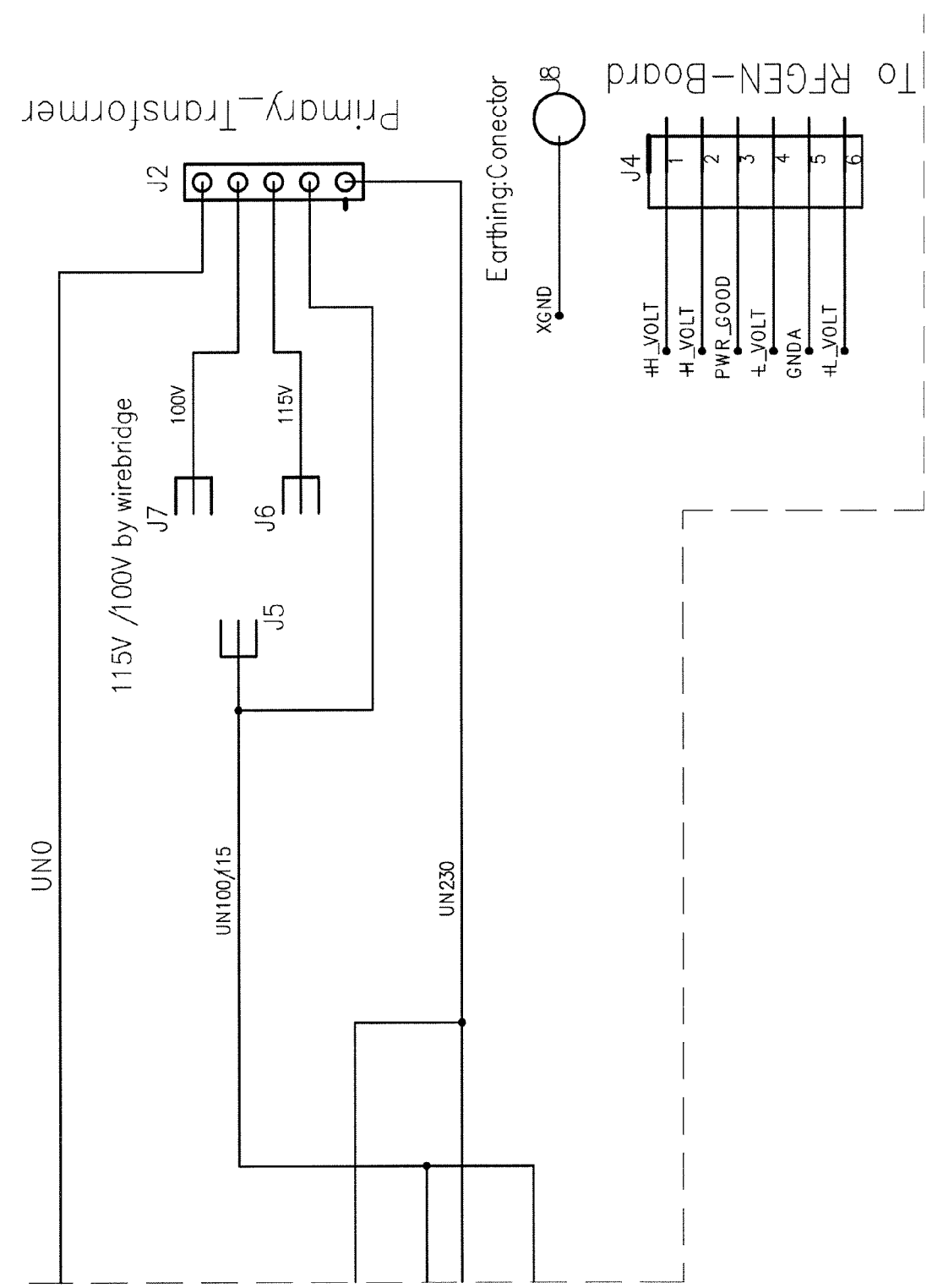
Figures 3, 60:
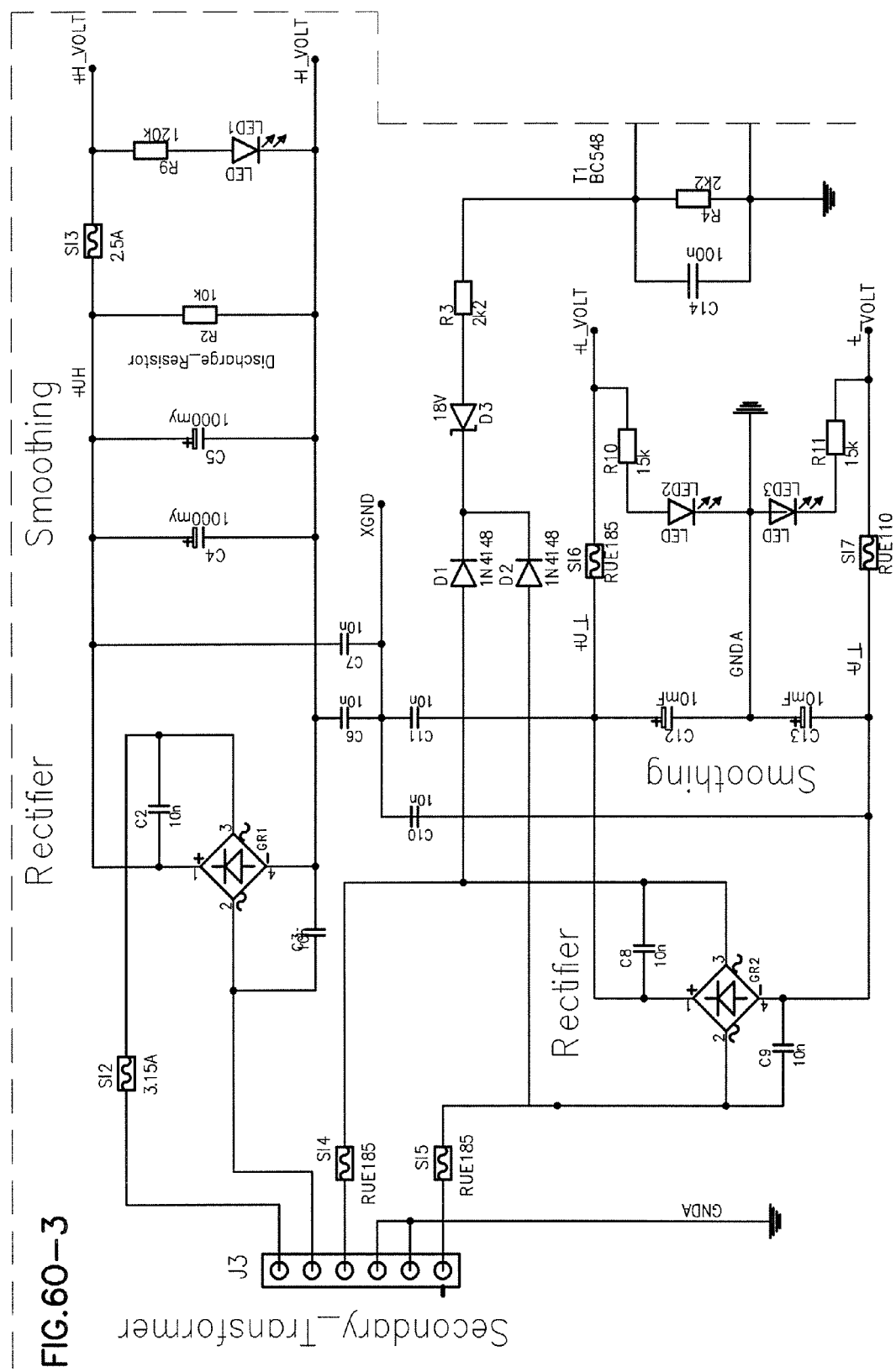
Figures 4, 60:
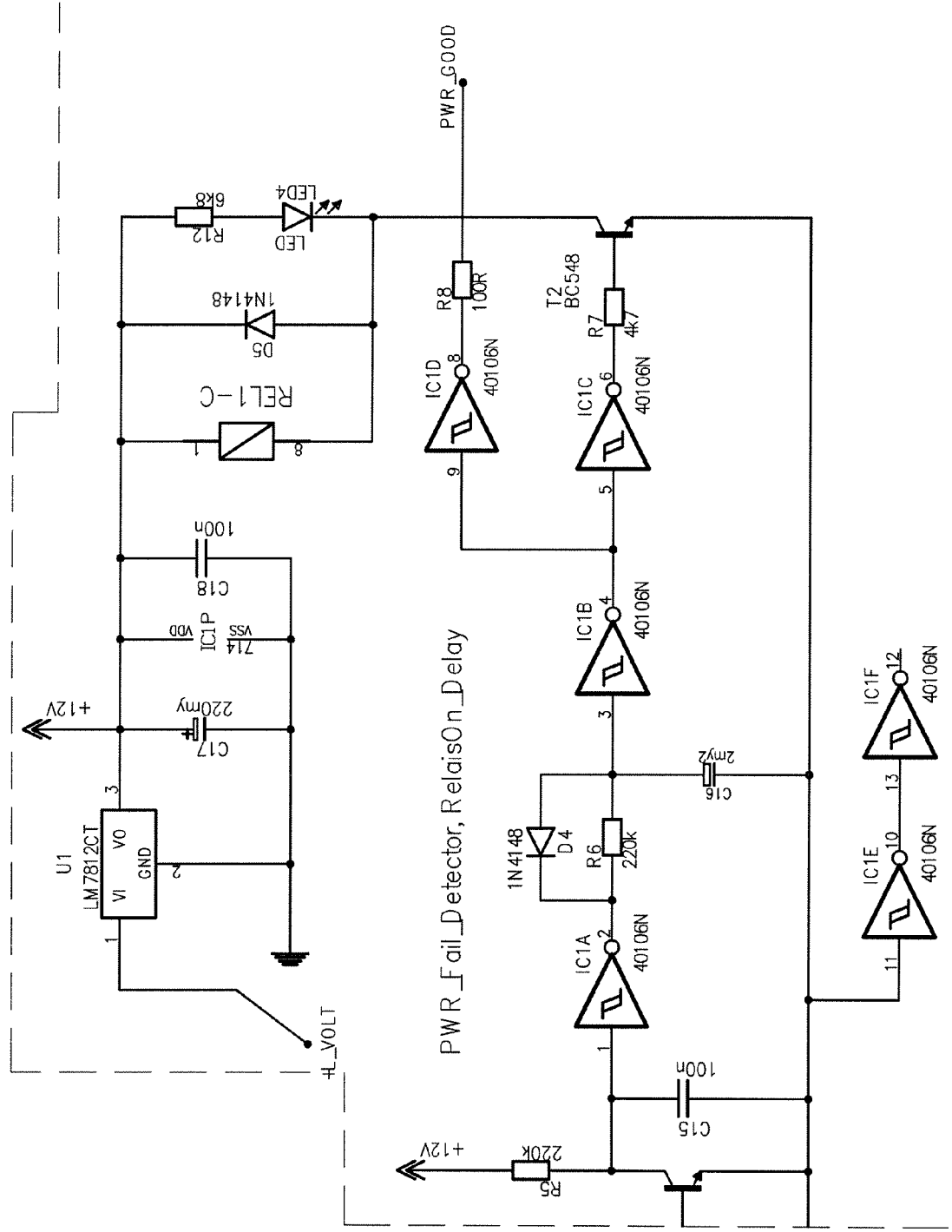

FIG. 3 shows the rear panel of electrosurgical unit 14. The rear panel of the electrosurgical unit 14 includes a speaker 60 and a volume control knob 62 to adjust the volume of the tone that will sound when the RF power is activated (RF power activation tone). The volume of the RF power activation tone is increased by turning the knob clockwise, and decreased by turning the knob counterclockwise. However, the electrosurgical unit 14 prevents this tone from being completely silenced.

Rear panel of electrosurgical unit 14 also includes a power cord receptacle 64 used to connect the main power cord to the electrosurgical unit 14 and an equipotential grounding lug connector 66 used to connect the electrosurgical unit 14 to earth ground using a suitable cable. The rear panel also includes a removable cap 68 for the installation of a bipolar footswitch socket connectable to an internal footswitch circuit of electrosurgical unit 14 so that the RF power may be activated by a footswitch in addition to a handswitch of device 30. Additionally, the rear panel also includes a fuse drawer 70 which includes which contains two extra fuses, consistent with the line voltage. Finally, the rear panel includes a name plate 72 which may provide information such as the model number, serial number, nominal line voltages, frequency, current and fuse rating information of the electrosurgical unit 14.

Figure 4:
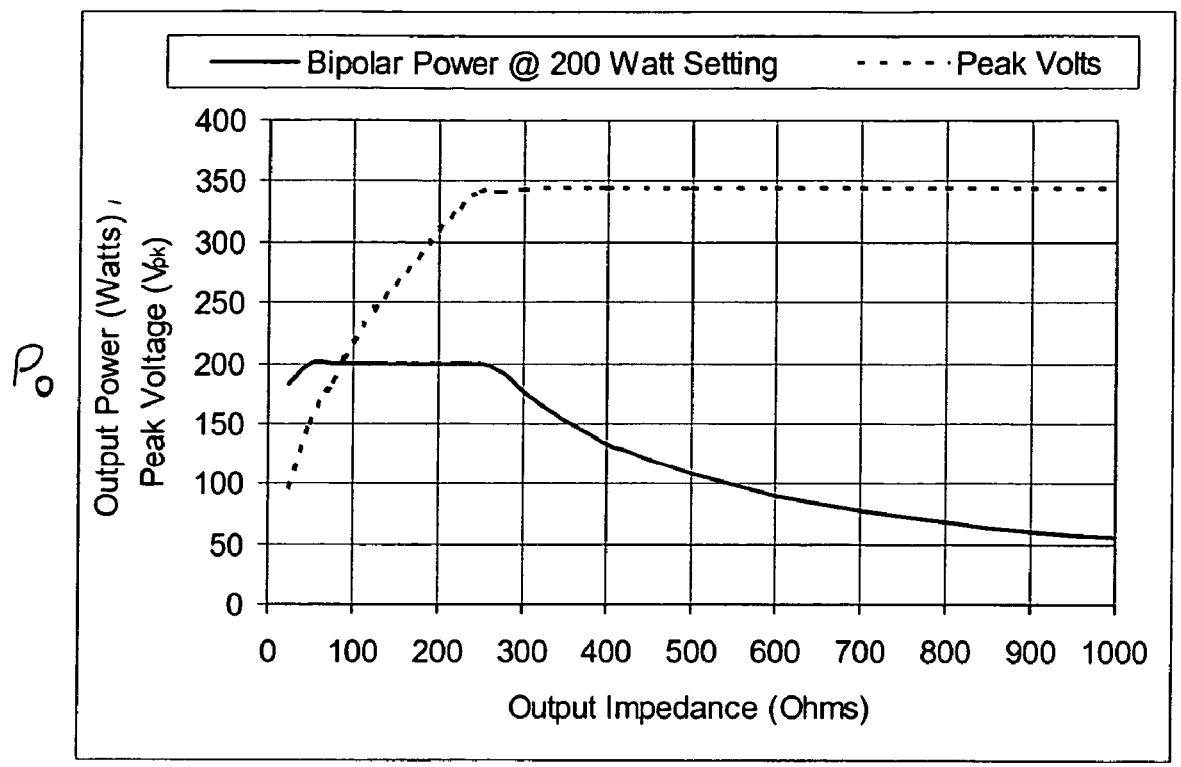
FIG. 4 is a graph of the RF power output versus impedance for the electrosurgical unit of FIG. 1.

The RF power output curve of electrosurgical unit 14 is shown in FIG. 4. Impedance Z, shown in units of ohms on the X-axis and output power $P_O$ is shown in units of watts on the Y-axis. In the illustrated embodiment, the bipolar electrosurgical power (RF) is set to 200 watts. As shown in the figure, for an RF power setting $P_S$ of 200 watts, the output power $P_O$ will remain constant with the set RF power $P_S$ as long as the impedance Z stays between the low impedance cut-off of 30 ohms and the high impedance cut-off of 250 ohms. Below an impedance Z of 30 ohms, the output power $P_O$ will decrease as shown by the low impedance ramp. Above an impedance Z of 250 ohms, the output power $P_O$ will also decrease as shown by the high impedance ramp.

Figure 5:
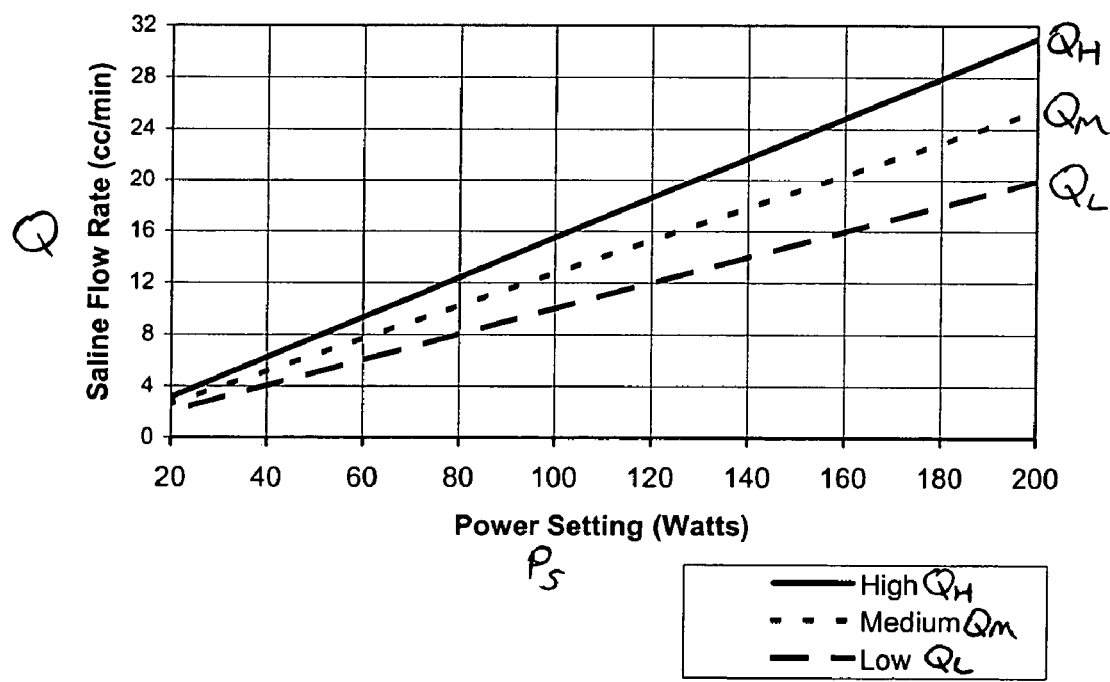
FIG. 5 is graph showing a relationship of fluid flow rate Q in units of cubic centimeters per minute (cc/min) on the Y-axis, and the RF power setting $P_S$ in units of watts on the X-axis.

Electrosurgical unit 14 has also been configured such that the pump speed, and therefore the throughput of fluid expelled by the pump, is predetermined based on two input variables, the RF power setting and the fluid flow rate setting. In FIG. 5 there is shown a relationship of fluid flow rate Q in units of cubic centimeters per minute (cc/min) on the Y-axis, and the RF power setting $P_S$ in units of watts on the X-axis. The relationship has been engineered to inhibit undesirable effects such as tissue desiccation, electrode sticking, smoke production and char formation, while at the same time not providing a fluid flow rate Q at a corresponding RF power setting $P_S$ which is so great as to provide too much electrical dispersion and cooling at the electrode/tissue interface. While not being bound to a particular theory, a more detailed discussion on how the fluid flow rate interacts with the radio frequency power, modes of heat transfer away from the tissue, fractional boiling of the fluid and various control strategies may be found in U.S. Publication Nos. 2001/0032002, published Oct. 18, 2001, and assigned to the assignee of the present invention and hereby incorporated by reference in its entirety to the extent it is consistent.

As shown, electrosurgical unit 14 has been configured to increase the fluid flow rate Q linearly with an increasing RF power setting $P_S$ for each of three fluid flow rate settings of low, medium and high corresponding to $Q_L$, $Q_M$ and $Q_H$, respectively. Conversely, electrosurgical unit 14 has been configured to decrease the fluid flow rate Q linearly with an decrease RF power setting $P_S$ for each of three fluid flow rate settings of low, medium and high corresponding to $Q_L$, $Q_M$ and $Q_H$, respectively. As shown, $Q_L$, $Q_M$ and $Q_H$ can be expressed as a function of the RF power setting $P_S$ by changing exemplary proportionality constants as follows:

$$Q_L = 0.1 \times P_S$$

$$Q_M = 0.1286 \times P_S$$

$$Q_H = 0.1571 \times P_S$$

FIG. 6 shows an exemplary block diagram of how electrosurgical unit 14 processes the inputs of RF power setting $P_S$ and the fluid flow rate setting, either $Q_L$, $Q_M$ or $Q_H$, to control the pump speed, and therefore the throughput of fluid expelled by the pump 32. As shown, user selected input values for the RF power setting $P_S$ and the fluid flow rate setting of either low, medium and high (corresponding to $Q_L$, $Q_M$ and $Q_H$), as well as activating the priming function, are entered into electrosurgical unit 14 by pushing corresponding switches for these parameters positioned on the front panel of the electrosurgical unit 14.

As shown in FIG. 6, the RF power setting switches 46a, 46b, the flow rate setting switches 52a, 52b, 52c and the priming switch 54 are all preferably part of a display panel module 40, preferably comprising a printed circuit board, which receives the inputs into electrosurgical unit 14.

The user selected input values for RF power, fluid flow rate and priming are then conveyed via corresponding input signals 41 to a main module 43 which preferably comprises a printed circuit board including a computer chip 45, a radiofrequency generator 47 and a pump controller 48. As shown, display panel module 40 and main module 43, as well as other components receive power from a power supply module 49, which also comprises a printed circuit board.

Computer chip 45 preferably comprises a micro-processor unit, a memory, and an input/output control unit. In this manner, the functional relationships between the radio-frequency power level and the flow of the fluid may be stored in the memory of the computer chip 45. While the functional relationships are preferably stored in the form of the foregoing equations, they may also be stored as numerical data points as part of a database look-up table.

As shown, the input signals 41 are received and processed by computer chip 45. More specifically, for example, from the input signal received corresponding to the fluid flow rate setting of either $Q_L$, $Q_M$ or $Q_H$, the computer chip 45 may first determine which of the above equations to apply. After determining which equation to apply, computer chip 45 may then apply the relationship to determine the output for flow of the fluid from the pump 32 based on the selected radio-frequency power level. Having determined this output, the computer chip 45 then sends output signals 51 and 53 corresponding to the selected radio-frequency power level and calculated output for flow of the fluid from the pump 32 to the radio-frequency generator 47 and pump controller 48, respectively. Thereafter, the pump controller 48 controls the speed of the pump drive shaft 55 by controlling the input voltage 59 to the pump motor 61 which rotates the drive shaft 55. More detailed drawings of exemplary electrosurgical unit 14 may be found in FIGS. 6A-6O.

Electrosurgical unit 14 can include a delay mechanism, such as a timer, to automatically keep the fluid flow on for several seconds after the RF power is deactivated to provide a post-treatment cooling. Electrosurgical unit 14 can also include a delay mechanism, such as a timer, to automatically turn on the fluid flow up to several seconds before the RF power is activated to inhibit the possibility of undesirable effects as tissue desiccation, electrode sticking, char formation and smoke production.

Electrosurgical unit 14 is particularly configured for use with bipolar devices. With a bipolar device, an alternating current electrical circuit is created between the first and second electrical poles of the device. An exemplary bipolar electrosurgical device of the present invention which may be used in conjunction with electrosurgical unit 14 of the present invention is shown at reference character 30a in FIG. 7. While various electrosurgical devices of the present invention are described herein with reference to use with electrosurgical unit, it should be understood that the description of the combination is for purposes of illustrating the system of the invention. Consequently, it should be understood that while the electrosurgical devices disclosed herein may be preferred for use with electrosurgical unit, it may be plausible to use other electrosurgical devices with electrosurgical unit such as monopolar devices, or it may be plausible to use the electrosurgical devices disclosed herein with another electrosurgical unit.

As shown, exemplary bipolar electrosurgical device 30a comprises two, preferably parallel, stationary arms 100a, 100b, which comprise rigid, self-supporting, hollow shafts 102a, 102b. Shafts 102a, 102b preferably comprise thick walled hypodermic stainless steel tubing. In this manner, the shafts 102a, 102b have sufficient rigidity to maintain their form during use of device 30a without kinking or significant bending.

Device 30a further comprises a proximal handle comprising mating handle portions 104a, 104b and arm tip portions as shown by circles 106a, 106b. Handle 104a, 104b is preferably made of a sterilizable, rigid, non-conductive material, such as a polymer (e.g., polycarbonate). Also, handle is preferably configured slender, along with the rest of the device, to facilitate a user of the device to hold and manipulate the device like a pen-type device. As indicated above, device 30a also comprises a flexible fluid delivery tubing 28 which is connectable to fluid source 22, preferably via a spike located at the end of drip chamber 26, and a cable 34 which is connectable to electrosurgical unit 14, which respectively provide fluid and RF power to arm tip portions 106a, 106b.

In this embodiment, cable 34 of device 30a comprises two insulated wires 34a, 34b connectable to electrosurgical unit 14 via two banana (male) plug connectors 37a, 37b. The banana plug connectors 37a, 37b are each assembled with wires 34a, 34b within the housings of plugs 36a, 36b. Wire conductors 35a, 35b of insulated wires 34a, 34b are connected distally to semi-circular terminals 39a, 39b which snap connect to a proximal portion of shafts 102a, 102b.

Arm tip portions 106a, 106b are retained in position relative to each other by a mechanical coupling device comprising a collar 108 and inhibited from separating relative to each other. As shown collar 108 comprises a polymer (e.g., acrylonitrile-butadiene-styrene or polycarbonate) and is located on the distal portion of arms 100a, 100b proximal the distal ends of the shafts 102a, 102b. Preferably the collar 108 comprises two apertures 112a, 112b, shown as opposing C-shapes, configured to receive a portion of the shafts 102a, 102b which are preferably snap-fit therein. Once the collar 108 is connected to the shafts 102a, 102b, preferably by a snap-fit connection, the collar 108 may be configured to slide along the length of the shafts 102a, 102b as to adjust or vary the location of the collar 108 on the shafts 102a, 102b. Alternatively, the location of the collar 108 may be fixed relative to the shafts 102a, 102b by welding, for example.

As shown in FIG. 7, arms 100a, 100b of device 30a are identical. At the end of arms 100a, 100b, device 30a comprises two side-by-side, spatially separated (by empty space) contact elements preferably comprising electrodes 114a, 114b which, as shown, comprise solid metal balls having a smooth, uninterrupted surface, the detail of which may be seen in FIG. 11.

Figure 9:
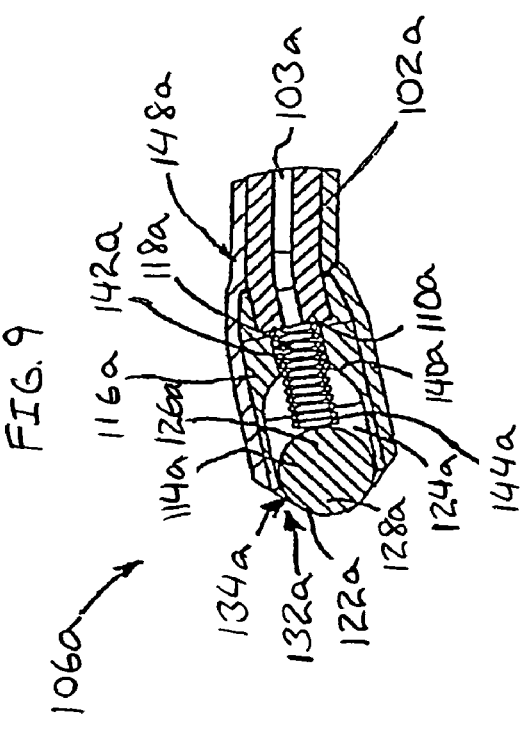
FIG. 9 is a close-up longitudinal cross-sectional view of the tip portion of the arm shown in FIG. 8 taken along line 9-9 of FIG. 10.
Figure 10:
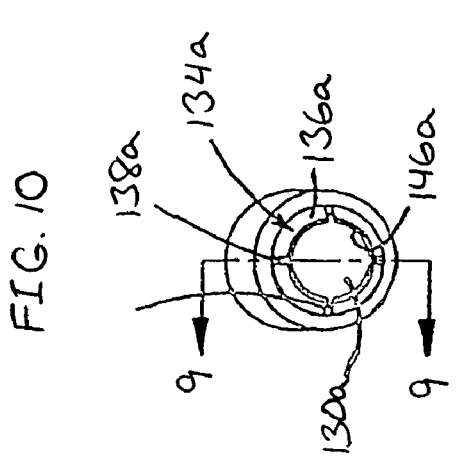
FIG. 10 is a distal end view of the arm shown in FIG. 8.
Figure 8:
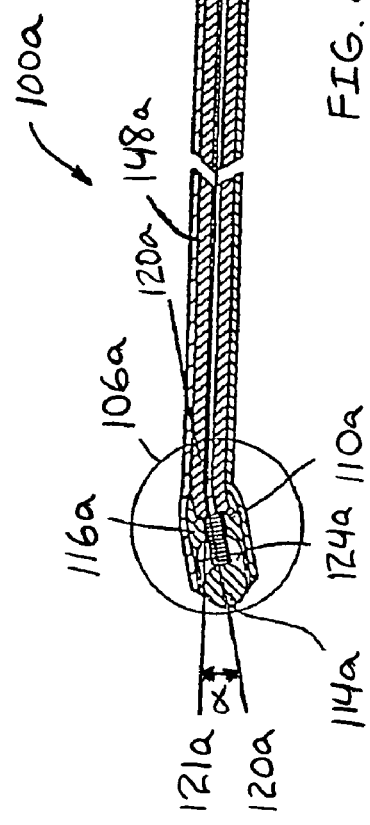
FIG. 8 is a longitudinal cross-sectional view of one arm of the device of FIG. 7.

FIGS. 8-10 show various views of an arm 100a of device 30a. Give the arms 100a, 100b are identical, the following description from arm 100a applies equally to arm 100b.

As best shown in FIGS. 8 and 9, tip portion 106a of arm 100a comprises a sleeve 116a having a uniform diameter along its longitudinal length, a spring 118a and a distal portion of shaft 102a. As shown in FIG. 8 the longitudinal axis 120a of the tip portion 106a may be configured at an angle α relative to the longitudinal axis of the proximal remainder of shaft 102a. Preferably, angle α is about 5 degrees to 90 degrees, and more preferably, angle α is about 8 degrees to 45 degrees.

As shown in FIGS. 8 and 9, electrode 114a comprises has a spherical shape with a corresponding spherical surface, a portion 122a of which is exposed to tissue at the distal end of device 30a. When electrode 114a is in the form of a sphere, the sphere may have any suitable diameter. Typically, the sphere has a diameter in the range between and including about 1 mm to about 7 mm, although it has been found that when a sphere is larger than about 4 mm or less than about 2 mm tissue treatment can be adversely effected (particularly tissue treatment time) due to an electrode surface that is respectively either to large or to small. Thus, preferably the sphere has a diameter in the range between and including about 2.5 mm to about 3.5 mm and, more preferably, about 3 mm.

It is understood that shapes other than a sphere can be used for the contact element. Examples of such shapes include oblong or elongated shapes. However, as shown in FIG. 8, preferably a distal end surface of the arm 100a provides a blunt, rounded surface which is non-pointed and non-sharp as shown by electrode 114a.

As shown in FIGS. 8 and 9, electrode 114a, is preferably located in a cavity 124a of cylindrical sleeve 116a providing a receptacle for electrode 114a. Among other things, sleeve 116a guides movement of electrode 114a, and also functions as a housing for retaining electrode 114a.

Also as shown in FIG. 9, a portion 126a of electrode 114a is retained within cavity 124a while another portion 128a extends distally through the fluid outlet opening provided by circular fluid exit hole 130a. Also as shown, sleeve 116a is connected, preferably via welding with silver solder, to the distal end 110a of shaft 102a. For device 30a, electrode 114a, sleeve 116a and shaft 102a preferably comprise an electrically conductive metal, which is also preferably non-corrosive. A preferred material is stainless steel. Other suitable metals include titanium, gold, silver and platinum. Shaft 102a preferably is stainless steel hypo-tubing.

Returning to cavity 124a, the internal diameter of cavity 124a surrounding electrode 114a is preferably slightly larger than the diameter of the sphere, typically by about 0.25 mm. This permits the sphere to freely rotate within cavity 124a. Consequently, cavity 124a of sleeve 116a also preferably has a diameter in the range of about 1 mm to about 7 mm.

As best shown in FIGS. 9 and 10, in order to retain electrode 114a, within the cavity 124a of sleeve 116a, preferably the fluid exit hole 130a, which ultimately provides a fluid outlet opening, of cavity 124a at its distal end 132a comprises a distal pinched region 134a which is reduced to a size smaller than the diameter of electrode 114a, to inhibit escape of electrode 114a from sleeve 116a. More preferably, the fluid exit hole 130a has a diameter smaller than the diameter of electrode 114a.

As best shown in FIG. 10, fluid exit hole 130a preferably has a diameter smaller than the diameter of electrode 114a, which can be accomplished by at least one crimp 136a located at the distal end 132a of sleeve 116a which is directed towards the interior of sleeve 116a and distal to the portion 126a of electrode 114a confined in cavity 124a. Where one crimp 136a is employed, crimp 136a may comprise a single continuous circular rim pattern. In this manner, the contact element portion extending distally through the fluid outlet opening (i.e., electrode portion 128a) provided by fluid exit hole 130a has a complementary shape to the fluid outlet opening provided by fluid exit hole 130a, here both circular.

As shown in FIG. 10, crimp 136a may have a discontinuous circular rim pattern where crimp 136a is interrupted by at least one rectangular hole slot 138a formed at the distal end 132a of sleeve 116a. Thus, the fluid outlet opening located at the distal end of the device 30a may comprise a first portion (e.g., the circular fluid exit hole portion 130a) and a second portion (e.g., the slot fluid exit hole portion 138a). As shown in FIG. 10, crimp 136a comprises at least four crimp sections forming a circular rim pattern separated by four discrete slots 138a radially located there between at 90 degrees relative to one another and equally positioned around the fluid outlet opening first portion. Slots 138a are preferably used to provide a fluid outlet opening or exit adjacent electrode 114a, when electrode 114a is fully seated (as discussed below) and/or when electrode 114a is not in use (i.e., not electrically charged) to keep surface portion 122a of the electrode surface of electrode 114a wet. Preferably, slots 138a have a width in the range between and including about 0.1 mm to 1 mm, and more preferably about 0.2 mm to 0.3 mm. As for length, slots 138a preferably have a length in the range between and including about 0.1 mm to 1 mm, and more preferably bout 0.4 mm to 0.6 mm.

Turning to the proximal end of the tip (comprising electrode 114a, sleeve 116a and spring 118a) of the device 30a, as shown in FIG. 9, preferably the portion of sleeve 116a proximal to electrode 114a, also has a proximal pinched region 140a which retains electrode 114a in the cavity 124a of sleeve 116a and inhibits escape of electrode 114a from the cavity 124a of sleeve 116a, such as a diameter smaller than the diameter of electrode 114a.

While distal pinched region 134a and proximal pinched region 140a may be used solely to support electrode 114a, in its position of use, the electrode may be further supported by a compression spring 118a as shown in FIG. 7. The use of spring 118a is preferred to provide a variable length support within the working length of the spring 118a for overcoming manufacturing tolerances (e.g., length) between the fixed supports (i.e., pinched regions 134a and 140a) of sleeve 116a. As for maintaining proper location of the spring 118a, sleeve 116a also comprises a lumen 142a as shown in FIG. 9, which, in addition to providing a direct passage for fluid, provides a guide tube for spring 118a.

In addition to the above, spring 118a provides a multitude of functions and advantages. For example, the configuration of the distal pinched region 134a, proximal pinched region 140a and spring 118a offers the ability to move electrode 114a distally and proximally within sleeve 116a. As shown in FIG. 9, spring 118a is located proximal to electrode 114a between a first load bearing surface comprising the electrode surface 144a and a second load bearing surface comprising the distal end 110a of shaft 102a. In this manner, spring 118a can be configured to provide a decompression force to seat electrode 114a against the distal pinched region 134a, in this case the perimeter edge 146a of crimp 136a, prior to use of electrosurgical device 30a.

Conversely, upon application of electrode 114a against a surface of tissue with sufficient force to overcome the compression force of the spring 118a, spring 118a compresses and electrode 114a retracts proximally away from distal pinched region 134a, in this case perimeter edge 146a of crimp 136a, changing the position thereof. In the above manner, the contact element comprising electrode 114a is retractable into the cavity 124a of the housing provided by sleeve 116a upon the application of a proximally directed force against surface 122a of the portion 128a of electrode 114a extending distally beyond the distal opening 130a located at the distal end 132a of the housing and spring 118a functions as a retraction biasing member.

By making electrode 114a positionable in the above manner via spring 118a, electrosurgical device 30a can be provided with a declogging mechanism. Such a mechanism can retract to provide access for unclogging fluid exit holes (e.g., 130a and 138a), which may become flow restricted as a result of loose debris (e.g., tissue, blood, coagula) becoming lodged therein. For example, when a biasing force, such as from a handheld cleaning device (e.g., brush) or from pushing the distal tip against a hard surface such as a retractor, is applied to surface 122a of electrode 114a which overcomes the compression force of the spring 118a causing the spring 118a to compress and electrode 114a to retract, the tip of the handheld cleaning device may by extended into the fluid exit hole 130a for cleaning the fluid exit hole 130a, perimeter edge 146a and slot 138a. Stated another way, electrode 118a, which can be positioned as outlined, provides a methodology for declogging a fluid exit hole by increasing the cross-sectional area of the fluid exit hole to provide access thereto.

Additionally, in various embodiments of device 30a, spring 118a comprises an electrical conductor, particularly when electrode 114a, is retracted to a non-contact position (i.e., not in contact) with sleeve 116a.

In other embodiments, proximal pinched region 140a may comprise one or more crimps similar to distal pinched region 134a, such that electrode 114a is retained in sleeve 116a both distally and proximally by the crimps. Also, in other embodiments, sleeve 116a may be disposed within shaft 102a rather than being connected to the distal end 110a of shaft 102a. Also, in still other embodiments, sleeve 116a may be formed unitarily (i.e., as a single piece or unit) with shaft 102a as a unitary piece.

In locations where shaft 102a and sleeve 116a are electrically conductive (for device 30a, preferably shaft 102a and sleeve 116a are completely electrically conductive and do not comprise non-conductive portions), an electrical insulator 148a (i.e., comprising non-conductive or insulating material) preferably surrounds shaft 102a and sleeve 116a along substantially its entire exposed length (e.g., the portion outside the confines of the handle 104a, 104b), terminating a short distance (e.g., at the proximal onset of crimp 136a or less than about 3 mm) from distal end 132a of sleeve 116a. Insulator 148a preferably comprises a shrink wrap polymer tubing.

In some embodiments, shaft 102a may be made of an electrical non-conducting material except for a portion at its distal end 110a that comes in contact with sleeve 116a. This portion of shaft 102a that contacts sleeve 116a should be electrically conducting. In this embodiment, the wire conductor 35a of insulated wire 34a extends to this electrically conducting portion of shaft 102a. In still other embodiments, shaft 102a may completely comprise a non-conducting material as where the wire conductor 35a from insulated wire 34a extends directly to sleeve 116a.

Figure 11:
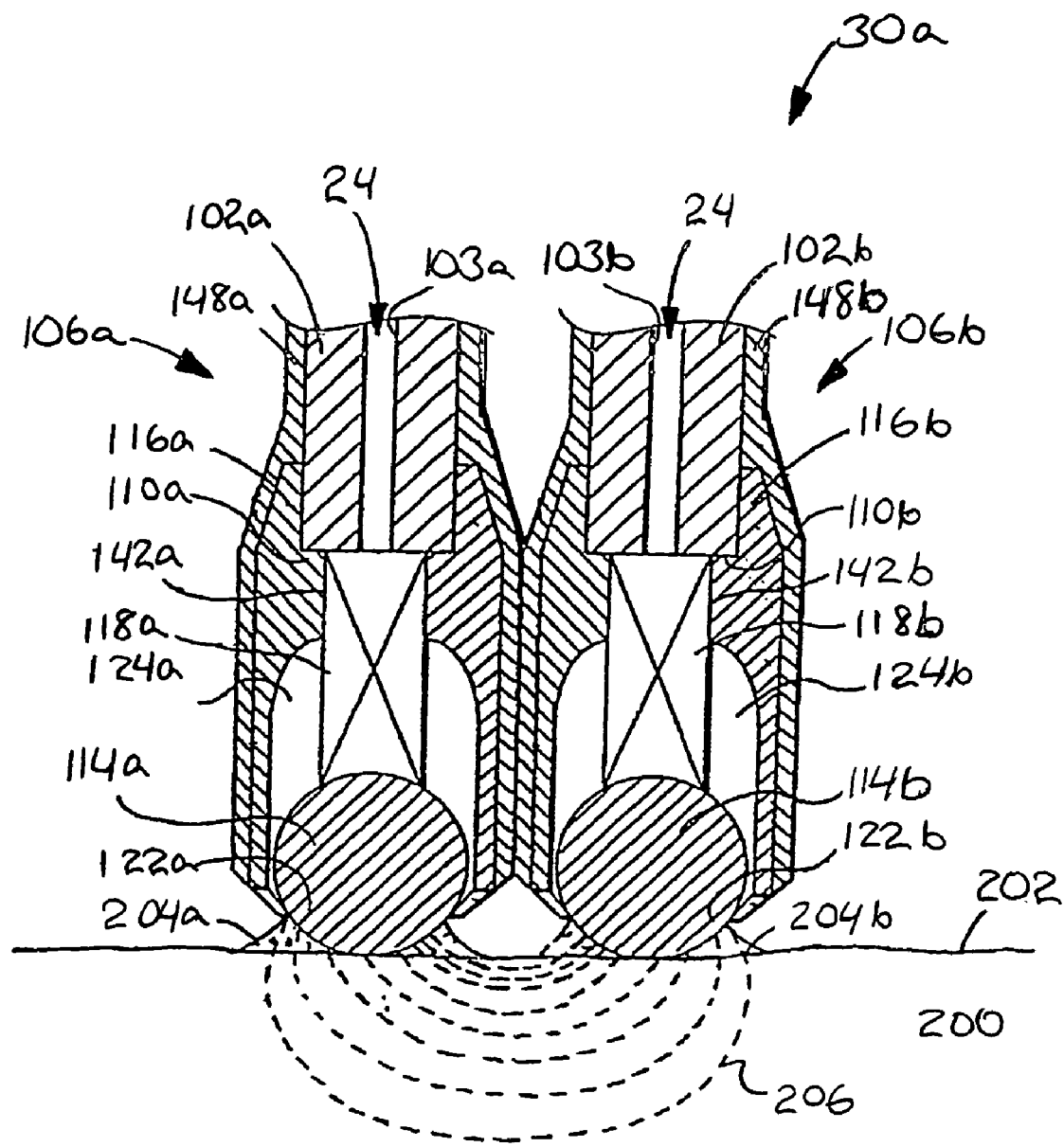
FIG. 11 is a close-up cross-sectional view of the tip portion of FIG. 7 assembled with a fluid coupling to a tissue surface of tissue.

As shown in FIG. 11, when device 30a is in use electrodes 114a, 114b are laterally spaced adjacent tissue surface 202 of tissue 200. Electrodes 114a, 114b are connected to electrosurgical unit 14 to provide RF power and form an alternating current electrical field in tissue 200 located between electrodes 114a and 114b. In the presence of alternating current, the electrodes 114a, 114b alternate polarity between positive and negative charges with current flow from the positive to negative charge. Without being bound to a particular theory, heating of the tissue is performed by electrical resistance heating. That is, the temperature of the tissue increases as a result of electric current flow through the tissue, with the electrical energy being absorbed from the voltage and transformed into thermal energy (i.e., heat) via accelerated movement of ions as a function of the tissue's electrical resistance.

During use of device 30a, fluid 24 from the fluid source 22 is first communicated through lumen 29 of delivery tubing 28. Delivery tubing 28 preferably feeds into an inlet lumen of a Y-splitter 150 (as shown in FIG. 7) which is in fluid communication with two outlet lumens therein to provide fluid communication to the lumens 154a, 154b of delivery tubing 152a, 152b to feed each arm 100a, 100b. Thereafter, the lumens 154a, 154b are preferably interference fit over the outside diameter of shafts 102a, 102b to provide a press fit seal there between. An adhesive may be used there between to strengthen the seal. Fluid 24 is then communicated down lumens 103a, 103b of shafts 102a, 102b through lumens 142a, 142b and cavities 124a, 124b of sleeves 116a, 116b where it is expelled from around and on the exposed surfaces 122a, 122b of electrodes 114a, 114b. This provides wet electrodes for performing electrosurgery.

The relationship between the material for electrodes 114a, 114b and their surfaces, and fluid 24 throughout the various embodiments should be such that the fluid 24 wets the surface of the electrodes 114a, 114b. Contact angle, θ, is a quantitative measure of the wetting of a solid by a liquid. It is defined geometrically as the angle formed by a liquid at the three phase boundary where a liquid, gas and solid intersect. In terms of the thermodynamics of the materials involved, contact angle θ involves the interfacial free energies between the three phases given by the equation $$\gamma_{LV} \cos\theta = \gamma_{SV} - \gamma_{SL}$$

where $\gamma_{LV}$, $\gamma_{SV}$ and $\gamma_{SL}$ refer to the interfacial energies of the liquid/vapor, solid/vapor and solid/liquid interfaces, respectively. If the contact angle θ is less than 90 degrees the liquid is said to wet the solid. If the contact angle is greater than 90 degrees the liquid is non-wetting. A zero contact angle θ represents complete wetting. Thus, preferably the contact angle is less than 90 degrees.

As shown in FIG. 11, during use of electrosurgical device 30a fluid couplings 204a, 204b preferably comprise discrete, localized webs and, as shown, typically form a triangular shaped webs or bead portions providing a film of fluid 24 between surface 202 of tissue 200 and electrodes 114a, 114b. When the user of electrosurgical device 30a places electrodes 114a, 114b at a tissue treatment site and moves electrodes 114a, 114b across the surface 202 of the tissue 200, fluid 24 is expelled around and on surfaces 122a, 122b of electrodes 114a, 114b at the distal ends 132a, 132b of sleeves 116a, 116b and onto the surface 202 of the tissue 200 via couplings 204a, 204b. At the same time, RF electrical energy, shown by electrical field lines 206, is provided to tissue 200 at tissue surface 202 and below tissue surface 202 into tissue 200 through fluid couplings 204a, 204b.

The fluid 24, in addition to providing an electrical coupling between electrosurgical device 30a and tissue 200, lubricates surface 202 of tissue 200 and facilitates the movement of electrodes 114a, 114b across surface 202 of tissue 200. During movement of electrodes 114a, 114b, electrodes 114a, 114b typically slide across surface 202 of tissue 200, but also may rotate as electrode 114a, 114b move across surface 202 of tissue 200. Typically the user of the electrosurgical device 30a slides electrodes 114a, 114b across surface 202 of tissue 200 back and forth with a painting motion while using fluid 24 as, among other things, a lubricating coating. In certain embodiments, the thickness of the fluid 24 between the distal end surface of electrodes 114a, 114b and surface 202 of tissue 200 at the outer edge of the couplings 204a, 204b is in the range between and including about 0.05 mm to 1.5 mm. Also, in certain embodiments, the distal end tips of electrodes 114a, 114b may contact surface 202 of tissue 200 without any fluid 24 in between.

To better inhibit fluid from the treatment site from inadvertently flowing into the handle 104a, 104b of device 30a, each arm 100a, 100b of device 30a may include a hollow cylindrical tubular seal 156a, 156b which forms a seal between the outer surface of insulators 148a, 148b and handle 104a, 104b. Furthermore, the proximal end portions of the tubular seals 156a, 156b, insulators 148a, 148b and shafts 102a, 102b may be received into cylindrical apertures 166a, 166b of a rubber bushing 164 to provide an additional seal.

Figure 12:
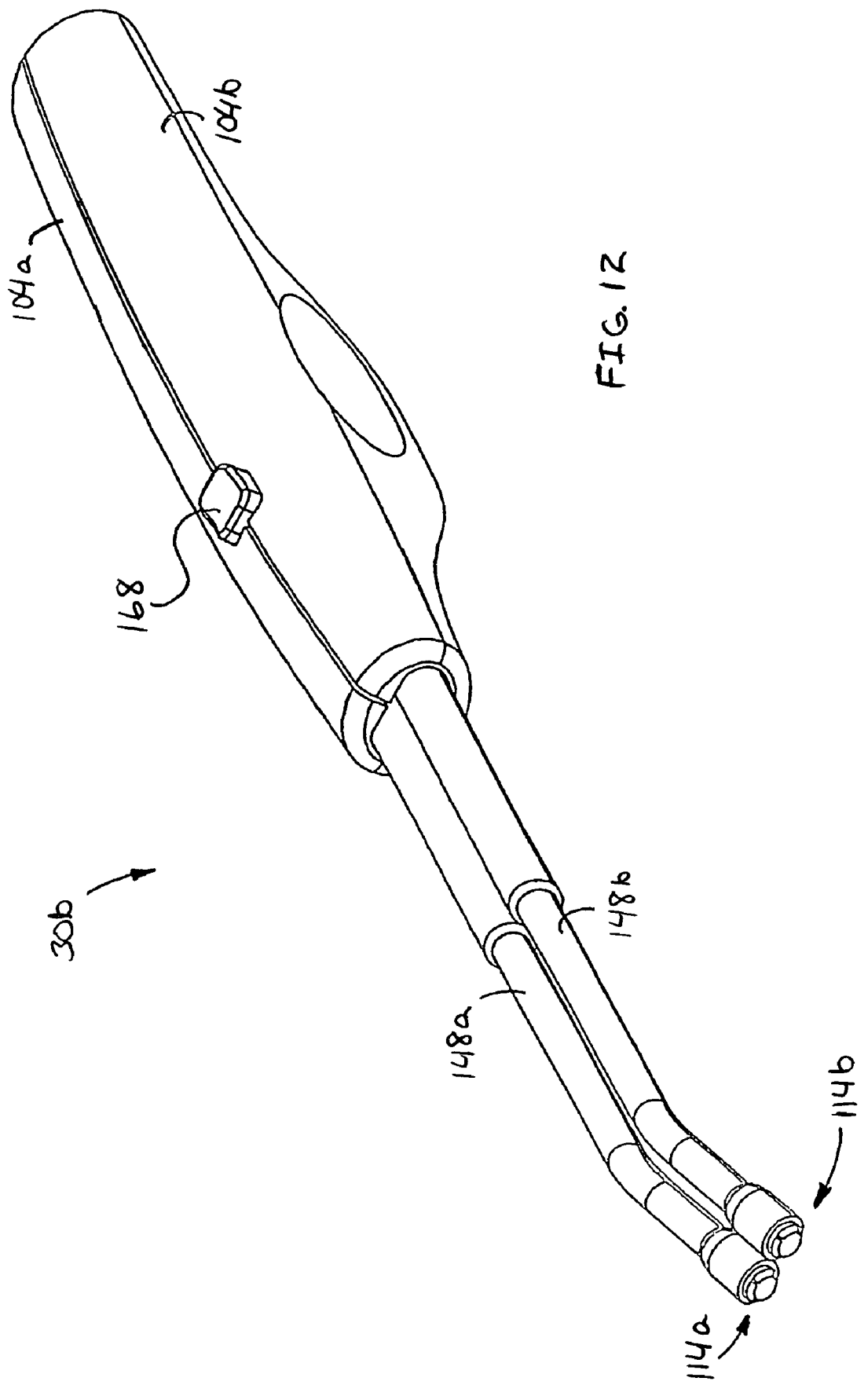
FIG. 12 is a perspective view of an alternative electrosurgical device according to the present invention.

FIG. 12 provides a perspective view of an alternative electrosurgical device according to the present invention. As shown in FIG. 12, device 30b includes a handswitch 168. Switch 168 preferably comprises a push button 169 and a dome switch 167 having two electrical contacts. The contacts preferably comprise upper and lower contacts disposed on a platform 171 in overlying relationship. Preferably the upper contact comprises a dome shaped configuration overlying and spaced from the lower contact which is flat. Preferably the contacts are spaced from one another by virtue of the domed configuration of the upper contact when the switch 168 is in an undepressed position, thus creating an open control circuit relative to switch 168. However, when the upper contact is pressed into a depressed position, the upper contact comes into contact with the lower contact thus closing the hand switch control circuit. The presence of the closed control circuit is then sensed by which then provides power to the electrodes 114a, 114b.

When a depression force is removed from the upper contact, the contact returns to its undepressed domed position as a result of its resiliency or elastic memory, thus returning switch 168 to its undepressed position and reopening the hand control circuit. The presence of the open control circuit is then sensed by electrosurgical unit 14 which then stops providing power to electrodes 114a, 114b.

In other embodiments, the tip portion 106 of the bipolar device comprises other configurations. Tip portion 106 of an exemplary bipolar electrosurgical device 30c of the present invention, which may be used in conjunction with the electrosurgical unit 14 of the present invention, is shown in FIG. 13.

Figure 13:
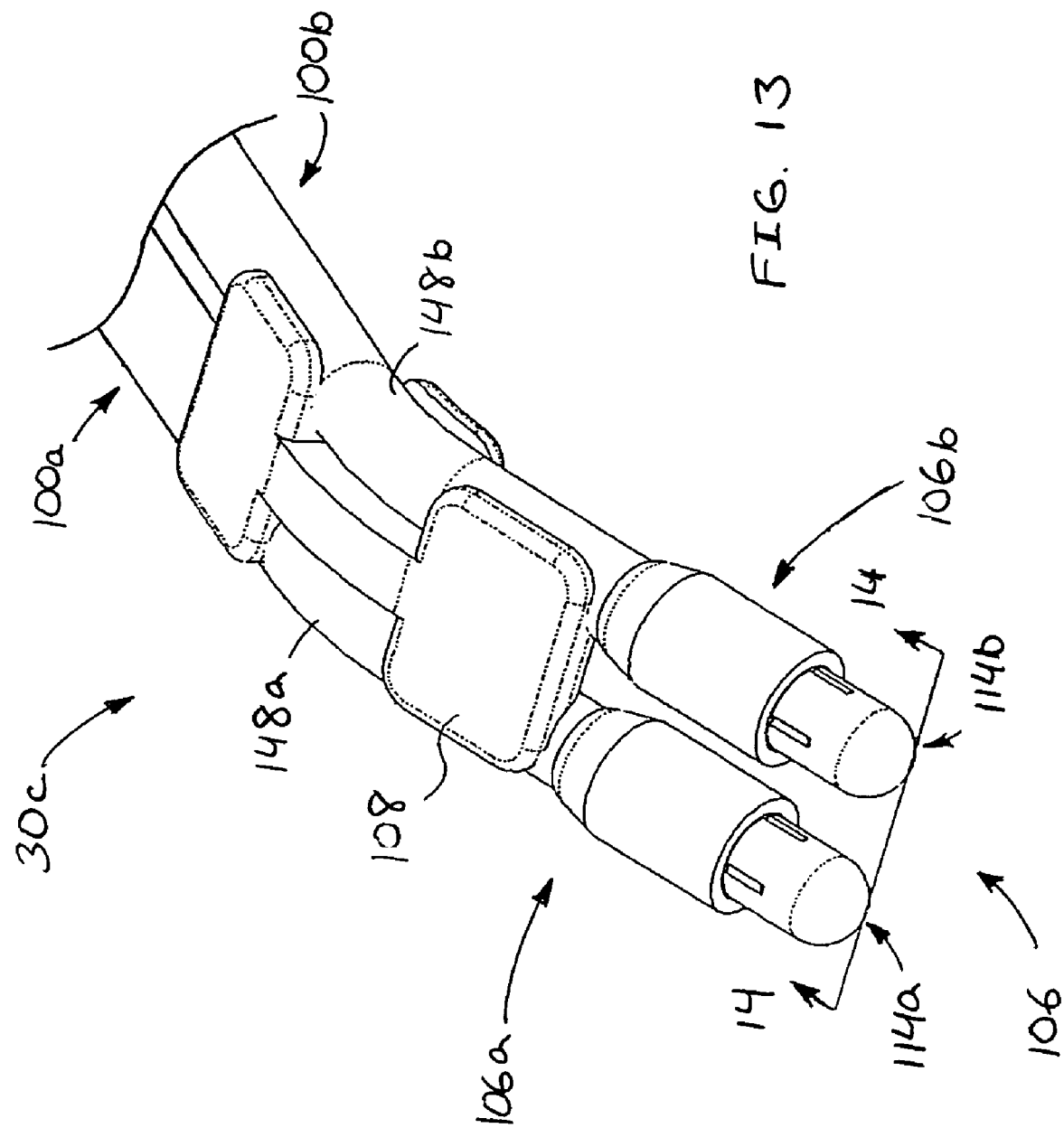
FIG. 13 is a close-up perspective view of an alternative tip portion.
Figure 14:
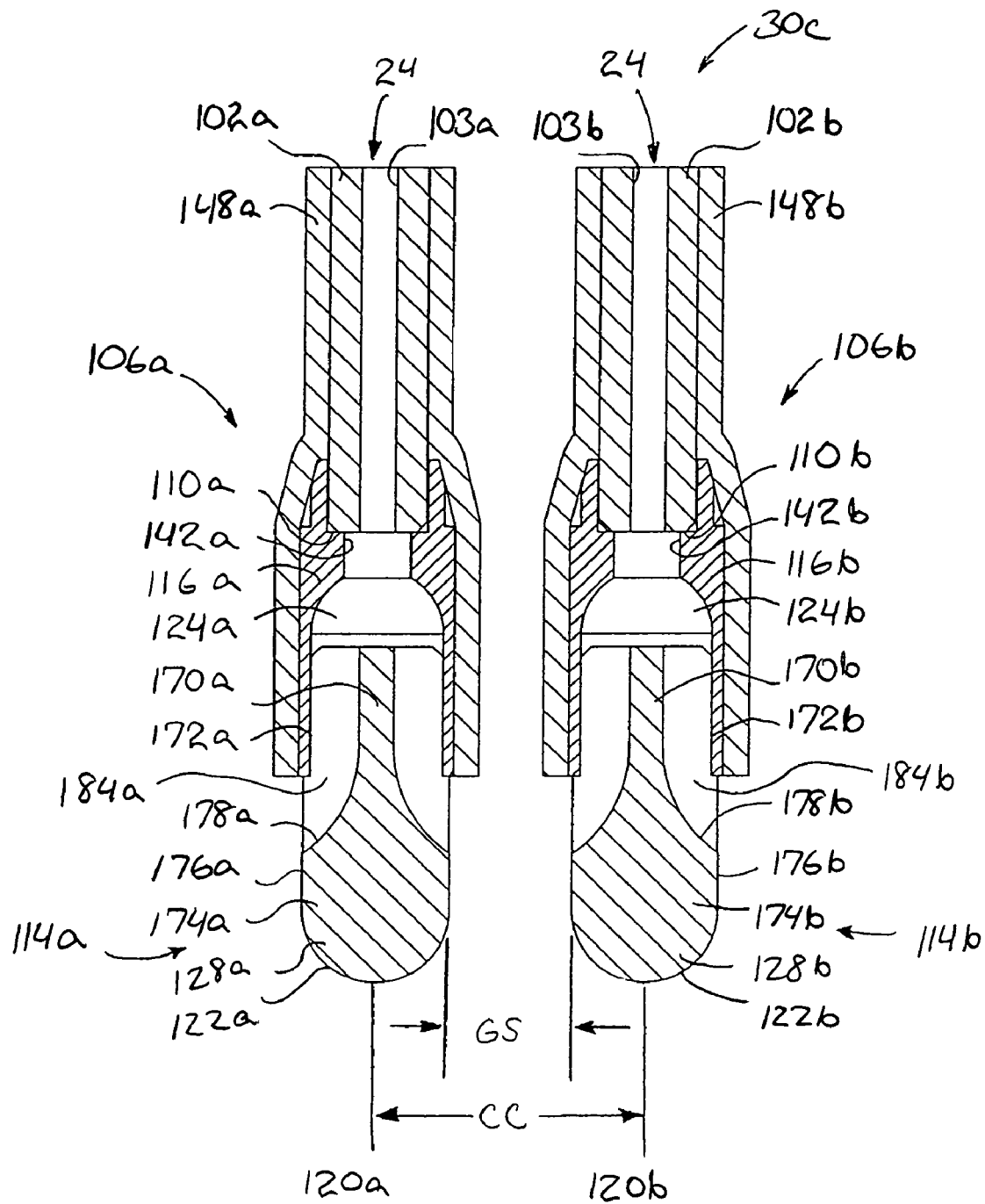
FIG. 14 is a close-up cross-sectional view of the tip portion of FIG. 13 taken along line 14-14 of FIG. 13.

As shown in FIGS. 13 and 14, similar to electrosurgical device 30a, device 30c comprises two, preferably parallel, stationary arms 100a, 100b, which comprise rigid, self-supporting, hollow shafts 102a, 102b. As with device 30a, shafts 102a, 102b preferably comprise thick walled hypodermic tubing to provide sufficient rigidity to maintain their form during use of device 30c without kinking or significant bending. Furthermore, arm tip portions 106a, 106b are retained in position relative to each other by a mechanical coupling device comprising a collar 108 and inhibited from separating relative to each other.

At the end of arms 100a, 100b, device 30c comprises two side-by-side, spatially separated (by empty space) contact elements preferably comprising electrodes 114a, 114b at the distal end of first arm tip portion 106a and second arm tip portion 106b, respectively.

As shown in FIG. 14, electrodes 114a, 114b are preferably located in cavities 124a, 124b of cylindrical sleeves 116a, 116b providing receptacles for electrodes 114a, 114b. Also as shown, sleeves 116a, 116b are connected, preferably via welding, to the distal ends 110a, 110b of shafts 102a, 102b. For device 30c, electrodes 114a, 114b, sleeves 116a, 116b, and shafts 102a, 102b are preferably made of an electrically conductive metal, which is also preferably non-corrosive. A preferred material is stainless steel. Other suitable metals may include titanium, gold, silver and platinum. Shafts 102a, 102b preferably comprise stainless steel hypo-tubing.

Electrodes 114a, 114b are preferably assembled within the cavities 124a, 124b of sleeves 116a, 116b via a mechanical press (interference) fit. In other embodiments, the electrodes 114a, 114b may be assembled to sleeves 116a, 116b by threaded engagement, adhesives and welding. In certain embodiments, electrodes 114a, 114b may be detachably assembled to sleeves 116a, 116b such that they may be removed from the sleeves 116a, 116b, preferably manually by human hand, so that device 30c may be used with multiple different contact elements/electrodes, or device 30c may be reuseable and used with disposable contact elements/electrodes.

Also as shown, electrodes 114a, 114b each preferably comprise a connector portion, preferably comprising a shank 170a, 170b which connects electrodes 114a, 114b to sleeves 116a, 116b, respectively. Among other things, the connector portion of electrodes 114a, 114b is preferably configured to form a connection with a mating connector portion of sleeves 116a, 116b. As shown, preferably the shank portions 170a, 170b are configured to extend into cavities 124a, 124b of sleeves 116a, 116b which comprise cylindrical receptacles and provide the mating connector portions for shanks 170a, 170b, respectively. More preferably, surfaces 172a, 172b of shank portions 170a, 170b are configured to mate against and form an interference fit with corresponding surfaces of cavities 124a, 124b to provide the connection, respectively. As shown, shank portions 170a, 170b are preferably cylindrical and located proximal and adjacent to cylindrical portions 174a, 174b of electrodes 114a, 114b. Shank portions 170a, 170b preferably have a diameter of about 1.6 mm.

Shank portions 170a, 170b preferably have a length in the range between and including about 2 mm to about 6 mm, and more preferably have a length in the range between and including about 2.5 mm to about 5 mm. Even more preferably, shanks 170a, 170b have a length of about 3 mm.

As shown in FIG. 14, electrodes 114a, 114b each preferably comprise a head portion with a surface devoid of edges (to provide a uniform current density) to treat tissue without cutting. As shown, electrodes 114a, 114b comprise a spherical portion 128a, 128b and a corresponding spherical surface portion 122a, 122b located at the distal end of device 30c which provide a smooth, blunt contour outer surface. More specifically, as shown, the spherical portions 128a, 128b and spherical surface portions 122a, 122b further provide a domed, hemisphere (i.e., less than a full sphere) and hemispherical surface portion comprising preferably about 180 degrees.

Also as shown, the head portion of electrodes 114a, 114b each preferably comprise a rectilinear cylindrical portion 174a, 174b and a corresponding cylindrical surface portion 176a, 176b located proximal and adjacent to the spherical portion 128a, 128b and spherical surface portion 122a, 122b, respectively.

In this embodiment, preferably cylindrical portions 174a, 174b have a diameter in the range between and including about 2.5 mm to about 5.0 mm, and more preferably have a diameter in the range between and including about 3.0 mm to about 4.0 mm, and even more preferably, about 3.5 mm.

With respect to length, preferably cylindrical portions 174a, 174b of device 30c have a length in the range between and including about 2 mm to about 6 mm, and more preferably have a length in the range between and including about 3 mm to about 5 mm. Even more preferably, cylindrical portions 174a, 174b have a length of about 4 mm.

As shown, electrodes 114a, 114b comprise at least one recess 178a, 178b which provides an elongated fluid flow channel for the distribution of fluid 24 onto and around electrodes 114a, 114b. As shown, electrodes 114a, 114b comprise a plurality of longitudinally directed recesses 178a, 178b and, more specifically, four recesses 178a, 178b equally spaced 90 degrees around the shanks 170a, 170b and a proximal portion of cylindrical portions 174a, 174b. Preferably, recesses 178a, 178b have a width in the range between and including about 0.1 mm to about 0.6 mm, and more preferably have a width of about 0.4 mm. Fluid outlet openings 184a, 184b are provided between the structure of electrodes 114a, 114b (i.e., recesses 178a, 178b) at the distal ends 110a, 110b of the shafts 102a, 102b. Consequently, fluid outlet openings 184a, 184b are partially defined by recesses 178a, 178b of electrodes 114a, 114b and partially by the distal ends 110a, 110b of the shafts 102a, 102b. The use of recesses 178a, 178b and fluid outlet openings 184a, 184b for the distribution of fluid 24 are generally preferred to the fluid outlets of devices 30a and 30b as they are proximal to the distal end of device 30c and, consequently, less apt to clog or otherwise become occluded during use of device 30c. When tissue overlies and occludes a recess for a portion of its longitudinal length, thus inhibiting fluid 24 from exiting therefrom, fluid 24 from the recess may still be expelled from device 30c after flowing longitudinally in the recess to a remote location where the recess is unoccluded and uninhibited to fluid flow exiting therefrom, or after the device is moved away from the occluding tissue.

For this embodiment, the longitudinal axes 120a, 120b of tip portions 106a, 106b and electrodes 114a, 114b are separated center-to-center CC about 6.5 mm. As a result, when cylindrical portions 174a 174b have a preferred diameter of 3.5 mm, the actual spatial gap separation GS between electrodes 114a, 114b is about 3 mm.

Figure 15:
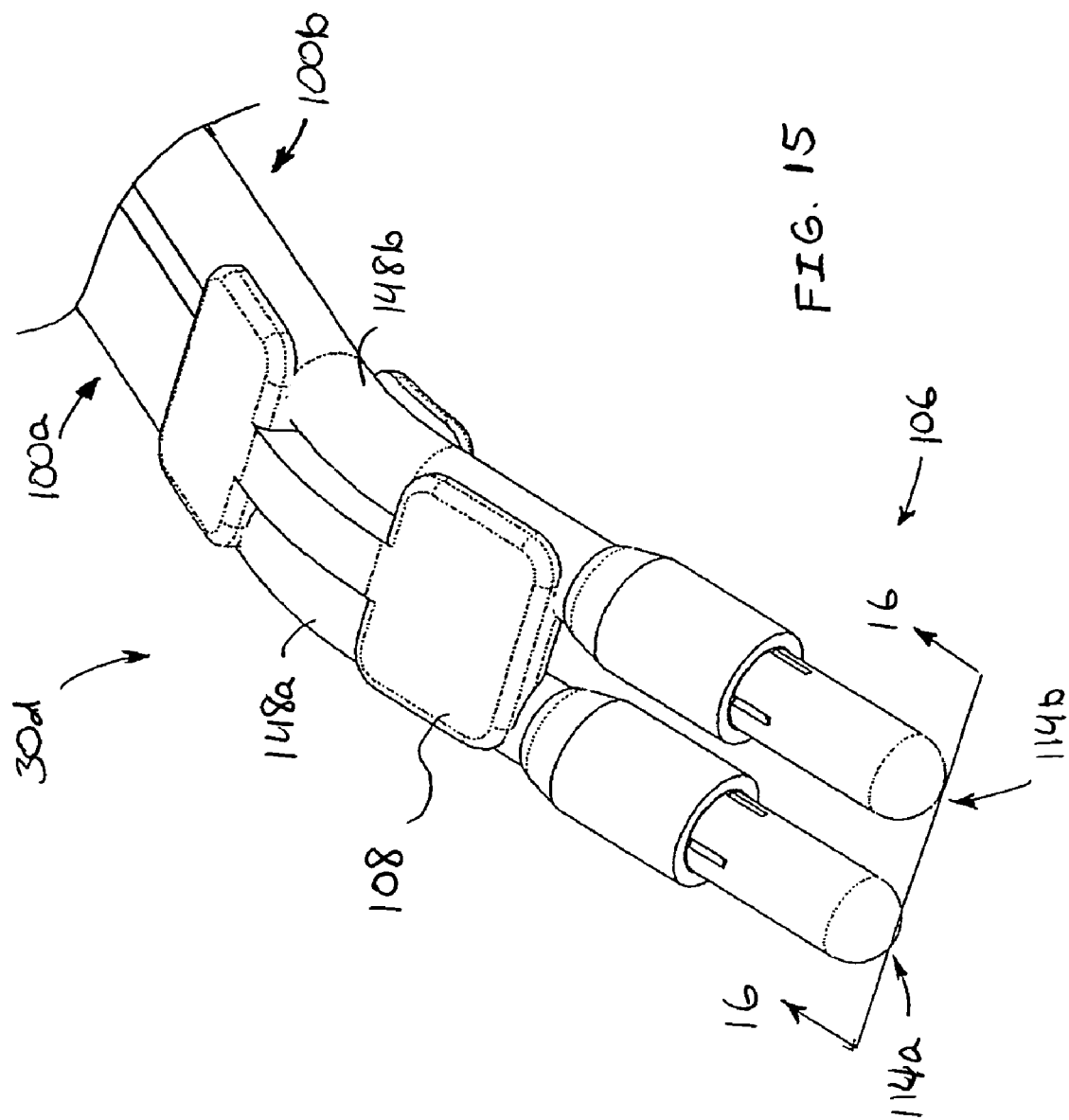
FIG. 15 is a close-up perspective view of an alternative tip portion.

A tip portion of another exemplary bipolar electrosurgical device 30d of the present invention, which may be used in conjunction with the electrosurgical unit 14 of the present invention, is shown at reference character 106 in FIG. 15.

Figure 16:
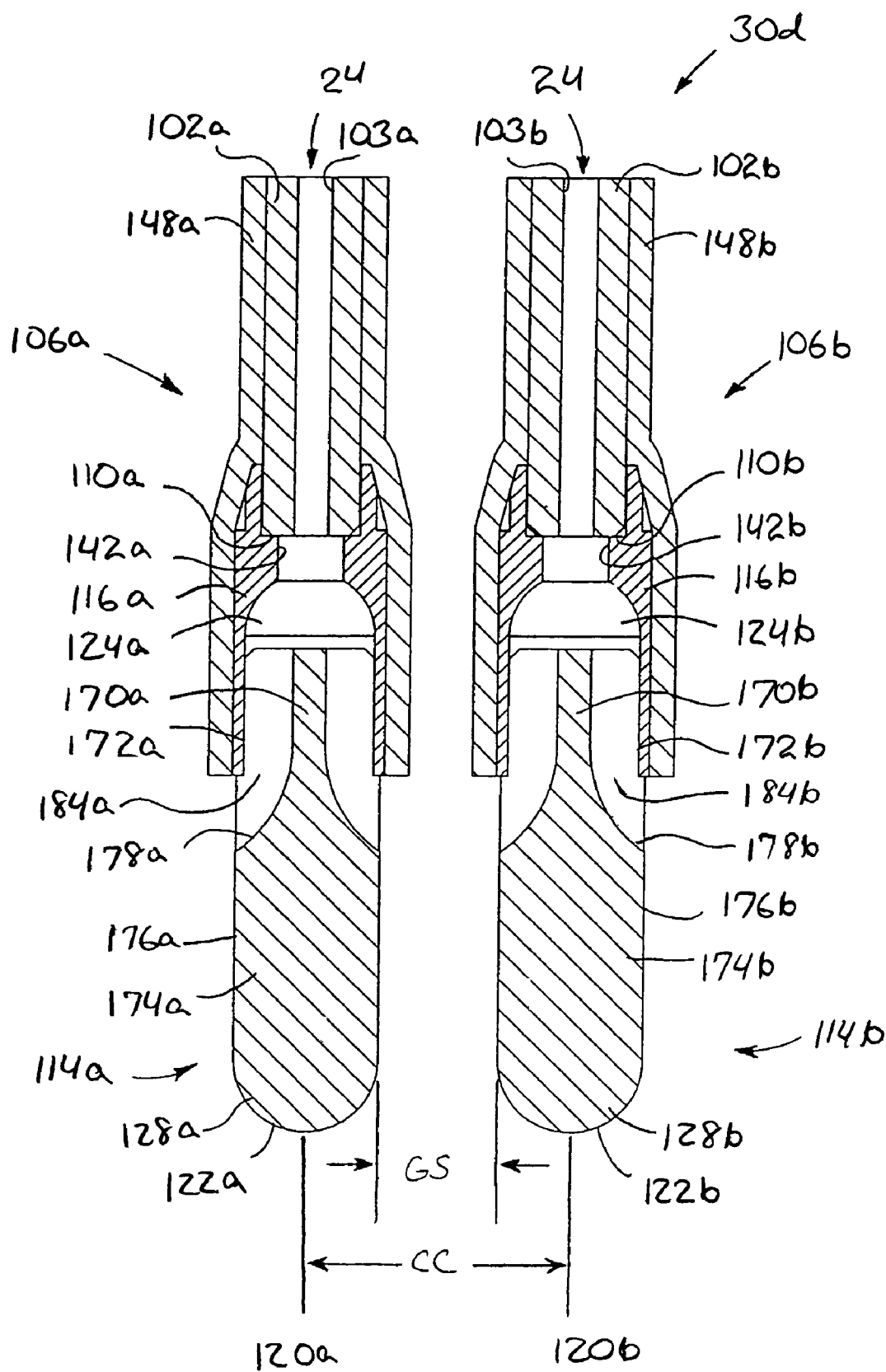
FIG. 16 is a close-up cross-sectional view of the tip portion of FIG. 15 taken along line 16-16 of FIG. 15.

As best shown in FIG. 16, in comparison with device 30c, the electrodes 114a, 114b of device 30d are of the same diameter and spacing. However, the length of electrodes 114a, 114b for device 30d are longer than the electrodes 114a, 114b of device 30c. With respect to length, preferably cylindrical portions 174a, 174b of device 30d have a length in the range between and including about 5 mm to about 10 mm, and more preferably have a length in the range between and including about 6 mm to about 8 mm. Even more preferably, cylindrical portions 174a, 174b have a length of about 7 mm.

Figure 17:
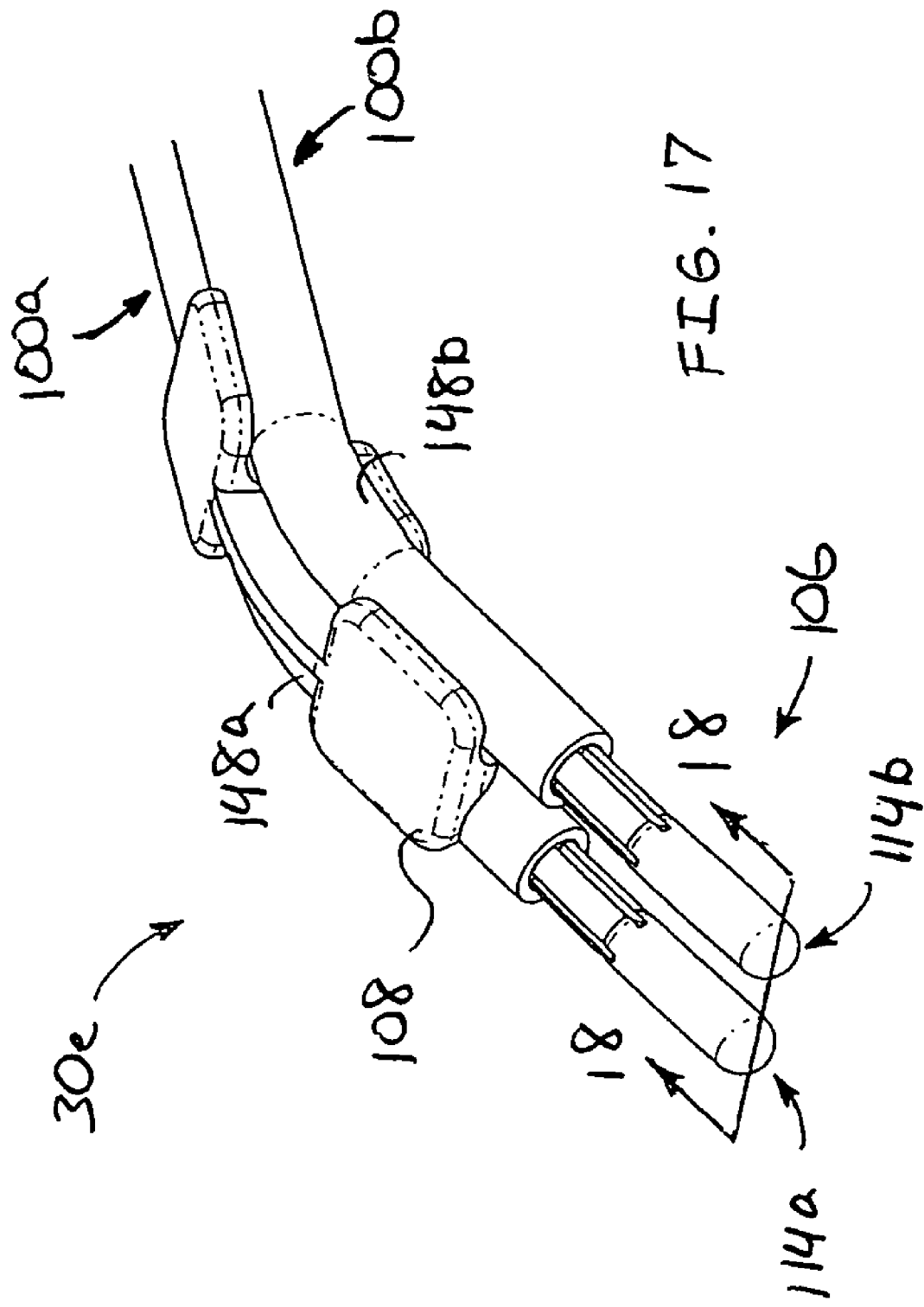
FIG. 17 is a close-up perspective view of an alternative tip portion.

A tip portion of another exemplary bipolar electrosurgical device 30e of the present invention, which may be used in conjunction with the electrosurgical unit 14 of the present invention, is shown at reference character 106 in FIG. 17.

Figure 18:
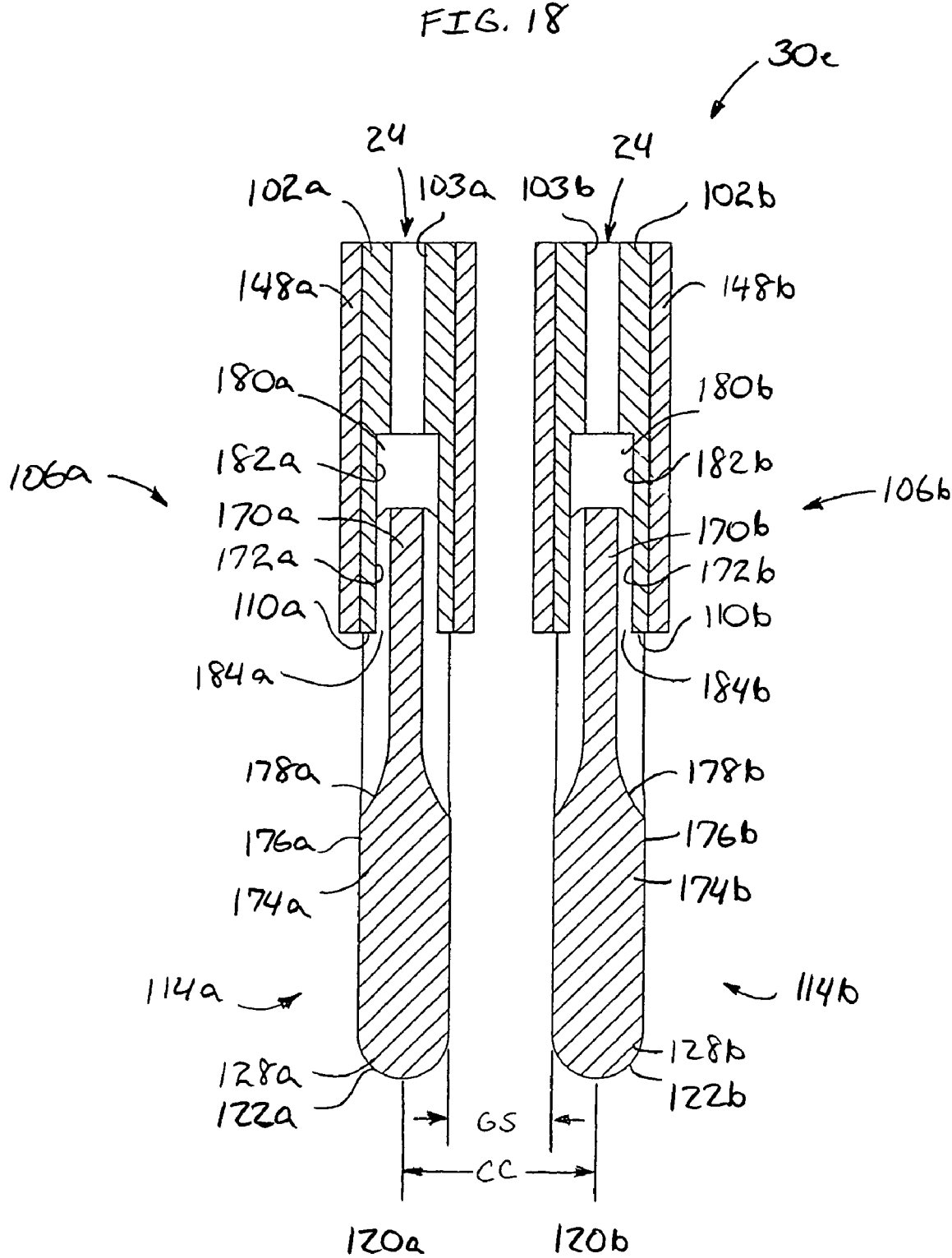
FIG. 18 is a close-up cross-sectional view of the tip portion of FIG. 17 taken along line 18-18 of FIG. 17.

As best shown in FIG. 18, the sleeves 116a, 116b used with embodiments 30a-30d have been eliminated from tip portions 106a, 106b of device 30e. Consequently, electrodes 114a, 114b are now assembled directly with shafts 102a, 102b, respectively. Electrodes 114a, 114b are preferably assembled adjacent the distal ends 110a, 110b of shafts 102a, 102b via a mechanical press (interference) fit. In other embodiments, the electrodes 114a, 114b may be assembled to shafts 102a, 102b by threaded engagement, adhesives and welding. In certain embodiments, electrodes 114a, 114b may be detachably assembled to shafts 102a, 102b such that they may be removed from the shafts 102a, 102b, preferably manually by human hand, so that device 30e may be used with multiple different contact elements/electrodes, or device 30e may be reuseable and used with disposable contact elements/electrodes.

Also as shown, electrodes 114a, 114b each preferably comprise a connector portion, preferably comprising a shank 170a, 170b which connects the electrodes 114a, 114b to shafts 102a, 102b, respectively. Among other things, the connector portion of electrodes 114a, 114b is preferably configured to form a connection with a mating connector portion of shafts 102a, 102b. As shown, preferably the shank portions 170a, 170b are configured to extend into cavities 180a, 180b of shafts 102a, 102b which comprise cylindrical receptacles and provide the mating connector portions for shanks 170a, 170b, respectively. More preferably, surfaces 172a, 172b of shank portions 170a, 170b are configured to mate against and form an interference fit with surfaces 182a, 182b of cavities 180a, 180b to provide the connection, respectively.

Electrodes 114a, 114b of device 30e comprise a spherical portion 128a, 128b and a corresponding spherical surface portion 122a, 122b located at the distal end of the device 30e which provide a smooth, blunt contour outer surface. More specifically, as shown, the spherical portions 128a, 128b and spherical surface portions 122a, 122b further provide a domed, hemisphere (i.e., less than a full sphere) and hemispherical surface portion comprising preferably about 180 degrees.

Electrodes 114a, 114b of device 30e each also comprise a rectilinear cylindrical portion 174a, 174b and a corresponding cylindrical surface portion 176a, 176b located proximal and adjacent to the spherical portion 128a, 128b and spherical surface portion 122a, 122b, respectively.

In this embodiment preferably cylindrical portions 174a, 174b have a diameter in the range between and including about 1.0 mm to about 3.5 mm, and more preferably have a diameter in the range between and including about 2.0 mm to about 2.5 mm, and even more preferably, about 2.3 mm.

With respect to length, preferably cylindrical portions 174a, 174b of device 30e have a length in the range between and including about 6 mm to about 14 mm, and more preferably have a length in the range between and including about 8 mm to about 12 mm. Even more preferably, cylindrical portions 174a, 174b have a length of about 10 mm.

As shown, electrodes 114a, 114b comprise at least one recess 178a, 178b which provides an elongated fluid flow channel for the distribution of fluid 24 onto and around electrodes 114a, 114b. As shown, electrodes 114a, 114b comprise a plurality of longitudinally directed recesses 178a, 178b and, more specifically, four recesses 178a, 178b equally spaced 90 degrees around the shanks 170a, 170b and a proximal portion of cylindrical portions 174a, 174b. Preferably, recesses 178a, 178b have a width in the range between and including about 0.1 mm to about 0.6 mm, and more preferably has a width of about 0.4 mm. Fluid outlet openings 184a, 184b are provided between the structure of electrodes 114a, 114b (i.e., recesses 178a, 178b) at the distal ends 110a, 110b of the shafts 102a, 102b.

For this embodiment, the longitudinal axes 120a, 120b of tip portions 106a, 106b and electrodes 114a, 114b are separated center-to-center CC about 4.4 mm. As a result, when cylindrical portions 174a, 174b have a preferred diameter of 2.3 mm, the actual spatial gap separation GS between electrodes 114a, 114b is about 2.1 mm.

Figure 19:
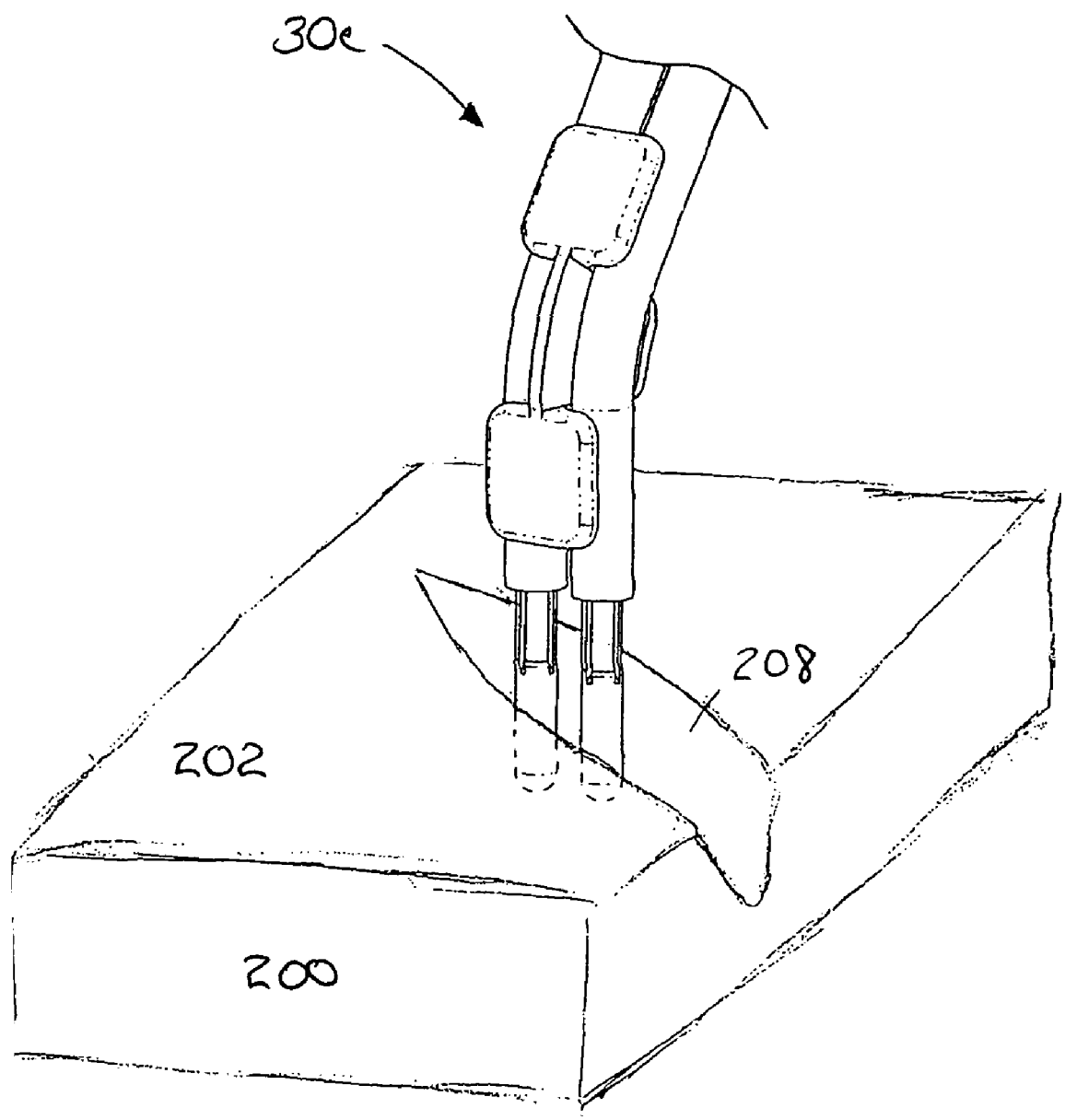
FIG. 19 is a close-up perspective view of the tip portion of FIG. 17 disposed in a tissue crevice.

As compared to devices 30c and 30d, the electrodes 114a, 114b of device 30e are longer and have a smaller diameter. Due to the longer length and narrower width of electrodes 114a, 114b, device 30e may be used in more narrow confines as compared to devices 30c and 30d. Furthermore, the corresponding longer recesses 178a, 178b and the more proximal position of fluid outlet openings 184a, 184b makes them even less apt to clog. This can be particularly advantageous where device 30e is used in narrow confines such as a tissue crevice 208 shown in FIG. 19.

Conversely, due to the larger spherical surface, devices 30c and 30d may be used to treat greater tissue surface areas than device 30e to paint over the raw, oozing surface 202 of tissue 200 to seal the tissue 200 against bleeding.

Figure 20:
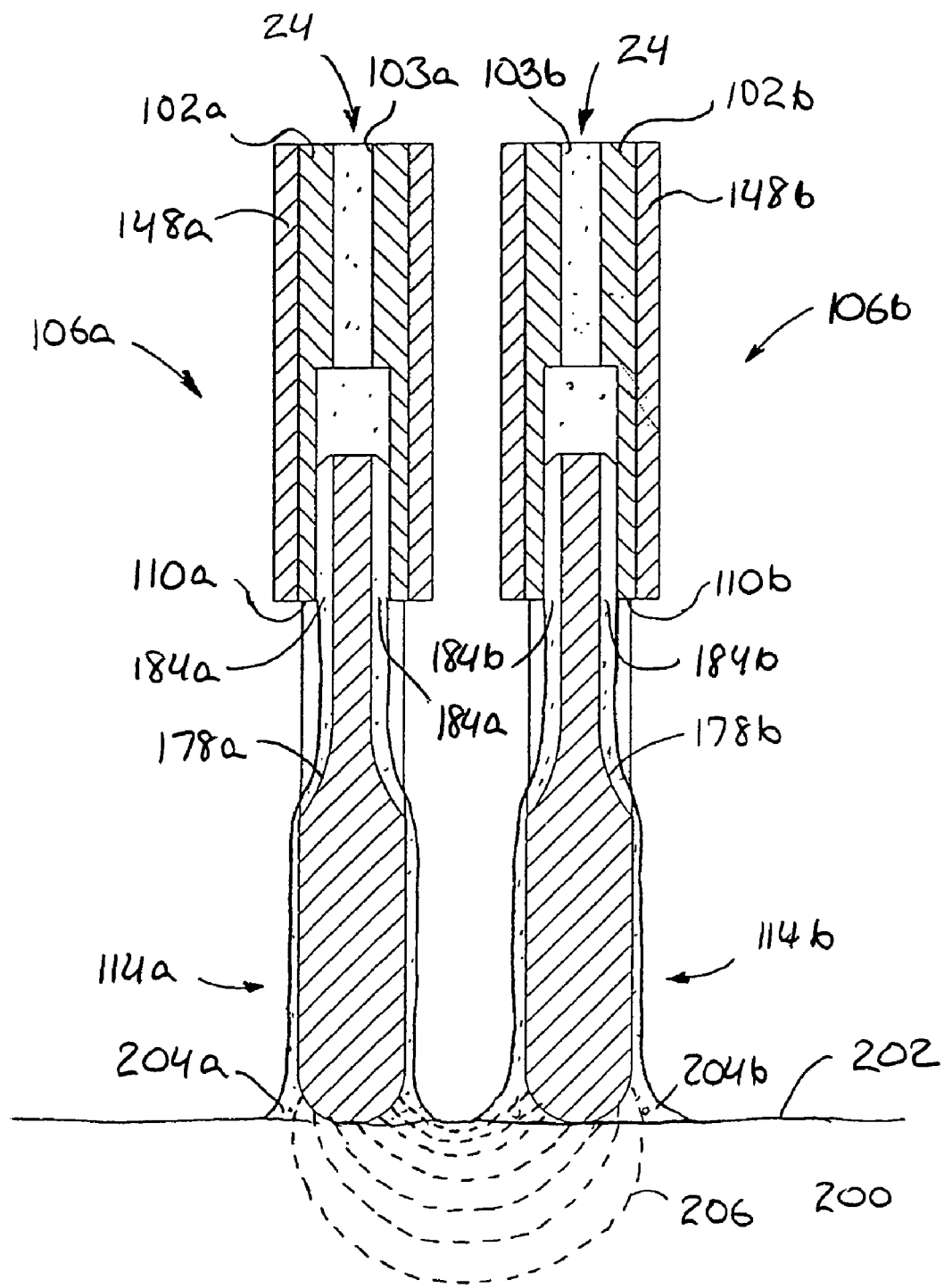
FIG. 20 is a close-up cross-sectional view of the tip portion of FIG. 17 with a fluid coupling to a tissue surface of tissue.

As shown in FIG. 20, one way in which device 30e (and similarly for devices 30c and 30d) may be used is with the longitudinal axis of electrodes 114a, 114b vertically orientated, and the spherical surfaces 122a, 122b of electrodes 114a, 114b laterally spaced adjacent tissue surface 202 of tissue 200. During use fluid 24 is communicated within the lumens 103a, 103b of the shafts 102a, 102b to recesses 178a, 178b of electrodes 114a, 114b and expelled from fluid outlet openings 184a, 184b.

As the user of device 30e places electrodes 114a, 114b at a tissue treatment site and moves electrodes 114a, 114b across surface 202 of tissue 200, fluid 24 is expelled from fluid outlet openings 184a, 184b and electrodes 114a, 114b onto surface 202 of tissue 200. At the same time, RF electrical energy, shown by electrical field lines 206, is provided to tissue 200 at tissue surface 202 and below tissue surface 202 into tissue 200 through fluid couplings 204a, 204b.

Fluid 24, in addition to providing an electrical coupling between the device 30e and tissue 200, lubricates surface 202 of tissue 200 and facilitates the movement of electrodes 114a, 114b across surface 202 of tissue 200. During movement of electrodes 114a, 114b, electrodes 114a, 114b typically slide across the surface 202 of tissue 200. Typically the user of device 30e slides electrodes 114a, 114b across surface 202 of tissue 200 back and forth with a painting motion while using fluid 24 as, among other things, a lubricating coating. Preferably the thickness of the fluid 24 between the distal end surface of electrodes 114a, 114b and surface 202 of tissue 200 at the outer edge of couplings 204a, 204b is in the range between and including about 0.05 mm to 1.5 mm. Also, in certain embodiments, the distal end tip of electrodes 114a, 114b may contact surface 202 of tissue 200 without any fluid 24 in between.

As shown in FIG. 20, fluid couplings 204a, 204b comprise discrete, localized webs and more specifically comprise triangular shaped webs or bead portions providing a film of fluid 24 between surface 202 of tissue 200 and electrodes 114a, 114b.

Figure 21:
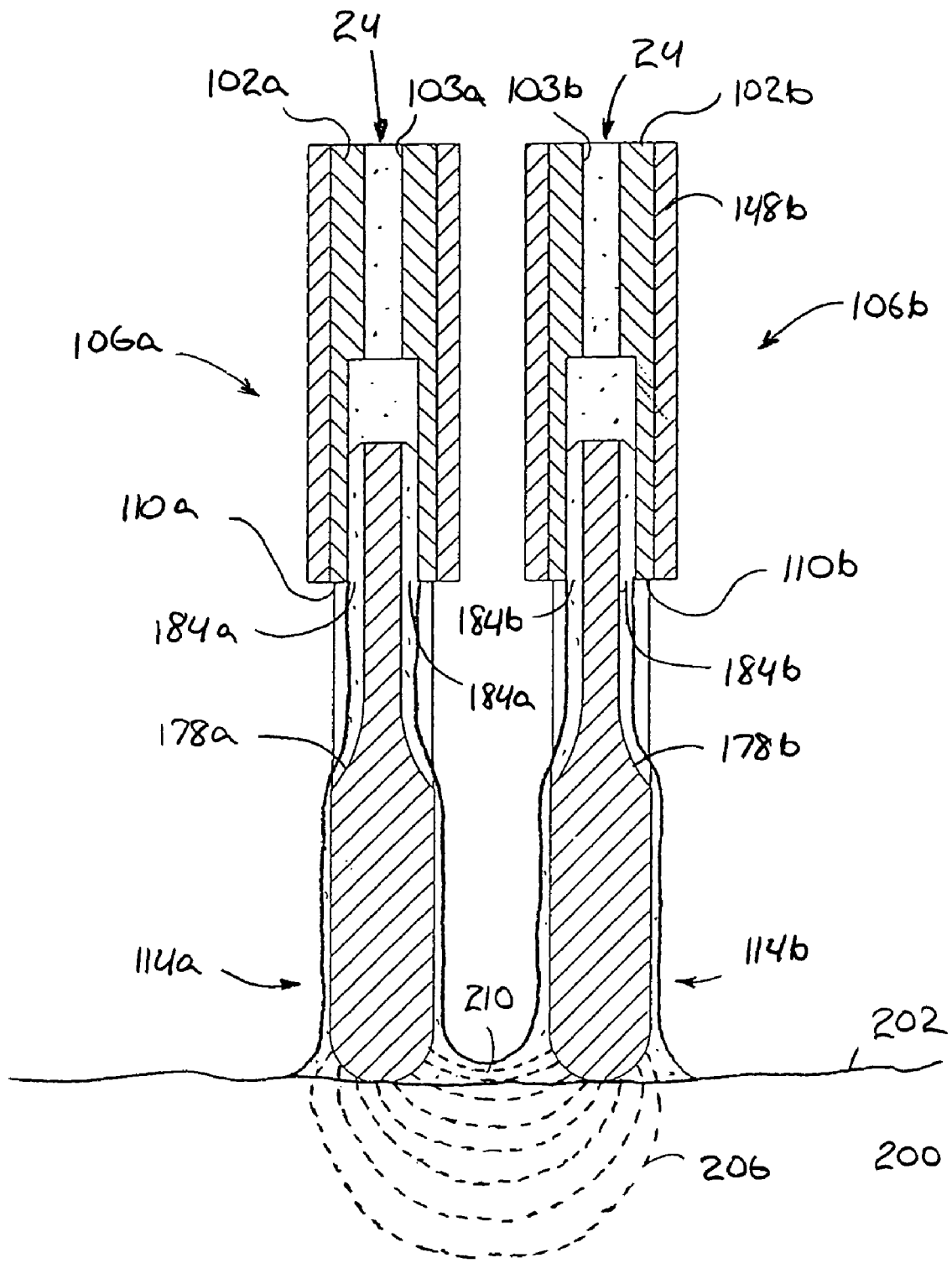
FIG. 21 is a close-up cross-sectional view of the tip portion of FIG. 17 with an alternative fluid coupling to a tissue surface of tissue.

As shown in FIG. 21, the fluid coupling for device 30e may also comprise a conductive fluid bridge 210 between electrodes 114a, 114b which rests on surface 202 of tissue 200 and forms a shunt between electrodes 114a, 114b. Given this scenario, a certain amount of RF energy may be diverted from going into tissue 200 and actually pass between electrodes 114a, 114b via the conductive fluid bridge 210. This loss of RF energy may slow down the process of coagulating and sealing the tissue and producing the desired hemostasis of the tissue.

In order to counteract the loss of energy through bridge 210, once enough energy has entered bridge 210 to boil fluid 24 of bridge 210, the loss of RF energy correspondingly decreases with the loss of bridge 210. Preferably energy is provided into fluid 24 of bridge 210 by means of heat dissipating from tissue 200.

Thus, where a high percentage of boiling of conductive fluid 24 of bridge 210 is created, the loss of RF energy through bridge 210 may either be reduced or eliminated because all the fluid 24 of bridge 210 boils off or a large fraction of boiling creates enough disruption in the continuity of bridge 210 to disrupt the electrical circuit through bridge 210.

Figure 22:
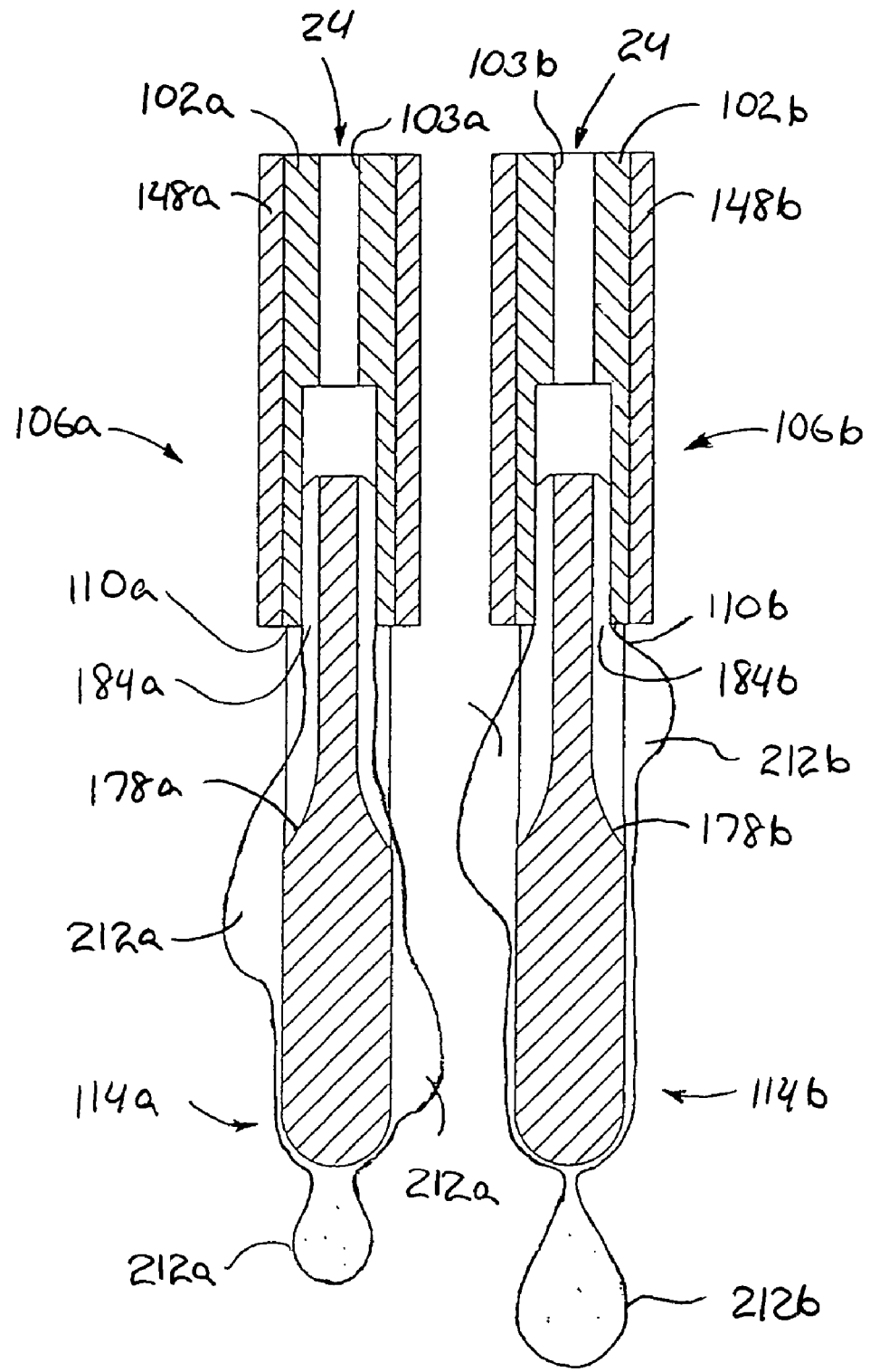
FIG. 22 is a close-up cross-sectional view of the tip portion of FIG. 17 with fluid droplets.
Figure 23:
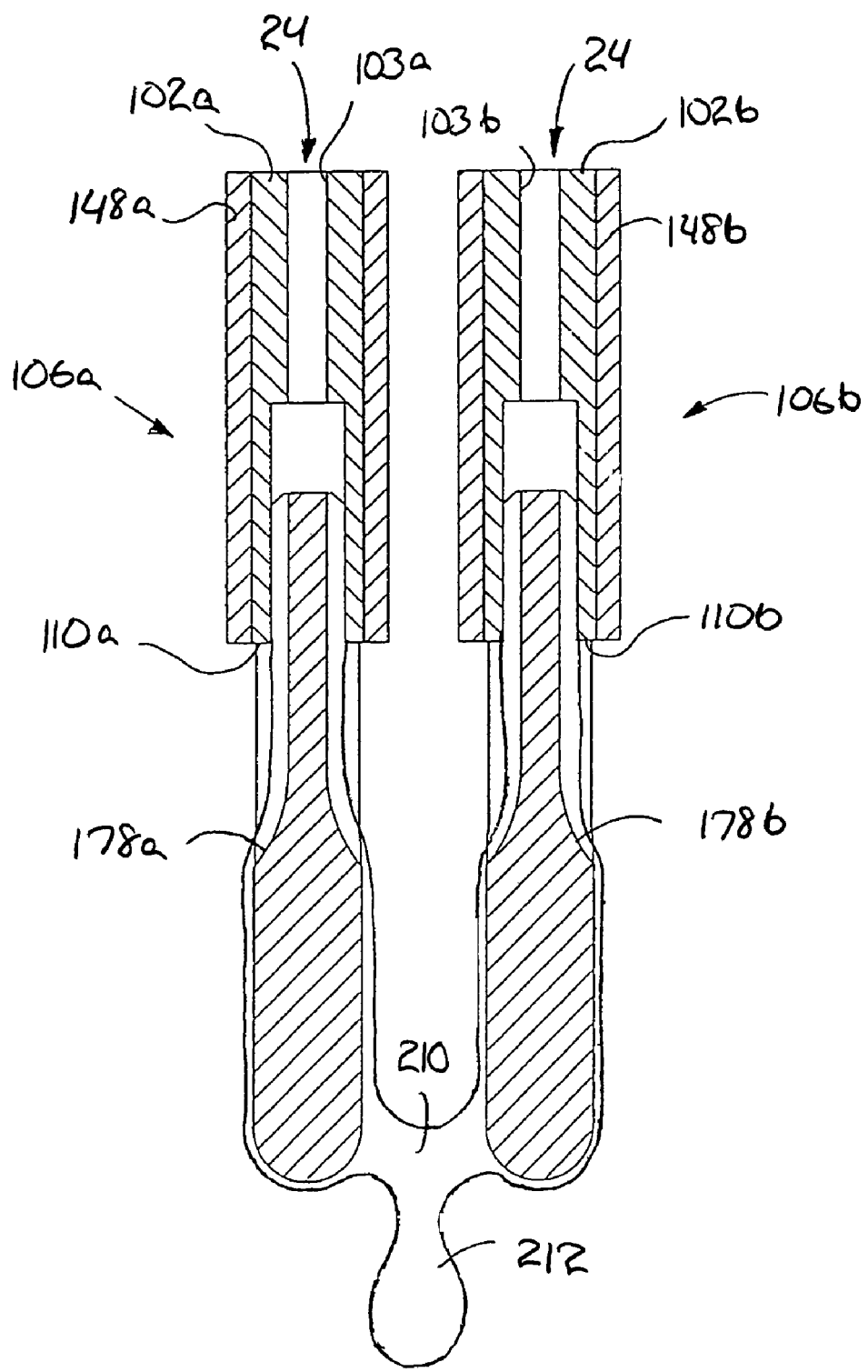
FIG. 23 is a close-up cross-sectional view of the tip portion of FIG. 17 with a fluid bridge between the electrodes.

Depending on the fluid flow rate, for example, fluid 24 expelled from fluid outlet openings 184a, 184b may form into droplets 212a, 212b which flow distally on electrodes 114a, 114b. As shown in FIG. 22, droplets 212a, 212b may form at varying times from fluid 24 expelled from any one of the fluid outlet openings 184a, 184b. Also, fluid 24 may be expelled in varying quantity from each of the fluid outlet openings 184a, 184b, depending on, for example, device orientation and varying fluid outlet sizes. With use of device 30e, the size of droplets 212a, 212b may also vary due to changes in the surface finish of the electrodes 114a, 114b, for example, as a result of being contaminated by blood and tissue.

When an unused device 30e is held in a normal (front end) use position with the longitudinal axes 120a, 120b of tip portions 106a, 106b pointed straight down (i.e. perpendicular to the earth) and with an adequate fluid flow rates of normal saline, the fluid 24 flowing down the electrodes 114a, 114b and dripping therefrom generally will remain separated as shown in FIG. 22. The same may also be said for devices 30c and 30d.

On occasion, for example when the orientation of the device is changed and the fluid flow rate increased, fluid 24 from certain of the fluid outlet openings 184a, 184b may merge into a bridge 210 between electrodes 114a, 114b. As shown in FIG. 21, this bridge 210 may drip from the device as droplet 212.

As indicated above, the formation of a bridge 210 between electrodes 114a, 114b forms a shunt between electrodes 114a, 114b, and a certain amount of RF energy may be diverted from going into tissue 200 and actually pass between electrodes 114a, 114b via the bridge 210. This loss of RF energy may slow down the process of coagulating and sealing the tissue and producing the desired hemostasis of the tissue. Also as indicated above, in order to decrease energy losses through the shunt it may be advantageous, as to increase the percentage of boiling of the conductive fluid to reduce the presence of a conductive fluid shunt. This may be achieved, for example, by decreasing the fluid flow rate or increasing the power level.

Another means to decrease energy losses through the shunt is to configure the tip portions 114a, 114b to reduce the merging of fluid 24 into bridge 210. For example, arranging the tip portions 106a, 106b with the electrodes 114a, 114b having a gap separation GS between electrodes 114a, 114b of at least about 2.0 mm has been found to reduce the merging of fluid 24 into bridge 210 as compared to a gap separation of 1.3 mm. Thus, the reduction in the merging of fluid 24 into bridge 210 may also be accomplished by the spacing of tip portions 106a, 106b.

Figure 24:
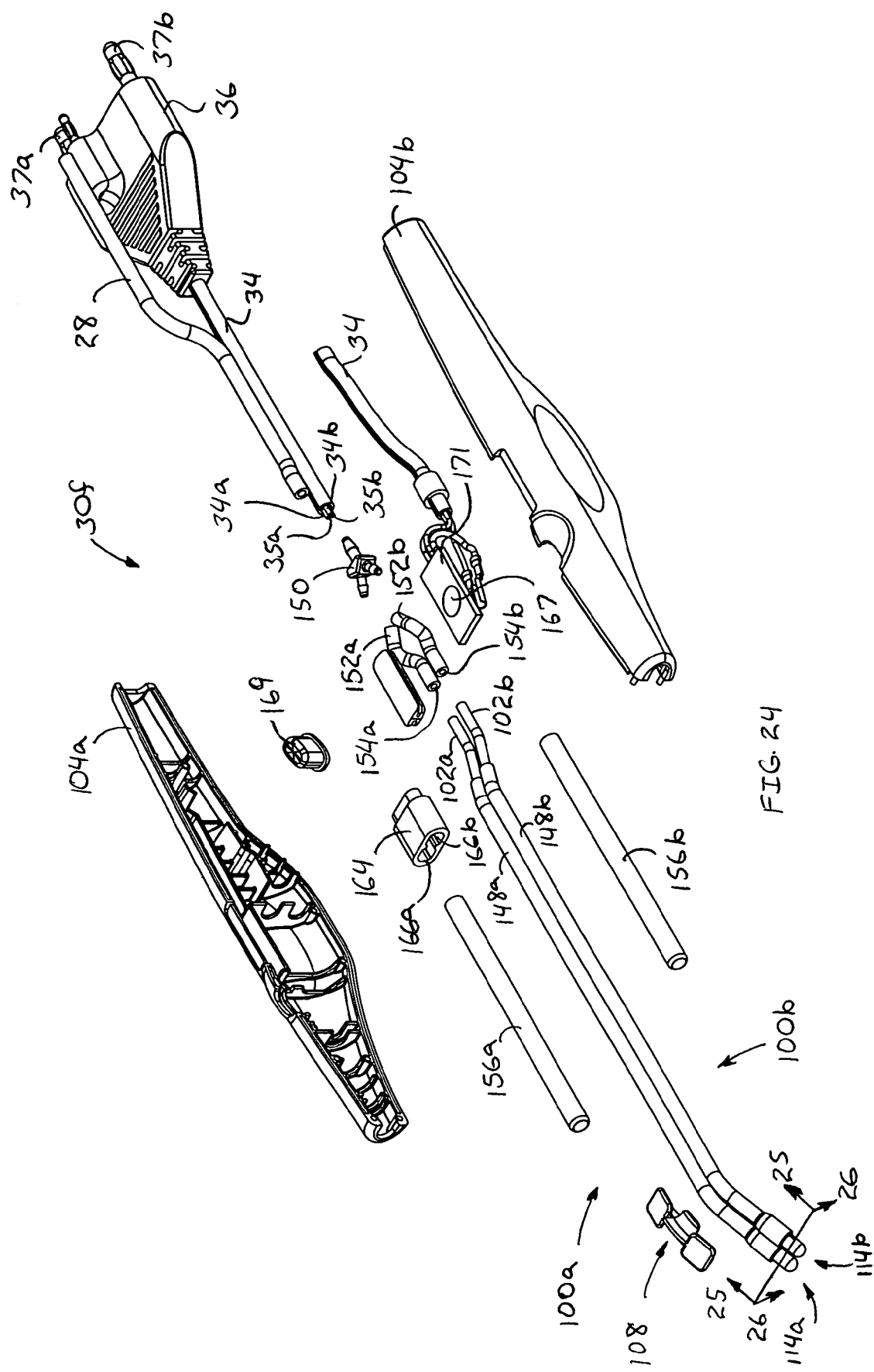
FIG. 24 is an exploded perspective view of an assembly of another electrosurgical device according to the present invention.

Yet another means to reduce the merging of fluid into bridge 210 may be accomplished by the specific location of fluid outlet openings 184a, 184b. An exemplary bipolar electrosurgical device of the present invention which may be used in conjunction with electrosurgical unit 14 of the present invention is shown at reference character 30f in FIGS. 24-26.

Figure 25:
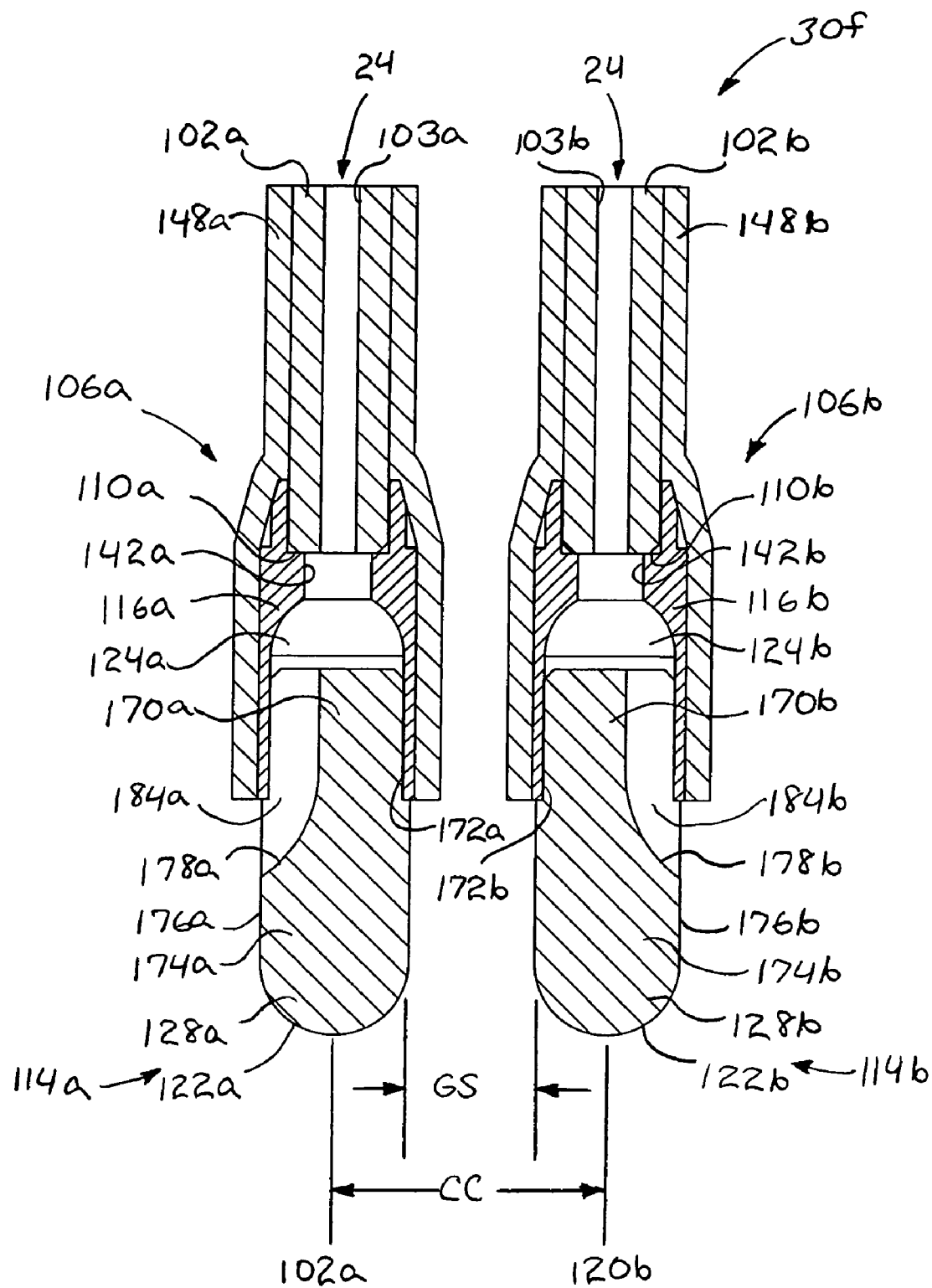
FIG. 25 is a close-up cross-sectional view of the tip portion of the device of FIG. 24 taken along line 25-25 of FIG. 24.
Figure 26:
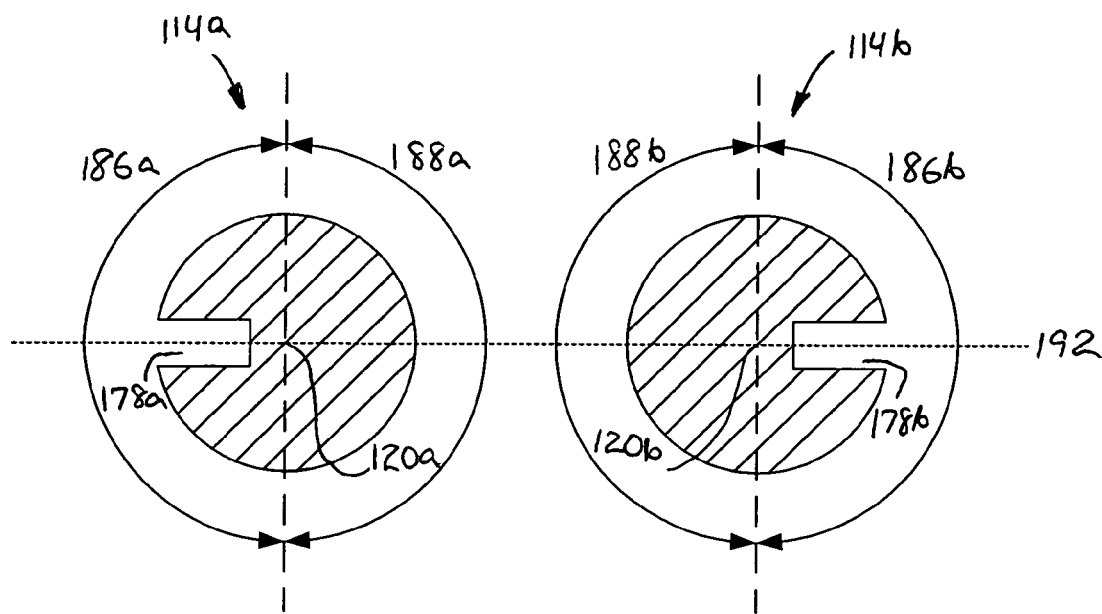
FIG. 26 is a close-up cross-sectional view of the tip portion of the device of FIG. 24 taken along line 26-26 of FIG. 24.

As best shown in FIGS. 25 and 26, the fluid outlet arrangement of device 30f expels fluid onto the electrodes 114a, 114b solely at locations remote from electrode surface portions alongside and facing each other. More particularly, fluid outlet opening 184a expels fluid onto electrode 114a at an electrode location remote from the surface portion of electrode 114a facing electrode 114b, and fluid outlet 184b expels fluid onto the electrode 114b at an electrode location remote from the surface portion of electrode 114b facing electrode 114a.

Even more particularly, fluid outlet opening 184a expels fluid onto a lateral surface portion 186a of electrode 114a, and fluid outlet opening 184b expels fluid onto a lateral surface portion 186b of electrode 114b. As shown in FIG. 26, the lateral surface portion 186a of electrode 114a comprises a semi-cylindrical surface portion of electrode 114a having a cylindrical arc of about 180 degrees, and the lateral surface portion 186b of electrode 114b is also provided by a semi-cylindrical surface portion of electrode 114b having a cylindrical arc of about 180 degrees.

Also as shown in FIG. 26, the surface portion of electrode 114a facing electrode 114b is provided by a medial surface portion 188a of electrode 114a, and the surface portion of electrode 114b facing electrode 114a is provided by a medial surface portion 188b of electrode 114b. As shown, the medial surface portion 188a of electrode 114a is provided by a semi-cylindrical surface portion of electrode 114a having a cylindrical arc of about 180 degrees, and the medial surface portion 188b of electrode 114b is also provided by a semi-cylindrical surface portion of electrode 114b having a cylindrical arc of about 180 degrees.

Figure 27:
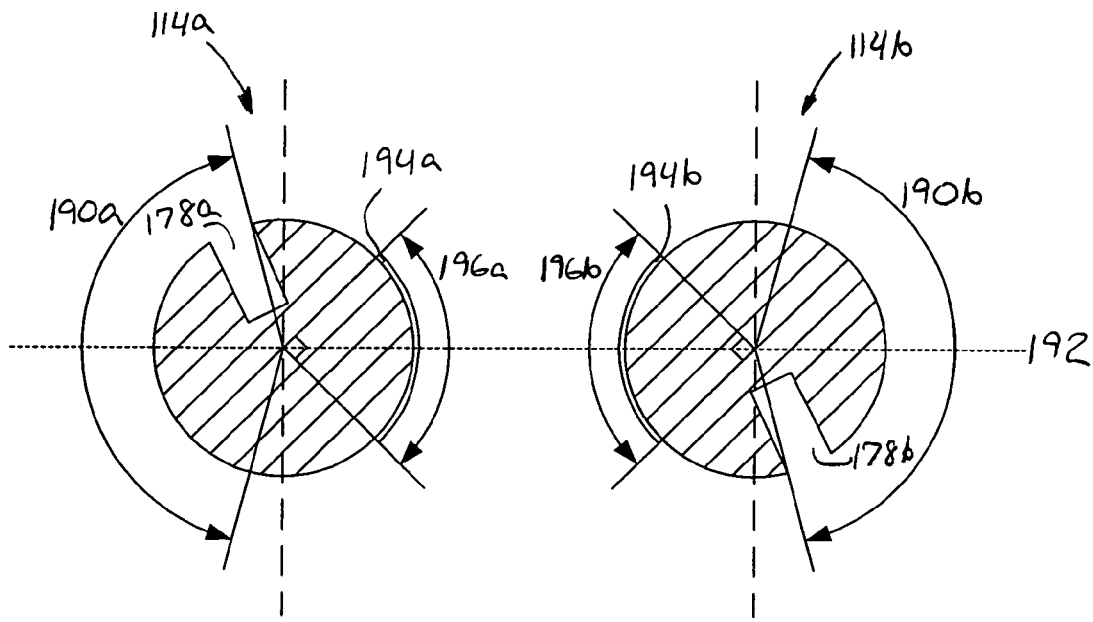
FIG. 27 is a close-up cross-sectional view of another embodiment of the tip portion of the device of FIG. 24 taken along line 26-26 of FIG. 24.

As shown in FIG. 27, a flat plane 192 passes through the longitudinal axis 120a of electrode 114a and the longitudinal axis 120b of electrode 114b. Fluid outlet opening 184a may be provided within a localized area 190a of the lateral surface portion 186a of electrode 114a which, as shown, comprises a cylindrical arc of about 150 degrees provided equally on each side of plane 192. Similarly, fluid outlet opening 184b may be provided within a localized area 190b of the lateral surface portion 186b of electrode 114b which, as shown, comprises a cylindrical arc of about 150 degrees provided equally on each side of plane 192. In other embodiments, the localized areas 190a, 190b of the lateral surface portions 186a, 186b may comprise narrower cylindrical arcs such as about 135, 120, 105, 90, 75, 60, 4530 and 15 degrees provided equally on each side of plane 192. In still other embodiments, the localized areas 190a, 190b of the lateral surface portions 186a, 186b may comprise wider cylindrical arcs such as about 155, 160, 165, 170 and 175 degrees provided equally on each side of plane 192. As best shown in FIGS. 25 and 26, both fluid outlet opening 184a and fluid outlet opening 184b are provided on the plane 192, which desirably places the fluid outlet openings 184a, 184b at the most extreme lateral area of electrodes 114a, 114b, respectively.

In certain embodiments, the electrodes 144a, 114b of device 30f may also have an electrically insulative coating thereon. As shown in FIG. 27, the medial surface portion 188a of electrode 114a has an electrically insulative coating 194a thereon, and the medial surface portion 188b of electrode 114b has an electrically insulative coating 194b thereon, both of which preferably terminate adjacent to the spherical distal end of their respective electrodes. As shown, coating 194a may be provided within a localized area 196a of the medial surface portion 188a of electrode 114a which, as shown, comprises a cylindrical arc of about 90 degrees provided equally on each side of plane 192. Similarly, coating 194b may be provided within a localized area 196b of the medial surface portion 188b of electrode 114b which, as shown, comprises a cylindrical arc of about 90 degrees provided equally on each side of plane 192. In still other embodiments, the localized areas 196a, 196b of the medial surface portions 188a, 188b may comprise wider or narrower cylindrical arcs the same as those listed above.

Figure 28:
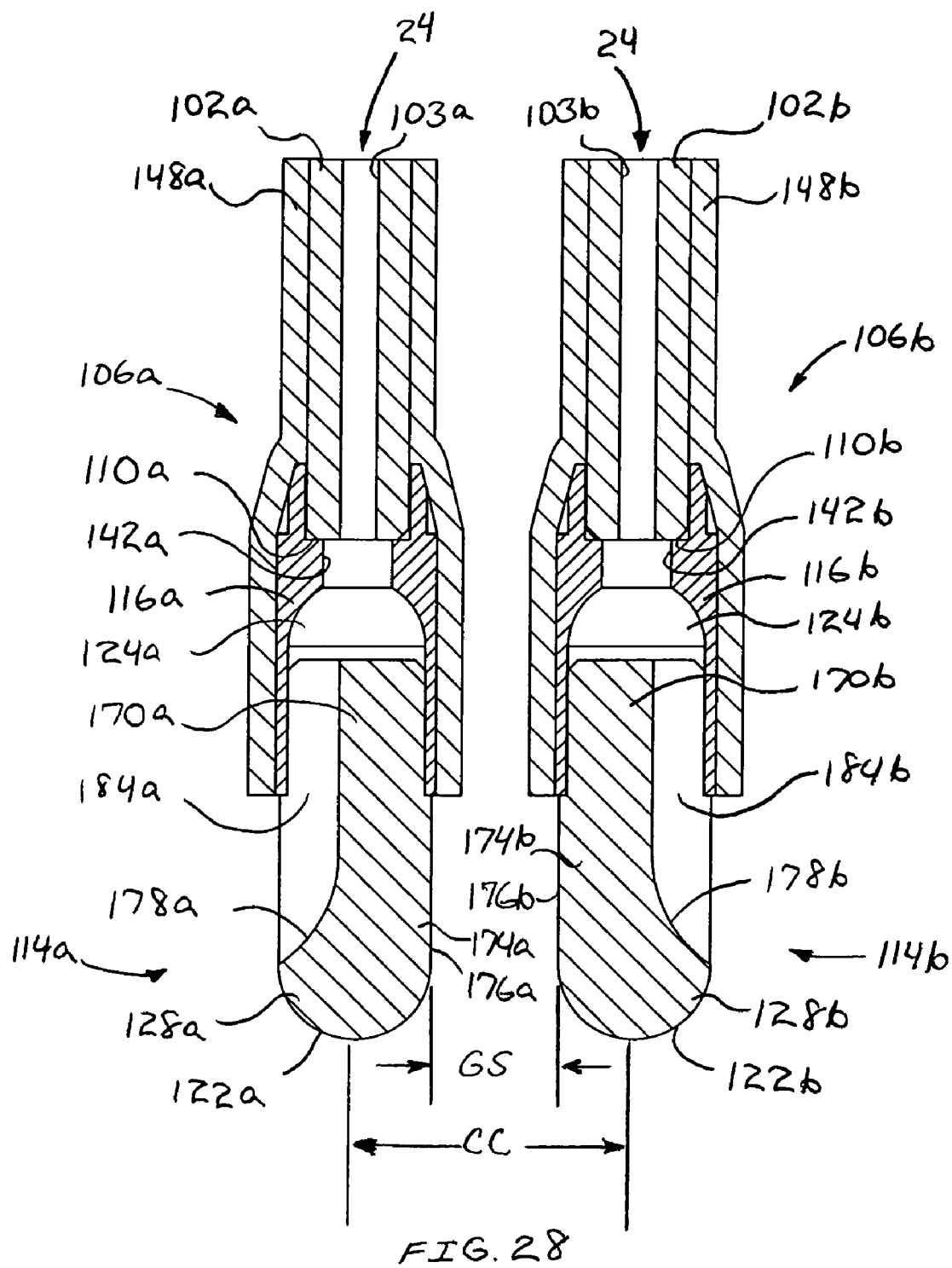
FIG. 28 is a close-up cross-sectional view of another embodiment of the tip portion of the device of FIG. 24 taken along line 25-25 of FIG. 24.

As best shown in FIG. 25, recesses 178a, 178b of electrodes 114a, 114b each provide a fluid flow channel which carries fluid expelled from the fluid outlet openings 184a, 184b distally along a length of electrodes 114a, 114b and remote from the surface portion the electrodes facing each other. Also as shown in FIG. 25, recesses 178a, 178b each terminate proximal to the spherical distal end of their respective electrodes. However, as shown in FIG. 28, in other embodiments recesses 178a, 178b each may terminate adjacent to the spherical distal end of their respective electrodes.

For device 30f, the longitudinal axes 120a, 120b of tip portions 106a, 106b and electrodes 114a, 114b are separated center-to-center CC about 6 mm. As a result, when cylindrical portions 174a 174b have a preferred diameter of 3.5 mm, the actual spatial gap separation GS between electrodes 114a, 114b is about 2.5 mm.

The bipolar devices disclosed herein are particularly useful as non-coaptive tissue sealers in providing hemostasis during surgery. In other words, grasping of the tissue is not necessary to shrink, coagulate and seal tissue against blood loss, for example, by shrinking collagen and associated lumens of blood vessels (e.g., arteries, veins) to provided the desired hemostasis of the tissue. Furthermore, the control system of the electrosurgical unit 12 is not necessarily dependent on tissue feedback such as temperature or impedance to operate. Thus, the control system of electrosurgical unit 12 may be open loop with respect to the tissue which simplifies use.

The bipolar devices disclosed herein are particularly useful to surgeons to achieve hemostasis after dissecting through soft tissue, as part of hip or knee arthroplasty. The tissue treating portions can be painted over the raw, oozing surface 202 of tissue 200 to seal the tissue 200 against bleeding, or focused on individual larger bleeding vessels to stop vessel bleeding. As part of the same or different procedure, bipolar devices 30a-30e are also useful to stop bleeding from the surface of cut bone tissue as part of any orthopaedic procedure that requires bone to be cut.

As is well known, bone, or osseous tissue, is a particular form of dense connective tissue consisting of bone cells (osteocytes) embedded in a matrix of calcified intercellular substance. Bone matrix mainly contains collagen fibers and the minerals calcium carbonate, calcium phosphate and hydroxyapatite. Among the many types of bone within the human body are compact bone and cancellous bone. Compact bone is hard, dense bone that forms the surface layers of bones and also the shafts of long bones. It is primarily made of haversian systems which are covered by the periosteum. Compact bone contains discrete nutrient canals through which blood vessels gain access to the haversian systems and the marrow cavity of long bones. For example, Volkmann's canals which are small canals found in compact bone through which blood vessels pass from the periosteum and connect with the blood vessels of haversian canals or the marrow cavity. Devices 30a-30e disclosed herein may be particularly useful to treat compact bone and to provide hemostasis and seal bleeding vessels (e.g. by shrinking to complete close) and other structures associated with Volkmann's canals and Haversian systems.

In contrast to compact bone, cancellous bone is spongy bone and forms the bulk of the short, flat, and irregular bones and the ends of long bones. The network of osseous tissue that makes up the cancellous bone structure comprises many small trabeculae, partially enclosing many intercommunicating spaces filled with bone marrow. Consequently, due to their trabecular structure, cancellous bones are more amorphous than compact bones, and have many more channels with various blood cell precursors mixed with capillaries, venules and arterioles. Devices 30a-30e disclosed herein may be particularly useful to treat cancellous bone and to provide hemostasis and seal bleeding structures such as the above micro-vessels (i.e. capillaries, venules and arterioles) in addition to veins and arteries. Devices 30a-30e may be particularly useful for use during orthopedic knee, hip, shoulder and spine procedures (e.g. arthroplasty).

During a knee replacement procedure, the condyle at the distal epiphysis of the femur and the tibial plateau at the proximal epiphysis of the tibia are often cut and made more planer with saw devices to ultimately provide a more suitable support structure for the femoral condylar prosthesis and tibial prosthesis attached thereto, respectively. The cutting of these long bones results in bleeding from the cancellous bone at each location. In order to seal and arrest the bleeding from the cancellous bone which has been exposed with the cutting of epiphysis of each long bone, bipolar device 30a-30e may be utilized, and more particularly devices 30c and 30d due to their electrode configuration. Thereafter, the respective prostheses may be attached.

Turning to a hip replacement procedure, the head and neck of the femur at the proximal epiphysis of the femur is removed, typically by cutting with a saw device, and the intertrochantic region of the femur is made more planer to provide a more suitable support structure for the femoral stem prosthesis subsequently attached thereto. With respect to the hip, a ball reamer is often used to ream and enlarge the acetabulum of the innominate (hip) bone to accommodate the insertion of an acetabular cup prosthesis therein, which will provide the socket into which the head of the femoral stem prosthesis fits. The cutting of the femur and reaming of the hip bone results in bleeding from the cancellous bone at each location. In order to seal and arrest the bleeding from the cancellous bone which has been cut and exposed, bipolar devices 30a-30e may be utilized, and more particularly devices 30c and 30d due to their electrode configuration. Thereafter, as with the knee replacement, the respective prostheses may be attached.

Bipolar devices 30a-30e may be utilized for treatment of connective tissues, such as for shrinking intervertebral discs during spine surgery. Intervertebral discs are flexible pads of fibrocartilaginous tissue tightly fixed between the vertebrae of the spine. The discs comprise a flat, circular capsule roughly an inch in diameter and about 0.25 inch thick, made of a tough, fibrous outer membrane called the annulus fibrosus, surrounding an elastic core called the nucleus pulposus.

Under stress, it is possible for the nucleus pulposus to swell and herniate, pushing through a weak spot in the annulus fibrosus membrane of the disc and into the spinal canal. Consequently, all or part of the nucleus pulposus material may protrude through the weak spot, causing pressure against surrounding nerves which results in pain and immobility.

Bipolar devices 30a-30e, and more particularly device 30e due to its size, may be utilized to shrink protruding and herniated intervertebral discs which, upon shrinking towards normal size, reduces the pressure on the surrounding nerves and relieves the pain and immobility. Devices 30a-30e may be applied via posterior spinal access under surgeon control for focal shrinking of the annulus fibrosus membrane.

Where an intervertebral disc cannot be repaired and must be removed as part of a discectomy, devices 30a-30e may be particularly useful to seal and arrest bleeding from the cancellous bone of opposing upper and lower vertebra surfaces (e.g. the cephalad surface of the vertebral body of a superior vertebra and the caudad surface of an inferior vertebra). Where the disc is removed from the front of the patient, for example, as part of an anterior, thoracic spine procedure, devices 30a-30e may also be particularly useful to seal and arrest bleeding from segmental vessels over the vertebral body.

Bipolar devices 30a-30e may be utilized to seal and arrest bleeding of epidural veins which bleed as a result of the removal of tissue around the dural membrane during, for example a laminectomy or other neurosurgical surgery. The epidural veins may start bleeding when the dura is retracted off of them as part of a decompression. Also during a laminectomy, devices 30a-30e may be used to seal and arrest bleeding from the vertebral arch and, in particular the lamina of the vertebral arch.

As established above, bipolar devices 30a-30e of the present invention inhibit such undesirable effects of tissue desiccation, electrode sticking, char formation and smoke generation, and thus do not suffer from the same drawbacks as prior art dry tip electrosurgical devices. The use of the disclosed devices can result in significantly lower blood loss during surgical procedures. Such a reduction in blood loss can reduce or eliminate the need for blood transfusions, and thus the cost and negative clinical consequences associated with blood transfusions, such as prolonged hospitalization.

While a preferred embodiment of the present invention has been described, it should be understood that various changes, adaptations and modifications can be made therein without departing from the spirit of the invention and the scope of the appended claims. The scope of the invention should, therefore, be determined not with reference to the above description, but instead should be determined with reference to the appended claims along with their full scope of equivalents. Furthermore, it should be understood that the appended claims do not necessarily comprise the broadest scope of the invention which the Applicant is entitled to claim, or the only manner(s) in which the invention may be claimed, or that all recited features are necessary.

All publications and patent documents cited in this application are incorporated by reference in their entirety for all purposes to the extent they are consistent.

What is claimed is:

1. An electrosurgical apparatus to provide controlled delivery of radio-frequency power and a fluid to an electrosurgical hand device to treat tissue, the apparatus comprising:
    a radio-frequency generator to deliver the radio-frequency power, the radio frequency power from the radio-frequency generator selectable at a radio-frequency power level;
    a pump to deliver the fluid;
    a primer to prime the hand device with the fluid;
    a control system to control a flow of the fluid delivered by the pump with a functional relationship between the radio-frequency power level and the flow of the fluid, the functional relationship to increase the flow of the fluid in response to an increase in the radio-frequency power level and to decrease the flow of the fluid in response to a decrease in the radio-frequency power level;
    a fluid flow selector which changes the functional relationship between the radiofrequency power level and the flow of the fluid; and
    wherein the functional relationship is stored in a memory of the apparatus for use by a microprocessor, the functional relationship in the form of a mathematical equation having a proportionality constant and the fluid flow selector changes the proportionality constant.

2. The apparatus of claim 1 wherein:
    the mathematical equation comprises a linear equation.

3. The apparatus of claim 1 wherein:
    the fluid flow selector provides a plurality of fluid flow settings.

4. The apparatus of claim 3 wherein:
    the plurality of fluid flow settings comprises a low fluid flow setting and a high fluid flow setting.

5. The apparatus of claim 1 wherein:
    the fluid flow selector comprises at least one switch.

6. The apparatus of claim 5 wherein:
    the at least one switch comprises a push switch.

7. The apparatus of claim 5 wherein:
    the at least one switch comprises a membrane switch.

8. The apparatus of claim 5 wherein:
    the at least one switch comprises a plurality of switches.

9. The apparatus of claim 1 wherein:
    the control system is open loop with respect to the tissue.

10. The apparatus of claim 1 wherein:
    the pump comprises a peristaltic pump.

11. The apparatus of claim 10 wherein:
    the peristaltic pump comprises a rotary peristaltic pump.

12. A bipolar electrosurgical device to treat tissue by moving along a tissue surface in a presence of radio frequency energy and a fluid provided simultaneously from the device, the device comprising:

a first electrode tip spaced next to a second electrode tip, a surface portion of the first electrode tip facing the second electrode tip and a surface portion of the second electrode tip facing the first electrode tip;

the first electrode tip having an electrically conductive spherical distal end;

the second electrode tip having an electrically conductive spherical distal end; and a fluid outlet arrangement, the fluid outlet arrangement to expel fluid onto the electrode tips solely at locations remote from the electrode tip surface portions facing each other.

13. The device of claim 12 wherein:
the fluid outlet arrangement having a first fluid outlet and a second fluid outlet;
the first fluid outlet to expel fluid onto the first electrode tip at a first electrode tip location remote from the surface portion of the first electrode tip facing the second electrode tip; and
the second fluid outlet to expel fluid onto the second electrode tip at a second electrode tip location remote from the surface portion of the second electrode tip facing the first electrode tip.

14. The device of claim 13 wherein:
the first fluid outlet to expel fluid onto the first electrode tip at a first electrode tip location remote from the surface portion of the first electrode tip facing the second electrode tip expels the fluid onto a lateral surface portion of the first electrode tip; and
the second fluid outlet to expel fluid onto the second electrode tip at a second electrode tip location remote from the surface portion of the second electrode tip facing the first electrode tip expels the fluid onto a lateral surface portion of the second electrode tip.

15. The device of claim 14 wherein:
the lateral surface portion of the first electrode tip comprises a semi-cylindrical surface portion having an arc of about 180 degrees; and
the lateral surface portion of the second electrode tip comprises a semi-cylindrical surface portion having an arc of about 180 degrees.

16. The device of claim 14 wherein:
a flat plane passes through a longitudinal axis of the first electrode tip and a longitudinal axis of the second electrode tip;
the first fluid outlet is provided within a localized area of the lateral surface portion of the first electrode tip, the localized area comprising a semi-cylindrical surface portion having an arc of about 180 degrees provided equally on each side of the plane; and
the second fluid outlet is provided within a localized area of the lateral surface portion of the second electrode tip, the localized area comprising a semi-cylindrical surface portion having an arc of about 180 degrees provided equally on each side of the plane.

17. The device of claim 14 wherein:
a flat plane passes through a longitudinal axis of the first electrode tip and a longitudinal axis of the second electrode tip;
the first fluid outlet is provided within a localized area of the lateral surface portion of the first electrode tip, the localized area comprising a semi-cylindrical surface portion having an arc of about 90 degrees provided equally on each side of the plane; and
the second fluid outlet is provided within a localized area of the lateral surface portion of the second electrode tip, the localized area comprising a semi-cylindrical surface portion having an arc of about 90 degrees provided equally on each side of the plane.

18. The device of claim 14 wherein:
a flat plane passes through a longitudinal axis of the first electrode tip and a longitudinal axis of the second electrode tip;
the first fluid outlet is provided on the plane; and
the second fluid outlet is provided on the plane.

19. The device of claim 13 wherein:
the first electrode tip location remote from the surface portion of the first electrode tip facing the second electrode tip is provided by a lateral surface portion of the first electrode tip; and
the second electrode tip location remote from the surface portion of the second electrode tip facing the first electrode tip is provided by a lateral surface portion of the second electrode tip.

20. The device of claim 19 wherein:
the lateral surface portion of the first electrode tip comprises a semi-cylindrical surface portion having an arc of about 180 degrees; and
the lateral surface portion of the second electrode tip comprises a semi-cylindrical surface portion having an arc of about 180 degrees.

21. The device of claim 13 wherein:
the first fluid outlet is at least partially defined by the first electrode tip; and
the second fluid outlet is at least partially defined by the second electrode tip.

22. The device of claim 13 wherein:
the first fluid outlet is located proximal to the first electrode tip spherical distal end; and
the second fluid outlet is located proximal to the second electrode tip spherical distal end.

23. The device of claim 13 wherein:
the first electrode tip further comprises a first electrode tip fluid flow channel in fluid communication with the first fluid outlet; and
the second electrode tip further comprises a second electrode tip fluid flow channel in fluid communication with the second fluid outlet.

24. The device of claim 23 wherein:
the first electrode tip fluid flow channel to carry fluid expelled from the first fluid outlet distally along a length of the first electrode tip and remote from the surface portion of the first electrode tip facing the second electrode tip; and
the second electrode tip fluid flow channel to carry fluid expelled from the second fluid outlet distally along a length of the second electrode tip and remote from the surface portion of the second electrode tip facing the first electrode tip.

25. The device of claim 23 wherein:
the first electrode tip fluid flow channel is provided by a first electrode tip elongated recess oriented longitudinally on the first electrode tip; and
the second electrode tip fluid flow channel is provided by a second electrode tip elongated recess oriented longitudinally on the second electrode tip.

26. The device of claim 25 wherein:
the first fluid outlet is at least partially defined by the first electrode tip elongated recess; and
the second fluid outlet is at least partially defined by the second electrode tip elongated recess.

27. The device of claim 25 wherein:
the first electrode tip elongated recess terminates adjacent to the first electrode tip spherical distal end; and the second electrode tip elongated recess terminates adjacent to the second electrode tip spherical distal end.

28. The device of claim 25 wherein:
the first electrode tip elongated recess terminates proximal to the first electrode tip spherical distal end; and
the second electrode tip elongated recess terminates proximal to the second electrode tip spherical distal end.

29. The device of claim 13 wherein:
the first electrode tip further comprises a surface having a contact angle with fluid expelled from the first fluid outlet onto the first electrode tip of less than 90 degrees; and
the second electrode tip further comprises a surface having a contact angle with fluid expelled from the second fluid outlet onto the second electrode tip of less than 90 degrees.

30. The device of claim 12 wherein:
the surface portion of the first electrode tip facing the second electrode tip is provided by a medial surface portion of the first electrode tip; and
the surface portion of the second electrode tip facing the first electrode tip is provided by a medial surface portion of the second electrode tip.

31. The device of claim 30 wherein:
the medial surface portion of the first electrode tip comprises a semi-cylindrical surface portion having an arc of about 180 degrees; and
the medial surface portion of the second electrode tip comprises a semi-cylindrical surface portion having an arc of about 180 degrees.

32. The device of claim 12 wherein:
the surface portion of the first electrode tip facing the second electrode tip and the surface portion of the second electrode tip facing the first electrode tip are mirror images of each other.

33. The device of claim 12 wherein:
the first electrode tip spherical distal end has a arc of about 180 degrees; and
the second electrode tip spherical distal end has a arc of about 180 degrees.

34. The device of claim 12 wherein:
the first electrode tip further comprises a first electrode tip cylindrical portion; and
the second electrode tip further comprises a second electrode tip cylindrical portion.

35. The device of claim 34 wherein:
the first electrode tip cylindrical portion is located proximally adjacent to the first electrode tip spherical distal end; and
the second electrode tip cylindrical portion is located proximally adjacent to the second electrode tip spherical distal end.

36. The device of claim 12 wherein:
the first electrode tip is provided at a distal end of a first stationary arm; and
the second electrode tip is provided at a distal end of a second stationary arm.

37. The device of claim 36 wherein:
the first stationary arm comprises a first shaft having a first shaft distal end, the first electrode tip extending distally beyond the first shaft distal end; and
the second stationary arm comprises a second shaft having a second shaft distal end, the second electrode tip extending distally beyond the second shaft distal end.

38. The device of claim 37 wherein:
the fluid outlet arrangement having a first fluid outlet and a second fluid outlet;
the first shaft further comprises a first shaft distal end opening;
the second shaft further comprises a second shaft distal end opening;
the first fluid outlet at least partially defined by the first shaft distal end opening; and
the second fluid outlet at least partially defined by the second shaft distal end opening.

39. The device of claim 37 wherein:
the fluid outlet arrangement having a first fluid outlet and a second fluid outlet;
the first shaft further comprises a first shaft fluid passage;
the second shaft further comprises a second shaft fluid passage;
the first shaft fluid passage in fluid communication with the first fluid outlet; and
the second shaft fluid passage in fluid communication with the second fluid outlet.

40. A bipolar electrosurgical device to treat tissue by moving along a tissue surface in a presence of radio frequency energy and a fluid provided simultaneously from the device, the device comprising:
a first electrode tip spaced next to a second electrode tip, a surface portion of the first electrode tip alongside the second electrode tip and a surface portion of the second electrode tip alongside the first electrode tip;
the first electrode tip having an electrically conductive spherical distal end;
the second electrode tip having an electrical conductive spherical distal end; and
a fluid outlet arrangement having a first fluid outlet and a second fluid outlet; the first fluid outlet to expel fluid onto the first electrode tip at a first electrode tip location remote from the surface portion of the first electrode tip alongside the second electrode tip; and
the second fluid outlet to expel fluid onto the second electrode tip at a second electrode tip location remote from the surface portion of the second electrode tip alongside the first electrode tip.

* * * * *